United States Patent
Rooney

(10) Patent No.: US 12,303,561 B2
(45) Date of Patent: May 20, 2025

(54) PROTEIN ANTIGENS AND USES THEREOF

(71) Applicant: BioNTech US Inc., Cambridge, MA (US)

(72) Inventor: Michael Steven Rooney, Boston, MA (US)

(73) Assignee: BioNTech US Inc., Cambridge, MA (US)

( * ) Notice: Subject to any disclaimer, the term of this patent is extended or adjusted under 35 U.S.C. 154(b) by 364 days.

(21) Appl. No.: 16/500,707

(22) PCT Filed: Apr. 3, 2018

(86) PCT No.: PCT/US2018/025933
§ 371 (c)(1),
(2) Date: Oct. 3, 2019

(87) PCT Pub. No.: WO2018/187356
PCT Pub. Date: Oct. 11, 2018

(65) Prior Publication Data
US 2023/0241207 A1    Aug. 3, 2023

Related U.S. Application Data

(60) Provisional application No. 62/480,593, filed on Apr. 3, 2017, provisional application No. 62/480,596, filed on Apr. 3, 2017, provisional application No. 62/480,597, filed on Apr. 3, 2017.

(51) Int. Cl.
| | |
|---|---|
| *A61K 39/245* | (2006.01) |
| *A61K 39/00* | (2006.01) |
| *A61K 45/06* | (2006.01) |
| *A61P 35/00* | (2006.01) |

(52) U.S. Cl.
CPC ........ *A61K 39/245* (2013.01); *A61K 39/0011* (2013.01); *A61K 39/4615* (2023.05); *A61K 39/4622* (2023.05); *A61K 39/4644* (2023.05); *A61K 45/06* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,683,195 A | 7/1987 | Mullis et al. | |
| 4,722,848 A | 2/1988 | Paoletti et al. | |
| 4,837,028 A | 6/1989 | Allen | |
| 5,019,369 A | 5/1991 | Presant et al. | |
| 5,204,253 A | 4/1993 | Sanford et al. | |
| 5,279,833 A | 1/1994 | Rose | |
| 5,580,859 A | 12/1996 | Felgner et al. | |
| 5,589,466 A | 12/1996 | Felgner et al. | |
| 5,973,007 A | 10/1999 | Demarchez et al. | |
| 6,406,705 B1 | 6/2002 | Davis et al. | |
| 7,026,443 B1* | 4/2006 | Sette | A61P 37/04 424/193.1 |
| 8,252,893 B2 | 8/2012 | Kim et al. | |
| 8,501,167 B2 | 8/2013 | Apelian et al. | |
| 8,999,937 B2 | 4/2015 | Srinivasan | |
| 9,862,927 B2 | 1/2018 | Banchereau et al. | |
| 11,135,262 B2* | 10/2021 | Jin | A61K 39/0011 |
| 2003/0124128 A1 | 7/2003 | Lillie et al. | |
| 2004/0029114 A1 | 2/2004 | Mack et al. | |
| 2004/0076955 A1 | 4/2004 | Mack et al. | |
| 2004/0087478 A1 | 5/2004 | Gillen et al. | |
| 2005/0222062 A1 | 10/2005 | Arai et al. | |
| 2005/0287127 A1 | 12/2005 | Li et al. | |
| 2007/0055049 A1 | 3/2007 | Grey et al. | |
| 2009/0136494 A1 | 5/2009 | Ponath et al. | |
| 2009/0270482 A1 | 10/2009 | Schuebeler et al. | |
| 2010/0105051 A1 | 4/2010 | Lillie et al. | |
| 2011/0092388 A1 | 4/2011 | Lillie et al. | |
| 2011/0097743 A1 | 4/2011 | Bihain et al. | |
| 2011/0182937 A1 | 7/2011 | Banchereau et al. | |
| 2011/0257890 A1 | 10/2011 | Weinschenk et al. | |
| 2012/0082691 A1 | 4/2012 | Rammensee | |
| 2012/0288509 A1 | 11/2012 | Schuebeler et al. | |
| 2012/0288539 A1 | 11/2012 | Eber | |
| 2013/0210014 A1 | 8/2013 | Sharman | |
| 2013/0323279 A1 | 12/2013 | Nixon et al. | |
| 2013/0338077 A1 | 12/2013 | Srinivasan | |
| 2014/0056986 A1 | 2/2014 | Desai et al. | |
| 2016/0122396 A1 | 5/2016 | Bunnik et al. | |
| 2016/0252511 A1 | 9/2016 | Czemiecki et al. | |

(Continued)

FOREIGN PATENT DOCUMENTS

| | | |
|---|---|---|
| CA | 2343602 A1 | 10/2001 |
| CN | 1299769 C | 2/2007 |

(Continued)

OTHER PUBLICATIONS

Ponti et al., Critical Reviews in Clinical Laboratory Sciences 2023, vol. 60, No. 8, 640-650 (Year: 2023).*
Pierce et al., Viruses 2024, 16, 803. https:/ /doi.org/10.3390/v16050803 (Year: 2024).*
Allison, "The Mode of Action of Immunological Adjuvants," Dev Biol Stand, 92: 3-11 (1998).
Coleman et al.: Human papillomavirus type 16 viral load is decreased following a therapeutic vaccination. Cancer Immunology Immunotherapy. 65(5):563-573 (2016).

(Continued)

*Primary Examiner* — Shanon A. Foley
*Assistant Examiner* — Myron G Hill
(74) *Attorney, Agent, or Firm* — Wilson Sonsini Goodrich & Rosati

(57) ABSTRACT

The field of the present invention relates to immunotherapeutic peptides, peptide binding agents, and their use, for example, in the immunotherapy of cancer.

24 Claims, No Drawings
Specification includes a Sequence Listing.

(56) References Cited

U.S. PATENT DOCUMENTS

| | | | |
|---|---|---|---|
| 2016/0317654 A1 | 11/2016 | Noelle et al. | |
| 2016/0331822 A1 | 11/2016 | Hacohen et al. | |
| 2016/0331834 A1 | 11/2016 | Mondoulet et al. | |
| 2016/0377631 A1 | 12/2016 | Kuchroo et al. | |
| 2017/0114413 A1 | 4/2017 | Hahn et al. | |
| 2017/0160269 A1 | 6/2017 | Linnemann et al. | |
| 2017/0204140 A1 | 7/2017 | Suphioglu | |
| 2017/0253633 A1 | 9/2017 | Mahr et al. | |
| 2017/0261508 A1 | 9/2017 | Czerniecki et al. | |
| 2018/0015161 A1* | 1/2018 | Weiner | C07K 16/2803 |
| 2018/0088121 A1 | 3/2018 | Gerhard et al. | |
| 2019/0099475 A1 | 4/2019 | Benz et al. | |

FOREIGN PATENT DOCUMENTS

| | | | |
|---|---|---|---|
| CN | 101885778 B | 10/2013 | |
| CN | 105693828 A | 6/2016 | |
| DE | 102008010954 A1 | 8/2009 | |
| EP | 1338606 A1 | 8/2003 | |
| EP | 1498145 A1 | 1/2005 | |
| EP | 2105511 A1 | 9/2009 | |
| EP | 2390363 A1 | 11/2011 | |
| EP | 1827385 B1 | 3/2013 | |
| JP | 2019513373 A | 5/2019 | |
| WO | WO-9106309 A1 | 5/1991 | |
| WO | WO-9324640 A2 | 12/1993 | |
| WO | WO-9403205 A1 | 2/1994 | |
| WO | WO-9420127 A1 | 9/1994 | |
| WO | WO-9507707 A1 | 3/1995 | |
| WO | WO-9618372 A2 | 6/1996 | |
| WO | WO20000587 A3 | 4/2000 | |
| WO | WO-0066153 A1 | 11/2000 | |
| WO | W02001/000225 | 1/2001 | |
| WO | WO-0119408 A1 | 3/2001 | |
| WO | WO2001055177 | 8/2001 | |
| WO | WO-2004011650 A2 | 2/2004 | |
| WO | WO-2004037175 A2 | 5/2004 | |
| WO | WO-2006121168 A1 | 11/2006 | |
| WO | WO-2007049737 A1 | 5/2007 | |
| WO | WO-2008096831 A1 | 8/2008 | |
| WO | WO-2010033949 A1 | 3/2010 | |
| WO | WO-2011146862 A1 | 11/2011 | |
| WO | WO-2012079000 A1 | 6/2012 | |
| WO | WO-2012095639 A2 | 7/2012 | |
| WO | WO-2012101112 A1 | 8/2012 | |
| WO | WO-2012159643 A1 | 11/2012 | |
| WO | WO-2012159754 A2 | 11/2012 | |
| WO | WO-2013026027 A1 | 2/2013 | |
| WO | WO-2013039889 A1 | 3/2013 | |
| WO | WO-2013086464 A1 | 6/2013 | |
| WO | WO-2013123031 A2 | 8/2013 | |
| WO | WO-2013151672 A2 | 10/2013 | |
| WO | WO-2013166321 A1 | 11/2013 | |
| WO | WO-2013173223 A1 | 11/2013 | |
| WO | WO-2013176915 A1 | 11/2013 | |
| WO | WO-2014011987 A1 | 1/2014 | |
| WO | WO-2014012051 A1 | 1/2014 | |
| WO | WO-2014018863 A1 | 1/2014 | |
| WO | WO-2014056986 A1 | 4/2014 | |
| WO | WO-2014134165 A1 | 9/2014 | |
| WO | WO-2014150924 A2 | 9/2014 | |
| WO | WO-2014172606 A1 | 10/2014 | |
| WO | WO-2014184744 A1 | 11/2014 | |
| WO | WO-2014191128 A1 | 12/2014 | |
| WO | WO-2014197369 A1 | 12/2014 | |
| WO | WO-2015085233 A1 | 6/2015 | |
| WO | WO-2015107081 A1 | 7/2015 | |
| WO | WO-2016011487 A1 | 1/2016 | |
| WO | WO-2016020710 A1 | 2/2016 | |
| WO | WO-2016100975 A1 | 6/2016 | |
| WO | WO-2016141324 A2 | 9/2016 | |
| WO | WO-2016144976 A1 | 9/2016 | |
| WO | WO-2016156478 A1 | 10/2016 | |
| WO | WO-2016187508 A2 | 11/2016 | |
| WO | WO-2016203577 A1 | 12/2016 | |
| WO | WO-2017004153 A1 | 1/2017 | |
| WO | WO-2017011710 A2 | 1/2017 | |
| WO | WO-2017069958 A2 | 4/2017 | |
| WO | WO-2017074788 A1 | 5/2017 | |
| WO | WO-2017088012 A1 | 6/2017 | |
| WO | WO-2017139694 A1 | 8/2017 | |
| WO | WO-2017148888 A1 | 9/2017 | |
| WO | WO-2017173321 A1 | 10/2017 | |
| WO | WO-2017180989 A2 | 10/2017 | |
| WO | WO-2017184590 A1 | 10/2017 | |
| WO | WO-2018037416 A1 | 3/2018 | |
| WO | WO-2018078053 A1 * | 5/2018 | A61K 31/16 |
| WO | WO-2018140391 A1 | 8/2018 | |

OTHER PUBLICATIONS

European Application No. 18720480.5 Search Report dated Nov. 8, 2023.
Greenfield et al.: A phase I dose-escalation clinical trial of a peptidebased human papillomavirus therapeutic vaccine with Candida skin test reagent as a novel vaccine adjuvant for treating women with biopsy-proven cervical intraepithelial neoplasia 2/3. Oncoimmunol 10:e1031439 (2015).
Yang et al.: Perspectives for therapeutic HPV vaccine development. Journal of Biomedical Science. 23(1):1-19 (2016).
Brito, Luis et al., Self-amplifying mRNA Vaccines,Adv. Genet. 2015; 89:179-233.
Busch et al., Degenerate binding of immunogenic peptides to HLA-DR proteins on B cell surfaces, Int. Immunol. 2:443 (1990).
Cai, A et al., Mutated BCR-ABL Generates Immunogenic T-Cell Epitopes in CML Patients, Clinical Cancer Research vol. 18, No. 20, Aug. 21, 2012.
Ceppellini et al., Binding of labelled influenza matrix peptide to Hla Dr in living B lymphoid cells, Nature 339:392 (1989).
Cerundolo et al., The binding affinity and dissociated rates of peptides for class I major histocompatibility complex molecules, Eur. Immunol., 21:2069-75 (1991).
Christnick et al., Peptide binding to class 1MHC on living cells and quantitation of complexes required for CTL lysis, Nature 352:67 (1991).
Del Guercio, M.F., et al., Binding of a peptide antigen to multiple HLA alleles allows definition of an A2-like supertype, J. Immunol. 154:685-693 (1995).
Deres, K., et al., In vivo priming of virus-specific cytotoxic T lymphocytes with synthetic peptide vaccine, Nature 342:561, 1989.
Dupont, J., et al., Artificial Antigen-Presenting Cells Transduces with Telomerase Efficiently Expand Epitope-Specific, Human Leukocyte Antigen-Restricted Cytotoxic T Cells, 2005 Cancer Res 65:5417-5427.
Dupuis, M., et al., Dendritic Cells Internalize Vaccine Adjuvant after Intramuscular Injection, Cell Immunol. 1998; 186(1):18-27.
Felgner et al., Lipofection: A highly efficient, lipid-mediated DNA-transfection procedure, Proc. Natl. Acad. Sci. USA 84: 7413-7414 (1987).
Fritsch, Edward F et al., HLA-binding properties of tumor neoepitopes in humans, Cancer Immunology Research, Jun. 2014, vol. 2, No. 6, Jun. 2014, pp. 522-529.
Gabrilovich, et al., "IL-12 and Mutant P53 Peptide-Pulsed Dendritic Cells for the Specific Immunotherapy of Cancer," J Immunother Emphasis Tumor Immunol, 19(6): 414-418 (1997).
Gamvrellis, A et al., Vaccines that facilitate antigen entry into dendritic cells, Immunol & Cell Biol. 2004; 82: 506-516.
Geall, A.J., et al. Nonviral delivery of self-amplifying RNA vaccines. Proc Natl Acad Sci U S A. Sep. 4, 2012;109(36):14604-9.
Hammer, J. et al., Precise prediction of major histocompatibility complex class Il-peptide interaction based on peptide side chain scanning, J. Exp. Med. 180:2353 (1994).
Hill et al., Conformational and structural characteristics of peptides binding to HLA-DR molecules, J. Immunol. 147:189 (1991).
Hill et al., Exploration of requirements for peptide binding to HLA DRB10101 and DRBI*0401, J. Immunol. 152, 2890 (1994).
International Search Report and Written Opinion for PCT/US16/033452 (WO2016/187508).

(56) References Cited

OTHER PUBLICATIONS

International Search Report and Written Opinion for PCT/US17/25462 (WO2017/173321).
International Search Report and Written Opinion for PCT/US18/025933 (WO2018/187356).
Khilko, Sergi N. et al., Direct Detection of Major Histocompatibility Complex Class I Binding to Antigenic Peptides Using Surface Plasmon Resonance, J. Biol. Chem. 268:15425 (1993).
Koide, Shohei et al., Target-Binding Proteins Based on the 10th Human Fibronectin Type III Domain (10Fn3), Methods Enzymol. 2012;503:135-56.
Krieg, Arthur M., Therapeutic potential of Toll-like receptor 9 activation, Nature Reviews, Drug Discovery, 5, Jun. 2006, 471-484).
Ljunggren et al., Empty MHC class I molecules come out in the cold, Nature 346:476 (1990).
Mannino & Gould-Fogerite, Lipsome mediated gene transfer, BioTechniques 6(7): 682-691 (1988).
Matteucci, et al. Synthesis of deoxyoligonucleotides on a polymer support. J. Am. Chem. Soc. 103(11):3185-3191, 1981.
Morgan, R. A., et al., (2006), Cancer Regression in Patients After Transfer of Genetically Engineered Lymphocytes, Science 314:126-129.
Mosca, Paul J. et al., Dendritic cell vaccines, Frontiers in Bioscience, (2007) 12:4050-4060).
Panelli, M. C., et al. (2000), A Tumor-Infiltrating from a Melanoma Metastasis with Decreased Expression of Melanoma Differentiation Antigens Recognizes MAGE-12, J Immunol 164:4382-4392.
Panelli, M. C., et al., (2000), Expansion of Tumor-T Cell Pairs from Fine Needle Aspirates of Melanoma Metastases, J Immunol 164:495-504.
Papanicolaou, G. A., et al., (2003), Rapid expansion of cytomegalovirus-specific cytotoxic T lymphocytes by artificial antigen-presenting cells expressing a single HLA allele, Blood 102:2498-2505).
Parker et al., The beta 2-microglobulin dissociation rate is an accurate measure of the stability of MHC Class I heterotrimers and depends on which peptide is bound, J. Immunol. 149:1896 (1992).
Reay, Phillip A. et al., (1992), pH dependence and exchange of high and low responder peptides binding to a class II MHC molecule, EMBO J. 11:2829-39.
Rooney, M. et al., Molecular and genetic properties of tumors associated with local immune cytolytic activity. Cell. Jan. 15, 2015; 160(1-2): 48-61.doi: 10.1016/j.cell.2014.12.033.
Sadelain et al. Targeting tumours with genetically enhanced T lymphocytes. Nat Rev Cancer 3(1):35-45 (2003).
Salter, Russell D. et al., Genes regulating HLA class I antigen expression in T-B lymphoblast hybrids, Immunogenetics 21:235-46 (1985).
Salter, Russell, et al., Impaired assembly and transport of HLA-A and -B antigens in a mutant TxB cell hybrid, EMBO J. 5:943-49 (1986).
Schumacher, Ton N.M., et al., (1990), Direct binding of peptide to empty MHC Class I molecules on intact cells and in vitro, Cell 62:563 (1990).
Sette, et al., (1994) Peptide binding to the most frequent HLA-A class I alleles measured by quantitative molecular bindings assays, Mol. Immunol. 31:813.
Sioud, Mouldy et al., A novel peptide carrier for efficient targeting of antigens and nucleic acids to dendritic cells, FASEB J 27: 3272-3283 (2013).
Southwood, Scott et al., Several Common HLA-DR Types Share Largely Overlapping Peptide Binding Repertoires, J. Immunol. 160:3363-3373, 1998).
Stover, C.K. et al., New use of BCG for recombinant vaccines, Nature 351:456-460 (1991).
Szoka, Comparative properties and methods of preparation of lipid vesicles (liposomes);Ann Rev Biophys Eng 9:467 (1980).
Townsend, A., et al., Assembly of MHC Class I molecules analyzed in vitro, Cell 62:285, Jul. 27, 1990.
Verhoef, et al., Des-enkephalin-Y-Error! Hyperlink reference not valid.endorphin (DEyE): Biotransformation in rat, dog, and human plasma, Eur. J. Drug Metab. Pharmacokinetics 11:291 (1986).
Wolff et al. Direct gene transfer into mouse muscle in vivo. Science 247:1465-1468 (1990).
Jaravine, V. et al., "Assessment of cancer and virus antigens for cross-reactivity in human tissues," Bioinformatics, 2016, vol. 33, No. 1, pp. 104-111.
Karran, L. et al., "Expression of a family of complementary-strand transcripts in Epstein-Barr virus-infected cells," Proc. Nati. Acad. Sci. USA, 1992, vol. 89, No. 17, pp. 8058-8062.
Riemer, A.B. et al., "A conserved E7-derived cytotoxic T lymphocyte epitope expressed on human papillomavirus 16-transformed HLA-A2+ epithelial cancers," J Biol Chem., 2010, vol. 285, No. 38, pp. 29608-29622.
Yao et al.: HPV-16 E6 and E7 protein T cell epitopes prediction analysis based on distributions of HLA-A loci across populations: An in silico approach. Elsevier, Vaccine 31(18): 2289-2294 (2013).
Acevedo et al., Analysis of the mechanisms mediating tumor-specific changes in gene expression in human liver tumors, Cancer Res, 68(8):2641-2651 (2008).
Acknowledgment of Receipt dated Jun. 28, 2017 for Response to Notices of Opposition of EP2569633.
Adams, Toll-like receptor agonists in cancer therapy, Immunotherapy, 1(6):949-964 (2009).
Adomas, et al. "Breast tumor specific mutation in GATA3 affects physiological mechanisms regulating transcription factor turnover," BMC Cancer 2014, 14:278.
Akiyama et al., GATA-4 and GATA-5 transcription factor genes and potential downstream antitumor target genes are epigenetically silenced in colorectal and gastric cancer, Mol Cell Biol, 23:8429-8439 (2003).
Alarcon et al., DNA vaccines: technology and application as anti-parasite and anti-microbial agents, Advances in Parasitology, 42:343-410 (1999).
Albert et al., "Direct Selection of Human Genomic Loci by Microarray Hybridization," Nat Methods, 4(11): 903-905 (2007).
Ali et al., In situ regulation of DC subsets and T cells mediates tumor regression in mice, Cancer Immunotherapy, 1(8):1-10 (2009).
Ali et al., "Infection-mimicking materials to program dendritic cells in situ," Nat Mater, 8:151-8 (2009).
Almeida et al., "CTdatabase: a knowledge-base of high- throughput and curated data on cancer-testis antigens," Nucleic acids research, 37:D816-819 (2008).
Altman et al., Phenotypic analysis of antigen-specific T lymphocytes, Science, 274(5284):94-6 (1996).
Alvarez, Present and future evolution of advanced breast cancer therapy, Breast Cancer Research, 12(Suppl 2):S1 (2010).
Alyea et al., "Toxicity and Efficacy of Defined Doses of CD4+ Donor Lymphocytes for Treatment of Relapse After Allogeneic Bone Marrow Transplant," Blood, 91(10):3671-3680 (1998).
Amara et al., "Control of a mucosal challenge and prevention of AIDS by a multiprotein DNA/MVA vaccine," Science, 292(5514):69-74 (2001).
Amato et al., "Vaccination of metastatic renal cancer patients with MVA-5T4: a randomized, double-blind, placebo-controlled phase III study," Clin Can Res, 16(22):5539-47 (2010).
Amato et al., "Vaccination of renal cell cancer patients with modified vaccinia ankara delivering tumor antigen 5T4 (TroVax) administered with interleukin 2: a phase II trial," Clin Cancer Res, 14(22):7504-10 (2008).
Anders et al., HTSeq-A Python framework to work with high-throughput sequencing data, Bioinformatics, 31(2):166-169 (2015).
Andersen et al., Parallel detection of antigen-specific T cell responses by combinatorial encoding of MHC multimers, Nature protocols, 7(5):891-902 (2012).
Anderson et al., "Next Generation DNA Sequencing and the Future of Genomic Medicine," Genes, 1:38-69 (2010).
Andreatta et al., Gapped sequence alignment using artificial neural networks: application to the MHC class I system, Bioinformatics 32(4):511-517 (2016).

(56) References Cited

OTHER PUBLICATIONS

Annunziata et al., "Frequent Engagement of the Classical and Alternative NF-KB Pathways by Diverse Genetic Abnormalities in Multiple Myeloma," Cancer Cell, 12(2):115-130 (2007).
Antoine et al., "The complete genomic sequence of the modified vaccinia Ankara strain: comparison with other orthopoxviruses," Virology, 244(2):365-96 (1998).
Antonis et al., "Vaccination with recombinant modified vaccinia virus Ankara expressing bovine respiratory syncytial virus (bRSV) proteins protects calves against RSV challenge," Vaccine, 25(25):4818-4827 (2007).
Attia et al., "Autoimmunity Correlates With Tumor Regression in Patients With Metastatic Melanoma Treated with Anti-Cytotoxic T-Lymphocyte Antigen-4," J Clin Oncol, 23.(25):6043-6053 (2005).
Aucouturier et al., "Adjuvants designed for veterinary and human vaccines," Vaccine, 19(17-19):2666-2672 (2001).
Austen et al., "Mutations in the ATM Gene Lead to Impaired Overall and Treatment-Free Survival that is Independent of IGVH Mutation Status in Patients with B-CLL," Blood, 106(9):3175-3182 (2005).
Ausubel, A botanical macroscope, Proceedings of the National Academy of Sciences, 106(31):12569-12570 (2009).
Avogadri et al. "Modulation of CTLA-4 and GITR for Cancer Immunotherapy," Curr Top Microbiol Immunol, 344:211 (2011).
Azvolinsky et al., "PD-1 Inhibitor MK-3475 Again Shows Promise in Advanced Melanoma," Cancer Network, 2013. [Retrieved online] http://www.cancernetwork.com/melanoma/pd-1-inhibitor-mk-3475-again-shows-promise-advanced-melanoma.
Bachem et al., "Superior antigen cross-presentation and XCR1 expression define human CD11c+ CD141+ cells as homologues of mouse CD8+ dendritic cells," Journal of Experimental Medicine, 207(6):1273-1281 (2010).
Bachireddy et al., "Reversal of in situ T cell exhaustion during effective human anti-leukemia responses to donor lymphocyte infusion," Blood, 123(9):1412-1421 (2013).
Backert et al., Immunoinformatics and epitope prediction in the age of genomic medicine, Genome Medicine, 7:119 (2015).
Baden et al., "First-in-human evaluation of the safety and immunogenicity of a recombinant adenovirus serotype 26 FfIV-1 Env vaccine (IPCAVD 001)," J Infect Dis, 207(2):240-247 (2012).
Balaggan et al., "Stable and efficient intraocular gene transfer using pseudotyped EIAV lentiviral vectors," J Gene Med, 8:275-285 (2005).
Balakrishnan et al., "Novel Somatic and Germline Mutations in Cancer Candidate Genes in Glioblastoma, Melanoma, and Pancreatic Carcinoma," Cancer Res, 67: 3545-3550 (2007).
Balazsi et al., Cellular decision making and biological noise: from microbes to mammals, Cell, 144(6):910-925 (2011).
Balch et al., Final version of 2009 AJCC melanoma staging and classification, Journal of clinical oncology, 27(36):6199-6206 (2009).
Barbie et al., Systematic RNA interference reveals that oncogenic KRAS-driven cancers require TBK1, Nature, 462:108-112 (2009).
Barretina et al., The Cancer Cell Line Encyclopedia enables predictive modelling of anticancer drug sensitivity, Nature, 483:603-607 (2012).
Baskar et al., "Autologous Lymphoma Vaccines Induce Human T Cell Responses Against Multiple, Unique Epitopes," J Clin Invest, 113:1498-1510 (2004).
Bassani-Sternberg et al., Mass Spectrometry of Human Leukocyte Antigen Class I Peptidomes Reveals Strong Effects of Protein Abundance and Turnover on Antigen Presentation, Mol Cell Proteomics, 14:658-673 (2015).
Baurain et al., "High Frequency of Autologous Anti-Melanoma CTL Directed Against an Antigen Generated by a Point Mutation in a New Helicase Gene," J Immunol, 164: 6057-6066 (2000).
Baylin, A decade of exploring the cancer epigenome-biological and translational implications, Nat Rev Cancer, 11:726-734 (2005).
Baylin, DNA methylation and gene silencing in cancer, Nat Clin Pract Oncol 2, Suppl 1, S4-11 (2005).
Beck et al., "Enterocolitis in Patients With Cancer After Antibody Blockade of Cytotoxicity TLymphocyte-Associated Antigen 4," J Clin Oncol, 24(15): 2283-2289 (2006).
Behrends et al., Network organization of the human autophagy system, Nature, 466(7302):68-76 (2010).
Bellucci et al., "Complete Response to Donor Lymphocyte Infusion in Multiple Myeloma is Associated with Antibody Responses to Highly Expressed Antigens," Blood, 103: 656-663 (2004).
Benson, Tandem repeats finder: a program to analyze DNA sequences, Nucleic acids research, 27(2):573-580 (1999).
Bentley et al., "Accurate Whole Human Genome Sequencing using Reversible Terminator Chemistry," Nature, 456(7218): 53-59 (2008).
Benton et al., Screening lambdagt recombinant clones by hybridization to single plaques in situ, Science, 196(4286):180-182 (1977).
Berg et al., Detection of artifacts and peptide modifications in liquid chromatography/mass spectrometry data using two-dimensional signal intensity map data visualization, Rapid Commun Mass Spectrom, 20(10):1558-1562 (2006).
Berger et al., Melanoma genome sequencing reveals frequent PREX2 mutations, Nature, 485(7399):502 (2012).
Berger et al., The genomic complexity of primary human prostate cancer, Nature, 470:214-220 (2011).
Berman et al., Regions of focal DNA hypermethylation and long-range hypomethylation in colorectal cancer coincide with nuclear lamina-associated domains, Nat Genet, 44:40-46 (2012).
Bettelli et al., "TH-17 cells in the circle of immunity and autoimmunity," Nat Immunol, 8:345-350 (2007).
Bhardwaj et al., "TLR Agonists: Are They Good Adjuvants?," Cancer J, 16:382-391 (2010).
Bindea et al., Spatiotemporal dynamics of intratumoral immune cells reveal the immune landscape in human cancer, Immunity, 39:782-795 (2013).
Bird, DNA methylation patterns and epigenetic memory, Genes Dev, 16:6-21 (2002).
Birrell et al., A genome-wide screen in Saccharomyces cerevisiae for genes affecting UV radiation sensitivity, Proceedings of the National Academy of Sciences 98(22):12608-12613 (2001).
Bishop et al., APOBEC-mediated editing of viral RNA, Science, 305:645 (2004).
Bisht et al., "Severe acute respiratory syndrome coronavirus spike protein expressed by attenuated vaccinia virus protectively immunizes mice," Proc Natl Acad Sci, 101:6641-46 (2004).
Blanchard et al., "Modified vaccinia virus Ankara undergoes limited replication in human cells and lacks several immunomodulatory proteins: implications for use as a human vaccine," Journal of General Virology, 79(5):1159-1167 (1998).
Bock et al., BiQ Analyzer: visualization and quality control for DNA methylation data from bisulfite sequencing, Bioinformatics, 21:4067-4068 (2005).
Bock et al., "Reference Maps of human ES and iPS cell variation enable high-throughput characterization of pluripotent cell lines," Cell, 144:439-452 (2011).
Boen et al., Identification of T Cell Ligands in a Library of Peptides Covalently Attached to Hla-DR4, J Immunol, 165:2040-2047 (2000).
Bogunovic et al., TLR4 engagement during TLR3-induced proinflammatory signaling in dendritic cells promotes IL-10-mediated suppression of antitumor immunity, Cancer Res, 71(16):5467-5476 (2011).
Bohm et al., DNA vector constructs that prime hepatitis B surface antigen-specific cytotoxic T lymphocyte and antibody responses in mice after intramuscular injection. Journal of immunological methods 193(1): 29-40 (1996).
Boisgerault et al., Definition of the HLA-A29 peptide ligand motif allows prediction of potential T-cell epitopes from the retinal soluble antigen, a candidate autoantigen in birdshot retinopathy, PNAS, 93:3466-3470 (1996).
Boisguerin et al., "Translation of genomis-guided RNA-based personalised cancer vaccines: towards the bedside," British J Cancer, 111:1469-1475 (2014).
Boller et al. Characterization of the antibody response specific for the human endogenous retrovirus HTDV/HERV-K, Journal of virology, 7I(6):4581-4588 (1997).

(56) References Cited

OTHER PUBLICATIONS

Boni et al. "Adoptive transfer of allogeneic tumor-specific T cells mediates effective regression of large tumors across major histocompatibility barriers," Blood, 112(12):4746-4754 (2008).
Boon et al., "Human T Cell Responses Against Melanoma," Annu Rev Immunol, 24: 175-208 (2006).
Boon, "Toward a Genetic Analysis of Tumor Rejection Antigens," Adv Cancer Res, 58:177-210 (1992).
Boquest et al., Isolation and transcription profiling of purified uncultured human stromal stem cells: alteration of gene expression after in vitro cell culture, Molecular biology of the cell, 16(3):1131-1141 (2005).
Boscardin et al., "Antigen targeting to dendritic cells elicits long-lived T cell help for antibody responses," Journal of Experimental Medicine, 203(3):599-606 (2006).
Bourdetsky et al., The nature and extent of contributions by defective ribosome products to the HLA peptidome, PNAS, III, E1591-E1599 (2014).
Bowerman et al., "Engineering the binding properties of the T cell receptor:peptide:MHC ternary complex that governs T cell activity," Mol Immunol, 46(15):3000-3008 (2009).
Boyle et al., "Gel-free multiplexed reduced representation bisulfite sequencing for large-scale DNA methylation profiling," Genome Biol, 13:R92 (2012).
Boyle et al., "Tapasin-related protein TAPBPR is an additional component of the MHC class I presentation pathway," Proceedings of the National Academy of Sciences, 110: 3465-3470 (2013).
Bozic et al., Dynamics of targeted cancer therapy, Trends Mol Med, 18:311-316 (2012).
Bozic et al., Evolutionary dynamics of cancer in response to targeted combination therapy, Elife, 2:e00747 (2013).
Brahmer et al. Safety and activity of anti-PD-L1 antibody in patients with advanced cancer. N Engl J Med 366(26):2455-2465 (2012).
Brandle et al., "A Mutated HLA-A2 Molecule Recognized by Autologous Cytotoxic T Lymphocytes on a Human Renal Cell Carcinoma," J Exp Med, 183: 2501-2508 (1996).
Bremel et al., An integrated approach to epitope analysis I: Dimensional reduction, visualization and prediction of MHC binding using amino acid principal components and regression approaches, Immunome Res, 6:7 (2010).
Brinckerhoff et al., "Melanoma Vaccines," Curr Opin Oncol, 12:163-173 (2000).
Broad Institute Article, Jan. 29, 2009, "Turning Cancer's Strength Into Weakness," (2009).
Brochier et al., "Large-scale eradication of rabies using recombinant vaccinia-rabies vaccine," Nature, 354:520-552 (1991).
Brown et al., Integrative genomic analysis implicates gain of PIK3CA at 3q26 and MYC at 8q24 in chronic lymphocytic leukemia, Clin Cancer Res, 8:3791-802 (2012).
Brown et al., "Neo-antigens predicted by tumor genome meta-analysis correlate with increased patient survival," Genome Res, 24(5):743-750 (2014).
Brunsvig et al., "Telomerase Peptide Vaccination: A Phase I/II Study in Patients with Non-Small Cell Lung Cancer," Cancer Immunol Immunother, 55(12): 1553-1564 (2006).
Buchschacher et al., "Human immunodeficiency virus vectors for inducible expression of foreign genes." Journal of virology, 66(5):2731-2739 (1992).
Buckwalter et al., "It is the antigen(s), stupid' and other lessons from over a decade of vaccitherapy of human cancer," Seminar in Immunology, 20(5):296-300 (2008).
Buller et al., "Decreased virulence of recombinant vaccinia virus expression vectors is associated with a thymidine kinase-negative phenotype," Nature, 317:813-815 (1985).
Buller et al., "Deletion of the vaccinia virus growth factor gene reduces virus virulence," Journal of virology, 62(3):866-874 (1988).
Burger et al., "Safety and activity of ibrutinib plus rituximab for patients with high-risk chronic lymphocytic leukaemia: a single-arm, phase 2 study," Lancet Oncology, 15(10):1090-1099 (2014).
Burger et al., B cell receptor signaling in chronic lymphocytic leukemia, Trends Immunol, 34:592-601 (2013).
Burkhardt et al., Autologous CLL cell vaccination early after transplant induces leukemia-specific T cells, The Journal of clinical investigation, 123(9):3756-3765 (2013).
Buser et al., Unique composite hematolymphoid tumor consisting of a pro-T lymphoblastic lymphoma and an indeterminate dendritic cell tumor: evidence for divergent common progenitor cell differentiation, Pathobiology, 81:199-205 (2014).
Byrd et al., Targeting BTK with ibrutinib in relapsed chronic lymphocytic leukemia, The New England journal of medicine, 369:32-42 (2013).
Bystryn et al., Double-blind trial of a polyvalent, shed-antigen, melanoma vaccine, Clin Cancer Res, 7(7):1882-1887 (2001).
Cahill et al., 450K-array analysis of chronic lymphocytic leukemia cells reveals global DNA methylation to be relatively stable over time and similar in resting and proliferative compartments, Leukemia, 27:150-158 (2013).
Cai et al., "Peptides Derived From Mutated BCR-ABL Elicit T Cell Immunity In CML Patients," BLOOD, 116(21): 388-388 (2010).
Cancer Genome Atlas Network, Comprehensive molecular portraits of human breast tumours, Nature, 490:61-70 (2012).
Cancer Genome Atlas Research Network, Comprehensive genomic characterization defines human glioblastoma genes and core pathways, Nature, 455(7216):1061-1068 (2008).
Cancer Genome Atlas Research Network, "Comprehensive genomic characterization of squamous cell lung cancers," Nature, 489, 519-525 (2012).
Cancer Genome Atlas Research Network, Comprehensive molecular characterization of clear cell renal cell carcinoma, Nature, 499:43-49 (2013).
Cancer Genome Atlas Research Network, Comprehensive molecular characterization of gastric adenocarcinoma, Nature, 513:202-209 (2014).
Cancer Genome Atlas Research Network, Genomic and epigenomic landscapes of adult de novo acute myeloid leukemia, New England Journal of Medicine, 368(22):2059-2074 (2013).
Cancer Genome Atlas Research Network, Integrated genomic analyses of ovarian carcinoma, Nature, 474: 609-615 (2011).
Carithers, L.J.., et al. (2015). A Novel Approach to High-Quality Postmortem Tissue Procurement: The GTEx Project. Biopreservation Biobanking 13, 311-319.
Caron et al., Analysis of MHC immunopeptidomes using mass spectrometry, Mol Cell Proteomics (2015), doi: 10.1074/mcp.0115. 052431.
Carpten et al., "A transforming mutation in the pleckstrin homology domain of AKT1 in cancer," Nature, 448(26):439-444 (2004).
Carreno et al., A dendritic cell vaccine increases the breadth and diversity of melanoma neoantigen-specific T cells, Science, 348(6239):803-808 (2015).
Carreno et al., "IL-12p70-producing patient DC vaccine elicits Tcl-polarized immunity," Journal of Clinical Investigation, 123(8):3383-94 (2013).
Carter et al., Absolute quantification of somatic DNA alterations in human cancer, Nat Biotechnol, 30:413-21 (2012).
Carter et al., Accurate estimation of homologue-specific DNA concentration-ratios in cancer samples allows long-range haplotyping, Nature Precedings, 59-87 (2011).
Carter et al., "Identification and validation of cell surface antigens for antibody targeting in oncology," Endocrine-Related Cancer, 11:659-687 (2004).
Caskey et al., "Synthetic double-stranded RNA induces innate immune responses similar to a live viral vaccine in humans," The Journal of experimental medicine, 208(12):2357-2366 (2011).
Castle et al., Exploiting the mutanome for tumor vaccination, Cancer research, 72(5):1081-1091 (2012).
CBOL Plant Working Group, A DNA barcode for land plants, PNAS, 106(31):12794-12797 (2009).
Chang et al., Immune selection of hot-spot beta 2-microglobulin gene mutations, HLA-A2 allospecificity loss, and antigen-processing machinery component down-regulation in melanoma cells derived from recurrent metastases following immunotherapy, Journal of immunology, 174:1462-1471 (2005).

(56) References Cited

OTHER PUBLICATIONS

Chang et al., "Peptide length-based prediction of peptide-MHC class II binding," Bioinformatics, 22(22): 2761-2767 (2006).
Chapman et al., Initial genome sequencing and analysis of multiple myeloma, Nature, 471:467-472 (2011).
Chatila, "The Regulatory T Cell Transcriptosome: E Pluribus Unum," Immunity, 27(5):693-695 (2007).
Cheever, Twelve immunotherapy drugs that could cure cancers, Immunological reviews, 222:357-368 (2008).
Chen, et al. "Hotspot mutations delineating diverse mutational signatures and biological utilities across cancer types," BMC Cenomics (2016)17(Suppl 2):394.
Chen et al., Impact of replication timing on non-CpG and CpG substitution rates in mammalian genomes, Genome Res, 20:447-457 (2010).
Chen et al., "Langerhans Cell Sarcoma Arising from Chronic Lymphocytic Lymphoma/Small Lymphocytic Leukemia: Lineage Analysis and BRAF V600E Mutation Study," N Am J Sci, 5:386-91 (2013).
Chen et al., Molecular mechanisms of T cell co-stimulation and co-inhibition, Nature reviews Immunology, 13:227-242 (2013).
Chen et al., Molecular Pharmaceutics, 3:109-111 (2010).
Chen et al., "Recombinant modified vaccinia virus Ankara expressing the spike glycoprotein of severe acute respiratory syndrome coronavirus induces protective neutralizing antibodies primarily targeting the receptor binding region," Journal of virology, 79.5:2678-2688 (2005).
Chianese-Bullock et al., "Multi-peptide vaccines vialed as peptide mixtures can be stable reagents for use in peptide-based immune therapies," Vaccine, 27(11):1764-1770 (2009).
Chiari et al., "Two Antigens Recognized by Autologous Cytolytic T Lymphocytes on a Melanoma Result from a Single Point Mutation in an Essential Housekeeping Gene," Cancer Res, 59:5785-5792 (1999).
Child et al., "Insertional inactivation of the large subunit of ribonucleotide reductase encoded by vaccinia virus is associated with reduced virulence in vivo," Virology, 174(2):625-629 (1990).
Chim et al., Epigenetic dysregulation of the Wnt signalling pathway in chronic lymphocytic leukaemia, J Clin Pathol, 61:1214-1219 (2008).
Chiron et al., Cell-cycle reprogramming for P13K inhibition overrides a relapse-specific C4815 Btk mutation revealed by longitudinal functional genomics in mantle cell lymphoma, Cancer Discov, 4:1022-35 (2014).
Chowell et al., TCR contact residue hydrophobicity is a hallmark of immunogenic CD8(+) T cell epitopes, PNAS, 112:E1754-E1762 (2015).
Christian et al., Targeting DNA double-strand breaks with TAL effector nucleases, Genetics, 186(2):757-761 (2010).
Christianson et al., Defining human ERAD networks through an integrative mapping strategy, Nat Cell Biol, 14:93-105 (2012).
Chroboczek et al., "The Sequence of the Genome of Adenovirus Type 5 and Its Comparison with the Genome of Adenovirus Type 2," Virology, 186:280-285 (1992).
Church, Genomes for all, Sci Am, 294(1):46-54 (2006).
Cibulskis et al., ContEst: estimating cross-contamination of human samples in next-generation sequencing data, Bioinformatics, 27:2601-2602 (2011).
Cibulskis et al. Sensitive detection of somatic point mutations in impure and heterogenous cencer samples. Nat Biotechnol 31:213-219 (2013).
Ciofani et al., "A Validated Regulatory Network for Th17 Cell Specification," Cell, 151(2):289-303 (2012).
Cleveland, Lowess: A program for smoothing scatterplots by robust locally weighted regression, The American Statistician, 35:54 (1981).
Clinical trial NCT 01970358, Patrick Ott, A Phase I Study With a Personalized NeoAntigen Cancer Vaccine in Melanoma, p. 1-6, Retrieved from https://clinicaltrials.gov/ct2/show/NCT01970358 downloaded Jun. 20, 2017.

Coffman et al., "Vaccine Adjuvants: Putting Innate Immunity to Work," Immunity 33:492-503 (2010).
Cohen, et al. "Shift in GATA3 functions, and GATA3 mutations, control progression and clinical presentation in breast cancer," Breast Cancer Research DOI 10.1186/s13058-014-0464-0.
Conlon et al., "Mouse, but not Human STING, Binds and Signals in Response to the Vascular Disrupting Agent 5,6-Dimethylxanthenone-4-Acetic Acid," Journal of Immunology, 190:5216-25 (2013).
Consolidated Table of Documents filed in Opposition to date in Response to Notices of Opposition of EP2569633 dated Jun. 28, 2017.
Corbett et al., "Aerosol immunization with NYVAC and MVA vectored vaccines is safe, simple, and immunogenic," Proc Natl Acad Sci, 105(6):2046-51 (2008).
Coulie et al., A mutated intron sequence codes for an antigenic peptide recognized by cytolytic T lymphocytes on a human melanoma, Proc Natl Acad Sci USA, 92(17):7976-7980 (1995).
Cox et al., "Induction of cytotoxic T lymphocytes by recombinant canarypox (ALVAC) and attenuated vaccinia (NYVAC) viruses expressing the HIV-1 envelope glycoprotein," Virology, 195(2):845-850 (1993).
Crozat et al., "The XC chemokine receptor 1 is a conserved selective marker of mammalian cells homologous to mouse CD8a+ dendritic cells," Journal of Experimental Medicine, 207(6):1283-1292 (2010).
CT-011 and p53 Genetic Vaccine for Advance Solid Tumor, National Library of Medicine, updated: Jun. 30, 2011, XP002738554.
Daheshia et al., "Suppression of ongoing ocular inflammatory disease by topical administration of plasmid DNA encoding IL-10," The Journal of Immunology 159(4):1945-1952 (1997).
De et al., Aberration in DNA methylation in B-cell lymphomas has a complex origin and increases with disease severity, PLoS Genet. 9:e1003137 (2013).
De Magalhaes et al., Next-generation sequencing in aging research: emerging applications, problems, pitfalls and possible solutions, Ageing Research Reviews, 9(3):315-323 (2010).
De Plaen et al., "Immunogenic (tum-) Variants of Mouse Tumor P815: Cloning of the Gene of Tum- Antigen P91A and Identification of the Tum- Mutation," PNAS, 85: 2274-2278 (1988).
Declaration by Professor John Haanen, M.D., Ph.D.
Declaration by Stephen Johnston filed during the prosecution of granted U.S. Pat. No. 8,796,414 Nov. 20, 2013.
Declaration of Dr. John C. Castle executed on Nov. 9, 2016.
Declaration of Dr Nir Hacohen on Feb. 16, 2014.
DeLuca et al., RNA-SeQC: RNA-seq metrics for quality control and process optimization, Bioinformatics, 28:1530-2 (2012).
Dengjel et al., "Glycan side chains on naturally presented MHC class II ligands," J. Mass Spectrom, 40:100-104 (2005).
Depristo et al. A framework for variation discovery and genotyping using next generation DNA sequencing data. Nat Genetics 43:491-498 (2011).
Dermer et al., "Another Anniversary for the War on Cancer," Biotech, 12:320 (1994).
Di Stasi et al., "Inducible apoptosis as a safety switch for adoptive cell therapy," New England Journal of Medicine, 365(18):1673-1683 (2011).
Didierlaurent et al., "Attenuated poxviruses expressing a synthetic HIV protein stimulate HLA-A2-restricted cytotoxic T-cell responses," Vaccine, 22(25-26):3395-3403 (2004).
Ding et al., "Genome remodelling in a basal-like breast cancer metastasis and xenograft," Nature, 464:999-1005 (2010).
Ding et al., Somatic mutations affect key pathways in lung adenocarcinoma, Nature, 455:1069-1075 (2008).
Dohner et al., Genomic aberrations and survival in chronic lymphocytic leukemia, The New England journal of medicine, 343:1910-1916 (2000).
Doody et al., "PRDMI/BLIMP-1 Modulates IFN--Dependent Control of the MHC Class I Antigen-Processing and Peptide-Loading Pathway," The Journal of Immunology, 179:7614-7623 (2007).
Dossinger et al., MHC multimer-guided and cell culture-independent isolation of functional T cell receptors from single cells facilitates TCR identification for immunotherapy, PloS one, 8(4):e61384 (2013).

(56) References Cited

OTHER PUBLICATIONS

Dreicer et al., "MVA-MUC1-IL2 vaccine immunotherapy (TG4010) improves PSA doubling time in patients with prostate cancer with biochemical failure," Investigational new drugs, 27(4):379-386 (2009).
Dubey et al., The immunodominant antigen of an ultraviolet-induced regressor tumor is generated by a somatic point mutation in the DEAD (SEQ ID No. 62) box helicase p68, The Journal of experimental medicine, 185(4):695-705 (1997).
DuPage et al., "Expression of tumour-specific antigens underlies cancer immunoediting," Nature, 482(7385):405-409 (2012).
Earl et al., "Immunogenicity of a highly attenuated MVA smallpox vaccine and protection against monkeypox," Nature, 428:182 (2004).
Eckhardt et al., DNA methylation profiling of human chromosomes 6, 20 and 22, Nat Genet, 38:1378-1385 (2006).
Eden et al., Discovering motifs in ranked lists of DNA sequences, PLoS computational biology, 3, e39 (2007).
Eden et al., GOrilla: a tool for discovery and visualization of enriched GO terms in ranked gene lists, BMCBioinformatics, 10:48 (2009).
Eggermont et al., Ulceration and stage are predictive of interferon efficacy in melanoma: results of the phase III adjuvant trials EORTC 18952 and EORTC 18991, EurJ Cancer, 48(2):218-225 (2012).
Ehrlich, DNA hypomethylation in cancer cells, Epigenomics, 1:239-259 (2009).
Eichmann et al., Identification and characterisation of peptide binding motifs of six autoimmune disease-associated human leukocyte antigen-class I molecules including HLA-B*39:06, Tissue Antigens 84(4):378-388 (2014).
Elias et al., Target-decoy search strategy for increased confidence in large-scale protein identifications by mass spectrometry, Nat Meth, 4:207-214 (2007).
Engelhard, "Structure of peptides associated with MHC class I molecules," Curr Opin Immunol, 6(1):13-23 (1994).
Engler et al., A one pot, one step, precision cloning method with high throughput capability, PloS one 3(11):e3647 (2008).
Engler et al., Golden gate shuffling: a one-pot DNA shuffling method based on type IIs restriction enzymes, PloS one, 4(5):e5553 (2009).
Erlich et al., "Next-generation sequencing for HLA typing of class I loci," BMC Genomics, 12:42 (2011).
Escobar et al., Bayesian density estimation and inference using mixtures, Journal of the American Statistical Association, 90:577-588 (1995).
Esteban, "Attenuated poxvirus vectors MVA and NYVAC as promising vaccine cadidates against HIV/AIDS," Human vaccines, 5(12):867-871 (2009).
Estep et al., "Mutation Analysis of Braf, MEK1 and MEK2 in 15 Ovarian Cancer Cell Lines: Implications for Therapy," PLOS One, 12:e1279 (2007).
European Search Report dated Oct. 24, 2019, for EP Appl. No. 177768116.
Extended European Search Report dated Apr. 11, 2016, which issued during prosecution of EP Application No. 15198284.0.
Extended European Search Report received for EP patent application No. EP11781409, mailed Apr. 10, 2014.
Extended Search Report in Corresponding European Application No. 11781409.5, dated Apr. 14, 2014.
Eyers et al., CONSeQuence: prediction of reference peptides for absolute quantitative proteomics using consensus machine learning approaches, Mol Cell Proteomics (2011); 10(11):M110.003384. doi: 10.1074/mcp.MI 10.003384. Epub Aug. 3, 2011.
Ezzell, "Cancer 'Vaccines': An idea whose time has come?," J NIH Res, 7:46 (1995).
Fais et al., Chronic lymphocytic leukemia B cells express restricted sets of mutated and unmutated antigen receptors, The Journal of clinical investigation, 102:1515-25 (1998).
Fan et al., The multi substrate adapter Gabl regulates hepatocyte growth factor (scatter factor)-c-Met signaling for cell survival and DNA repair, Molecular and Cellular Biology, 21:4968-4984 (2001).

Fantom Consortium et al., A promoter-level mammalian expression atlas, Nature, 507:462-470 (2014).
Farsaci et al., Consequence of dose scheduling of sunitinib on host immune response elements and vaccine combination therapy, Int J Cancer, 130:1948-1959 (2012).
Feigner et al., Lipofection: A Highly Efficient, Lipid-Mediated DNA-Transfection Procedure, PNAS, 84(21): 7413-7417 (1987).
Feng, Du et al., The Significance and Therapeutic Potential of GATA3 Expression and Mutation in Breast Cancer: A Systematic Review, Medicinal Research Reviews, vol. 35, No. 6, Nov. 1, 1015, pp. 1300-1315, XP002791786.
Ferrier-Rembert et al., Short-and long-term immunogenicity and protection induced by non-replicating smallpox vaccine candidates in mice and comparison with the traditional 1st generation vaccine, Vaccine, 26(14):1794-1804 (2008).
Final Rejection for U.S. Appl. No. 15/187,174, Compositions and Methods of Identifying Tumor Specific Neoantigens, dated Oct. 12, 2018.
Finke et al., Sunitinib Reverses Type-1 Immune Suppression and Decreases T-Regulatory Cells in Renal Cell Carcinoma Patients, Clin Cancer Res, 14(20):6674-6682 (2008).
Fisher et al., A scalable, fully automated process for construction of sequence-ready human exome targeted capture libraries, Genome Biol, 12:R1 (2011).
Flaherty et al., From genes to drugs: targeted strategies for melanoma, Nat Rev Cancer, 12(5):349-361 (2012).
Flexner et al., "Prevention of vaccinia virus infection in imiminodeficient mice by vector-directed IL-2 expression," Nature, 330(6145):259-262 (1987).
Flynn et al., Immunization with HIV Gag targeted to dendritic cells followed by recombinant New York vaccinia virus induces robust T-cell immunity in nonhuman primates, Proc Natl Acad Sci, 108(17):7131-7136 (2011).
Forconi et al., Genome-wide DNA analysis identifies recurrent imbalances predicting outcome in chronic lymphocytic leukaemia with 17p deletion, British journal of haematology, 143:532-6 (2008).
Fransen et al., Controlled local delivery of CTLA-4 blocking antibody induces CD8+ T-cell-dependent tumor eradication and decreases risk of toxic side effects, Clin Cancer Res, 19(19):5381-5389 (2013).
Frederick et al., "BRAF inhibition is associated with enhanced melanoma antigen expression and a more favorable tumor microenvironment in patients with metastatic melanoma," Clin Cancer Res, 19:1225-1231 (2013).
Friedberg et al., Inhibition of Syk with fostamatinib disodium has significant clinical activity in non-Hodgkin lymphoma and chronic lymphocytic leukemia, Blood, 115:2578-2585 (2011).
Fritsch et al., "Personal neoantigen cancer vaccines: The momentum builds," Oncoimmunology, 3(6):e29311 (2014).
Fritsch et al., Translational repression of MCL-1 couples stress-induced elF2 alpha phosphorylation to mitochondria! apoptosis initiation, The Journal of biological chemistry, 282:22551-62 (2007).
Fruci et al., Altered expression of endoplasmic reticulum aminopeptidases ERAP1 and ERAP2 in transformed non-lymphoid human tissues, J Cell Physiol, 216(3):742-749 (2008).
Fukami, et al. GATA3 abnormalities in six patients with HDR syndrome, Endocrine Journal 2011, 58 (2), 117-121.
Furman et al., Ibrutinib resistance in chronic lymphocytic leukemia, The New England journal of medicine, 370(24):2352 (2014).
Furman et al., Idelalisib and rituximab in relapsed chronic lymphocytic leukemia, The New England journal of medicine, 370:997-1007 (2014).
Fusaro et al., Prediction of high-responding peptides for targeted protein assays by mass spectrometry, Nat Biotechnol, 27(2):190-198 (2009).
Fynan et al., "DNA vaccines: protective immunizations by parenteral, mucosal, and gene-gun inoculations," PNAS, 90 (24): 11478-82 (1993).
Gallego-Gomez et al., "Differences in virus-induced cell morphology and in virus maturation between MVA and other strains (WR, Ankara, and NYCBH) of vaccinia virus in infected human cells," Journal of virology, 77(19):10606-10622 (2003).

(56) References Cited

OTHER PUBLICATIONS

Gallois et al., A needle in the 'cancer vaccine' haystack, Nature medicine, 16(8):854-856 (2010).
Gao et al., Integrative analysis of complex cancer genomics and clinical profiles using the cBioPortal, Science signaling, 6(269):pi1 (2013).
Garcia-Marco et al., Frequent Somatic Deletion of the 13q12.3 locus Encompassing BRCA2 in Chronic Lymphocytic Leukemia, Blood, 88: 1568-1575 (1996).
Garimella et al., Identification of novel molecular regulators of tumor necrosis factor-related apoptosis-inducing ligand (TRAIL)-induced apoptosis in breast cancer cells by RNAi screening, Breast cancer research, 16(2):R41 (2014).
Garofalo et al., miR-221&222 regulate TRAIL resistance and enhance tumorigenicity through PTEN and TIMP3 downregulation, Cancer Cell, 16(6):498-509 (2009).
Garraway et al., Lessons from the cancer genome, Cell, 153:17-37 (2013).
Gaucher et al., Yellow fever vaccine induces integrated multilineage and polyfunctional immune responses, The Journal of experimental medicine, 205(13):3119-3131 (2008).
Gazdar, Activating and resistance mutations of EGFR in non-small-cell lung cancer: role in clinical response to EGFR tyrosine kinase inhibitors, Oncogene, 28:S24-S31 (2009).
Gevaert et al., Protein identification methods in proteomics, Electrophoresis: An International Journal, 21(6):1145-1154 (2000).
Gherardi et al., Prime-boost immunization schedules based on influenza virus and vaccinia virus vectors potentiate cellular immune responses against human immunodeficiency virus Env protein systemically and in the genitorectal draining lymph nodes, Journal of virology, 77(12):7048-7057 (2003).
Ghiringhelli et al., "Metronomic cyclophosphamide regimen selectively depletes CD4+CD25+ regulatory T cells and restores T and NK effector functions in end stage cancer patients," Cancer Immunol Immunother, 56:641-648 (2007).
Giaever et al., Functional profiling of the Saccharomyces cerevisiae genome, Nature, 418(6896):387-391 (2002).
Giannopoulos et al., Peptide vaccination elicits leukemia-associated antigen-specific cytotoxic CD8+ T-cell responses in patients with chronic lymphocytic leukemia, Leukemia, 24(4):798-805 (2010).
Gibbs et al., Abundant quantitative trait loci exist for DNA methylation and gene expression in human brain, PLoS genetics, 6:e1000952 (2010).
Gibney et al., "Safety and efficacy of adjuvant anti-PD1 therapy (nivolumab) in combination with vaccine in resected high-risk metastatic melanoma.," J Clin Oncol, Abstract 9056 (2013).
Gilboa, "The Makings of a Tumor Rejection Antigen," Immunity, 11: 263-270 (1999).
Gluzman, Yakov, SV40-transformed simian cells support the replication of early SV40 mutants, Cell, 23:175-182 (1981).
Gnirke et al., "Solution Hybrid Selection with Ultra-Long Oligonucleotides for Massively Parallel Targeted Sequencing," Nat Biotechnol, 27(2): 182-189 (2009).
Goebel et al., "The complete DNA sequence of vaccinia virus," Virology, 179(1):247-266 (1990).
Gomez et al., "Efficient CD8+ T cell response to the HIV-env V3 loop epitope from multiple virus isolates by a DNA prime/vaccinia virus boost (rWR and rMVA strains) immunization regime and enhancement by the cytokine IFN-y," Virus research, 105:11-22 (2004).
Gomez et al., Head-to-head comparison on the immunogenicity of two HIV/AIDS vaccine candidates based on the attenuated poxvirus strains MVA and NYVAC co-expressing in a single locus the HIV-1 BX08 gp120 and HIV-111IB Gag-Pol-Nef proteins of Glade B, Vaccine, 25(15):2863-2885 (2007).
Gomez et al., MVA and NYVAC as vaccines against emergent infectious diseases and cancer, Current gene therapy, 11(:3):189-217 (2011).
Gomez et al., The poxvirus vectors MVA and NYVAC as gene delivery systems for vaccination against infectious diseases and cancer, Current gene therapy, 8(2):97-120 (2008).
Gomez et al., Virus distribution of the attenuated MVA and NYVAC poxvirus strains in mice, Journal of General Virology, 88(9):2473-2478 (2007).
Gotter et al., "Medullary Epithelial Cells of the Human Thymus Express a Highly Diverse Selection of Tissue-specific Genes Colocalized in Chromosomal Clusters," J Exp Med, 199(2):155-166 (2004).
Goya et al., "SNVMix:predicting single nucleotide variants from next-generation sequencing of tumors," Bioinformatics, Original Paper, 26(6): 730-736 (2010).
Greco et al., Improving the safety of cell therapy with the TK-suicide gene, Front Pharmacol, 6:95 (2015).
Greenman et al., Patterns of somatic mutation in human cancer genomes, Nature, 446:153-158 (2007).
Gregoriadis et al., "Improving the therapeutic efficacy of peptides and proteins: A role for polysialic acids," Int J Pharmaceutics, 300(1-2):125-30 (2005).
Gros et al. PD-1 identifies the patient-specific CD8+ tumor-reactive repertoire infiltrating human tumors. The Journal of clinical investigation, 124(5):2246-2259 (2014).
Grunstein et al., Colony hybridization: a method for the isolation of cloned DNAs that contain a specific gene, PNAS, 72(10):3961-3965 (1975).
GTEx Consortium, The Genotype-Tissue Expression (GTEx) project, Nature genetics, 45:580-585 (2013).
Guasp et al., The Peptidome of Behcet's Disease-Associated HLA-B*51 :01 Includes Two Subpeptidomes Differentially Shaped by Endoplasmic Reticulum Aminopeptidase 1, Arthritis Rheumatol, 68:505-515 (2016).
Gubin et al., Checkpoint blockade cancer immunotherapy targets tumor-specific mutant antigens, Nature, 515:577-581 (2014).
Gueguen et al., An Antigen Recognized by Autologous CTLs on a Human Bladder Carcinoma, J Immunol, 160(12): 6188-6194 (1998).
Guo et al., Different length peptids bind to HLA-Aw68 similarity at their ends but bulge on in the middle, Nature, 360:364-366 (1992).
Guo et al., Droplet microfluidics for high-throughput biological assays, Lab Chip, 12:2146-55 (2012).
Guruprasad et al., Correlation between stability of a protein and its dipeptide composition: a novel approach for predicting in vivo stability of a protein from its primary sequence, Protein Eng, 4(2):155-161 (1990).
Gustin, et al. GATA3 frameshift mutation promotes tumor grouwth in human luminal breast cancer cells and induces transcriptional changes seen in primary GATA3 mutant breast cancers, Oncotarget, 2017, vol. 8, (No. 61), pp. 103415-103427.
Guthals et al., Shotgun Protein Sequencing with Meta-contig Assembly, Molecular and Cellular Proteomics, 1(10):1084-96 (2012).
Hacohen et al., "Getting Personal with Neoantigen-Based Therapeutic Cancer Vaccines," Cancer Immunol. Res, 1(1):11-15 (2013).
Hadrup et al., Parallel detection of antigen-specific T-eeil responses by multidimensional encoding of MHC multimers, Nature Methods, 6(7):520-26 (2009).
Halabi et al., "Prognostic model for predicting survival in men with hormone-refractory metastatic prostate cancer," Journal of Clinical Oncology, 21(7):1232-1237 (2003).
Hall, Advanced sequencing technologies and their wider impact in microbiology, Journal of experimental biology, 210(9):1518-1525 (2007).
Han et al., Linking T-Cell Receptor Sequence to Fucntional Phenotype at the Single-Cell Level, Nat Biotechnol, 32:684-692 (2014).
Hanahan et al., Hallmarks of cancer: the next generation, Cell, 144:646-674 (2011).
Hansen et al., Increased methylation variation in epigenetic domains across cancer types, Nat Genet, 43:768-775 (2011).
Hanzelmann et al., GSVA: gene set variation analysis for microarray and RNA-Seq data, BMC bioinformatics, 14:7 (2013).
Harndahl et al., Peptide-MHC class I stability is a better predictor than peptide affinity of CTL immunogenicity, Eur J Immunol, 42:1405-1416 (2012).

(56) References Cited

OTHER PUBLICATIONS

Harndahl et al., Real-time, High-Throughput Measurements of Peptide-MHC-I Dissociation Using a Scintillation Proximity Assay, J Immunol Methods, 374:5-12 (2011).
Harris et al., Comparison of sequencing-based methods to profile DNA methylation and identification of monoallelic epigenetic modifications, Nat Biotechnol, 28:1097-1105 (2010).
Harris et al., RNA editing enzyme APOBECI and some of its homologs can act as DNA mutators, Molecular cell, 1095):1247-1253 (2002).
Heemskerk et al., The cancer antigenome, EMBO Journal, 32(2):194-203 (2013).
Hel et al., "Potentiation of simian immunodeficiency virus (SIV)-specific CD4+ and CD8+ T cell responses by a DNA-SIV and NYVAC-SIV prime/boost regimen," The Journal of Immunology, 167(12):7180-7191 (2001).
Herbeuval et al., HAART reduces death ligand but not death receptors in lymphoid tissue of HIV-infected patients and simian immunodeficiency virus-infected macaques, AIDS, 23:35-40 (2009).
Herbst et al., "Predictive Correlates of Response to the Anti-PD-L1 Antibody MPDL3280A in Cancer Patients," Nature, 515(7528):563-567 (2014).
Herman et al., "Differences in the Recognition by CTL of Peptides Presented by the HLAB* 4402 and the HLA-B*4403 Molecules Which Differ by a Single Amino Acid," Tissue Antigens, 53: 111-121 (1999).
Herman et al., ibrutinib-induced lymphocytosis in patients with chronic lymphocytic leukemia: correlative analyses from a phase II study, Leukemia, 28:2188 (2014).
Hersey et al., "Phase I/II study of treatment with dendritic cell vaccines in patient with disseminated melanoma," Cancer Immunol Immunoother, 53:125-134 (2004).
HHS Public Access "Cmprehensive molecular portraits of human breast tumors," Nature Oct. 4, 2012; 490(7418): 61-70. doi:10.1038/nature11412.
Hickman et al., Toward a Definition of Self: Proteomic Evaluation of the Class I Peptide Repertoire, J Immunol, 172:2944-2952 (2004).
Hinrichs et al., Exploiting the curative potential of adoptive T-cell therapy for cancer, Immunological reviews, 257:56-71 (2014).
Hocker et al., "Ultraviolet Radiation and Melanoma: A Systematic Review and Analysis of Reported Sequence Variants," Hum Mutat, 28(6): 578-588 (2007).
Hodi et al., "Biologic Activity of Cytotoxic T Lymphocyte-Associated Antigen 4 Antibody Blockade in Previously Vaccinated Metastatic Melanoma and Ovarian Carcinoma Patients," PNAS, 100: 4712-4717 (2003).
Hodi et al., "Immunologic and Clinical Effects of Antibody Blockade of Cytotoxic T Lymphocyte-Associated Antigen 4 in Previously Vaccinated Cancer Patients," PNAS, 105: 3005-3010 (2008).
Hodi et al., "Improved Survival with Ipilimumab in Patients with Metastatic Melanoma," New Engl J Med, 363:711-723 (2010).
Hombrink et al., High-Throughput Identification of Potential Minor Histocompatibility Antigens by MHC Tetramer-Based Screening: Feasibility and Limitations, Plos One, 6(8):1-11 (2011).
Hombrink et al., Identification of Biological Relevant Minor Histocompatibility Antigens within the B-lymphocyte—Derived HLA-Ligandome Using a Reverse Immunology Approach, Clin Cancer Res, 21(9):2177-2186 (2015).
Honig et al., "Phase 1 clinical trial of a recombinant canarypoxvirus (ALVAC) vaccine expressing human carcinoembryonic antigen and the B7.1 co- stimulatory molecule," Cancer Immunol Immunother, 49:504-514 (2000).
Honigberg et al., The Bruton tyrosine kinase inhibitor PCI-32765 blocks B-cell activation and is efficacious in models of autoimmune disease and B-cell malignancy, PNAS, 107:13075-13080 (2010).
Hoof, et al. NetMHCpan, a method for MHC class I binding prediction beyond humans. Immunogenetics. 61.1 (2009):1-13. doi: 10.1007/s00251-008-0341-z. Epub Nov. 12, 2008.
Huang et al., "Mucosal priming with replicative Tiantan vaccinia and systemic boosting with DNA vaccine raised strong mucosal and systemic HIV-specific immune responses," Vaccine, 25(52):8874-8884 (2007).
Huang et al., "T Cells Associated With Tumor Regression Recognize Frameshifted Products of the CDKN2A Tumor Suppressor Gene Locus and a Mutated HLA Class I Gene Product," J Immunol, 172(10):6057-6064 (2004).
Humphries et al., "Lineage tracing reveals multipotent stem cells maintain human adenomas and the pattern of clonal expansion in tumor evolution," PNAS, 110(27):e2490-e2499 (2013).
Hunt et al., Characterization of peptides bound to the class I MHC molecule HLA- A2.1 by mass spectrometry, Science, 255:1261-1263 (1992).
Hutchings et al., "Combination of protein and viral vaccines induces potent cellular and humoral immune responses and enhanced protection from murine malaria challenge," Infect Immun, 75(12):5819-26 (2007).
Illingworth et al., Orphan CpG islands identify numerous conserved promoters in the mammalian genome, PLoS Genet, 6(9):e1001134 (2010).
Illumina, Immunotherapy, the Next Generation of Cancer Treatment, NGS-guided assessment of interactions between tumors and the immune system leads to new discoveries in immuno-oncology, (2016).
Inokuchi et al., DCC protein expression in hematopoietic cell populations and its relation to leukemogenesis, J Clin Invest, 97:852-857 (1996).
Intellectual Property Policy for Partners-Affiliated Hospitals and Institutions, Aug. 15, 2002.
International Preliminary Report on Patentability for International Application No. PCT/US2011/036665 issued Nov. 20, 2012.
International Preliminary Report on Patentability for International Application No. PCT/US2014/033185 issued Oct. 22, 2015.
International Preliminary Report on Patentability for International Application No. PCT/US2014/067146 dated May 31, 2016.
International Preliminary Report on Patentability for International Application No. PCT/US2014/068746 dated Jun. 7, 2016.
International Preliminary Report on Patentability for International Application No. PCT/US2014/068893 dated Jun. 7, 2016.
International Preliminary Report on Patentability for International Application No. PCT/US2014/071707 issued Jun. 21, 2016.
Ishihama et al., Exponentially Modified Protein Abundance Index (emPAI) for Estimation of Absolute Protein Amount in Proteomics by the Number of Sequenced Peptides per Protein, Mol Cell Proteomics, 4:1265-1272 (2005).
Izeradjene et al., Casein kinase II (CK2) enhances death-inducing signaling complex (DISC) activity in TRAIL-induced apoptosis in human colon carcinoma cell lines, Oncogene, 24:2050-2058 (2005).
Jaatinen et al., Global gene expression profile of human cord blood-derived CD133+ cells, Stem Cells, 24:631-641 (2006).
Jarmalavicius et al., High Immunogenicity of the Human Leukocyte Antigen Peptidomes of Melanoma Tumor Cells, J Biol Chem, 287(40):33401-33411 (2012).
Jayasinghe, et al "Systematic Analysis of Splice-Site-creating Mutations in Cancer" Cell Reports (2018) 23, 270-281.
Jeffery et al., The Influence of HLA Class I Alleles and Heterozygosity on the Outcome of Human T Cell Lymphotropic Virus Type I Infection, J Immunol, 165:7278-7284 (2000).
Jemal et al., Cancer statistics, 2007, CA: a cancer journal for clinicians, 57:43-66 (2007).
Jennewein et al., Sumoylation of peroxisome proliferator-activated receptor gamma by apoptotic cells prevents lipopolysaccharide-induced NCoR removal from kappaB binding sites mediating transrepression of proinflammatory cytokines, Journal of immunology, 181:5646-5652 (2008).
Johnson et al., Discovery of Naturally Processed and HLA-Presented Class I Peptides from Vaccinia Virus Infection using Mass Spectrometry for Vaccine Development, Vaccine, 28(1):38-47 (2009).
Johnson et al., Single-cell perforin and granzyme expression reveals the anatomical localization of effector CD8+ T cells in influenza virus-infected mice, PNAS, 100:2657-2662 (2003).

(56) References Cited

OTHER PUBLICATIONS

Jones et al., Functions of DNA methylation: islands, start sites, gene bodies and beyond, Nat Rev Genet, 13:484-492 (2012).
Jones et al., InterProScan 5: genome-scale protein function classification, Bioinformatics, 30:1236-1240 (2014).
Jones et al., The epigenomics of cancer, Cell, 128:683-692 (2007).
Kalaora et al., Use of HLA peptidomics and whole exome sequencing to identify human immunogenic neo-antigens, Oncotarget, 7(5):5110-5117 (2016).
Kandoth et al., "Mutational landscape and significance across 12 major cancer types," Nature, 502:333-339 (2013).
Kannan et al., Vaccination strategies in follicular lymphoma, Current hematologic malignancy reports, 4(4):189-195 (2009).
Karnani et al., Pan-S replication patterns and chromosomal domains defined by genome-tiling arrays of ENCODE genomic areas, Genome research, 17:865-876 (2007).
Karolchik et al., The UCSC Table Browser data retrieval tool, Nucleic acids research, 32:D493-496 (2004).
Kawai et al., TLR signaling, Seminars in immunology, 19(1):24-32 (2007).
Kenter et al., Vaccination against HPV-16 oncoproteins for vulvar intraepithelial neoplasia, New England Journal of Medicine, 361(19):1838-1847 (2009).
Keskin et al., Neoantigen vaccine generates intratumoral T cell responses in phase Ib glioblastoma trial, Nature, 565(7738):234-239 (2019).
Khong et al., Natural selection of tumor variants in the generation of "tumor escape" phenotypes, Nature immunology, 3:999-1005 (2002).
Kim et al., A Myc network accounts for similarities between embryonic stem and cancer cell transcription programs, Cell, 143:313-324 (2010).
Kim et al., mTOR inhibitors radiosensitize PTEN-deficient non-small-cell lung cancer cells harboring an EGFR activating mutation by inducing autophagy, J Cell Biochem, 114(6):1248-1256 (2013).
Kim et al., Positional Bias of MHC Class I Restricted T-Cell Epitopes in Viral Antigens Is Likely due to a Bias in Conservation, PLoS Comput Biol, 9:e1002884 (2013).
Kim et al., TopHat2: accurate alignment of transcriptomes in the presence of insertions, deletions and gene fusions, Genome biology, 14:R36 (2013).
Kimmel et al., [54] Identification and characterization of specific clones: Strategy for confirming the validity of presumptive clones, Methods in enzymology, 152:507-511 (1987).
Kirkwood et al., High- and Low-dose Interferon Alpha-2b in Highisk Melanoma: First Analysis of Intergroup Trial E1690/S9111/C9190, J Clin Oncol, 18:2444-2458 (2000).
Kirkwood et al., Interferon alfa-2b Adjuvant Therapy of High- Risk Resected Cutaneous Melanoma: The Eastern Cooperative Oncology Group Trial EST 1684, J Clin Oncol, 14:7-17 (1996).
Klebanoff et al., Therapeutic cancer vaccines:are we there yet?, Immunol Rev, 239(1):27-44 (2011).
Klein et al., Droplet Barcoding for Single-Cell Transcriptomics Applied to Embryonic Stem Cells, Cell, 161:1187-1201 (2015).
Kloor et al., Immune evasion of microsatellite unstable colorectal cancers, International journal of cancer, 127:1001-1010 (2010).
Klug et al., Characterization of MHC Ligands for Peptide Based Tumor Vaccination, Current Pharmaceutical Design, 15(28): 3221-3236 (2009).
Koch, Combining morphology and DNA barcoding resolves the taxonomy of Western Malagasy Liotrigona Moure, 1961, African Invertebrates, 51(2):413-421 (2010).
Kreso et al., Variable clonal repopulation dynamics influence chemotherapy response in colorectal cancer, Science, 339:543-548 (2013).
Kress et al., DNA barcodes: Genes, genomics, and bioinformatics, PNAS, 105(8):2761-2762 (2008).
Kress et al., Use of DNA barcodes to identify flowering plants, PNAS, 102(23):8369-8374 (2005).
Kulis et al., Epigenomic analysis detects widespread gene-body DNA hypomethylation in chronic lymphocytic leukemia, Nat Genet, 44:1236-1242 (2012).
Lahaye et al., DNA barcoding the floras of biodiversity hotspots, PNAS, 105(8):2923-2928 (2008).
Landan et al., Epigenetic polymorphism and the stochastic formation of differentially methylated regions in normal and cancerous tissues, Nat Genet, 44:1207-1214 (2012).
Landau et al., Clonal evolution in hematological malignancies and therapeutic implications, Leukemia, 28:34-43 (2014).
Landau et al., Evolution and impact of subclonal mutations in chronic lymphocytic leukemia, Cell, 152(4):714-726 (2013).
Langmead et al., Fast gapped-read alignment with Bowtie 2, Nature methods, 9:357-359 (2012).
Langmead et al., Ultrafast and memory-efficient alignment of short DNA sequences to the human genome, Genome Biology, 10:R25 (2009).
Lata et al., MHCBN 4.0: A database of MHC/TAP binding peptides and T-cell epitopes, BMC Research Notes, 2(1): 61 (2009).
Lawrence et al., Discovery and saturation analysis of cancer genes across 21 tumour types, Nature, 505:495-501 (2014).
Lawrence et al., Mutational heterogeneity in cancer and the search for new cancer-associated genes, Nature, 499:214-218 (2013).
Le et al., Evaluation of Ipilimumab in combination with allogeneic pancreatic tumor cells transfected with a GM-CSF gene in previously treated pancreatic cancer, J Immunother, 36(7):382-389 (2013).
Lee et al., Sequential amplification of cloned DNA as tandem multimers using class-IIS restriction enzymes, Genetic Analysis: Biomolecular Engineering, 13(6):139-145 (1996).
Leffers et al., "Immunization with a P53 synthetic long peptide vaccine induces P530specific immune responses in ovarian cancer patients, a phase II trial," Int J Cancer, 125(9):2104-2113 (2009).
Leffers et al., Long Oterm clinical and immunological effects of p530SLPO vaccine in patients with ovarian cancer, Int J Cancer, 130(1):105-112 (2012).
Lemay et al., Dok-3, a Novel Adapter Molecule Involved in the Negative Regulation of Immunoreceptor Signaling, Mol Cell Biol, 20:2743-2754 (2000).
Lewintre et al., Analysis of chronic lymphotic leukemia transcriptomic profile: differences between molecular subgroups, Leuk Lymphoma, 50:68-79 (2009).
Li et al., Fast and accurate short read alignment with Burrows-Wheeler Transform, Bioinformatics, 25(14):1754-1760 (2009).
Li et al., Inactivating mutations of the chromatin remodeling gene ARID2 in hepatocellular carcinoma, Nature Genetics, 43:828-829 (2011).
Li et al., Mapping short DNA sequencing reads and calling variants using mapping quality scores, Genome Res, 18:1851-1858 (2008).
Li et al., RSEM: accurate transcript quantification from RNA-Seq data with or without a reference genome, BMC Bioinformatics, 12:323 (2011).
Li et al., The Sequence Alignment/Map format and SAMtools, Bioinformatics, 25(16):2078-2079 (2009).
Li et al., Fast and accurate long-read alignment with Burrows-Wheeler transform, Bioinformatics, 26(5):589-595 (2010).
Liggins et al., MORC4, a novel member of the MORC family, is highly expressed in a subset of diffuse large B-cell lymphomas, Brit J Haematol, 138:479-486 (2007).
Lim et al., Transcriptome analyses of mouse and human mammary cell subpopulations reveal multiple conserved genes and pathways, Breast Cancer Res, 12:R21 (2010).
Lin et al., Relevance of the immunoglobulin VH somatic mutation status in patients with chronic lymphocytic leukemia treated with fludarabine, cyclophosphamide, and rituximab (FCR) or related chemoimmunotherapy regimens, Blood, 113:3168-71 (2009).
Linardou et al., Assessment of somatic k-RAS mutations as a mechanism associated with resistance to EGFR-targeted agents: a systematic review and meta-analysis of studies in advanced non-small-cell lung cancer and metastatic colorectal cancer, Lancet Oncol, 9(10):962-972 (2008).
Linardou et al., Somatic EGFR mutations and efficacy of tyrosine kinase inhibitors in NSCLC, Nat Rev Clin Oncol, 6(6):352-366 (2009).

(56) References Cited

OTHER PUBLICATIONS

Link et al., Electric control of droplets in microfluidic devices, Angew Chem Int Ed Engl, 45(16):2556-2560 (2006).
Liu et al., Systematic identification of type I and type II interferon-induced antiviral factors, PNAS, 109(11):4239-4244 (2012).
Livak et al. Methods for qPCR gene expression profiling applied to 1440 lymphoblastoid single cells, Methods, 59(1):71-79 (2013).
Llobet et al., CK2 controls TRAIL and Fas sensitivity by regulating FLIP levels in endometrial carcinoma cells, Oncogene, 27:2513-2524 (2008).
Lohr et al., Discovery and prioritization of somatic mutations in diffuse large B-cell lymphoma (DLBCL) by whole-exome sequencing, PNAS, 109(10):3879-3884 (2012).
Lorente et al., "Diversity of Natural Self-Derived Ligands Presented by Different HLA Class I Molecules in Transporter Antigen Processing-Deficient Cells," PLoS One 8:e59118 (2013).
Lu et al., Mutated regions of nucleophosmin 1PPP1R3B Is Recognized by T Cells Used to Treat a Melanoma Patient Who Experienced a Durable Complete Tumor Regression, J Immunol, 190(12):6034-6042 (2013).
Lucas et al., About human tumor antigens to be used in immunotherapy, Semin Immunol, 20(5):301-307 (2008).
Lund et al., Coordination of early protective immunity to viral infection by regulatory T cells, Science, 320(5880):1220-1224 (2008).
Luo et al. Machine learning methods for Predicting hla—Peptide Binding activity, Bioinformatics and Biology Insights, 9(s3):2I-29 (2015).
Ma, Novor: Real-Time Peptide de Novo Sequencing Software, J Am Soc Mass Spectrom, 26:1885-1894 (2015).
Macosko et al., Highly Parallel Genome-wide Expression Profiling of Individual Cells Using Nanoliter Droplets, Cell, 161(5):1202-1214 (2015).
Maegawa et al., Age-related epigenetic drift in the pathogenesis of MDS and AML, Genome Res, 24:580-591 (2014).
Mair, et al. "Gain-and Loss0of-Function Mutations in the Breast Cancer Gene GATA3 Result in Differential Drug Sensitivity," PLOS Genetics.
Manghera et al., Endogenous retrovirus-K promoter: a landing strip for inflammatory transcription factors?, Retrovirol, 10:16 (2013).
Marabelle et al., Depleting tumor-specific Tregs at a single site eradicates disseminated tumors, J Clin Invest, 1123(6):2447-2463(2013).
Marcais et al., A fast, lock-free approach for efficient parallel counting of occurrences of k-mers, Bioinformatics, 27(6):764-770 (2011).
Mayer et al., A revised nomenclature for transcribed human endogenous retroviral loci, Mobile DNA, 2:7 (2011).
Mazutis et al., Single-cell analysis and sorting using droplet-based microfluidics, Nat Protoc, 8:870-891 (2013).
McCormack et al., HLA-A*3101 and Carbamazepine-Induced Hypersensitivity Reactions in Europeans, New Engl J Med, 364:1134-1143 (2011).
McDermott et al., Immune Therapy for Kidney Cancer: A Second Dawn?, Semin Oncol, 40(4):492-498 (2013).
McFadden et al., Genetic and clonal dissection of murine small cell lung carcinoma progression by genome sequencing, Cell, 156(6):1298-1311 (2014).
McKenna et al., The Genome Analysis Toolkit: a MapReduce framework for analyzing next-generation DNA sequencing data, Genome Res, 20(9):1297-1303 (2010).
McMurtrey et al., Toxoplasma gondii peptide ligands open the gate of the HLA class I binding groove, eLife 5:e12556 (2016).
Medema et al., Immune Escape of Tumors in Vivo by Expression of Cellular Flice-Inhibitory Protein, J Exp Med, 190:1033-1038 (1999).
Meissner et al., Genome-scale DNA methylation maps of pluripotent and differentiated cells, Nature, 454:766-770 (2008).
Menke et al., Genetic interactions between the Wilms' tumor 1 gene and the p53 gene, Cancer Res, 62(22):6615-6620 (2002).

Mermel et al., GISTIC2.0 facilitates sensitive and confident localization of the targets of focal somatic copy-number alteration in human cancers, Genome Biol, 12:R41 (2011).
Messmer et al., In vivo measurements document the dynamic cellular kinetics of chronic lymphocytic leukemia B cells, J Clin Invest, 115(3):755-764 (2005).
Milner et al., The Effect of Proteasome Inhibition on the Generation of the Human Leukocyte Antigen (HLA) Peptidome, Mol Cell Proteomics, 12:1853-1864 (2013).
Milner et al., The Turnover Kinetics of Major Histocompatibility Complex Peptides of Human Cancer Cells, Mol Cell Proteomics, 5:357-365 (2006).
Missale et al., HLA-A31- and HLA-Aw68-restricted cytotoxic T cell responses to a single hepatitis B virus nucleocapsid epitope during acute viral hepatitis, J Exp Med, 177(3):751-762 (1993).
Mocellin et al., Interferon Alpha Adjuvant Therapy in Patients With High-Risk Melanoma: A Systematic Review and Meta-analysis, JNCI, 102(7):493-501 (2010).
Mommen et al., "Expanding the detectable HLA peptide repertoire using electron-transfer/higher-energy collision dissociation (EThcD)," PNAS III, 4507-4512 (2014).
Mommen et al., Sampling From the Proteome to the Human Leukocyte Antigen-DR (HLA-DR) Ligandome Proceeds Via High Specificity, Mol Cell Proteomics MCP, 15:1412-1423 (2016).
Morison et al., A census of mammalian imprinting, Trends Genet, 21(8):457-465 (2005).
Morozov et al., The Transmembrane Protein of the Human Endogenous Retrovirus—K (HERV-K) Modulates Cytokine Release and Gene Expression, PloS one 8(8):e70399 (2013).
Morton et al., Prolonged Survival of Patients Receiving Active Immunotherapy With Canvaxin Therapeutic Polyvalent Vaccine After Complete Resection of Melanoma Metastatic to Regional Lymph Nodes, Ann Surg, 236(4):438-448 (2002).
Mosmann et al., THI and TH2 Cells: Different Patterns of Lymphokine Secretion Lead to Different Functional Properties, Ann Rev Immunol, 7:145-173 (1989).
Muntel et al., Abundance-based Classifier for the Prediction of Mass Spectrometric Peptide Detectability Upon Enrichment (PPA), Mol Cell Proteomics, 14:430-440 (2015).
Ng et al., Dereplication and de novo sequencing of nonribosomal peptides, Nat Meth, 6:596-599 (2009).
Nielsen et al., NetMHCpan, a Method for Quantitative Predictions of Peptide Binding to Any HLA-A and -B Locus Protein of Known Sequence, PloS one, 2:e796 (2007).
Nielsen et al., NetMHCpan-3.0; improved prediction of binding to MHC class I molecules integrating information from multiple receptor and peptide length datasets, Genome Medicine, 8:33 (2016).
Nielsen et al., The role of the proteasome in generating cytotoxic T-cell epitopes: insights obtained from improved predictions of proteasomal cleavage, Immunogenetics, 57:33-41 (2005).
Non-Final Office Action dated Jun. 27, 2019 for U.S. Appl. No. 15/575,328.
Non-Final Office Action for U.S. Appl. No. 13/108,610, Compositions and Methods of Identifying Tumor Specific Neoantigens, dated Aug. 15, 2013.
Non-Final Office Action for U.S. Appl. No. 13/108,610, Compositions and Methods of Identifying Tumor Specific Neoantigens, dated Dec. 3, 2014.
Non-Final Office Action for U.S. Appl. No. 14/794,449, Compositions and Methods of Identifying Tumor Specific Neoantigens, dated Dec. 29, 2016.
Non-Final Office Action for U.S. Appl. No. 14/794,449, "Compositions and Methods of Identifying Tumor Specific Neoantigens," dated Jul. 24, 2018.
Non-Final Office Action for U.S. Appl. No. 14/877,125, Compositions and Methods for Personalized Neoplasia Vaccines, dated Mar. 27, 2017.
Non-Final Office Action for U.S. Appl. No. 14/877,125, "Compositions and Methods for Personalized Neoplasia Vaccines," dated Nov. 2, 2018.
Non-Final Office Action for U.S. Appl. No. 15/038,504, Compositions and Methods for Diagnosing, Evaluating and Treating Cancer by Means of the DNA Methyl, dated Sep. 6, 2017.

(56) References Cited

OTHER PUBLICATIONS

Non-Final Office Action for U.S. Appl. No. 15/102,129, Formulations for Neoplasia Vaccines, dated Dec. 17, 2018.
Non-Final Office Action for U.S. Appl. No. 15/102,129, Formulations for Neoplasia Vaccines, dated Jul. 28, 2017.
Non-Final Office Action for U.S. Appl. No. 15/102,129, Formulations for Neoplasia Vaccines, dated Mar. 7, 2018.
Non-Final Office Action for U.S. Appl. No. 15/105,961, Combination Therapy With Neoantigen Vaccine, dated Jan. 8, 2019.
Non-Final Office Action for U.S. Appl. No. 15/105,961, Combination Therapy With Neoantigen Vaccine, dated Nov. 20, 2017.
Non-Final Office Action for U.S. Appl. No. 15/187,174, "Compositions and Methods of Identifying Tumor Specific Neoantigens," dated Dec. 5, 2016.
Non-Final Office Action for U.S. Appl. No. 15/187,174, Compositions and Methods of Identifying Tumor Specific Neoantigens, dated Jan. 22, 2018.
Non-Final Office Action for U.S. Appl. No. 15/513,127, Use of Clonal Evolution Analysis for Ibrutinib Resistance in Chronic Lymphocytic Leukemia Patients, dated Nov. 26, 2018.
Non-Final Office Action for U.S. Appl. No. 15/537,785, Methods for Profiling the T Cell Repertoire, dated Dec. 21, 2018.
Non-Final Office Action for U.S. Appl. No. 16/181,098, Compositions and Methods of Identifying Tumor Specific Neoantigens, dated Jan. 31, 2019.
Notice of Allowance for U.S. Appl. No. 13/108,610, Compositions and Methods of Identifying Tumor Specific Neoantigens, mailed Jun. 11, 2015.
Notice of Allowance for U.S. Appl. No. 13/108,610, Compositions and Methods of Identifying Tumor Specific Neoantigens, mailed May 12, 2015.
Notice of Allowance for U.S. Appl. No. 15/102,129, Formulations for Neoplasia Vaccines, mailed Oct. 12, 2018.
Novershtern et al., Densely Interconnected Transcriptional Circuits Control Cell States in Human Hematopoiesis, Cell, 144(2):296-309 (2011).
Oh et al., Neutrophil isolation protocol, J Vis Exp (2008).
Ohnishi et al., Premature Termination of Reprogramming In Vivo Leads to Cancer Development through Altered Epigenetic Regulation, Cell, 156(4):663-677 (2014).
Okada et al., Induction of CD8+ T-Cell Responses Against Novel Glioma-Associated Antigen Peptides and Clinical Activity by Vaccinations With a-Type 1 Polarized Dendritic Cells and Polyinosinic-Polycytidylic Acid Stabilized by Lysine and Carboxymethylcellulose in Patients With Recurrent Malignant Glioma, J Clin Oncol, 29(3):330-336 (2011).
Oshiumi et al., Dead/H Box 3 (DDX3) helicase binds the RIG-I adaptor IPS-1 to up-regulate IFN-beta-inducing potential, Eur J Immunol, 40:940-948 (2010).
Ott et al., CTLA-4 and PD-1/PD-L1 Blockade: New Immunotherapeutic Modalities with Durable Clinical Benefit in Melanoma Patients, Clin Cancer Res, 19(19):5300-5309 (2013).
Padgett et al., Creating seamless junctions independent of restriction sites in PCR cloning, Gene, 168:31-35 (1996).
Pages, et al., Effector Memory T Cells, Early Metastasis, and Survival in Colorectal Cancer, New Engl J Med, 353:2654-2666 (2005).
PAIR Assignment Register extract (accessed Oct. 20, 2016).
PCT/US2017/025462 International Search Report dated Sep. 11, 2017.
PCT/US2018/025933 International Search Report and Written Opinion dated Oct. 9, 2018.
Pei et al., Genome-wide DNA methylation analysis reveals novel epigenetic changes in chronic lymphocytic leukemia, Epigenetics, 7:567-578 (2012).
Peitras, Richard J., Biologic Basis of Sequential and Combination Therapies for Hormone- Response Breast Cancer, The Oncologist, 2006; 11:704-717.
Peng et al., DOK3 Negatively Regulates LPS Responses and Endotoxin Tolerance, PloS one 7:e39967 (2012).

Perez et al., p63 consensus DNA-binding site: identification, analysis and application into a p63MH algorithm, Oncogene, 26:7363-7370 (2007).
Pieters et al., On guard: coronin proteins in innate and adaptive immunity, Nat Rev Immunol, 13:510-518 (2013).
Pirard et al., Interferon Alpha as Adjuvant Postsurgical Treatment of Melanoma: A Meta-Analysis, Dermatology, 208(1):43-48 (2004).
Powell et al., NCoR1 Mediates Papillomavirus E8AE2C Transcriptional Repression, J Virol, 84:4451-4460 (2010).
Prints-outs from the UniProtKB database concerning the CEP170, Parva and FLT3 genes.
Pujadas et al., Regulated noise in the epigenetic landscape of development and disease, Cell, 148(6):1123-1131 (2012).
Qin et al., Soft lithography for micro- and nanoscale patterning, Nat Protoc, 5:491-502 (2010).
Quesada et al., "Exome sequencing identifies recurrent mutations of the splicing factor SF3B1 gene in chronic lymphocytic leukemia," Nat Genet, 44:47-52 (2012).
Quezada et al., CTLA4 blockade and GM-CSF combination immunotherapy alters the intratumor balance of effector and regulatory T cells, J Clin Invest, 116(7):1935-1945 (2006).
Ramskold et al., Full-length mRNA-Seq from single-cell levels of RNA and individual circulating tumor cells, Nat Biotechnol, 30:777-782 (2012).
Rassenti et al., Relative value of ZAP-70, CD38, and immunoglobulin mutation status in predicting aggressive disease in chronic lymphocytic leukemia, Blood, 112:1923-1930 (2008).
Raval et al., Downregulation of Death-Associated Protein Kinase 1 (DAPK1) in Chronic Lymphocytic Leukemia, Cell, 129(5):879-890 (2007).
Ravi et al., Sensitization of Tumor Cells to Apo2 Ligand/TRAIL-induced Apoptosis by Inhibition of Casein Kinase II, Cancer Res, 62(15):4180-4185 (2002).
Richter et al., Mechanistic Determinants of Biotherapeutics Absorption Following SC Administration, The AAPS Journal, 14(3):559-568 (2012).
Rini et al., Biology and Treatment of Advanced Renal Cell Carcinoma: A Global Perspective, Semin Oncol, 40(4):419-420 (2013).
Robbins et al., Mining exomic sequencing data to identify mutated antigens recognized by adoptively transferred tumor-reactive T cells, Nat Med, 19(6):747-752 (2013).
Robinson et al., A phase I-II trial of multiple-dose polyriboinosic-polyribocytidylic acid in patients with leukemia or solid tumors, J Natl Cancer Inst, 57(3):599-602 (1976).
Robinson et al., "DNA vaccines for viral infections: Basic studies and applications," Adv Virus Res, 55:1-74 (2000).
Robinson et al., edgeR: a Bioconductor package for differential expression analysis of digital gene expression data, Bioinformatics, 26(1):139-140 (2010).
Robinson et al., Integrative genomics viewer, Nat Biotechnol, 29:24-26 (2011).
Rosenberg, Raising the Bar: The Curative Potential of Human Cancer Immunotherapy, Sci Transl Med, 4(127):127ps128 (2012).
Rossi et al., Integrated mutational and cytogenetic analysis identifies new prognostic subgroups in chronic lymphocytic leukemia, Blood, 121:1403-1412 (2013).
Rubin et al., Mutation patterns in cancer genomes, PNAS, 106(51):21766-21770 (2009).
Rubio-Moscardo et al., Characterization of 8p21.3 chromosomal deletions in B-cell lymphoma: TRAIL-R1 and TRAIL-R2 as candidate dosage-dependent tumor suppressor genes, Blood, 106:3214-3222 (2005).
Rutledge et al., Tumor-Infiltrating Lymphocytes in Glioblastoma Are Associated with Specific Genomic Alterations and Related to Transcriptional Class, Clin Cancer Res, 19:4951-4960 (2013).
Sahin et al., Personalized RNA mutanome vaccines mobilize polyspecific therapeutic immunity against cancer, Nature, 547(7662):222-226 (2017).
Salem et al., Defining the Antigen-Specific T-Cell Response to Vaccination and Poly(I:C)/TLR3 Signaling: Evidence of Enhanced Primary and Memory CD8 T-Cell Responses and Antitumor Immunity, J Immunother, 28(3):220-228 (2005).

(56) References Cited

OTHER PUBLICATIONS

Samuels et al., Oncogenic P13K and its role in cancer, Curr Opin Oncol, 18:77-82n (2006).
Sato et al., Discovery of Novel Targets for Aberrant Methylation in Pancreatic Carcinoma Using High-Throughput Microarrays, Cancer Res, 63(13):3735-3742 (2003).
Saturno et al., Combining TRAIL with P13 Kinase or HSP90 inhibitors enhances apoptosis in colorectal cancer cells via suppression of survival signaling, Oncotarget, 4(8):1185-1198 (2013).
Saunders et al. Strelka: accurate somatic small-variant calling from sequenced tumor-normal sample pairs. Bioinformatic, 28(14):1811-1817 (2012).
Schmitt et al., Transcriptional Profiling of Human Endogenous Retrovirus Group HERV-K(HML-2) Loci in Melanoma, Genome Biol Evol, 5(2):307-328 (2013).
Schreiber et al., Cancer Immunoediting: Integrating Immunity's Roles in Cancer Suppression and Promotion, Science, 331(6024):1565-1570 (2011).
Schumacher et al., Prognostic Significance of Activated CD8+ T Cell Infiltrations within Esophageal Carcinomas, Cancer Res, 61(10):3932-3936 (2001).
Schuster et al., Vaccination With Patient-Specific Tumor-Derived Antigen in First Remission Improves Disease-Free Survival in Follicular Lymphoma, J Clin Oncol, 29(20):2787-2794 (2011).
Seberg et al., How Many Loci Does it Take to DNA Barcode a Crocus?, PLoS One 4(2):e4598 (2009).
Secchiero et al., Aberrant expression of TRAIL in B chronic lymphocytic leukemia (B-CLL) cells, J Cell Physiol, 205(2):246-252 (2005).
Sensi et al., Unique tumor antigens: evidence for immune control of genome integrity and immunogenic targets for T cell-mediated patient-specific immunotherapy, Clin Cancer, Res 12:5023-5032 (2006).
Shah et al., Multiple BCR-ABL kinase domain mutations confer polyclonal resistance to the tyrosine kinase inhibitor imatinib (STI571) in chronic phase and blast crisis chronic myeloid leukemia, Cancer Cell, 2(2):117-125 (2002).
Shalek et al., Single-cell RNA-seq reveals dynamic paracrine control of cellular variation, Nature, 510(7505):363-369 (2014).
Shannon, A Mathematical Theory of Communication, Bell System Technical Journal, 27(3):379-423 (1948).
Shao et al., Clonally related histiocytic/dendritic cell sarcoma and chronic lymphocytic leukemia/small lymphocytic lymphoma: a study of seven cases, Mod Pathol, 24:1421-1432 (2011).
Shendure et al., Next-generation DNA sequencing, Nat Biotechnol, 26(10):1135-1145 (2008).
Shipony et al., Dynamic and static maintenance of epigenetic memory in pluripotent and somatic cells, Nature, 513:115-119 (2014).
Sidney et al., HLA class I supertypes: a revised and updated classification, BMC Immunol, 9:1 (2008).
Siegel et al., Cancer statistics, 2013, CA, 63(1):11-30 (2013).
Simmons et al., Local secretion of anti-CTLA-4 enhances the therapeutic efficacy of a cancer immunotherapy with reduced evidence of systemic autoimmunity, Cancer Immunol Immunother, 57(8):1263-1270 (2008).
Simpson et al., Cancer/testis antigens, gametogenesis and cancer, Nat Rev Cancer, 5:615-625 (2005).
Simpson et al., "Fc-dependent depletion of tumor-infiltrating regulatory T cells co-defines the efficacy of anti-CTLA-4 therapy against melanoma," J Exp Med, 210(9):1695-1710 (2013).
Slingluff et al., Randomized Multicenter Trial of the Effects of Melanoma-Associated Helper Peptides and Cyclophosphamide on the Immunogenicity of a Multipeptide Melanoma Vaccine, J Clin Oncol, 29(21):2924-2932 (2011).
Smith et al., Comparison of biosequences, Adv Appl Math, 2(4):482-489 (1981).
Smoley et al., "Standardization of fluorescence in situ hybridization studies on chronic lymphocytic leukemia (CLL) blood and marrow cells by the CLL Research Consortium," Cancer Genet Cytogenet, 203(2):141-148 (2010).
Soares et al., A subset of dendritic cells induces CD4+ T cells to produce IFN-gamma by an IL-12-independent but CD70-dependent mechanism in vivo, J Exp Med, 2215(11):1095-1106 (2007).
Soininen et al., Analysing diet of small herbivores: the efficiency of DNA barcoding coupled with high-throughput pyrosequencing for deciphering the composition of complex plant mixtures, Front Zool, 6:16 (2009).
Song et al., c-Cbl acts as a mediator of Src-induced activation of the PI3K-Akt signal transduction pathway during TRAIL treatment, Cellular Signalling, 22(3):377-385 (2010).
Song, Shengli et al., Full screening and accurate subtyping of HLA-A*02 alleles through group-specific amplification and monoallelic sequencing, Cellular & Molecular Immunology (2013) 10, 490-496.
Sosman et al., A phase 2 trial of complete resection for stage IV melanoma: results of Southwest Oncology Group Clinical Trial S9430, Cancer, 117(20):4740-4706 (2011).
Speetjens et al., Induction of p53-Specific Immunity by a p53 Synthetic Long Peptide Vaccine in Patients Treated for Metastatic Colorectal Cancer, Clin Cancer Res, 15(3):1086-1095 (2009).
Spencer et al., Non-genetic origins of cell-to-cell variability in TRAIL-induced apoptosis, Nature, 459:428-432 (2009).
Spranger et al., Up-regulation of PD-LI, IDO, and Tregs in the melanoma tumor microenvironment is driven by CD8+ T cells, Sci Trans! Med, 5(200):200ra116 (2013).
Srivastava et al., Modeling the Repertoire of True Tumor-Specific Mhc I Epitopes in a Human Tumor, PLOS one, 4(7):e6094 (2009).
Srivastava, Therapeutic Cancer Vaccines, Curr Opin Immunol, 18: 201-205 (2006).
Stransky et al., The Mutational Landscape of Head and Neck Squamous Cell Carcinoma, Science, 333:1157-1160 (2011).
Stranzl et al., NetCTLpan: pan-specific MHC class I pathway epitope predictions, Immunogenetics, 62(6):357-368 (2010).
Su et al., Next-generation sequencing and its applications in molecular diagnostics Exp Rev Mol Diagn, 11(3):333-343 (2011).
Subramanian et al., Gene set enrichment analysis: a knowledge-based approach for interpreting genome-wide expression profiles, PNAS, 102:15545-15550 (2005).
Sun et al., Material bionics and Thinking Innovation, 176-177 (2012).
Suzuki et al., A Novel Glycosylphosphatidyl Inositol-Anchored Protein on Human Leukocytes: A Possible Role for Regulation of Neutrophil Adherence and Migration, J Immunol, 162(7):4277-4284 (1999).
Sykulev et al., Evidence that a Single Peptide-MHC Complex on a Target Cell Can Elicit a Cytolytic T Cell Response, Immunity, 4:565-571 (1996).
Takaku, et al. "GATA3 in Breast Cancer: tumor suppressor or oncogene?" HHS Public Access, 2015.
Takaku, et al. "GATA3 zinc finger 2 mutations reprogram the breast cancer transcriptional network," Nature Communications, (2018)9:1059.
Tang et al., NeoantigenR: An annotation based pipeline for tumor neoantigen identification from sequencing data, bioRxiv preprint first posted online Aug. 8, 2017.
Tang et al., The landscape of viral expression and host gene fusion and adaptation in human cancer, Nat Commun, 4:2513 (2013).
Ten Bosch et al., Keeping Up With the Next Generation: Massively Parallel Sequencing in Clinical Diagnostics, J Mol Diagn, 10(6):484-492 (2008).
Teng et al., A human TAPBP (TAPASIN)-related gene, TAPBP-R, Eur J Immunol, 32:1059-1068 (2002).
Testori et al., Phase III comparison of vitespen, an autologous tumor-derived heat shock protein gp96 peptide complex vaccine, with physician's choice of treatment for stage IV melanoma: the C-100-21 Study Group, J Clin Oncol, 26(6):955-962 (2008).
Textor et al., "Human NK cells are alerted to induction of p53 in cancer cells by upregulation of the NKG2D ligands ULBPI and ULBP2," Cancer Res, 71:5998-6009 (2011).

(56) References Cited

OTHER PUBLICATIONS

Timp et al., Cancer as a dysregulated epigenome allowing cellular growth advantage at the expense of the host, Nat Rev Cancer, 13:497-510 (2013).
Topalian et al., Safety, Activity, and Immune Correlates of Anti-PD-1 Antibody in Cancer, N Engl J Med, 366(26):2443-2454 (2012).
Topalian et al., Survival, Durable Tumor Remission, and Long-Term Safety in Patients With Advanced Melanoma Receiving Nivolumab, J Clin Oncol, 32(10):1020-1030 (2014).
Tough et al., Induction of bystander T cell proliferation by viruses and type I interferon in vivo, Science, 272(5270):1947-1950 (1996).
Tran et al., Cancer Immunotherapy Based on Mutation-Specific CD4+ T Cells in a Patient with Epithelial Cancer, Science, 344(6184):641-645 (2014).
Trolle et al., Automated benchmarking of peptide-MHC class I binding predictions, Bioinformatics, 31(13):2174-2181 (2015).
Trumpfheller et al., ntensified and protective CD4+ T cell immunity in mice with anti-dendritic cell HIV gag fusion antibody vaccine, J Exp Med, 203(3):607-617 (2006).
Trumpfheller et al., The microbial mimic poly IC induces durable and protective CD4+ T cell immunity together with a dendritic cell targeted vaccine, PNAS, 105(7):2574-2579 (2008).
Tucker et al., Massively Parallel Sequencing: The Next Big Thing in Genetic Medicine, Am J Hum Genet, 85(2):142-154 (2009).
Turchaninova et al., Pairing of T-cell receptor chains via emulsion PCR, Eur J Immunol, 43:2507-2515 (2013).
Uderhardt et al., 12/15-lipoxygenase orchestrates the clearance of apoptotic cells and maintains immunologic tolerance, Immunity, 36(5):834-846 (2012).
Usary, et al. "Mutation of GATA3 in human breast tumors," Oncogene (2004) 23, 7669-7678.
Ushijima et al., Fidelity of the methylation pattern and its variation in the genome, Genome research, 13:868-874 (2005).
Uyttenhove et al., Evidence for a tumoral immune resistance mechanism based on tryptophan degradation by indoleamine 2,3 -di oxygenase, Nature medicine, 9:1269-1274 (2003).
Vaishampayan et al., Active immunotherapy of metastatic melanoma with allogeneic melanoma lysates and interferon alpha, Clin Cancer Res, 8(12):3696-3701 (2002).
Van Buuren et al., High sensitivity of cancer exome-based CD8 T cell neo-antigen identification, OncoImmunology, 3(5):e28836 (2014).
Van Elsas et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation, Journal of Experimental Medicine, 190(3):355-366 (1999).
Van Poelgeest et al., HPV16 synthetic long peptide (HPV16-SLP) vaccination therapy of patients with advanced or recurrent HPV16-induced gynecological carcinoma, a phase II trial, J Trans! Med, 11:88 (2013).
Van Rooij et al., Tumor exome analysis reveals neoantigen-specific T-cell reactivity in an ipilimumab-responsive melanoma, Journal of clinical oncology: official journal of the American Society of Clinical Oncology, 31:32 (2013).
Vermeij et al., Potentiation of a p53-SLP vaccine by cyclophosphamide in ovarian cancer: a single-arm phase II study, Int J Cancer, 131(5):E670-680 (2012).
Vogel et al., Mass Spectrometry Reveals Changes in MHC I Antigen Presentation After Lentivector Expression of a Gene Regulation System, Molecular Therapy—Nucleic Acids, 2:e75 (2013).
Wahl et al., [43] Molecular hybridization of immobilized nucleic acids: Theoretical concepts and practical considerations, Methods in enzymology, Academic Press, 152:399-407 (1987).
Wang et al., Functional Polymeric Material, 1-44 (2010).
Wang et al., Role of protein kinase CK2 in the regulation of tumor necrosis factor-related apoptosis inducing ligand-induced apoptosis in prostate cancer cells, Cancer research, 66:2242-2249 (2006).

Wang et al., SF3B1 and other novel cancer genes in chronic lymphocytic leukemia, N Engl J Med, 365:2497-2506 (2011).
Wang et al., Widespread plasticity in CTCF occupancy linked to DNA methylation, Genome Res, 22:1680-1688 (2012).
Weber et al., Assembly of Designer TAL Effectors by Golden Gate Cloning, PLoS One, 6:e19722 (2001).
Welters et al., Induction of tumor-specific CD4+ and CD8+ T-cell immunity in cervical cancer patients by a human papillomavirus type 16 E6 and E7 long peptides vaccine, Clinical cancer research, 14(1):178-187 (2008).
Welters et al., Success or failure of vaccination for HPV16-positive vulvar lesions correlates with kinetics and phenotype of induced T-cell responses, PNAS, 107(26):11895-11899 (2010).
Wheatley et al., Does adjuvant interferon-alpha for high-risk melanoma provide a worthwhile benefit? A meta-analysis of the randomised trials, Cancer treatment reviews, 29(4):241-252 (2003).
Widschwendter et al., Epigenetic stem cell signature in cancer, Nat Genet, 39:157-158 (2007).
Wierda et al., Multivariable model for time to first treatment in patients with chronic lymphocytic leukemia, J Clin Oncol, 29:4088-4095 (2011).
Winzeler et al., Functional characterization of the S. cerevisiae genome by gene deletion and parallel analysis, science, 285(5429):901-906 (1999).
Wolchok et al., "Nivolumab plus ipilimumab in advanced melanoma," N Engl J Med, 369(2):122-133 (2013).
Wong et al., Module map of stem cell genes guides creation of epithelial cancer stem cells, Cell Stem Cell, 2:333-344 (2008).
Woodfine et al., Quantitative analysis of DNA methylation at all human imprinted regions reveals preservation of epigenetic stability in adult somatic tissue, Epigenetics & chromatin, 4:1 (2011).
Woyach et al., Resistance mechanisms for the Bruton's tyrosine kinase inhibitor ibrutinib, The New England journal of medicine, 370:2286-94 (2014).
Wraith, The Future of Immunotherapy: A 20-Year Perspective, Front Immunol, 8:1668 (2017).
Xi et al., BSMAP: whole genome bisulfite sequence MAPping program, BMC bioinformatics, 10:232 (2009).
Xie et al., Stepwise reprogramming of B cells into macrophages, Cell, 117(5):663-676 (2004).
Xu et al., Design of 240,000 orthogonal 25mer DNA barcode probes, Proceedings of the National Academy of Sciences, pnas-0812506106 (2009).
Yan et al., PBAF chromatin-remodeling complex requires a novel specificity subunit, BAF200, to regulate expression of selective interferon-responsive genes, Genes & development, 19(14):1662-1667 (2005).
Yang, et al. "HDR syndrome with a novel mutation in GATA3 mimicking a congenital X-linked stapes gusher: a case report," BMC Medical Genetics (2017) 18:121.
Yang et al., Meta-analysis followed by replication identifies loci in or near CDKN1B, TET3, CD80, DRAM1, and ARID5B as associated with systemic lupus erythematosus in Asians, American journal of human genetics, 92:41-51 (2013).
Ye, et al. "Systematic Discovery of Complex Indels in Human Cancers," Nat Med. Jan. 2016; 22(1): 97-104.
Yoshihara, K. et al., Inferring tumour purity and stromal and immune cell admixture from expression data,: Nature communications 4:2612 (2013).
Yoshitake et al., Cross0 linking of GPI 080, a possible regulatory molecule of cell adhesion, induces upO regulation of CD11b/CD18 expression on neutrophil surfaces and shedding of LO selectin, Journal of leukocyte biology, 71(2):205-211 (2002).
Young et al., Resurrection of endogenous retroviruses in antibody-deficient mice, Nature, 491(7426):774 (2012).
Yu et al., Nucleic acid-sensing Toll-like receptors are essential for the control of endogenous retrovirus viremia and ERV-induced tumors, Immunity, 37(5):867-879 (2012).
Yuille et al., TCL1 is activated by chromosomal rearrangement or by hypomethylation, Genes, Chromosomes and Cancer, 30(4):336-341 (2001).
Zeestraten et al., "Addition of interferon-alpha to the p53-SLP(R) vaccine results in increased production of interferon-gamma in

(56) References Cited

OTHER PUBLICATIONS vaccinated colorectal cancer patients: a phase 1/11 clinical trial," Int J Cancer, 132(7):1581-1591 (2013).

Zhang et al., Machine learning competition in immunology-prediction of HLA class I binding peptides, J Immunol Methods 374:1-4 (2009).

Zhang et al., Oncology, 1-44 (2005).

Zhang et al., The impact of next-generation sequencing on genomics, J Genet Genomics, 38(3):95-109 (2011).

Zhou et al., A hypermorphic missense mutation in PLCG2, encoding phospholipase Cgamma2, causes a dominantly inherited autoinflammatory disease with immunodeficiency, Am J Hum Genet, 91:713-20 (2012).

Zhu et al., Toll like receptor-3 ligand poly-ICLC promotes the efficacy of peripheral vaccinations with tumor antigen-derived peptide epitopes in murine CNS tumor models, Journal of translational medicine, 5:10 (2007).

Ziller et al., Charting a dynamic DNA methylation landscape of the human genome, Nature, 500:477-481 (2013).

Zorn et al., A natural cytotoxic T cell response in a spontaneously regressing human melanoma targets a neoantigen resulting from a somatic point mutation, Eur J Immunol, 29(2):592-601 (1999).

Zwaveling et al., Established human papillomavirus type 16-expressing tumors are effectively eradicated following vaccination with long peptides, J Immunol, 169(1):350-358 (2002).

Japanese Patent Application No. 2023-90878 Office Action dated May 20, 2024.

\* cited by examiner

PROTEIN ANTIGENS AND USES THEREOF

CROSS REFERENCE

This application is a National Stage Entry of International Application No. PCT/US2018/025933, filed Apr. 3, 2018, which claims priority to U.S. Provisional Application No. 62/480,593, filed Apr. 3, 2017, U.S. Provisional Application No. 62/480,596, filed Apr. 3, 2017, and U.S. Provisional Application No. 62/480,597, filed Apr. 3, 2017, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 14, 2018, is named 50401-705_602_SL.txt and is 265,859 bytes in size.

FIELD

The field of the present invention relates to immunotherapeutic peptides, nucleic acids encoding the peptides, peptide binding agents, and their use, for example, in the immunotherapy of cancer. In one aspect, the invention provides non-mutated protein epitopes expressed in cancer cells, useful alone or in combination with other tumor-associated peptides, anti-cancer, or immunomodulatory agents to treat cancer.

BACKGROUND

Tumor vaccines are typically composed of tumor antigens and immunostimulatory molecules (e.g., adjuvants, cytokines or TLR ligands) that work together to induce antigen-specific cytotoxic T cells (CTLs) that recognize and lyse tumor cells. Such vaccines contain either shared tissue restricted tumor antigens or a mixture of shared and patient-specific antigens in the form of whole tumor cell preparations. The shared tissue restricted tumor antigens are ideally immunogenic proteins with selective expression in tumors across many individuals and are commonly delivered to patients as synthetic peptides or recombinant proteins. In contrast, whole tumor cell preparations are delivered to patients as autologous irradiated cells, cell lysates, cell fusions, heat-shock protein preparations or total mRNA. Since whole tumor cells are isolated from the autologous patient, the cells may include patient-specific tumor antigens as well as shared tumor antigens. Finally, there is a third class of tumor antigens, neoantigens, which consists of proteins with tumor-specific mutations (which can be patient-specific or shared) that result in altered amino acid sequences. Accordingly, there is still a need for developing additional cancer therapeutics.

SUMMARY

Provided herein an isolated antigenic peptide comprising an epitope from a sequence in Table 1 or 2. The present disclosure is also directed to an isolated antigenic peptide 100 amino acids or less in length which comprises an epitope from a sequence in Table 1 or 2. The present disclosure is also directed to an isolated antigenic peptide comprising an epitope from a sequence in Table 3 or 4. The present disclosure is also directed to an isolated antigenic peptide 100 amino acids or less in length which comprises an epitope from a sequence in Table 3 or 4. The present disclosure is also directed to an isolated antigenic peptide comprising an epitope from a sequence in Table 5 or 6. The present disclosure is also directed to an isolated antigenic peptide 100 amino acids or less in length which comprises an epitope from a sequence in Table 5 or 6.

In one embodiment, the isolated antigenic peptide is a retroviral antigen. In another embodiment, the isolated antigenic peptide is a non-mutated overexpressed antigen. In another embodiment, the isolated antigenic peptide is a viral antigen.

In one embodiment, the isolated antigenic peptide is between about 5 to about 50 amino acids in length. In another embodiment, the isolated antigenic peptide is between about 15 to about 35 amino acids in length. In another embodiment, the isolated antigenic peptide is about 15 amino acids or less in length. In another embodiment, the isolated antigenic peptide is between about 8 and about 11 amino acids in length. In another embodiment, the isolated antigenic peptide is 9 or 10 amino acids in length. In one embodiment, the isolated antigenic peptide binds major histocompatibility complex (MHC) class I. In another embodiment, the isolated antigenic peptide binds MHC class I with a binding affinity of less than about 500 nM.

In one embodiment, the isolated antigenic peptide is about 30 amino acids or less in length. In another embodiment, the isolated antigenic peptide is between about 6 and about 25 amino acids in length. In another embodiment, the isolated antigenic peptide is between about 15 and about 24 amino acids in length. In another embodiment, the isolated antigenic peptide is between about 9 and about 15 amino acids in length. In one embodiment, the isolated antigenic peptide binds MHC class II. In another embodiment, the isolated antigenic peptide binds MHC class II with a binding affinity of less than about 1000 nM.

In one embodiment, the isolated antigenic peptide further comprises flanking amino acids. In another embodiment, the flanking amino acids are not native flanking amino acids. In one embodiment, the isolated antigenic peptide is linked to at least a second antigenic peptide. In another embodiment, the peptides are linked using a poly-glycine or poly-serine linker. In another embodiment, the second antigenic peptide binds MHC class I or class II with a binding affinity of less than about 1000 nM. In another embodiment, the second antigenic peptide binds MHC class I or class II with a binding affinity of less than about 500 nM. In another embodiment, both of the epitopes bind to human leukocyte antigen (HLA)-A, -B, -C, -DP, -DQ, or -DR. In another embodiment, the isolated antigenic peptide binds a class I HLA and the second antigenic peptide binds a class II HLA. In another embodiment, the isolated antigenic peptide binds a class II HLA and the second antigenic peptide binds a class I HLA.

In one embodiment, the isolated antigenic peptide further comprises modifications which increase in vivo half-life, cellular targeting, antigen uptake, antigen processing, MHC affinity, MHC stability, or antigen presentation. In another embodiment, the modification is conjugation to a carrier protein, conjugation to a ligand, conjugation to an antibody, PEGylation, polysialylation HESylation, recombinant PEG mimetics, Fc fusion, albumin fusion, nanoparticle attachment, nanoparticulate encapsulation, cholesterol fusion, iron fusion, acylation, amidation, glycosylation, side chain oxidation, phosphorylation, biotinylation, the addition of a surface active material, the addition of amino acid mimetics, or the addition of unnatural amino acids. In one embodiment, the cells that are targeted are antigen presenting cells.

In another embodiment, the antigen presenting cells are dendritic cells. In another embodiment, the dendritic cells are targeted using DEC205, XCR1, CD197, CD80, CD86, CD123, CD209, CD273, CD283, CD289, CD184, CD85h, CD85j, CD85k, CD85d, CD85g, CD85a, CD141, CD11c, CD83, TSLP receptor, or CD1a marker. In another embodiment, the dendritic cells are targeted using the CD141, DEC205, or XCR1 marker.

In one embodiment, provided herein is an in vivo delivery system comprising an isolated antigenic peptide described herein. In another embodiment, the delivery system includes cell-penetrating peptides, nanoparticulate encapsulation, virus like particles, or liposomes. In another embodiment, the cell-penetrating peptide is TAT peptide, herpes simplex virus VP22, transportan, or Antp.

In one embodiment, provided herein is a cell comprising an isolated antigenic peptide described herein. In another embodiment, the cell is an antigen presenting cell. In another embodiment, the cell is a dendritic cell.

In one embodiment, provided herein is a composition comprising an isolated antigenic peptide described herein. In another embodiment, the composition comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 of the isolated antigenic peptides comprising a tumor-specific epitope defined in Table 1 or 2. In another embodiment, the composition comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 of the isolated antigenic peptides comprising a tumor-specific epitope defined in Table 3 or 4. In another embodiment, the composition comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 of the isolated antigenic peptides comprising a tumor-specific epitope defined in Table 5 or 6. In another embodiment, the composition comprises between 2 and 20 antigenic peptides. In another embodiment, the composition further comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25, at least 26, at least 27, at least 28, at least 29, or at least 30 additional antigenic peptides. In another embodiment, the composition comprises between about 4 and about 20 additional antigenic peptides. In another embodiment, the additional antigenic peptide is specific for an individual patient's tumor. In another embodiment, an antigenic peptide is selected by identifying differences in expression between the transcriptome or proteome of the patient's tumor sample and the transcriptome or proteome of a non-tumor sample. In another embodiment, the samples are fresh or formalin-fixed paraffin embedded tumor tissues, freshly isolated cells, or circulating tumor cells. In some embodiments, the sequences of the antigenic peptides are determined by Next Generation Sequencing.

In one embodiment, provided herein is an isolated polynucleotide encoding the isolated antigenic peptide described herein. In another embodiment, the isolated polynucleotide is RNA, optionally a self-amplifying RNA. In another embodiment, the RNA is modified to increase stability, increase cellular targeting, increase translation efficiency, adjuvanticity, cytosol accessibility, and/or decrease cytotoxicity. In another embodiment, the modification is conjugation to a carrier protein, conjugation to a ligand, conjugation to an antibody, codon optimization, increased GC-content, incorporation of modified nucleosides, incorporation of 5'-cap or cap analog, and/or incorporation of an unmasked poly-A sequence.

In one embodiment, provided herein is a cell comprising a polynucleotide described herein.

In one embodiment, provided herein is a vector comprising a polynucleotide described herein. In another embodiment, the polynucleotide is operably linked to a promoter. In another embodiment, the vector is a self-amplifying RNA replicon, plasmid, phage, transposon, cosmid, virus, or virion. In another embodiment, the vector is an adeno-associated virus, herpesvirus, lentivirus, or pseudotypes thereof.

In one embodiment, provided herein is an in vivo delivery system comprising an isolated polynucleotide described herein. In another embodiment, the delivery system includes spherical nucleic acids, viruses, virus-like particles, plasmids, bacterial plasmids, or nanoparticles.

In one embodiment, provided herein is a cell comprising a vector or delivery system described herein. In another embodiment, the cell is an antigen presenting cell. In another embodiment, the cell is a dendritic cell. In another embodiment, the cell is an immature dendritic cell.

In one embodiment, provided herein is a composition comprising at least one polynucleotide described herein. In another embodiment, the composition comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 of the isolated polynucleotides. In another embodiment, the composition comprises between about 2 and about 20 polynucleotides. In another embodiment, the composition further comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 additional antigenic polynucleotides encoding for additional antigenic peptides. In another embodiment, the composition comprises between about 4 and about 20 additional antigenic polynucleotides. In another embodiment, the isolated polynucleotides and the additional antigenic polynucleotides are linked. In another embodiment, the polynucleotides are linked using nucleic acids that encode a poly-glycine or poly-serine linker. In another embodiment, at least one of the additional antigenic peptide is specific for an individual patient's tumor. In another embodiment, an antigenic peptide is selected by identifying differences in expression between the transcriptome or proteome of the patient's tumor sample and the transcriptome or proteome of a non-tumor sample. In another embodiment, the samples are fresh or formalin-fixed paraffin embedded tumor tissues, freshly isolated cells, or circulating tumor cells. In some embodiments, the sequences of the antigenic peptides are determined by Next Generation Sequencing.

In one embodiment, provided herein is a T cell receptor (TCR) capable of binding at least one antigenic peptide described herein. In another embodiment, the TCR is capable of binding the isolated antigenic peptide in the context of MHC class I or class II.

In one embodiment, provided herein is a chimeric antigen receptor comprising: (i) a T cell activation molecule; (ii) a transmembrane region; and (iii) an antigen recognition moiety capable of binding an isolated antigenic peptide described herein. In another embodiment, CD3-zeta is the T cell activation molecule. In another embodiment, the chimeric antigen receptor further comprises at least one costimulatory signaling domain. In another embodiment, the signaling domain is CD28, 4-1BB, ICOS, OX40, ITAM, or Fe epsilon RI-gamma. In another embodiment, the antigen recognition moiety is capable of binding the isolated antigenic peptide in the context of MHC class I or class II. In another embodiment, the chimeric antigen receptor comprises the CD3-zeta, CD28, CTLA-4, ICOS, BTLA, KIR, LAG3, CD137, OX40, CD27, CD40L, Tim-3, A2aR, or PD-1 transmembrane region. In another embodiment, the tumor-specific epitope is located in the extracellular domain of a tumor associated polypeptide.

In one embodiment, provided herein is a T cell comprising the T cell receptor or chimeric antigen receptor described herein. In one embodiment, the T cell is a helper or cytotoxic T cell.

In one embodiment, provided herein is a nucleic acid comprising a promoter operably linked to a polynucleotide encoding a T cell receptor described herein. In another embodiment, the TCR is capable of binding the at least one antigenic peptide in the context of major histocompatibility complex (MHC) class I or class II. In one embodiment, the nucleic acid comprises a promoter operably linked to a polynucleotide encoding a chimeric antigen receptor described herein. In another embodiment, the antigen recognition moiety is capable of binding the at least one antigenic peptide in the context of major histocompatibility complex (MHC) class I or class II. In another embodiment, the tumor-specific epitope is located in the extracellular domain of a tumor associated polypeptide. In another embodiment, the nucleic acid comprises the CD3-zeta, CD28, CTLA-4, ICOS, BTLA, KIR, LAG3, CD137, OX40, CD27, CD40L, Tim-3, A2aR, or PD-1 transmembrane region.

In one embodiment, provided herein is an antibody capable of binding at least one antigenic peptide listed in Table 1 or 2. In another embodiment, provided herein is an antibody capable of binding at least one antigenic peptide listed in Table 3 or 4. In another embodiment, provided herein is an antibody capable of binding at least one antigenic peptide listed in Table 5 or 6. In another embodiment, the at least one antigenic peptide listed in Table 1 or 2 is a retroviral antigenic peptide. In another embodiment, the at least one antigenic peptide listed in Table 3 or 4 is a non-mutated overexpressed antigenic peptide. In another embodiment, the at least one antigenic peptide listed in Table 5 or 6 is a viral antigenic peptide.

In one embodiment, provided herein is a modified cell transfected or transduced with a nucleic acid described herein. In another embodiment, the modified cell is a T cell, tumor infiltrating lymphocyte, NK-T cell, TCR-expressing cell, CD4+ T cell, CD8+ T cell, or NK cell.

In one embodiment, provided herein is a composition comprising a T cell receptor or chimeric antigen receptor described herein. In another embodiment, a composition comprises autologous patient T cells containing a T cell receptor or chimeric antigen receptor described herein. In another embodiment, the composition further comprises an immune checkpoint inhibitor. In another embodiment, the composition further comprises at least two immune checkpoint inhibitors. In another embodiment, each of the immune checkpoint inhibitors inhibits a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands or a combination thereof. In another embodiment, each of the immune checkpoint inhibitors interacts with a ligand of a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands or a combination thereof.

In one embodiment, the composition further comprises an immune modulator or adjuvant. In another embodiment, the immune modulator is a co-stimulatory ligand, a TNF ligand, an Ig superfamily ligand, CD28, CD80, CD86, ICOS, CD40L, OX40, CD27, GITR, CD30, DR3, CD69, or 4-1BB. In another embodiment, the immune modulator is at least one cancer cell or cancer cell extract. In another embodiment, the cancer cell is autologous to the subject in need of the composition. In another embodiment, the cancer cell has undergone lysis or been exposed to UV radiation. In another embodiment, the composition further comprises an adjuvant. In another embodiment, the adjuvant is selected from the group consisting of: Poly(I:C), Poly-ICLC, STING agonist, 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312 VG, Montanide ISA 206 VG, Montanide ISA 50 V2, Montanide ISA 51 VG, OK-432, OM-174, OM-197-MP-EC, ISA-TLR2 agonist, ONTAK, PepTel®. vector system, PLG microparticles, resiquimod, SRL172, virosomes and other virus-like particles, YF-17D, VEGF trap, R848, beta-glucan, Pam3Cys, Pam3CSK4, acrylic or methacrylic polymers, copolymers of maleic anhydride, and QS21 stimulon. In another embodiment, the adjuvant induces a humoral when administered to a subject. In another embodiment, the adjuvant induces a T helper cell type 1 when administered to a subject.

In one embodiment, provided herein is a method of inhibiting growth of a tumor cell expressing a tumor-specific epitope defined in Table 1 or 2, comprising contacting a tumor cell with a peptide, polynucleotide, delivery system, vector, composition, antibody, or cells of the invention. In another embodiment, provided herein is a method of inhibiting growth of a tumor cell expressing a tumor-specific epitope defined in Table 3 or 4, comprising contacting the tumor cell with the peptide, polynucleotide, delivery system, vector, composition, antibody, or cells of the invention. In another embodiment, provided herein is a method of inhibiting growth of a tumor cell expressing a tumor-specific epitope defined in Table 5 or 6, comprising contacting the tumor cell with the peptide, polynucleotide, delivery system, vector, composition, antibody, or cells of the invention.

In one embodiment, provided herein is a method of treating cancer or initiating, enhancing, or prolonging an anti-tumor response in a subject in need thereof comprising administering to the subject the peptide, polynucleotide, vector, composition, antibody, or cells described herein. In one embodiment, the cancer is selected from the group consisting of CRC, head and neck, stomach, lung squamous, lung adeno., Prostate, Bladder. stomach, renal cell carcinoma, and uterine. In one embodiment, the cancer is selected from the group consisting of melanoma, lung squamous, DLBCL, uterine, head and neck, uterine, liver, and CRC. In one embodiment, the cancer is selected from the group consisting of cervical, head and neck, anal, stomach, Burkitt's lymphoma, and nasopharyngeal carcinoma.

In one embodiment, the subject is a human. In another embodiment, the subject has cancer. In another embodiment, the cancer is selected from the group consisting of urogenital, gynecological, lung, gastrointestinal, head and neck cancer, malignant glioblastoma, malignant mesothelioma, non-metastatic or metastatic breast cancer, malignant melanoma, triple-negative breast cancer (TNBC), smoldering myeloma (SMM), Merkel Cell Carcinoma or bone and soft tissue sarcomas, hematologic neoplasias, multiple myeloma, acute myelogenous leukemia, chronic myelogenous leukemia, myelodysplastic syndrome and acute lymphoblastic leukemia, non-small cell lung cancer (NSCLC), breast cancer, metastatic colorectal cancers, hormone sensitive or hormone refractory prostate cancer, colorectal cancer, ovarian cancer, hepatocellular cancer, renal cell cancer, pancreatic cancer, gastric cancer, esophageal cancers, hepatocellular cancers, cholangiocellular cancers, head and neck squamous cell cancer soft tissue sarcoma, and small cell lung cancer. In another embodiment, the subject has undergone surgical removal of the tumor. In another embodiment, the peptide, polynucleotide, vector, composition, or cells is administered via intravenous, intraperitoneal, intratumoral, intradermal, or subcutaneous administration. In another embodiment, the peptide, polynucleotide, vector, composition, or cells is administered into an anatomic site that drains into a lymph node basin. In another embodiment, the administration is into multiple lymph node basins. In another embodiment, the administration is by a subcutaneous or intradermal route.

In one embodiment of the method, a peptide is administered. In another embodiment, the administration is intratumorally. In another embodiment of the method, a polynucleotide, optionally RNA, is administered. In another embodiment, the polynucleotide is administered intravenously. In one embodiment of the method, a cell is administered. In another embodiment, the cell is a T cell or dendritic cell. In another embodiment, the peptide or polynucleotide comprises an antigen presenting cell targeting moiety.

One embodiment of the method further comprises administering at least one immune checkpoint inhibitor to a subject. In another embodiment, the checkpoint inhibitor is a biologic therapeutic or a small molecule. In another embodiment, the checkpoint inhibitor is selected from the group consisting of a monoclonal antibody, a humanized antibody, a fully human antibody and a fusion protein or a combination thereof. In another embodiment, the checkpoint inhibitor inhibits a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands or a combination thereof. In another embodiment, the checkpoint inhibitor interacts with a ligand of a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands or a combination thereof. In another embodiment, two or more checkpoint inhibitors are administered. In another embodiment, the checkpoint inhibitors are: (i) ipilimumab or tremelimumab, and (ii) nivolumab. In another embodiment, the checkpoint inhibitor and the composition are administered simultaneously or sequentially in any order. In another embodiment, the peptide, polynucleotide, vector, composition, or cells is administered prior to the checkpoint inhibitor. In another embodiment, the peptide, polynucleotide, vector, composition, or cells is administered after the checkpoint inhibitor. In another embodiment, administration of the checkpoint inhibitor is continued throughout antigen peptide, polynucleotide, vector, composition, or cell therapy. In another embodiment, the antigen peptide, polynucleotide, vector, composition, or cell therapy is administered to subjects that only partially respond or do not respond to checkpoint inhibitor therapy. In another embodiment, the composition is administered intravenously or subcutaneously. In another embodiment, the checkpoint inhibitor is administered intravenously or subcutaneously. In another embodiment, the checkpoint inhibitor is administered subcutaneously within about 2 cm of the site of administration of the composition. In another embodiment, the composition is administered into the same draining lymph node as the checkpoint inhibitor.

In one embodiment of the method, an additional agent is administered. In another embodiment, the agent is a chemotherapeutic agent, an immunomodulatory drug, an immune metabolism modifying drug, a targeted therapy, radiation an anti-angiogenesis agent, or an agent that reduces immune-suppression. In another embodiment, the chemotherapeutic agent is an alkylating agent, a topoisomerase inhibitor, an anti-metabolite, or an anti-mitotic agent. In another embodiment, the additional agent is an anti-glucocorticoid induced tumor necrosis factor family receptor (GITR) agonistic antibody or antibody fragment, ibrutinib, docetaxel, cisplatin, or cyclophosphamide. In another embodiment, the administration elicits a CD4+ T cell immune response. In another embodiment, the administration elicits a CD4+ T cell immune response and a CD8+ T cell immune response.

In one embodiment, provided herein is a method for stimulating an immune response in a subject, comprising administering an effective amount of modified cells or composition described herein. In another embodiment, the immune response is cytotoxic and/or humoral immune response. In another embodiment, the method stimulates a T cell-mediated immune response in a subject. In another embodiment, the T cell-mediated immune response is directed against a target cell. In another embodiment, the target cell is a tumor cell. In another embodiment, the modified cells are transfected or transduced in vivo. In another embodiment, the modified cells are transfected or transduced ex vivo. In another embodiment, the modified cells are autologous patient T cells. In another embodiment, the autologous patient T cells are obtained from a patient that has received an antigen peptide or nucleic acid vaccine. In another embodiment, the antigen peptide or nucleic acid vaccine comprises at least one personalized antigen. In another embodiment, the antigen peptide or nucleic acid vaccine comprises at least one additional antigenic peptide listed in Table 1 or 2. In another embodiment, the antigen peptide or nucleic acid vaccine comprises at least one additional antigenic peptide listed in Table 3 or 4. In another embodiment, the antigen peptide or nucleic acid vaccine comprises at least one additional antigenic peptide listed in Table 5 or 6. In another embodiment, the at least one additional antigenic peptide listed in Table 1 or 2 is a retroviral antigenic peptide. In another embodiment, the at least one additional antigenic peptide listed in Table 3 or 4 is a non-mutated overexpressed antigenic peptide. In another embodiment, the at least one additional antigenic peptide listed in Table 5 or 6 is a viral antigenic peptide. In another embodiment, the patient received a chemotherapeutic agent, an immunomodulatory drug, an immune metabolism modifying drug, targeted therapy or radiation prior to and/or during receipt of the antigen peptide or nucleic acid vaccine. In another embodiment, the patient receives treatment with at least one checkpoint inhibitor. In another embodiment, the autologous T cells are obtained from a patient that has already received at least one round of T cell therapy containing an antigen. In another embodiment, the method further comprises adoptive T cell therapy. In another embodiment, the adoptive T cell therapy comprises autologous T-cells. In another embodiment, the autologous T-cells are targeted against tumor antigens. In another embodiment, the adoptive T cell therapy further comprises allogenic T-cells. In another embodiment, the allogenic T-cells are targeted against tumor antigens. In another embodiment, the adoptive T cell therapy is administered before the checkpoint inhibitor.

In one embodiment, provided herein is a method for evaluating the efficacy of treatment comprising: (i) measuring the number or concentration of target cells in a first sample obtained from the subject before administering the modified cell, (ii) measuring the number concentration of target cells in a second sample obtained from the subject after administration of the modified cell, and (iii) determining an increase or decrease of the number or concentration of target cells in the second sample compared to the number or concentration of target cells in the first sample. In another embodiment, the treatment efficacy is determined by monitoring a clinical outcome; an increase, enhancement or prolongation of anti-tumor activity by T cells; an increase in the number of anti-tumor T cells or activated T cells as compared with the number prior to treatment; B cell activity; CD4 T cell activity; or a combination thereof. In another embodiment, the treatment efficacy is determined by monitoring a biomarker. In another embodiment, the biomarker is selected from the group consisting of CEA, Her-2/neu, bladder tumor antigen, thyroglobulin, alpha-fetoprotein, PSA, CA 125, CA19.9, CA 15.3, leptin, prolactin, osteopontin, IGF-II, CD98, fascin, sPIgR, 14-3-3 eta, troponin I, and b-type natriuretic peptide. In another embodiment, the clinical outcome is selected from the group consisting of tumor regression; tumor shrinkage; tumor necrosis; anti-tumor response by the immune system; tumor expansion, recurrence or spread; or a combination thereof. In another embodiment, the treatment effect is predicted by presence of T cells or by presence of a gene signature indicating T cell inflammation or a combination thereof.

In one embodiment, provided herein is a method of treating cancer or initiating, enhancing, or prolonging an anti-tumor response in a subject in need thereof comprising administering to the subject: (a) the peptide, polynucleotide, vector, composition, antibody, or cells described herein; and (b) at least one checkpoint inhibitor. In another embodiment, the method further comprises administration of an immunomodulator or adjuvant. In another embodiment, the immunomodulator or adjuvant is selected from the group consisting of Poly(I:C), Poly-ICLC, STING agonist, 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312 VG, Montanide ISA 206 VG, Montanide ISA 50 V2, Montanide ISA 51 VG, OK-432, OM-174, OM-197-MP-EC, ISA-TLR2 agonist, ONTAK, PepTel® vector system, PLG microparticles, resiquimod, SRL172, virosomes and other virus-like particles, YF-17D, VEGF trap, R848, beta-glucan, Pam3Cys, Pam3CSK4, acrylic or methacrylic polymers, copolymers of maleic anhydride, and QS21 stimulon. a co-stimulatory ligand, a TNF ligand, an Ig superfamily ligand, CD28, CD80, CD86, ICOS, CD40L, OX40, CD27, GITR, CD30, DR3, CD69, or 4-1BB. In another embodiment, the immunomodulator or adjuvant is Poly-ICLC. In another embodiment, the checkpoint inhibitor is an anti-PD1 antibody or antibody fragment. In another embodiment, the inhibitor of the PD-1 pathway is nivolumab. In another embodiment, the checkpoint inhibitor is an anti-CTLA4 antibody or antibody fragment. In another embodiment, the anti-CTLA4 antibody is ipilimumab or tremelimumab. In another embodiment, the method comprises administering both an anti-PD1 antibody and an anti-CTLA4 antibody. In another embodiment, the administration of the checkpoint inhibitor is initiated before initiation of administration of the peptide, polynucleotide, vector, composition, antibody, or cell. In another embodiment, the administration of the checkpoint inhibitor is initiated after initiation of administration of the peptide, polynucleotide, vector, composition, antibody, or cell. In another embodiment, the administration of the checkpoint inhibitor is initiated simultaneously with the initiation of administration of the peptide, polynucleotide, vector, composition, antibody, or cell. In another embodiment, the peptide, polynucleotide, vector, composition, antibody, or cell is administered intravenously or subcutaneously. In another embodiment, the checkpoint inhibitor is administered intravenously or subcutaneously. In another embodiment, the checkpoint inhibitor is administered subcutaneously within about 2 cm of the site of administration of the peptide, polynucleotide, vector, composition, antibody, or cell. In another embodiment, the peptide, polynucleotide, vector, composition, antibody, or cell is administered into the same draining lymph node as the checkpoint inhibitor.

In one embodiment of the therapeutic methods, the additional therapeutic agent is for example, a chemotherapeutic or biotherapeutic agent, radiation, or immunotherapy. Any suitable therapeutic treatment for a particular cancer may be administered. Examples of chemotherapeutic and biotherapeutic agents include, but are not limited to, an angiogenesis inhibitor, such as hydroxy angiostatin K 1-3, DL-a-Difluoromethyl-ornithine, endostatin, fumagillin, genistein, minocycline, staurosporine, and thalidomide; a DNA intercalator/cross-linker, such as Bleomycin, Carboplatin, Carmustine, Chlorambucil, Cyclophosphamide, cis-Diammineplatinum (II) dichloride (Cisplatin), Melphalan, Mitoxantrone, and Oxaliplatin; a DNA synthesis inhibitor, such as (±)-Amethopterin (Methotrexate), 3-Amino-1,2,4-benzotriazine 1,4-dioxide, Aminopterin, Cytosine β-D-arabinofuranoside, 5-Fluoro-5'-deoxyuridine, 5-Fluorouracil, Ganciclovir, Hydroxyurea, and Mitomycin C; a DNA-RNA transcription regulator, such as Actinomycin D, Daunorubicin, Doxorubicin, Homoharringtonine, and Idarubicin; an enzyme inhibitor, such as S(-+-)-Camptothecin, Curcumin, (−)-Deguelin, 5,6-Dichlorobenzimidazole 1-β-D-ribofuranoside, Etoposide, Formestane, Fostriecin, Hispidin, 2-Immo-1-imidazolidineacetic acid (Cyclocreatine), Mevinolin, Trichostatin A, Tyrphostin AG 34, and Tyrphostin AG 879; a gene regulator, such as 5-Aza-2'-deoxycytidine, 5-Azacytidine, Cholecalciferol (Vitamin D3), 4-Hydroxytamoxifen, Melatonin, Mifepristone, Raloxifene, all trans-Retinal (Vitamin A aldehyde), Retinoic acid all trans (Vitamin A acid), 9-cis- Retinoic Acid, 13-cis-Retinoic acid, Retinol (Vitamin A), Tamoxifen, and Troglitazone; a microtubule inhibitor, such as Colchicine, docetaxel, Dolastatin15, Nocodazole, Paclitaxel, Podophyllotoxin, Rhizoxin, Vinblastine, Vincristine, Vindesine, and Vinorelbine (Navelbine); and an unclassified therapeutic agent, such as 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone, Pifithrin-a, Rapamycin, Sex hormone-binding globulin, Thapsigargin, and Urinary trypsin inhibitor fragment (Bikunin). The therapeutic agent may be altretamine, amifostine, asparaginase, capecitabine, cladribine, cisapride, cyiarahirse, dacarbazine (DT1C), dactinomycin, dronabinol, epoetin alpha, "filgrastim, fludarabine, gemcitabine, granisetron, ifosfamide, irinotecan, lansoprazole, levamisole, leucovorin, megestrol, mesna, metoclopramide, mitotane, omeprazole, ondansetron, pilocarpine, prochlorperazine, or topotecan hydrochloride. The therapeutic agent may be a monoclonal antibody such as rituximab (Rituxan®), alemtuzumab (Campath®), Bevacizumab (Avastin®), Cetuximab (Erbitux®), panitumumab (Vectibix®), and trastuzumab (Herceptin®), Vemurafenib (Zelboraf®) imatinib mesylate (Gleevec®), erlotinib (Tarceva®), gefitinib (Iressa®), Vismodegib (Erivedge™), 90Y-ibritumomab tiuxetan, 1311-tositumomab, ado-trastuzumab emtansine, lapatinib (Tykerb®), pertuzumab (Perjeta™), ado-trastuzumab emtansine (Adcyla™), regorafenib (Stivarga®), sunitinib (Sutent®), Denosumab (Xgeva®), sorafenib (Nexavar®), pazopanib (Votrient®), axitinib (Inita®), dasatinib (Sprycel®), nilotinib (Tasigna®), bosutinib (Bosulif®), ofatumumab (Arzerra®), obinutuzumab (Gazyva™), ibrutinib (Imbruvica™), idelalisib (Zydelig®), crizotinib (Xalkori®), erlotinib (Tarceva®), afatimb dimaleate (Giiotrif®), ceritinib (LDK378/Zykadia), Tositumomab and 1311-tositumomab (Bexxar®), ibritumomab tiuxetan (Zevalin®), brentuximab vedotin (Adcetris®), bortezomib (Velcade®), siltuximab (Sylvant™), trametinib (Ekinist®), dabrafenib (Tafmlar®), pembrolizumab (Keytruda®), carfilzomib (Kyprolis®), Ramucirumab (Cyramza™), Cabozantinib (Cometriq™), vandetanib (Caprelsa®), Optionally, the therapeutic agent is a neoantigen. The therapeutic agent may be a cytokine such as interferons (INFs), interleukins (ILs), or hematopoietic growth factors. The therapeutic agent may be INF-α, IL-2, Aldesleukin, IL-2, Erythropoietin, Granulocyte-macrophage colony-stimulating factor (GM-CSF) or granulocyte colony-stimulating factor. The therapeutic agent may be a targeted therapy such as toremifene (Fareston®), fulvestrant (Faslodex®), anastrozole (Arimidex®), exemestane (Aromasin®), letrozole (Femara®), ziv-aflibercept (Zaltrap®), Alitretinoin (Panretin®), temsirolimus (Torisel®), Tretinoin (Vesanoid®), denileukin diftitox (Ontak®), vorinostat (Zoinza®), romidepsin (Istodax®), bexarotene (Targretin®), pralatrexate (Foiotyn®), lenalidomide (Revlimid®), belinostat (Beleodaq™), lenalidomide (Revlimid®), pomalidomide (Pomalyst®), Cabazitaxel (Jevtana®), enzalutamide (Xtandi®), abiraterone acetate (Zytiga®), radium 223 chloride (Xofigo®), or everolimus (Afinitor®). Additionally, the therapeutic agent may be an epigenetic targeted drug such as HDAC inhibitors, kinase inhibitors, DNA methyltransferase inhibitors, histone demethylase inhibitors, or histone methylation inhibitors. The epigenetic drugs may be Azacitidine (Vidaza), Decitabine (Dacogen), Vorinostat (Zolinza), Romidepsin (Istodax), or Ruxolitinib (Jakafi). For prostate cancer treatment, a preferred chemotherapeutic agent with which anti-CTLA-4 can be combined is paclitaxel (TAXOL).

In one embodiment, provided herein is a kit comprising any antigen therapeutic described herein.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

DETAILED DESCRIPTION

Described herein are novel immunotherapeutic agents and uses thereof based on the discovery of non-mutated protein epitopes expressed in cancer cells. Accordingly, the invention described herein provides peptides, polynucleotides encoding the peptides, and peptide binding agents, that can be used, for example, to stimulate an immune response to a tumor associated antigen, to create an immunogenic composition or cancer vaccine for use in treating disease.

I. Definitions

To facilitate an understanding of the present invention, a number of terms and phrases are defined below.

"Non-mutated protein antigens" refer to antigens expressed in cancers either specifically or at a level higher than in non-cancer tissue. They include, but are not limited to, antigens of exogenous viruses, antigens of endogenous retroviruses and overexpressed antigens that do not comprise somatic mutations.

"Viral antigens" refer to antigens encoded by a exogenous virus.

"Retroviral antigens" refer to antigens encoded by an endogenous retroviral sequence.

"Non-mutated overexpressed antigens" refer to non-mutated antigens encoded by a genome of a cancer cell that are expressed at a level higher than in non-cancer tissue.

A "tumor-specific epitope" refers to an epitope that is either not expressed in non-cancer or germline cells but is found expressed in cancer cells, or that is expressed at a higher level in cancer cells than in non-cancer cells.

A "reference" can be used to correlate and compare the results obtained in the methods of the invention from a tumor specimen. Typically the "reference" may be obtained on the basis of one or more normal specimens, in particular specimens which are not affected by a cancer disease, either obtained from a patient or one or more different individuals, for example, healthy individuals, in particular individuals of the same species. A "reference" can be determined empirically by testing a sufficiently large number of normal specimens.

The term "mutation" refers to a change of or difference in the nucleic acid sequence (nucleotide substitution, addition or deletion) compared to a reference. A "somatic mutation" can occur in any of the cells of the body except the germ cells (sperm and egg) and therefore are not passed on to children. These alterations can (but do not always) cause cancer or other diseases. In some embodiments, a mutation is a non-synonymous mutation. The term "non-synonymous mutation" refers to a mutation, for example, a nucleotide substitution, which does result in an amino acid change such as an amino acid substitution in the translation product.

Throughout this disclosure, "binding data" results can be expressed in terms of "$IC_{50}$." $IC_{50}$ is the concentration of the tested peptide in a binding assay at which 50% inhibition of binding of a labeled reference peptide is observed. Given the conditions in which the assays are run (i.e., limiting HLA protein and labeled reference peptide concentrations), these values approximate $K_D$ values. Assays for determining binding are well known in the art and are described in detail, for example, in PCT publications WO 94/20127 and WO 94/03205, and other publications such Sidney et al., Current Protocols in Immunology 18.3.1 (1998); Sidney, et al., J. Immunol. 154:247 (1995); and Sette, et al., Mol. Immunol. 31:813 (1994). Alternatively, binding can be expressed relative to binding by a reference standard peptide. For example, can be based on its $IC_{50}$, relative to the $IC_{50}$ of a reference standard peptide.

Binding can also be determined using other assay systems including those using: live cells (e.g., Ceppellini et al., Nature 339:392 (1989); Christnick et al., Nature 352:67 (1991); Busch et al., Int. Immunol. 2:443 (1990); Hill et al., J. Immunol. 147:189 (1991); del Guercio et al., J. Immunol. 154:685 (1995)), cell free systems using detergent lysates (e.g., Cerundolo et al., J. Immunol. 21:2069 (1991)), immobilized purified MHC (e.g., Hill et al., J. Immunol. 152, 2890 (1994); Marshall et al., J. Immunol. 152:4946 (1994)), ELISA systems (e.g., Reay et al., EMBO J. 11:2829 (1992)), surface plasmon resonance (e.g., Khilko et al., J. Biol. Chem. 268:15425 (1993)); high flux soluble phase assays (Hammer et al., J. Exp. Med. 180:2353 (1994)), and measurement of class I MHC stabilization or assembly (e.g., Ljunggren et al., Nature 346:476 (1990); Schumacher et al., Cell 62:563 (1990); Townsend et al., Cell 62:285 (1990); Parker et al., J. Immunol. 149:1896 (1992)).

"Cross-reactive binding" indicates that a peptide is bound by more than one HLA molecule; a synonym is degenerate binding.

The term "derived" when used to discuss an epitope is a synonym for "prepared." A derived epitope can be isolated from a natural source, or it can be synthesized according to standard protocols in the art. Synthetic epitopes can comprise artificial amino acid residues "amino acid mimetics," such as D isomers of natural occurring L amino acid residues or non-natural amino acid residues such as cyclohexylalanine. A derived or prepared epitope can be an analog of a native epitope.

A "diluent" includes sterile liquids, such as water and oils, including those of petroleum, animal, vegetable or synthetic origin, such as peanut oil, soybean oil, mineral oil, sesame oil and the like. Water is also a diluent for pharmaceutical compositions. Saline solutions and aqueous dextrose and glycerol solutions can also be employed as diluents, for example, in injectable solutions.

An "epitope" is the collective features of a molecule, such as primary, secondary and tertiary peptide structure, and charge, that together form a site recognized by, for example, an immunoglobulin, T cell receptor, HLA molecule, or chimeric antigen receptor. Alternatively, an epitope can be defined as a set of amino acid residues which is involved in recognition by a particular immunoglobulin, or in the context of T cells, those residues necessary for recognition by T cell receptor proteins, chimeric antigen receptors, and/or Major Histocompatibility Complex (MHC) receptors. Epitopes can be prepared by isolation from a natural source, or they can be synthesized according to standard protocols in the art. Synthetic epitopes can comprise artificial amino acid residues, "amino acid mimetics," such as D isomers of naturally-occurring L amino acid residues or non-naturally-occurring amino acid residues such as cyclohexylalanine. Throughout this disclosure, epitopes may be referred to in some cases as peptides or peptide epitopes.

It is to be appreciated that proteins or peptides that comprise an epitope or an analog described herein as well as additional amino acid(s) are still within the bounds of the invention. In certain embodiments, the peptide comprises a fragment of an antigen.

In certain embodiments, there is a limitation on the length of a peptide of the invention. The embodiment that is length-limited occurs when the protein or peptide comprising an epitope described herein comprises a region (i.e., a contiguous series of amino acid residues) having 100% identity with a native sequence. In order to avoid the definition of epitope from reading, e.g., on whole natural molecules, there is a limitation on the length of any region that has 100% identity with a native peptide sequence. Thus, for a peptide comprising an epitope described herein and a region with 100% identity with a native peptide sequence, the region with 100% identity to a native sequence generally has a length of: less than or equal to 600 amino acid residues, less than or equal to 500 amino acid residues, less than or equal to 400 amino acid residues, less than or equal to 250 amino acid residues, less than or equal to 100 amino acid residues, less than or equal to 85 amino acid residues, less than or equal to 75 amino acid residues, less than or equal to 65 amino acid residues, and less than or equal to 50 amino acid residues. In certain embodiments, an "epitope" described herein is comprised by a peptide having a region with less than 51 amino acid residues that has 100% identity to a native peptide sequence, in any increment down to 5 amino acid residues; for example 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 or 1 amino acid residues.

"Human Leukocyte Antigen" or "HLA" is a human class I or class II Major Histocompatibility Complex (MHC) protein (see, e.g., Stites, et al., IMMUNOLOGY, 8TH ED., Lange Publishing, Los Altos, Calif. (1994).

An "HLA supertype or HLA family", as used herein, describes sets of HLA molecules grouped on the basis of shared peptide-binding specificities. HLA class I molecules that share somewhat similar binding affinity for peptides bearing certain amino acid motifs are grouped into such HLA supertypes. The terms HLA superfamily, HLA supertype family, HLA family, and HLA xx-like molecules (where "xx" denotes a particular HLA type), are synonyms.

The terms "identical" or percent "identity," in the context of two or more peptide sequences or antigen fragments, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

An "immunogenic" peptide or an "immunogenic" epitope or "peptide epitope" is a peptide that comprises an allele-specific motif such that the peptide will bind an HLA molecule and induce a cell-mediated or humoral response, for example, cytotoxic T lymphocyte (CTL), helper T lymphocyte (HTL) and/or B lymphocyte response. Thus, immunogenic peptides described herein are capable of binding to an appropriate HLA molecule and thereafter inducing a CTL (cytotoxic) response, or a HTL (and humoral) response, to the peptide.

As used herein, a "chimeric antigen receptor" or "CAR" refers to an antigen binding protein in that includes an immunoglobulin antigen binding domain (e.g., an immunoglobulin variable domain) and a T cell receptor (TCR) constant domain. As used herein, a "constant domain" of a TCR polypeptide includes a membrane-proximal TCR constant domain, and may also include a TCR transmembrane domain and/or a TCR cytoplasmic tail. For example, in some embodiments, the CAR is a dimer that includes a first polypeptide comprising a immunoglobulin heavy chain variable domain linked to a TCR-beta constant domain and a second polypeptide comprising an immunoglobulin light chain variable domain (e.g., a κ or λ variable domain) linked to a TCRα constant domain. In some embodiments, the CAR is a dimer that includes a first polypeptide comprising a immunoglobulin heavy chain variable domain linked to a TCRα constant domain and a second polypeptide comprising an immunoglobulin light chain variable domain (e.g., a κ or λ variable domain) linked to a TCRβ constant domain.

The phrases "isolated" or "biologically pure" refer to material which is substantially or essentially free from components which normally accompany the material as it is found in its native state. Thus, isolated peptides described herein do not contain some or all of the materials normally associated with the peptides in their in situ environment. An "isolated" epitope refers to an epitope that does not include the whole sequence of the antigen from which the epitope was derived. Typically the "isolated" epitope does not have attached thereto additional amino acid residues that result in a sequence that has 100% identity over the entire length of a native sequence. The native sequence can be a sequence such as a tumor-associated antigen from which the epitope is derived. Thus, the term "isolated" means that the material is removed from its original environment (e.g., the natural environment if it is naturally occurring). For example, a naturally-occurring polynucleotide or peptide present in a living animal is not isolated, but the same polynucleotide or peptide, separated from some or all of the coexisting materials in the natural system, is isolated. Such a polynucleotide could be part of a vector, and/or such a polynucleotide or peptide could be part of a composition, and still be "isolated" in that such vector or composition is not part of its natural environment. Isolated RNA molecules include in vivo or in vitro RNA transcripts of the DNA molecules described herein, and further include such molecules produced synthetically.

"Major Histocompatibility Complex" or "MHC" is a cluster of genes that plays a role in control of the cellular interactions responsible for physiologic immune responses. In humans, the MHC complex is also known as the human leukocyte antigen (HLA) complex. For a detailed description of the MHC and HLA complexes, see, Paul, FUNDAMENTAL IMMUNOLOGY, 3.sup.RD ED., Raven Press, New York (1993).

A "native" or a "wild type" sequence refers to a sequence found in nature. Such a sequence can comprise a longer sequence in nature.

A "T-cell epitope" is to be understood as meaning a peptide sequence which can be bound by the MHC molecules of class I or II in the form of a peptide-presenting MHC molecule or MHC complex and then, in this form, be recognized and bound by cytotoxic T-lymphocytes or T-helper cells, respectively.

A "receptor" is to be understood as meaning a biological molecule or a molecule grouping capable of binding a ligand. A receptor may serve, to transmit information in a cell, a cell formation or an organism. The receptor comprises at least one receptor unit, for example, where each receptor unit may consist of a protein molecule. The receptor has a structure which complements that of a ligand and may complex the ligand as a binding partner. The information is transmitted in particular by conformational changes of the receptor following complexation of the ligand on the surface of a cell. In some embodiments, a receptor is to be understood as meaning in particular proteins of MHC classes I and II capable of forming a receptor/ligand complex with a ligand, in particular a peptide or peptide fragment of suitable length.

A "ligand" is to be understood as meaning a molecule which has a structure complementary to that of a receptor and is capable of forming a complex with this receptor. In some embodiments, a ligand is to be understood as meaning a peptide or peptide fragment which has a suitable length and suitable binding motifs in its amino acid sequence, so that the peptide or peptide fragment is capable of forming a complex with proteins of MHC class I or MHC class II.

In some embodiments, a "receptor/ligand complex" is also to be understood as meaning a "receptor/peptide complex" or "receptor/peptide fragment complex", including a peptide- or peptide fragment-presenting MHC molecule of class I or of class II.

"Proteins or molecules of the major histocompatibility complex (MHC)", "MHC molecules", "MHC proteins" or "HLA proteins" are to be understood as meaning proteins capable of binding peptides resulting from the proteolytic cleavage of protein antigens and representing potential lymphocyte epitopes, (e.g., T cell epitope and B cell epitope) transporting them to the cell surface and presenting them there to specific cells, in particular cytotoxic T-lymphocytes, T-helper cells, or B cells. The major histocompatibility complex in the genome comprises the genetic region whose gene products expressed on the cell surface are important for binding and presenting endogenous and/or foreign antigens and thus for regulating immunological processes. The major histocompatibility complex is classified into two gene groups coding for different proteins, namely molecules of MHC class I and molecules of MHC class II. The cellular biology and the expression patterns of the two MHC classes are adapted to these different roles.

The terms "peptide" and "peptide epitope" are used interchangeably with "oligopeptide" in the present specification to designate a series of residues connected one to the other, typically by peptide bonds between the α-amino and carboxyl groups of adjacent amino acid residues.

"Synthetic peptide" refers to a peptide that is obtained from a non-natural source, e.g., is man-made. Such peptides can be produced using such methods as chemical synthesis or recombinant DNA technology. "Synthetic peptides" include "fusion proteins."

A "PanDR binding" peptide, a "PanDR binding epitope" is a member of a family of molecules that binds more than one HLA class II DR molecule.

"Pharmaceutically acceptable" refers to a generally non-toxic, inert, and/or physiologically compatible composition or component of a composition.

A "pharmaceutical excipient" or "excipient" comprises a material such as an adjuvant, a carrier, pH-adjusting and buffering agents, tonicity adjusting agents, wetting agents, preservatives, and the like. A "pharmaceutical excipient" is an excipient which is pharmaceutically acceptable.

The term "motif" refers to a pattern of residues in an amino acid sequence of defined length, for example, a peptide of less than about 15 amino acid residues in length, or less than about 13 amino acid residues in length, for example, from about 8 to about 13 amino acid residues (e.g., 8, 9, 10, 11, 12, or 13) for a class I HLA motif and from about 6 to about 25 amino acid residues (e.g., 6, 7, 8, 9, 10, 11, 12, 13, 14, 15, 16, 17, 18, 19, 20, 21, 22, 23, 24, or 25) for a class II HLA motif, which is recognized by a particular HLA molecule. Motifs are typically different for each HLA protein encoded by a given human HLA allele. These motifs differ in their pattern of the primary and secondary anchor residues. In some embodiments, an MHC class I motif identifies a peptide of 9, 10, or 11 amino acid residues in length.

A "supermotif" is a peptide binding specificity shared by HLA molecules encoded by two or more HLA alleles. In some embodiments, a supermotif-bearing peptide described herein is recognized with high or intermediate affinity (as defined herein) by two or more HLA antigens.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

According to the invention, the term "vaccine" relates to a pharmaceutical preparation (pharmaceutical composition) or product that upon administration induces an immune response, for example, a cellular or humoral immune response, which recognizes and attacks a pathogen or a diseased cell such as a cancer cell. A vaccine may be used for the prevention or treatment of a disease. The term "individualized cancer vaccine" or "personalized cancer vaccine" concerns a particular cancer patient and means that a cancer vaccine is adapted to the needs or special circumstances of an individual cancer patient.

A "protective immune response" or "therapeutic immune response" refers to a CTL and/or an HTL response to an antigen derived from an pathogenic antigen (e.g., a tumor antigen), which in some way prevents or at least partially arrests disease symptoms, side effects or progression. The immune response can also include an antibody response which has been facilitated by the stimulation of helper T cells.

"Antigen processing" or "processing" refers to the degradation of a polypeptide or antigen into procession products, which are fragments of said polypeptide or antigen (e.g., the degradation of a polypeptide into peptides) and the association of one or more of these fragments (e.g., via binding) with MHC molecules for presentation by cells, for example, antigen presenting cells, to specific T cells.

"Antigen presenting cells" (APC) are cells which present peptide fragments of protein antigens in association with MHC molecules on their cell surface. Some APCs may activate antigen specific T cells. Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen presenting cell. An additional co-stimulatory signal is then produced by the antigen presenting cell, leading to activation of the T cell. The expression of co-stimulatory molecules is a defining feature of professional antigen-presenting cells.

The main types of professional antigen-presenting cells are dendritic cells, which have the broadest range of antigen presentation, and are probably the most important antigen presenting cells, macrophages, B-cells, and certain activated epithelial cells.

Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of antitumoral immunity.

Dendritic cells are conveniently categorized as "immature" and "mature" cells, which can be used as a simple way to discriminate between two well characterized phenotypes. However, this nomenclature should not be construed to exclude all possible intermediate stages of differentiation.

Immature dendritic cells are characterized as antigen presenting cells with a high capacity for antigen uptake and processing, which correlates with the high expression of Fcy receptor and mannose receptor. The mature phenotype is typically characterized by a lower expression of these markers, but a high expression of cell surface molecules responsible for T cell activation such as class I and class II MHC, adhesion molecules (e. g. CD54 and CD11) and costimulatory molecules (e. g., CD40, CD80, CD86 and 4-1 BB).

The term "residue" refers to an amino acid residue or amino acid mimetic residue incorporated into a peptide or protein by an amide bond or amide bond mimetic, or nucleic acid (DNA or RNA) that encodes the amino acid or amino acid mimetic.

The nomenclature used to describe peptides or proteins follows the conventional practice wherein the amino group is presented to the left (the amino- or N-terminus) and the carboxyl group to the right (the carboxy- or C-terminus) of each amino acid residue. When amino acid residue positions are referred to in a peptide epitope they are numbered in an amino to carboxyl direction with position one being the residue located at the amino terminal end of the epitope, or the peptide or protein of which it can be a part.

In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three letter or single letter designations. The L-form of an amino acid residue is represented by a capital single letter or a capital first letter of a three-letter symbol, and the D-form for those amino acid residues having D-forms is represented by a lower case single letter or a lower case three letter symbol. However, when three letter symbols or full names are used without capitals, they can refer to L amino acid residues. Glycine has no asymmetric carbon atom and is simply referred to as "Gly" or "G". The amino acid sequences of peptides set forth herein are generally designated using the standard single letter symbol. (A, Alanine; C, Cysteine; D, Aspartic Acid; E, Glutamic Acid; F, Phenylalanine; G, Glycine; H, Histidine; I, Isoleucine; K, Lysine; L, Leucine; M, Methionine; N, Asparagine; P, Proline; Q, Glutamine; R, Arginine; S, Serine; T, Threonine; V, Valine; W, Tryptophan; and Y, Tyrosine.)

The terms "polynucleotide" and "nucleic acid" are used interchangeably herein and refer to polymers of nucleotides of any length, and include DNA and RNA, for example, mRNA. The nucleotides can be deoxyribonucleotides, ribonucleotides, modified nucleotides or bases, and/or their analogs, or any substrate that can be incorporated into a polymer by DNA or RNA polymerase. In some embodiments, the polynucleotide and nucleic acid can be in vitro transcribed mRNA. In some embodiments, the polynucleotide that is administered is mRNA.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software that can be used to obtain alignments of amino acid or nucleotide sequences are well-known in the art. These include, but are not limited to, BLAST, ALIGN, Megalign, BestFit, GCG Wisconsin Package, and variations thereof. In some embodiments, two nucleic acids or polypeptides described herein are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 residues, at least about 60-80 residues in length or any integral value 2 between. In some embodiments, identity exists over a longer region than 60-80 residues, such as at least about 80-100 residues, and in some embodiments the sequences are substantially identical over the full length of the sequences being compared, such as the coding region of a nucleotide sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Methods of identifying nucleotide and amino acid conservative substitutions which do not eliminate peptide function are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells, or compositions include those which have been purified to a degree that they are no longer in a form in which they are found in nature. In some embodiments, a polypeptide, antibody, polynucleotide, vector, cell, or composition which is isolated is substantially pure. In one embodiment, an "isolated polynucleotide" encompasses a PCR or quantitative PCR reaction comprising the polynucleotide amplified in the PCR or quantitative PCR reaction.

The term "substantially pure" as used herein refers to material which is at least 50% pure (i.e., free from contaminants), at least 90% pure, at least 95% pure, at least 98% pure, or at least 99% pure.

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The terms "effective amount" or "therapeutically effective amount" or "therapeutic effect" refer to an amount of a therapeutic effective to "treat" a disease or disorder in a subject or mammal. The therapeutically effective amount of a drug has a therapeutic effect and as such can prevent the development of a disease or disorder; slow down the development of a disease or disorder; slow down the progression of a disease or disorder; relieve to some extent one or more of the symptoms associated with a disease or disorder; reduce morbidity and mortality; improve quality of life; or a combination of such effects.

The terms "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus those in need of treatment include those already with the disorder; those prone to have the disorder; and those in whom the disorder is to be prevented.

As used in the present disclosure and claims, the singular forms "a", "an" and "the" include plural forms unless the context clearly dictates otherwise.

It is understood that terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. Nothing herein is intended as a promise.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Non-Mutated Protein Antigens Expressed in Cancer Cells

Applicants have discovered antigens expressed by cancer cells encoded by the following genes: ERVH-2 matrix protein, ERVH-2 gag, ERVH48-1 coat protein, ERVH48-1 syncytin, ERVE-4 reverse transcriptase, ERVK-5 gag, env, pol protein, and ERVI-1 envelope protein.

Applicants have discovered antigens expressed by cancer encoded by the following genes: TYR, MAGEC1, MAGEA10, MAGEB17, MAGEA4, MABEB16, MAGEA1, MAGEA8, MAGEB4, CT45A5, ALPPL2, MMP13, CTAG1B, DCT, CLDN6, MLANA, AFP, DKK4, ASCL2, GAGE1, GAGE10, SLC45A2, PAGE5, PAGE2, and PMEL.

Applicants have discovered antigens expressed by cancer encoded by the following genes: HPV-16, E6, HPV-16 E7, EBV LF2, EBV BALF5, EBV RPMS1, EBV A73, EBV BALF4, EBV BALF3, and EBV BARF0.

Non-Mutated Protein Epitope Polypeptides

In aspects, the invention provides isolated peptides that comprise a non-mutated protein epitope expressed in a cancer cell. In some embodiments, the non-mutated protein epitope is a retroviral antigen. In some embodiments, the non-mutated protein epitope is a non-mutated overexpressed antigen. In some embodiments, the non-mutated protein epitope is a viral antigen.

In aspects, the invention provides an isolated peptide that comprises a peptide from Tables 1-6. The term "peptide" is used in the present specification to designate a series of residues, typically L-amino acids, connected one to the other, typically by peptide bonds between the α-amino and carboxyl groups of adjacent amino acids. Similarly, the term "polypeptide" is used in the present specification to designate a series of residues, e.g., L-amino acids, connected one to the other, typically by peptide bonds between the α-amino and carboxyl groups of adjacent amino acids. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

In some embodiments, sequencing methods are used to identify tumor specific epitopes. Any suitable sequencing method can be used according to the invention, for example, Next Generation Sequencing (NGS) technologies. Third Generation Sequencing methods might substitute for the NGS technology in the future to speed up the sequencing step of the method. For clarification purposes: the terms "Next Generation Sequencing" or "NGS" in the context of the present invention mean all novel high throughput sequencing technologies which, in contrast to the "conventional" sequencing methodology known as Sanger chemistry, read nucleic acid templates randomly in parallel along the entire genome by breaking the entire genome into small pieces. Such NGS technologies (also known as massively parallel sequencing technologies) are able to deliver nucleic acid sequence information of a whole genome, exome, transcriptome (all transcribed sequences of a genome) or methylome (all methylated sequences of a genome) in very short time periods, e.g. within 1-2 weeks, for example, within 1-7 days or within less than 24 hours and allow, in principle, single cell sequencing approaches. Multiple NGS platforms which are commercially available or which are mentioned in the literature can be used in the context of the invention e.g. those described in detail in WO 2012/159643.

In certain embodiments a non-mutated protein epitope peptide described herein molecule can comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino acid residues, and any range derivable therein. In specific embodiments, a non-mutated protein epitope peptide molecule is equal to or less than 100 amino acids.

In some embodiments, non-mutated protein epitope peptides and polypeptides described herein for MHC Class I are 13 residues or less in length and usually consist of between about 8 and about 11 residues, particularly 9 or 10 residues. In some embodiments, non-mutated protein epitope peptides and polypeptides described herein for MHC Class II are 9-24 residues in length.

A longer non-mutated protein epitope peptide can be designed in several ways. In some embodiments, when HLA-binding peptides are predicted or known, a longer non-mutated protein epitope peptide could consist of (1) individual binding peptides with extensions of 2-5 amino acids toward the N- and C-terminus of each corresponding peptide; or (2) a concatenation of some or all of the binding peptides with extended sequences for each. In some embodiments, use of a longer peptide is presumed to allow for endogenous processing by patient cells and can lead to more effective antigen presentation and induction of T cell responses. In some embodiments, two or more peptides can be used, where the peptides overlap and are tiled over the long non-mutated protein epitope peptide.

In some embodiments, the non-mutated protein epitope peptides and polypeptides bind an HLA protein (e.g., HLA class I or HLA class II). In specific embodiments the non-mutated protein epitope peptide or polypeptide has an $IC_{50}$ of at least less than 5000 nM, at least less than 500 nM, at least less than 100 nM, at least less than 50 nM or less.

In some embodiments, a non-mutated protein epitope peptide described herein can comprise carriers such as those well known in the art, e.g., thyroglobulin, albumins such as human serum albumin, tetanus toxoid, polyamino acid residues such as poly L-lysine, poly L-glutamic acid, influenza virus proteins, hepatitis B virus core protein, and the like.

In some embodiments, a non-mutated protein epitope peptide described herein can be modified by terminal-$NH_2$ acylation, e.g., by alkanoyl ($C_1$-$C_{20}$) or thioglycolyl acetylation, terminal-carboxyl amidation, e.g., ammonia, methylamine, etc. In some embodiments these modifications can provide sites for linking to a support or other molecule.

In some embodiments, a non-mutated protein epitope peptide described herein can contain modifications such as but not limited to glycosylation, side chain oxidation, biotinylation, phosphorylation, addition of a surface active material, e.g. a lipid, or can be chemically modified, e.g., acetylation, etc. Moreover, bonds in the peptide can be other than peptide bonds, e.g., covalent bonds, ester or ether bonds, disulfide bonds, hydrogen bonds, ionic bonds, etc.

In some embodiments, a non-mutated protein epitope peptide described herein can contain substitutions to modify a physical property (e.g., stability or solubility) of the resulting peptide. For example, non-mutated protein epitope peptides can be modified by the substitution of a cysteine (C) with α-amino butyric acid ("B"). Due to its chemical nature, cysteine has the propensity to form disulfide bridges and sufficiently alter the peptide structurally so as to reduce binding capacity. Substituting α-amino butyric acid for C not only alleviates this problem, but actually improves binding and crossbinding capability in certain instances. Substitution of cysteine with α-amino butyric acid can occur at any residue of a non-mutated protein epitope peptide, e.g., at either anchor or non-anchor positions of an epitope or analog within a peptide, or at other positions of a peptide.

In some embodiments, a non-mutated protein epitope peptide described herein can comprise amino acid mimetics or unnatural amino acid residues, e.g. D- or L-naphylalanine; D- or L-phenylglycine; D- or L-2-thienylalanine; D- or L-1, -2, 3-, or 4-pyrenylalanine; D- or L-3 thienylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-.rho.-fluorophenylalanine; D- or L-.rho.-biphenyl-phenylalanine; D- or L-ρ-methoxybiphenylphenylalanine; D- or L-2-indole(allyl)alanines; and, D- or L-alkylalanines, where the alkyl group can be a substituted or unsubstituted methyl, ethyl, propyl, hexyl, butyl, pentyl, isopropyl, iso-butyl, sec-isotyl, iso-pentyl, or a nonacidic amino acid residues. Aromatic rings of a non-natural amino acid include, e.g., thiazolyl, thiophenyl, pyrazolyl, benzimidazolyl, naphthyl, furanyl, pyrrolyl, and pyridyl aromatic rings. Modified peptides that have various amino acid mimetics or unnatural amino acid residues are particularly useful, as they tend to manifest increased stability in vivo. Such peptides can also possess improved shelf-life or manufacturing properties.

Peptide stability can be assayed in a number of ways. For instance, peptidases and various biological media, such as human plasma and serum, have been used to test stability. See, e.g., Verhoef, et al., Eur. J. Drug Metab. Pharmacokinetics 11:291 (1986). Half-life of the peptides described herein is conveniently determined using a 25% human serum (v/v) assay. The protocol is as follows: pooled human serum (Type AB, non-heat inactivated) is dilapidated by centrifugation before use. The serum is then diluted to 25% with RPMI-1640 or another suitable tissue culture medium. At predetermined time intervals, a small amount of reaction solution is removed and added to either 6% aqueous trichloroacetic acid (TCA) or ethanol. The cloudy reaction sample is cooled (4° C.) for 15 minutes and then spun to pellet the precipitated serum proteins. The presence of the peptides is then determined by reversed-phase HPLC using stability-specific chromatography conditions.

In some embodiments, a non-mutated protein epitope peptide described herein can be in solution, lyophilized, or can be in crystal form.

In some embodiments, a non-mutated protein epitope peptide described herein can be prepared synthetically, by recombinant DNA technology or chemical synthesis, or can be isolated from natural sources such as native tumors or pathogenic organisms. Epitopes can be synthesized individually or joined directly or indirectly in a peptide. Although a non-mutated protein epitope peptide described herein will be substantially free of other naturally occurring host cell proteins and fragments thereof, in some embodiments the peptide can be synthetically conjugated to be joined to native fragments or particles.

In some embodiments, a non-mutated protein epitope peptide described herein can be prepared in a wide variety of ways. In some embodiments, the peptides can be synthesized in solution or on a solid support according to conventional techniques. Various automatic synthesizers are commercially available and can be used according to known protocols. (See, for example, Stewart & Young, SOLID PHASE PEPTIDE SYNTHESIS, 2D. ED., Pierce Chemical Co., 1984). Further, individual peptides can be joined using chemical ligation to produce larger peptides that are still within the bounds of the invention.

Alternatively, recombinant DNA technology can be employed wherein a nucleotide sequence which encodes a peptide inserted into an expression vector, transformed or transfected into an appropriate host cell and cultivated under conditions suitable for expression. These procedures are generally known in the art, as described generally in Sambrook et al., MOLECULAR CLONING, A LABORATORY MANUAL, Cold Spring Harbor Press, Cold Spring Harbor, N.Y. (1989). Thus, recombinant peptides, which comprise or consist of one or more epitopes described herein, can be used to present the appropriate T cell epitope.

In one aspect, the invention described herein also provides compositions comprising one, at least two, or more than two non-mutated protein epitope peptides. In some embodiments a composition described herein contains at least two distinct peptides. In some embodiments, the at least two distinct peptides are derived from the same polypeptide. By distinct polypeptides is meant that the peptide vary by length, amino acid sequence or both. The peptides are derived from any polypeptide known to or have been found to contain a tumor specific epitope.

Non-Mutated Protein Epitope Polynucleotides

Polynucleotides encoding each of the peptides described herein are also part of the invention. As appreciated by one of ordinary skill in the art, various nucleic acids will encode the same peptide due to the redundancy of the genetic code. Each of these nucleic acids falls within the scope of the present invention. This embodiment of the invention comprises DNA and RNA, for example, mRNA, and in certain embodiments a combination of DNA and RNA. In one embodiment, the mRNA is a self-amplifying mRNA. (Brito et al., Adv. Genet. 2015; 89:179-233). It is to be appreciated that any polynucleotide that encodes a peptide described herein falls within the scope of this invention.

The term "RNA" includes and in some embodiments relates to "mRNA". The term "mRNA" means "messenger-RNA" and relates to a "transcript" which is generated by using a DNA template and encodes a peptide or polypeptide. Typically, an mRNA comprises a 5'-UTR, a protein coding region, and a 3'-UTR. mRNA only possesses limited half-life in cells and in vitro. In one embodiment, the mRNA is self-amplifying mRNA. In the context of the present invention, mRNA may be generated by in vitro transcription from a DNA template. The in vitro transcription methodology is known to the skilled person. For example, there is a variety of in vitro transcription kits commercially available.

The stability and translation efficiency of RNA may be modified as required. For example, RNA may be stabilized and its translation increased by one or more modifications having a stabilizing effects and/or increasing translation efficiency of RNA. Such modifications are described, for example, in PCT/EP2006/009448 incorporated herein by reference. In order to increase expression of the RNA used according to the present invention, it may be modified within the coding region, i.e. the sequence encoding the expressed peptide or protein, without altering the sequence of the expressed peptide or protein, so as to increase the GC-content to increase mRNA stability and to perform a codon optimization and, thus, enhance translation in cells.

The term "modification" in the context of the RNA used in the present invention includes any modification of an RNA which is not naturally present in said RNA. In one embodiment of the invention, the RNA used according to the invention does not have uncapped 5'-triphosphates. Removal of such uncapped 5'-triphosphates can be achieved by treating RNA with a phosphatase. The RNA according to the invention may have modified ribonucleotides in order to increase its stability and/or decrease cytotoxicity. For example, in one embodiment, in the RNA used according to the invention 5-methylcytidine is substituted partially or completely, for example, completely, for cytidine. Alternatively or additionally, in one embodiment, in the RNA used according to the invention pseudouridine is substituted partially or completely, for example, completely, for uridine.

In one embodiment the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, to the 7-methylguanosine cap (m G). In the context of the present invention, the term "5'-cap" includes a 5'-cap analog that resembles the RNA cap structure and is modified to possess the ability to stabilize RNA and/or enhance translation of RNA if attached thereto, in vivo and/or in a cell.

In certain embodiments, an mRNA encoding a non-mutated protein epitope is administered to a subject in need thereof. In one embodiment, the invention provides RNA, oligoribonucleotide, and polyribonucleotide molecules comprising a modified nucleoside, gene therapy vectors comprising same, gene therapy methods and gene transcription silencing methods comprising same. In one embodiment, the mRNA to be administered comprises at least one modified nucleoside.

The polynucleotides encoding peptides described herein can be synthesized by chemical techniques, for example, the phosphotriester method of Matteucci, et al., J. Am. Chem. Soc. 103:3185 (1981). Polynucleotides encoding peptides comprising or consisting of an analog can be made simply by substituting the appropriate and desired nucleic acid base(s) for those that encode the native epitope.

A large number of vectors and host systems suitable for producing and administering a non-mutated protein epitope peptide described herein are known to those of skill in the art, and are commercially available. The following vectors are provided by way of example. Bacterial: pQE70, pQE60, pQE-9 (Qiagen), pBS, pD10, phagescript, psiX174, pBluescript SK, pbsks, pNH8A, pNH16a, pNH18A, pNH46A (Stratagene); ptrc99a, pKK223-3, pKK233-3, pDR540, pRIT5 (Pharmacia); pCR (Invitrogen). Eukaryotic: pWL-NEO, pSV2CAT, pOG44, pXT1, pSG (Stratagene) pSVK3, pBPV, pMSG, pSVL (Pharmacia); p75.6 (Valentis); pCEP (Invitrogen); pCEI (Epimmune). However, any other plasmid or vector can be used as long as it is replicable and viable in the host.

As representative examples of appropriate hosts, there can be mentioned: bacterial cells, such as *E. coli, Bacillus subtilis, Salmonella typhimurium* and various species within the genera *Pseudomonas, Streptomyces,* and *Staphylococcus*; fungal cells, such as yeast; insect cells such as *Drosophila* and Sf9; animal cells such as COS-7 lines of monkey kidney fibroblasts, described by Gluzman, Cell 23:175 (1981), and other cell lines capable of expressing a compatible vector, for example, the C127, 3T3, CHO, HeLa and BHK cell lines or Bowes melanoma; plant cells, etc. The selection of an appropriate host is deemed to be within the scope of those skilled in the art from the teachings herein.

Thus, the present disclosure is also directed to vectors, and expression vectors useful for the production and administration of the non-mutated protein epitope peptides described herein, and to host cells comprising such vectors.

Host cells are genetically engineered (transduced or transformed or transfected) with the vectors which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the polynucleotides. The culture conditions, such as temperature, pH and the like, are those previously used with the host cell selected for expression, and will be apparent to the ordinarily skilled artisan.

For expression of the non-mutated protein epitope peptides described herein, the coding sequence will be provided operably linked start and stop codons, promoter and terminator regions, and in some embodiments, and a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), acid phosphatase, or heat shock proteins, among others. The heterologous structural sequence is assembled in appropriate phase with translation initiation and termination sequences, and in some embodiments, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Yeast, insect or mammalian cell hosts can also be used, employing suitable vectors and control sequences. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. Such promoters can also be derived from viral sources, such as, e.g., human cytomegalovirus (CMV-IE promoter) or herpes simplex virus type-1 (HSV TK promoter). Nucleic acid sequences derived from the SV40 splice, and polyadenylation sites can be used to provide the nontranscribed genetic elements.

Polynucleotides encoding on-mutated protein epitope peptides described herein can also comprise a ubiquitination signal sequence, and/or a targeting sequence such as an endoplasmic reticulum (ER) signal sequence to facilitate movement of the resulting peptide into the endoplasmic reticulum.

Polynucleotides described herein can be administered and expressed in human cells (e.g., immune cells, including dendritic cells). A human codon usage table can be used to guide the codon choice for each amino acid. Such polynucleotides comprise spacer amino acid residues between epitopes and/or analogs, such as those described above, or can comprise naturally-occurring flanking sequences adjacent to the epitopes and/or analogs (and/or CTL, HTL, and B cell epitopes).

In some embodiments, a non-mutated protein epitope peptide described herein can also be administered/expressed by viral or bacterial vectors. Examples of expression vectors include attenuated viral hosts, such as vaccinia or fowlpox. As an example of this approach, vaccinia virus is used as a vector to express nucleotide sequences that encode the non-mutated protein epitope peptides described herein. Vaccinia vectors and methods useful in immunization protocols are described in, e.g., U.S. Pat. No. 4,722,848. Another vector is BCG (Bacille Calmette Guerin). BCG vectors are described by Stover et al., Nature 351:456-460 (1991). A wide variety of other vectors useful for therapeutic administration or immunization of the non-mutated protein epitope polypeptides described herein, e.g. adeno and adeno-associated virus vectors, retroviral vectors, *Salmonella typhi* vectors, detoxified anthrax toxin vectors, Sendai virus vectors, poxvirus vectors, canarypox vectors, and fowlpox vectors, and the like, will be apparent to those skilled in the art from the description herein. In some embodiments, the vector is Modified Vaccinia Ankara (VA) (e.g. Bavarian Noridic (MVA-BN)).

Standard regulatory sequences well known to those of skill in the art can be included in the vector to ensure expression in the human target cells. Several vector elements are desirable: a promoter with a downstream cloning site for polynucleotide, e.g., minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences. In some embodiments, the promoter is the CMV-IE promoter.

Polynucleotides described herein can comprise one or more synthetic or naturally-occurring introns in the transcribed region. The inclusion of mRNA stabilization sequences and sequences for replication in mammalian cells can also be considered for increasing polynucleotide expression.

In addition, a polynucleotide described herein can comprise immunostimulatory sequences (ISSs or CpGs). These sequences can be included in the vector, outside the polynucleotide coding sequence to enhance immunogenicity.

Non-Mutated Protein Epitope Binding Peptides

In certain embodiments, the present invention provides a binding protein (e.g., an antibody or antigen-binding fragment thereof), or a T cell receptor (TCR), or a chimeric antigen receptor (CAR) capable of binding with a high affinity to a non-mutated protein epitope peptide:human leukocyte antigen (HLA) complex. In some embodiments, the present invention provides a CAR that is capable of binding with a high affinity to a non-mutated protein epitope peptide derived from the extracellular domain of a protein. In certain embodiments, an antigen-specific binding protein or TCR or CAR as described herein includes variant polypeptide species that have one or more amino acid substitutions, insertions, or deletions in the native amino acid sequence, provided that the binding protein retains or substantially retains its specific binding function. Conservative substitutions of amino acids are well known and may occur naturally or may be introduced when the binding protein or TCR is recombinantly produced. Amino acid substitutions, deletions, and additions may be introduced into a protein using mutagenesis methods known in the art (see, e.g., Sambrook et al., Molecular Cloning: A Laboratory Manual, 3d ed., Cold Spring Harbor Laboratory Press, N Y, 2001). Oligonucleotide-directed site-specific (or segment specific) mutagenesis procedures may be employed to provide an altered polynucleotide that has particular codons altered according to the substitution, deletion, or insertion desired. Alternatively, random or saturation mutagenesis techniques, such as alanine scanning mutagenesis, error prone polymerase chain reaction mutagenesis, and oligonucleotide-directed mutagenesis may be used to prepare immunogen polypeptide variants (see, e.g., Sambrook et al., supra).

A variety of criteria known to persons skilled in the art indicate whether an amino acid that is substituted at a particular position in a peptide or polypeptide is conservative (or similar). For example, a similar amino acid or a conservative amino acid substitution is one in which an amino acid residue is replaced with an amino acid residue having a similar side chain. Similar amino acids may be included in the following categories: amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine) In certain circumstances, substitution of glutamine for glutamic acid or asparagine for aspartic acid may be considered a similar substitution in that glutamine and asparagine are amide derivatives of glutamic acid and aspartic acid, respectively. As understood in the art "similarity" between two polypeptides is determined by comparing the amino acid sequence and conserved amino acid substitutes thereto of the polypeptide to the sequence of a second polypeptide (e.g., using GENEWORKS, Align, the BLAST algorithm, or other algorithms described herein and practiced in the art).

In certain embodiments, a non-mutated protein epitope specific binding protein, TCR or CAR is capable of (a) specifically binding to an antigen:HLA complex on a cell surface independent or in the absence of CD8. In certain embodiments, a non-mutated protein epitope specific binding protein is a T cell receptor (TCR), a chimeric antigen receptor or an antigen-binding fragment of a TCR, any of which can be chimeric, humanized or human. In further embodiments, an antigen-binding fragment of the TCR comprises a single chain TCR (scTCR).

In certain embodiments, there is provided a composition comprising a non-mutated protein epitope-specific binding protein or high affinity recombinant TCR according to any one of the above embodiments and a pharmaceutically acceptable carrier, diluent, or excipient.

Methods useful for isolating and purifying recombinantly produced soluble TCR, by way of example, can include obtaining supernatants from suitable host cell/vector systems that secrete the recombinant soluble TCR into culture media and then concentrating the media using a commercially available filter. Following concentration, the concentrate can be applied to a single suitable purification matrix or to a series of suitable matrices, such as an affinity matrix or an ion exchange resin. One or more reverse phase HPLC steps may be employed to further purify a recombinant polypeptide. These purification methods can also be employed when isolating an immunogen from its natural environment. Methods for large scale production of one or more of the isolated/recombinant soluble TCR described herein include batch cell culture, which is monitored and controlled to maintain appropriate culture conditions. Purification of the soluble TCR may be performed according to methods described herein and known in the art.

III. Immunogenic and Vaccine Compositions

In one embodiment, provided herein is an immunogenic composition, e.g., a vaccine composition capable of raising a non-mutated protein epitope-specific response (e.g., a humoral or cell-mediated immune response). In some embodiments, the immunogenic composition comprises non-mutated protein epitope therapeutics (e.g., peptides, polynucleotides, TCR, CAR, cells containing TCR or CAR, dendritic cell containing polypeptide, dendritic cell containing polynucleotide, antibody, etc.) described herein corresponding to tumor specific non-mutated protein epitope identified herein.

A person skilled in the art will be able to select non-mutated protein epitope therapeutics by testing, for example, the generation of T-cells in vitro as well as their efficiency and overall presence, the proliferation, affinity and expansion of certain T-cells for certain peptides, and the functionality of the T-cells, e.g. by analyzing the IFN-γ production or tumor killing by T-cells. The most efficient peptides can then combined as an immunogenic composition.

In one embodiment of the present invention the different non-mutated protein epitope peptides and/or polypeptides are selected so that one immunogenic composition comprises non-mutated protein epitope peptides and/or polypeptides capable of associating with different MHC molecules, such as different MHC class I molecule. In some embodiments, an immunogenic composition comprises non-mutated protein epitope peptides and/or polypeptides capable of associating with the most frequently occurring MHC class I molecules. Hence immunogenic compositions described herein comprise different peptides capable of associating with at least 2, at least 3, or at least 4 MHC class I or class II molecules.

In one embodiment, an immunogenic composition described herein is capable of raising a specific cytotoxic T-cells response, specific helper T-cell response, or a B cell response.

In some embodiments, an immunogenic composition described herein can further comprise an adjuvant and/or a carrier. Examples of useful adjuvants and carriers are given herein below. Polypeptides and/or polynucleotides in the composition can be associated with a carrier such as e.g. a protein or an antigen-presenting cell such as e.g. a dendritic cell (DC) capable of presenting the peptide to a T-cell or a B cell. In further embodiments, DC-binding peptides are used as carriers to target the non-mutated protein epitope peptides and polynucleotides encoding the non-mutated protein epitope peptides to dendritic cells (Sioud et al. FASEB J 27: 3272-3283 (2013)).

In embodiments, the non-mutated protein epitope polypeptides or polynucleotides can be provided as antigen presenting cells (e.g., dendritic cells) containing such polypeptides or polynucleotides. In other embodiments, such antigen presenting cells are used to stimulate T cells for use in patients.

In some embodiments, the antigen presenting cells are dendritic cells. In related embodiments, the dendritic cells are autologous dendritic cells that are pulsed with the non-mutated protein epitope peptide or nucleic acid. The non-mutated protein epitope peptide can be any suitable peptide that gives rise to an appropriate T-cell response. T-cell therapy using autologous dendritic cells pulsed with peptides from a tumor associated antigen is disclosed in Murphy et al. (1996) The Prostate 29, 371-380 and Tjua et al. (1997) The Prostate 32, 272-278. In some embodiments, the T cell is a CTL. In some embodiments, the T cell is a HTL.

Thus, one embodiment of the present invention an immunogenic composition containing at least one antigen presenting cell (e.g., a dendritic cell) that is pulsed or loaded with one or more non-mutated protein epitope polypeptides or polynucleotides described herein. In embodiments, such APCs are autologous (e.g., autologous dendritic cells). Alternatively, peripheral blood mononuclear cells (PBMCs) isolated from a patient can be loaded with non-mutated protein epitope peptides or polynucleotides ex vivo. In related embodiments, such APCs or PBMCs are injected back into the patient.

The polynucleotide can be any suitable polynucleotide that is capable of transducing the dendritic cell, thus resulting in the presentation of a non-mutated protein epitope peptide and induction of immunity. In one embodiment, the polynucleotide can be naked DNA that is taken up by the cells by passive loading. In another embodiment, the polynucleotide is part of a delivery vehicle, for example, a liposome, virus like particle, plasmid, or expression vector. In another embodiment, the polynucleotide is delivered by a vector-free delivery system, for example, high performance electroporation and high-speed cell deformation). In embodiments, such antigen presenting cells (APCs) (e.g., dendritic cells) or peripheral blood mononuclear cells (PBMCs) are used to stimulate a T cell (e.g., an autologous T cell). In related embodiments, the T cell is a CTL. In other related embodiments, the T cell is an HTL. Such T cells are then injected into the patient. In some embodiments, CTL is injected into the patient. In some embodiments, HTL is injected into the patient. In some embodiments, both CTL and HTL are injected into the patient. Administration of either therapeutic can be performed simultaneously or sequentially and in any order.

The pharmaceutical compositions (e.g., immunogenic compositions) described herein for therapeutic treatment are intended for parenteral, topical, nasal, oral or local administration. In some embodiments, the pharmaceutical compositions described herein are administered parenterally, e.g., intravenously, subcutaneously, intradermally, or intramuscularly. In embodiments, the composition can be administered intratumorally. The compositions can be administered at the site of surgical excision to induce a local immune response to the tumor. In some embodiments, described herein are compositions for parenteral administration which comprise a solution of the non-mutated protein epitope peptides and immunogenic compositions are dissolved or suspended in an acceptable carrier, for example, an aqueous carrier. A variety of aqueous carriers can be used, e.g., water, buffered water, 0.9% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of non-mutated protein epitope peptides and polynucleotides described herein in the pharmaceutical formulations can vary widely, i.e., from less than about 0.1%, usually at or at least about 2% to as much as 20% to 50% or more by weight, and will be selected by fluid volumes, viscosities, etc., according to the particular mode of administration selected.

The non-mutated protein epitope peptides and polynucleotides described herein can also be administered via liposomes, which target the peptides to a particular cells tissue, such as lymphoid tissue. Liposomes are also useful in increasing the half-life of the peptides. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the DEC205 antigen, or with other therapeutic or immunogenic compositions. Thus, liposomes filled with a desired peptide or polynucleotide described herein can be directed to the site of lymphoid cells, where the liposomes then deliver the selected therapeutic/immunogenic polypeptide/polynucleotide compositions. Liposomes can be formed from standard vesicle-forming lipids, which generally include neutral and negatively charged phospholipids and a sterol, for example, cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9; 467 (1980), U.S. Pat. Nos. 4,235,871, 4,501,728, 4,501,728, 4,837,028, and 5,019,369.

For targeting to the immune cells, a non-mutated protein epitope polypeptides or polynucleotides to be incorporated into the liposome for cell surface determinants of the desired immune system cells. A liposome suspension containing a peptide can be administered intravenously, locally, topically, etc. in a dose which varies according to, inter alia, the manner of administration, the polypeptide or polynucleotide being delivered, and the stage of the disease being treated.

In some embodiments, non-mutated protein epitope polypeptides and polynucleotides are targeted to dendritic cells. In one embodiment, the non-mutated protein epitope polypeptides and polynucleotides are target to dendritic cells using the markers DEC205, XCR1, CD197, CD80, CD86, CD123, CD209, CD273, CD283, CD289, CD184, CD85h, CD85j, CD85k, CD85d, CD85g, CD85a, TSLP receptor, or CD1a.

For solid compositions, conventional or nanoparticle nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more non-mutated protein epitope polypeptides or polynucleotides described herein at a concentration of 25%-75%.

For aerosol administration, the non-mutated protein epitope polypeptides or polynucleotides can be supplied in finely divided form along with a surfactant and propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute 0.1%-20% by weight of the composition, or 0.25-5%. The balance of the composition can be propellant. A carrier can also be included as desired, as with, e.g., lecithin for intranasal delivery.

Additional methods for delivering the non-mutated protein epitope polynucleotides described herein are also known in the art. For instance, the nucleic acid can be delivered directly, as "naked DNA". This approach is described, for instance, in Wolff et al., Science 247: 1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles.

For therapeutic or immunization purposes, mRNA encoding the non-mutated protein epitope peptides, or peptide binding agents can also be administered to the patient. In one embodiment, the mRNA is self-amplifying RNA. In a further embodiment, the self-amplifying RNA is a part of a synthetic lipid nanoparticle formulation (Geall et al., Proc Natl Acad Sci USA. 109: 14604-14609 (2012)).

The nucleic acids can also be delivered complexed to cationic compounds, such as cationic lipids. Lipid-mediated gene delivery methods are described, for instance, in WO 96/18372, WO 93/24640; Mannino & Gould-Fogerite, BioTechniques 6(7): 682-691 (1988); U.S. Pat. No. 5,279,833; WO 91/06309; and Felgner et al., Proc. Natl. Acad. Sci. USA 84: 7413-7414 (1987).

The non-mutated protein epitope peptides and polypeptides described herein can also be expressed by attenuated viruses, such as vaccinia or fowlpox. This approach involves the use of vaccinia virus as a vector to express nucleotide sequences that encode the peptide described herein. Upon introduction into an acutely or chronically infected host or into a noninfected host, the recombinant vaccinia virus expresses the immunogenic peptide, and thereby elicits a host CTL response. Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vectors useful for therapeutic administration or immunization of the peptides described herein will be apparent to those skilled in the art from the description herein.

Adjuvants are any substance whose admixture into the immunogenic composition increases or otherwise modifies the immune response to the therapeutic agent. Carriers are scaffold structures, for example a polypeptide or a polysaccharide, to which a non-mutated protein epitope polypeptide or polynucleotide, is capable of being associated. Optionally, adjuvants are conjugated covalently or non-covalently to the polypeptides or polynucleotides described herein.

The ability of an adjuvant to increase the immune response to an antigen is typically manifested by a significant increase in immune-mediated reaction, or reduction in disease symptoms. For example, an increase in humoral immunity can be manifested by a significant increase in the titer of antibodies raised to the antigen, and an increase in T-cell activity can be manifested in increased cell proliferation, or cellular cytotoxicity, or cytokine secretion. An adjuvant can also alter an immune response, for example, by changing a primarily humoral or T helper 2 response into a primarily cellular, or T helper 1 response.

Suitable adjuvants are known in the art (see, WO 2015/095811) and include, but are not limited to poly(I:C), poly-ICLC, STING agonist, 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, Lipo-Vac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel®. vector system, PLG microparticles, resiquimod, SRL172, virosomes and other virus-like particles, YF-17D, VEGF trap, R848, beta-glucan, Pam3Cys, Pam3CSK4, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Adjuvants also include incomplete Freund's or GM-CSF. Several immunological adjuvants (e.g., MF59) specific for dendritic cells and their preparation have been described previously (Dupuis M, et al., Cell Immunol. 1998; 186(1):18-27; Allison A C; Dev Biol Stand. 1998; 92:3-11) (Mosca et al. Frontiers in Bioscience, 2007; 12:4050-4060) (Gamvrellis et al. Immunol & Cell Biol. 2004; 82: 506-516). Also cytokines can be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, PGE1, PGE2, IL-1, IL-1b, IL-4, IL-6 and CD40L) (U.S. Pat. No. 5,849,589 incorporated herein by reference in its entirety) and acting as immunoadjuvants (e.g., IL-12) (Gabrilovich D I, et al., J Immunother Emphasis Tumor Immunol. 1996 (6):414-418).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. Importantly, it enhances dendritic cell maturation and differentiation, resulting in enhanced activation of TH1 cells and strong cytotoxic T-lymphocyte (CTL) generation, even in the absence of CD4 T-cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enabled the antigen doses to be reduced with comparable antibody responses to the full-dose vaccine without CpG in some experiments (Arthur M. Krieg, Nature Reviews, Drug Discovery, 5, June 2006, 471-484). U.S. Pat. No. 6,406,705 B1 describes the combined use of CpG oligonucleotides, non-nucleic acid adjuvants and an antigen to induce an antigen-specific immune response. A commercially available CpG TLR9 antagonist is dSLIM (double Stem Loop Immunomodulator) by Mologen (Berlin, GERMANY), which is a component of the pharmaceutical composition described herein. Other TLR binding molecules such as RNA binding TLR 7, TLR 8 and/or TLR 9 can also be used.

Other examples of useful adjuvants include, but are not limited to, chemically modified CpGs (e.g. CpR, Idera), Poly(I:C)(e.g. polyi:CI2U), non-CpG bacterial DNA or RNA, ssRNA40 for TLR8, as well as immunoactive small molecules and antibodies such as cyclophosphamide, sunitinib, bevacizumab, celebrex, NCX-4016, sildenafil, tadalafil, vardenafil, sorafenib, XL-999, CP-547632, pazopanib, ZD2171, AZD2171, ipilimumab, tremelimumab, and SC58175, which can act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim).

In some embodiments, an immunogenic composition according to the present invention can comprise more than one different adjuvants. Furthermore, the invention encompasses a therapeutic composition comprising any adjuvant substance including any of the above or combinations thereof. It is also contemplated that the non-mutated protein epitope therapeutic (e.g., a humoral or cell-mediated immune response). In some embodiments, the immunogenic composition comprises non-mutated protein epitope therapeutics (e.g., peptides, polynucleotides, TCR, CAR, cells containing TCR or CAR, dendritic cell containing polypeptide, dendritic cell containing polynucleotide, antibody, etc.) and the adjuvant can be administered separately in any appropriate sequence.

A carrier can be present independently of an adjuvant. The function of a carrier can for example be to increase the molecular weight of in particular mutant in order to increase their activity or immunogenicity, to confer stability, to increase the biological activity, or to increase serum half-life. Furthermore, a carrier can aid presenting peptides to T-cells. The carrier can be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. In one embodiment, the carrier comprises a human fibronectin type III domain (Koide et al. Methods Enzymol. 2012; 503:135-56). For immunization of humans, the carrier must be a physiologically acceptable carrier acceptable to humans and safe. However, tetanus toxoid and/or diptheria toxoid are suitable carriers in one embodiment of the invention. Alternatively, the carrier can be dextrans for example sepharose.

In some embodiments, the polypeptides can be synthesized as multiply linked peptides as an alternative to coupling a polypeptide to a carrier to increase immunogenicity. Such molecules are also known as multiple antigenic peptides (MAPS).

IV. Combinations of CTL Peptides and HTL Peptides

Immunogenic or vaccine compositions comprising the non-mutated protein epitope polypeptides and polynucleotides described herein, or analogs thereof, which have immunostimulatory activity can be modified to provide desired attributes, such as improved serum half-life, or to enhance immunogenicity.

For instance, the ability of the non-mutated protein epitope peptides to induce CTL activity can be enhanced by linking the peptide to a sequence which contains at least one epitope that is capable of inducing a T helper cell response. In one embodiment, CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus can be a hetero- or homo-oligomer. When present, the spacer will usually be at least one or two residues, more usually three to six residues. Alternatively, the CTL peptide can be linked to the T helper peptide without a spacer.

Although the CTL peptide epitope can be linked directly to the T helper peptide epitope, CTL epitope/HTL epitope conjugates can be linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus can be a hetero- or homo-oligomer. When present, the spacer will usually be at least one or two residues, more usually three to six residues. The CTL peptide epitope can be linked to the T helper peptide epitope either directly or via a spacer either at the amino or carboxy terminus of the CTL peptide. The amino terminus of either the immunogenic peptide or the T helper peptide can be acylated.

HTL peptide epitopes can also be modified to alter their biological properties. For example, peptides comprising HTL epitopes can contain D-amino acids to increase their resistance to proteases and thus extend their serum half-life. Also, the epitope peptides can be conjugated to other molecules such as lipids, proteins or sugars, or any other synthetic compounds, to increase their biological activity. For example, the T helper peptide can be conjugated to one or more palmitic acid chains at either the amino or carboxyl termini.

In certain embodiments, the T helper peptide is one that is recognized by T helper cells present in the majority of the population. This can be accomplished by selecting amino acid sequences that bind to many, most, or all of the HLA class II molecules. These are known as "loosely HLA-restricted" or "promiscuous" T helper sequences. Examples of amino acid sequences that are promiscuous include sequences from antigens such as tetanus toxoid at positions 830-843 (QYIKANSKFIGITE (SEQ ID NO: 1)), *Plasmodium falciparum*: CS protein at positions 378-398 (DIEKKIAKMEKASSVFNVVNS (SEQ ID NO: 2)), and *Streptococcus* 18 kD protein at positions 116 (GAVDSILGGVATYGAA (SEQ ID NO: 3)). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE, Epimmune, Inc., San Diego, CA) are designed to bind most HLA-DR (human HLA class II) molecules. For instance, a pan-DR-binding epitope peptide having the formula: aKXVWANTLKAAa (SEQ ID NO: 4), where "X" is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

In some embodiments it can be desirable to include in a non-mutated protein epitope therapeutic (e.g., peptides, polynucleotides, TCR, CAR, cells containing TCR or CAR, dendritic cell containing polypeptide, dendritic cell containing polynucleotide, antibody, etc.) in pharmaceutical compositions (e.g., immunogenic compositions) at least one component of which primes cytotoxic T lymphocytes. Lipids have been identified as agents capable of priming CTL in vivo against viral antigens. For example, palmitic acid residues can be attached to the ε- and α-amino groups of a lysine residue and then linked, e.g., via one or more linking residues such as Gly, Gly-Gly-, Ser, Ser-Ser, or the like, to an immunogenic non-mutated protein epitope peptide. The lipidated peptide can then be administered either directly in a micelle or particle, incorporated into a liposome, or emulsified in an adjuvant. In one embodiment, a particularly effective immunogenic construct comprises palmitic acid attached to ε- and α-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine (P3CSS) can be used to prime virus specific CTL when covalently attached to an appropriate peptide. (See, e.g., Deres, et al., Nature 342:561, 1989). Non-mutated protein epitope peptides described herein can be coupled to P3CSS, for example, and the lipopeptide administered to an individual to specifically prime a CTL response to the target antigen. Moreover, because the induction of neutralizing antibodies can also be primed with P3CSS-conjugated epitopes, two such compositions can be combined to more effectively elicit both humoral and cell-mediated responses to infection.

As noted herein, additional amino acids can be added to the termini of a non-mutated protein epitope peptide to provide for ease of linking peptides one to another, for coupling to a carrier support or larger peptide, for modifying the physical or chemical properties of the peptide or oligopeptide, or the like. Amino acids such as tyrosine, cysteine, lysine, glutamic or aspartic acid, or the like, can be introduced at the C- or N-terminus of the peptide or oligopeptide. However, it is to be noted that modification at the carboxyl terminus of a T cell epitope can, in some cases, alter binding characteristics of the peptide. In addition, the peptide or oligopeptide sequences can differ from the natural sequence by being modified by terminal-NH2 acylation, e.g., by alkanoyl (C1-C20) or thioglycolyl acetylation, terminal-carboxyl amidation, e.g., ammonia, methylamine, etc. In some instances these modifications can provide sites for linking to a support or other molecule.

An embodiment of an immunogenic composition described herein comprises ex vivo administration of a cocktail of epitope-bearing non-mutated protein epitope polypeptide or polynucleotides to PBMC, or isolated DC therefrom, from the patient's blood. A pharmaceutical to facilitate harvesting of dendritic cells (DCs) can be used, including GM-CSF, IL-4, IL-6, IL-1β, and TNFα. After pulsing the DCs with peptides or polynucleotides encoding the peptides, and prior to reinfusion into patients, the DC are washed to remove unbound peptides. In this embodiment, a vaccine or immunogenic composition comprises peptide-pulsed DCs which present the pulsed peptide epitopes complexed with HLA molecules on their surfaces. The composition is then administered to the patient. In other embodiments, such pulsed DCs are used to stimulate T cells suitable for use in T cell therapy.

V. Multi-Epitope Immunogenic Compositions

A number of different approaches are available which allow simultaneous delivery of multiple epitopes. Nucleic acids encoding the non-mutated protein epitope peptides described herein are a particularly useful embodiment of the invention. In one embodiment, the nucleic acid is RNA. In some embodiments, minigene constructs encoding a non-mutated protein epitope peptide comprising one or multiple epitopes described herein are used to administer nucleic acids encoding the non-mutated protein epitope peptides described herein uses.

The use of multi-epitope minigenes is described An, L. and Whitton, J. L., J. Virol. 71:2292, 1997; Thomson, S. A. et al., J. Immunol. 157:822, 1996; Whitton, J. L. et al., J. Virol. 67:348, 1993; Hanke, R. et al., Vaccine 16:426, 1998. For example, a multi-epitope DNA plasmid encoding supermotif- and/or motif-bearing antigen peptides, a universal helper T cell epitope (or multiple tumor associated antigen HTL epitopes), and an endoplasmic reticulum-translocating signal sequence can be engineered.

The immunogenicity of a multi-epitopic minigene can be tested in transgenic mice to evaluate the magnitude of immune response induced against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a cell mediated and/or humoral response and 2.) that the induced immune cells recognized cells expressing the encoded epitopes.

For example, to create a DNA sequence encoding the selected non-mutated protein epitope (minigene) for expression in human cells, the amino acid sequences of the epitopes can be reverse translated. A human codon usage table can be used to guide the codon choice for each amino acid. These non-mutated protein epitope-encoding DNA sequences can be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, a ubiquitination signal sequence, and/or an endoplasmic reticulum targeting signal. In addition, HLA presentation of CTL and HTL epitopes can be improved by including synthetic (e.g. poly-alanine) or naturally-occurring flanking sequences adjacent to the CTL or HTL epitopes; these larger peptides comprising the epitope(s) are within the scope of the invention.

The minigene sequence can be converted to DNA by assembling oligonucleotides that encode the plus and minus strands of the minigene. Overlapping oligonucleotides (30-100 bases long) can be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art can be included in the vector to ensure expression in the target cells. For example, a promoter with a down-stream cloning site for minigene insertion; a polyadenylation signal for efficient transcription termination; an E. coli origin of replication; and an E. coli selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications can be used to optimize minigene expression and immunogenicity. In some cases, introns are utilized for efficient gene expression, and one or more synthetic or naturally-occurring introns could be incorporated into the transcribed region of the minigene. The inclusion of mRNA stabilization sequences and sequences for replication in mammalian cells can also be considered for increasing minigene expression.

Once an expression vector is selected, the minigene can be cloned into the polylinker region downstream of the promoter. This plasmid is transformed into an appropriate E. coli strain, and DNA is prepared using standard techniques. The orientation and DNA sequence of the minigene, as well as all other elements included in the vector, can be confirmed using restriction mapping and DNA sequence analysis. Bacterial cells harboring the correct plasmid can be stored as a master cell bank and a working cell bank.

In addition, immunomodulatory sequences appear to play a role in the immunogenicity of DNA vaccines. These sequences can be included in the vector, outside the minigene coding sequence, if desired to enhance immunogenicity. In one embodiment, the sequences are immunostimulatory. In another embodiment, the sequences are ISSs or CpGs.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins. Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) can be beneficial in certain diseases.

Therapeutic quantities of plasmid DNA can be produced for example, by fermentation in E. coli, followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valencia, California). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA can be used. A variety of methods have been described, and new techniques can become available. Cationic lipids can also be used in the formulation (see, e.g., as described by WO 93/24640; Mannino & Gould-Fogerite, BioTechniques 6(7): 682 (1988); U.S. Pat. No. 5,279,833; WO 91/06309; and Felgner, et al., Proc. Nat'l Acad. Sci. USA 84:7413 (1987). In addition, glycolipids, fusogenic liposomes, peptides and compounds referred to collectively as protective, interactive, non-condensing compounds (PINC) could also be complexed to purified plasmid DNA to influence variables such as stability, intramuscular dispersion, or trafficking to specific organs or cell types.

In another embodiment, the nucleic acid is introduced into cells by use of high-speed cell deformation. During high-speed deformation, cells are squeezed such that temporary disruptions occur in the cell membrane, thus allowing the nucleic acid to enter the cell. Alternatively, protein can be produced from expression vectors—in a bacterial expression vector, for example, and the proteins can then be delivered to the cell;

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes can be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (IP) for lipid-complexed DNA). An exemplary protocol is twenty-one days after immunization, splenocytes are harvested and restimulated for 1 week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is evaluated in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

VI. Cells

In one aspect, the present invention also provides cells expressing a non-mutated protein epitope-recognizing receptor that activates an immunoresponsive cell (e.g., T cell receptor (TCR) or chimeric antigen receptor (CAR)), and methods of using such cells for the treatment of a disease that requires an enhanced immune response.

Such cells include genetically modified immunoresponsive cells (e.g., T cells, Natural Killer (NK) cells, cytotoxic T lymphocytes (CTL) cells, helper T lymphocyte (HTL) cells) expressing an antigen-recognizing receptor (e.g., TCR or CAR) that binds one of the non-mutated protein epitope peptides described herein, and methods of use therefore for the treatment of neoplasia and other pathologies where an increase in an antigen-specific immune response is desired. T cell activation is mediated by a TCR or a CAR targeted to an antigen.

The present invention provides cells expressing a combination of an antigen-recognizing receptor that activates an immunoresponsive cell (e.g., TCR, CAR) and a chimeric co-stimulating receptor (CCR), and methods of using such cells for the treatment of a disease that requires an enhanced immune response. In one embodiment, tumor antigen-specific T cells, NK cells, CTL cells or other immunoresponsive cells are used as shuttles for the selective enrichment of one or more co-stimulatory ligands for the treatment or prevention of neoplasia. Such cells are administered to a human subject in need thereof for the treatment or prevention of a particular cancer.

In one embodiment, the tumor antigen-specific human lymphocytes that can be used in the methods of the invention include, without limitation, peripheral donor lymphocytes genetically modified to express chimeric antigen receptors (CARs) (Sadelain, M., et al. 2003 Nat Rev Cancer 3:35-45), peripheral donor lymphocytes genetically modified to express a full-length tumor antigen-recognizing T cell receptor complex comprising the a and p heterodimer (Morgan, R. A., et al. 2006 Science 314:126-129), lymphocyte cultures derived from tumor infiltrating lymphocytes (TILs) in tumor biopsies (Panelli, M. C., et al. 2000 J Immunol 164:495-504; Panelli, M. C., et al. 2000 J Immunol 164:4382-4392), and selectively in vitro-expanded antigen-specific peripheral blood leukocytes employing artificial antigen-presenting cells (AAPCs) or pulsed dendritic cells (Dupont, J., et al. 2005 Cancer Res 65:5417-5427; Papanicolaou, G. A., et al. 2003 Blood 102:2498-2505). The T cells may be autologous, allogeneic, or derived in vitro from engineered progenitor or stem cells.

Co-Stimulatory Ligands

In one embodiment, the cells of the invention are provided with at least one co-stimulatory ligand which is a non-antigen specific signal important for full activation of an immune cell. Co-stimulatory ligands include, without limitation, tumor necrosis factor (TNF) ligands, cytokines (such as IL-2, IL-12, IL-15 or IL21), and immunoglobulin (Ig) superfamily ligands.

Tumor necrosis factor (TNF) is a cytokine involved in systemic inflammation and stimulates the acute phase reaction. Its primary role is in the regulation of immune cells. Tumor necrosis factor (TNF) ligands share a number of common features. The majority of the ligands are synthesized as type II transmembrane proteins containing a short cytoplasmic segment and a relatively long extracellular region. TNF ligands include, without limitation, nerve growth factor (NGF), CD4OL (CD40L)/CD154, CD137L/ 4-1BBL, tumor necrosis factor alpha (TNFα), CD134L/ OX4OL/CD252, CD27L/CD70, Fas ligand (FasL), CD30L/ CD153, tumor necrosis factor β3 (TNF(3)/lymphotoxin-alpha (LTa), lymphotoxin-beta (ur(3), CD257/1B cell-activating factor (BAFF)/Blys/THANK/Ta11-1, glucocorticoid-induced TNF Receptor ligand (GITRL), and TNF-related apoptosis-inducing ligand (TRAIL), LIGHT (TNFSF14). The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, without limitation, CD80 and CD86, both ligands for CD28.

Compositions comprising genetically modified immunoresponsive cells of the invention can be provided systemically or directly to a subject for the treatment of a neoplasia. In one embodiment, cells of the invention are directly injected into an organ of interest (e.g., an organ affected by a tumor). Alternatively, compositions comprising genetically modified immunoresponsive cells are provided indirectly to the organ of interest, for example, by administration into the circulatory system (e.g., the tumor vasculature). Expansion and differentiation agents can be provided prior to, during or after administration of the cells to increase production of T cells, NK cells, or CTL cells in vitro or in vivo.

The modified cells can be administered in any physiologically acceptable vehicle, normally intravascularly, although they may also be introduced into bone or other convenient site where the cells may find an appropriate site for regeneration and differentiation (e.g., thymus). Genetically modified immunoresponsive cells of the invention can comprise a purified population of cells. Those skilled in the art can readily determine the percentage of genetically modified immunoresponsive cells in a population using various well-known methods, such as fluorescence activated cell sorting (FACS). Dosages can be readily adjusted by those skilled in the art (e.g., a decrease in purity may require an increase in dosage). The cells can be introduced by injection, catheter, or the like. If desired, factors can also be included, including, but not limited to, interleukins, e.g. IL-2, IL-3, IL-6, and IL-11, as well as the other interleukins, the colony stimulating factors, such as G-, M- and GM-CSF, interferons, e.g. γ-interferon and erythropoietin.

Compositions of the invention include pharmaceutical compositions comprising genetically modified immunoresponsive cells or their progenitors and a pharmaceutically acceptable carrier. Administration can be autologous or heterologous. For example, immunoresponsive cells, or progenitors can be obtained from one subject, and administered to the same subject or a different, compatible subject. Peripheral blood derived immunoresponsive cells of the invention or their progeny (e.g., in vivo, ex vivo or in vitro derived) can be administered via localized injection, including catheter administration, systemic injection, localized injection, intravenous injection, or parenteral administration. When administering a therapeutic composition of the present invention (e.g., a pharmaceutical composition containing a genetically modified immunoresponsive cell), it will generally be formulated in a unit dosage injectable form (solution, suspension, emulsion).

VII. Methods of Use and Pharmaceutical Compositions

The non-mutated protein epitope therapeutics (e.g., peptides, polynucleotides, TCR, CAR, cells containing TCR or CAR, dendritic cell containing polypeptide, dendritic cell containing polynucleotide, antibody, etc.) described herein are useful in a variety of applications including, but not limited to, therapeutic treatment methods, such as the treatment of cancer. In some embodiments, the therapeutic treatment methods comprise immunotherapy. In certain embodiments, a non-mutated protein epitope peptide is useful for activating, promoting, increasing, and/or enhancing an immune response, redirecting an existing immune response to a new target, increasing the immunogenicity of a tumor, inhibiting tumor growth, reducing tumor volume, increasing tumor cell apoptosis, and/or reducing the tumorigenicity of a tumor. The methods of use can be in vitro, ex vivo, or in vivo methods.

In some aspects, the present invention provides methods for activating an immune response in a subject using a non-mutated protein epitope therapeutic described herein. In some embodiments, the invention provides methods for promoting an immune response in a subject using a non-mutated protein epitope therapeutic described herein. In some embodiments, the invention provides methods for increasing an immune response in a subject using a non-mutated protein epitope peptide described herein. In some embodiments, the invention provides methods for enhancing an immune response using a non-mutated protein epitope peptide. In some embodiments, the activating, promoting, increasing, and/or enhancing of an immune response comprises increasing cell-mediated immunity. In some embodiments, the activating, promoting, increasing, and/or enhancing of an immune response comprises increasing T-cell activity or humoral immunity. In some embodiments, the activating, promoting, increasing, and/or enhancing of an immune response comprises increasing CTL or HTL activity. In some embodiments, the activating, promoting, increasing, and/or enhancing of an immune response comprises increasing NK cell activity. In some embodiments, the activating, promoting, increasing, and/or enhancing of an immune response comprises increasing T-cell activity and increasing NK cell activity. In some embodiments, the activating, promoting, increasing, and/or enhancing of an immune response comprises increasing CTL activity and increasing NK cell activity. In some embodiments, the activating, promoting, increasing, and/or enhancing of an immune response comprises inhibiting or decreasing the suppressive activity of Tregs. In some embodiments, the immune response is a result of antigenic stimulation. In some embodiments, the antigenic stimulation is a tumor cell. In some embodiments, the antigenic stimulation is cancer.

In some embodiments, the invention provides methods of activating, promoting, increasing, and/or enhancing of an immune response using a non-mutated protein epitope therapeutic described herein. In some embodiments, a method comprises administering to a subject in need thereof a therapeutically effective amount of a non-mutated protein epitope therapeutic that delivers a non-mutated protein epitope polypeptide or polynucleotide to a tumor cell. In some embodiments, a method comprises administering to a subject in need thereof a therapeutically effective amount of a non-mutated protein epitope therapeutic that binds the tumor associated antigen and is internalized by the tumor cell. In some embodiments, a method comprises administering to a subject in need thereof a therapeutically effective amount of a non-mutated protein epitope polypeptide that is internalized by a tumor cell, and the non-mutated protein epitope peptide is processed by the cell. In some embodiments, a method comprises administering to a subject in need thereof a therapeutically effective amount of a non-mutated protein epitope polypeptide that is internalized by a tumor cell, and an antigenic peptide is presented on the surface of the tumor cell. In some embodiments, a method comprises administering to a subject in need thereof a therapeutically effective amount of a non-mutated protein epitope polypeptide that is internalized by the tumor cell, is processed by the cell, and an antigenic peptide is presented on the surface of the tumor cell.

In some embodiments, a method comprises administering to a subject in need thereof a therapeutically effective amount of a non-mutated protein epitope polypeptide or polynucleotide described herein that delivers an exogenous polypeptide comprising at least one antigenic peptide to a tumor cell, wherein the antigenic peptide is presented on the surface of the tumor cell. In some embodiments, the antigenic peptide is presented on the surface of the tumor cell in complex with a MHC class I molecule. In some embodiments, the antigenic peptide is presented on the surface of the tumor cell in complex with a MHC class II molecule.

In some embodiments, a method comprises contacting a tumor cell with a non-mutated protein epitope polypeptide or polynucleotide described herein that delivers an exogenous polypeptide comprising at least one antigenic peptide to the tumor cell, wherein the antigenic peptide is presented on the surface of the tumor cell. In some embodiments, the antigenic peptide is presented on the surface of the tumor cell in complex with a MHC class I molecule. In some embodiments, the antigenic peptide is presented on the surface of the tumor cell in complex with a MHC class II molecule.

In some embodiments, a method comprises administering to a subject in need thereof a therapeutically effective amount of a non-mutated protein epitope polypeptide or polynucleotide described herein that delivers an exogenous polypeptide comprising at least one antigenic peptide to a tumor cell, wherein the antigenic peptide is presented on the surface of the tumor cell, and an immune response against the tumor cell is induced. In some embodiments, the immune response against the tumor cell is increased. In some embodiments, the non-mutated protein epitope polypeptide or polynucleotide delivers an exogenous polypeptide comprising at least one antigenic peptide to a tumor cell, wherein the antigenic peptide is presented on the surface of the tumor cell, and tumor growth is inhibited.

In some embodiments, a method comprises administering to a subject in need thereof a therapeutically effective amount of a non-mutated protein epitope polypeptide or polynucleotide described herein that delivers an exogenous polypeptide comprising at least one antigenic peptide to a tumor cell, wherein the antigenic peptide is presented on the surface of the tumor cell, and T-cell killing directed against the tumor cell is induced. In some embodiments, T-cell killing directed against the tumor cell is enhanced. In some embodiments, T-cell killing directed against the tumor cell is increased.

In some embodiments, a method of increasing an immune response in a subject comprises administering to the subject a therapeutically effective amount of a non-mutated protein epitope therapeutic described herein, wherein the agent is an antibody that specifically binds the non-mutated protein epitope described herein. In some embodiments, a method of increasing an immune response in a subject comprises administering to the subject a therapeutically effective amount of the antibody.

The present invention provides methods of redirecting an existing immune response to a tumor. In some embodiments, a method of redirecting an existing immune response to a tumor comprises administering to a subject a therapeutically effective amount of a non-mutated protein epitope therapeutic described herein. In some embodiments, the existing immune response is against a virus. In some embodiments, the virus is selected from the group consisting of: measles virus, varicella-zoster virus (VZV; chickenpox virus), influenza virus, mumps virus, poliovirus, rubella virus, rotavirus, hepatitis A virus (HAV), hepatitis B virus (HBV), Epstein Barr virus (EBV), and cytomegalovirus (CMV). In some embodiments, the virus is varicella-zoster virus. In some embodiments, the virus is cytomegalovirus. In some embodiments, the virus is measles virus. In some embodiments, the existing immune response has been acquired after a natural viral infection. In some embodiments, the existing immune response has been acquired after vaccination against a virus. In some embodiments, the existing immune response is a cell-mediated response. In some embodiments, the existing immune response comprises cytotoxic T-cells (CTLs) or HTLs.

In some embodiments, a method of redirecting an existing immune response to a tumor in a subject comprises administering a fusion protein comprising (i) an antibody that specifically binds a non-mutated protein epitope and (ii) at least one non-mutated protein epitope peptide described herein, wherein (a) the fusion protein is internalized by a tumor cell after binding to the tumor-associated antigen; (b) the non-mutated protein epitope peptide is processed and presented on the surface of the tumor cell associated with a MHC class I molecule; and (c) the non-mutated protein epitope peptide/MHC Class I complex is recognized by cytotoxic T-cells. In some embodiments, the cytotoxic T-cells are memory T-cells. In some embodiments, the memory T-cells are the result of a vaccination with the non-mutated protein epitope peptide.

The present invention provides methods of increasing the immunogenicity of a tumor. In some embodiments, a method of increasing the immunogenicity of a tumor comprises contacting the tumor or tumor cells with an effective amount of a non-mutated protein epitope therapeutic described herein. In some embodiments, a method of increasing the immunogenicity of a tumor comprises administering to a subject a therapeutically effective amount of a non-mutated protein epitope therapeutic described herein.

The present invention also provides methods for inhibiting growth of a tumor using a non-mutated protein epitope therapeutic described herein. In certain embodiments, a method of inhibiting growth of a tumor comprises contacting a cell mixture with a non-mutated protein epitope therapeutic in vitro. For example, an immortalized cell line or a cancer cell line mixed with immune cells (e.g., T-cells) is cultured in medium to which a non-mutated protein epitope peptide is added. In some embodiments, tumor cells are isolated from a patient sample such as, for example, a tissue biopsy, pleural effusion, or blood sample, mixed with immune cells (e.g., T-cells), and cultured in medium to which an antigen therapeutic is added. In some embodiments, a non-mutated protein epitope therapeutic increases, promotes, and/or enhances the activity of the immune cells. In some embodiments, a non-mutated protein epitope therapeutic inhibits tumor cell growth. In some embodiments, a non-mutated protein epitope therapeutic activates killing of the tumor cells.

In certain embodiments, the subject is a human. In certain embodiments, the subject has a tumor or the subject had a tumor which was at least partially removed.

In some embodiments, a method of inhibiting growth of a tumor comprises redirecting an existing immune response to a new target, comprising administering to a subject a therapeutically effective amount of a non-mutated protein epitope therapeutic, wherein the existing immune response is against an antigenic peptide delivered to the tumor cell by the non-mutated protein epitope peptide.

In certain embodiments, the tumor comprises cancer stem cells. In certain embodiments, the frequency of cancer stem cells in the tumor is reduced by administration of the non-mutated protein epitope therapeutic. In some embodiments, a method of reducing the frequency of cancer stem cells in a tumor in a subject, comprising administering to the subject a therapeutically effective amount of a non-mutated protein epitope therapeutic is provided.

In addition, in some aspects the invention provides a method of reducing the tumorigenicity of a tumor in a subject, comprising administering to the subject a therapeutically effective amount of a non-mutated protein epitope therapeutic described herein. In certain embodiments, the tumor comprises cancer stem cells. In some embodiments, the tumorigenicity of a tumor is reduced by reducing the frequency of cancer stem cells in the tumor. In some embodiments, the methods comprise using the non-mutated protein epitope therapeutic described herein. In certain embodiments, the frequency of cancer stem cells in the tumor is reduced by administration of a non-mutated protein epitope therapeutic described herein.

In some embodiments, the tumor is a solid tumor. In certain embodiments, the tumor is a tumor selected from the group consisting of: colorectal tumor, pancreatic tumor, lung tumor, ovarian tumor, liver tumor, breast tumor, kidney tumor, prostate tumor, neuroendocrine tumor, gastrointestinal tumor, melanoma, cervical tumor, bladder tumor, glioblastoma, and head and neck tumor. In certain embodiments, the tumor is a colorectal tumor. In certain embodiments, the tumor is an ovarian tumor. In some embodiments, the tumor is a breast tumor. In some embodiments, the tumor is a lung tumor. In certain embodiments, the tumor is a pancreatic tumor. In certain embodiments, the tumor is a melanoma tumor. In some embodiments, the tumor is a solid tumor.

The present invention further provides methods for treating cancer in a subject comprising administering to the subject a therapeutically effective amount of a non-mutated protein epitope therapeutic described herein.

In some embodiments, a method of treating cancer comprises redirecting an existing immune response to a new target, the method comprising administering to a subject a therapeutically effective amount of non-mutated protein epitope therapeutic, wherein the existing immune response is against an antigenic peptide delivered to the cancer cell by the non-mutated protein epitope peptide.

The present invention provides for methods of treating cancer comprising administering to a subject a therapeutically effective amount of a non-mutated protein epitope therapeutic described herein (e.g., a subject in need of treatment). In certain embodiments, the subject is a human. In certain embodiments, the subject has a cancerous tumor. In certain embodiments, the subject has had a tumor at least partially removed.

In certain embodiments, the cancer is a cancer selected from the group consisting of colorectal cancer, renal cancer, pancreatic cancer, lung cancer, ovarian cancer, liver cancer, breast cancer, kidney cancer, prostate cancer, gastrointestinal cancer, melanoma, cervical cancer, neuroendocrine cancer, bladder cancer, glioblastoma, triple-negative breast cancer (TNBC), smoldering myeloma (SMM), and head and neck cancer. In certain embodiments, the cancer is pancreatic cancer. In certain embodiments, the cancer is ovarian cancer. In certain embodiments, the cancer is colorectal cancer. In certain embodiments, the cancer is breast cancer. In certain embodiments, the cancer is prostate cancer. In certain embodiments, the cancer is lung cancer. In certain embodiments, the cancer is melanoma. In some embodiments, the cancer is a solid cancer. In some embodiments, the cancer comprises a solid tumor.

In some embodiments, the cancer is a hematologic cancer. In some embodiment, the cancer is selected from the group consisting of: acute myelogenous leukemia (AML), Hodgkin lymphoma, multiple myeloma, T-cell acute lymphoblastic leukemia (T-ALL), chronic lymphocytic leukemia (CLL), hairy cell leukemia, chronic myelogenous leukemia (CML), non-Hodgkin lymphoma, diffuse large B-cell lymphoma (DLBCL), mantle cell lymphoma (MCL), and cutaneous T-cell lymphoma (CTCL).

In some embodiments, the non-mutated protein epitope therapeutic is administered as a combination therapy. Combination therapy with two or more therapeutic agents uses agents that work by different mechanisms of action, although this is not required. Combination therapy using agents with different mechanisms of action can result in additive or synergetic effects. Combination therapy can allow for a lower dose of each agent than is used in monotherapy, thereby reducing toxic side effects and/or increasing the therapeutic index of the agent(s). Combination therapy can decrease the likelihood that resistant cancer cells will develop. In some embodiments, combination therapy comprises a therapeutic agent that affects the immune response (e.g., enhances or activates the response) and a therapeutic agent that affects (e.g., inhibits or kills) the tumor/cancer cells.

In some embodiments, the combination of an agent described herein and at least one additional therapeutic agent results in additive or synergistic results. In some embodiments, the combination therapy results in an increase in the therapeutic index of the agent. In some embodiments, the combination therapy results in an increase in the therapeutic index of the additional therapeutic agent(s). In some embodiments, the combination therapy results in a decrease in the toxicity and/or side effects of the agent. In some embodiments, the combination therapy results in a decrease in the toxicity and/or side effects of the additional therapeutic agent(s).

In certain embodiments, in addition to administering a non-mutated protein epitope therapeutic described herein, the method or treatment further comprises administering at least one additional therapeutic agent. An additional therapeutic agent can be administered prior to, concurrently with, and/or subsequently to, administration of the agent. In some embodiments, the at least one additional therapeutic agent comprises 1, 2, 3, or more additional therapeutic agents.

Therapeutic agents that can be administered in combination with the non-mutated protein epitope therapeutic described herein include chemotherapeutic agents. Thus, in some embodiments, the method or treatment involves the administration of an agent described herein in combination with a chemotherapeutic agent or in combination with a cocktail of chemotherapeutic agents. Treatment with an agent can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in The Chemotherapy Source Book, 4th Edition, 2008, M. C. Perry, Editor, Lippincott, Williams & Wilkins, Philadelphia, PA.

Useful classes of chemotherapeutic agents include, for example, anti-tubulin agents, auristatins, DNA minor groove binders, DNA replication inhibitors, alkylating agents (e.g., platinum complexes such as cisplatin, mono(platinum), bis (platinum) and tri-nuclear platinum complexes and carboplatin), anthracyclines, antibiotics, anti-folates, antimetabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In certain embodiments, the second therapeutic agent is an alkylating agent, an antimetabolite, an antimitotic, a topoisomerase inhibitor, or an angiogenesis inhibitor.

Chemotherapeutic agents useful in the instant invention include, but are not limited to, alkylating agents such as thiotepa and cyclosphosphamide (CYTOXAN); alkyl sulfonates such as busulfan, improsulfan and piposulfan; aziridines such as benzodopa, carboquone, meturedopa, and uredepa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT11; topoisomerase inhibitor RFS 2000; difluoromethylomithine (DMFO); retinoic acid; esperamicins; capecitabine (XELODA); and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4 hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above. In certain embodiments, the additional therapeutic agent is cisplatin. In certain embodiments, the additional therapeutic agent is carboplatin.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In some embodiments, the additional therapeutic agent is irinotecan.

In certain embodiments, the chemotherapeutic agent is an anti-metabolite. An anti-metabolite is a chemical with a structure that is similar to a metabolite utilized for normal biochemical reactions, yet different enough to interfere with one or more normal functions of cells, such as cell division. Anti-metabolites include, but are not limited to, gemcitabine, fluorouracil, capecitabine, methotrexate sodium, raltitrexed, pemetrexed, tegafur, cytosine arabinoside, thioguanine, 5-azacytidine, 6 mercaptopurine, azathioprine, 6-thioguanine, pentostatin, fludarabine phosphate, and cladribine, as well as pharmaceutically acceptable salts, acids, or derivatives of any of these. In certain embodiments, the additional therapeutic agent is gemcitabine.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (ABRAXANE), DHA-paclitaxel, or PG-paclitaxel. In certain alternative embodiments, the antimitotic agent comprises a vinca alkaloid, such as vincristine, vinblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In certain embodiments, the additional therapeutic agent is paclitaxel. In some embodiments, the additional therapeutic agent is albumin-bound paclitaxel.

In some embodiments, an additional therapeutic agent comprises an agent such as a small molecule. For example, treatment can involve the combined administration of an agent of the present invention with a small molecule that acts as an inhibitor against tumor-associated antigens including, but not limited to, EGFR, HER2 (ErbB2), and/or VEGF. In some embodiments, an agent is administered in combination with a protein kinase inhibitor selected from the group consisting of: gefitinib (IRESSA), erlotinib (TARCEVA), sunitinib (SUTENT), lapatanib, vandetanib (ZACTIMA), AEE788, CI-1033, cediranib (RECENTIN), sorafenib (NEXAVAR), and pazopanib (GW786034B). In some embodiments, an additional therapeutic agent comprises an mTOR inhibitor. In another embodiment, the additional therapeutic agent is chemotherapy or other inhibitors that reduce the number of Treg cells. In certain embodiments, the therapeutic agent is cyclophosphamide or an anti-CTLA4 antibody. In another embodiment, the additional therapeutic reduces the presence of myeloid-derived suppressor cells. In a further embodiment, the additional therapeutic is carbotaxol. In another embodiment, the additional therapeutic agent shifts cells to a T helper 1 response. In a further embodiment, the additional therapeutic agent is ibrutinib.

In some embodiments, an additional therapeutic agent comprises a biological molecule, such as an antibody. For example, treatment can involve the combined administration of an agent of the present invention with antibodies against tumor-associated antigens including, but not limited to, antibodies that bind EGFR, HER2/ErbB2, and/or VEGF. In certain embodiments, the additional therapeutic agent is an antibody specific for a cancer stem cell marker. In certain embodiments, the additional therapeutic agent is an antibody that is an angiogenesis inhibitor (e.g., an anti-VEGF or VEGF receptor antibody). In certain embodiments, the additional therapeutic agent is bevacizumab (AVASTIN), ramucirumab, trastuzumab (HERCEPTIN), pertuzumab (OMNITARG), panitumumab (VECTIBIX), nimotuzumab, zalutumumab, or cetuximab (ERBITUX).

In certain embodiments, an additional therapeutic agent comprises a second immunotherapeutic agent. In some embodiments, the additional immunotherapeutic agent includes, but is not limited to, a colony stimulating factor, an interleukin, an antibody that blocks immunosuppressive functions (e.g., an anti-CTLA-4 antibody, anti-CD28 antibody, anti-CD3 antibody, anti-PD-1 antibody, anti-PD-L1 antibody, anti-TIGIT antibody), an antibody that enhances immune cell functions (e.g., an anti-GITR antibody, an anti-OX-40 antibody, an anti-CD40 antibody, or an anti-4-1BB antibody), a toll-like receptor (e.g., TLR4, TLR7, TLR9), a soluble ligand (e.g., GITRL, GITRL-Fc, OX-40L, OX-40L-Fc, CD40L, CD40L-Fc, 4-1BB ligand, or 4-1BB ligand-Fc), or a member of the B7 family (e.g., CD80, CD86). In some embodiments, the additional immunotherapeutic agent targets CTLA-4, CD28, CD3, PD-1, PD-L1, TIGIT, GITR, OX-40, CD-40, or 4-1BB.

In some embodiments, the additional therapeutic agent is an immune checkpoint inhibitor. In some embodiments, the immune checkpoint inhibitor is an anti-PD-1 antibody, an anti-PD-L1 antibody, an anti-CTLA-4 antibody, an anti-CD28 antibody, an anti-TIGIT antibody, an anti-LAG3 antibody, an anti-TIM3 antibody, an anti-GITR antibody, an anti-4-1BB antibody, or an anti-OX-40 antibody. In some embodiments, the additional therapeutic agent is an anti-TIGIT antibody. In some embodiments, the additional therapeutic agent is an anti-PD-1 antibody selected from the group consisting of: nivolumab (OPDIVO), pembrolizumab (KEYTRUDA), pidilizumab, MEDI0680, REGN2810, BGB-A317, and PDR001. In some embodiments, the additional therapeutic agent is an anti-PD-L1 antibody selected from the group consisting of: BMS935559 (MDX-1105), atezolizumab (MPDL3280A), durvalumab (MEDI4736), and avelumab (MSB0010718C). In some embodiments, the additional therapeutic agent is an anti-CTLA-4 antibody selected from the group consisting of: ipilimumab (YERVOY) and tremelimumab. In some embodiments, the additional therapeutic agent is an anti-LAG-3 antibody selected from the group consisting of: BMS-986016 and LAG525. In some embodiments, the additional therapeutic agent is an anti-OX-40 antibody selected from the group consisting of: MED16469, MED10562, and MOXR0916. In some embodiments, the additional therapeutic agent is an anti-4-1BB antibody selected from the group consisting of: PF-05082566.

In some embodiments, the non-mutated protein epitope therapeutic can be administered in combination with a biologic molecule selected from the group consisting of: adrenomedullin (AM), angiopoietin (Ang), BMPs, BDNF, EGF, erythropoietin (EPO), FGF, GDNF, granulocyte colony stimulating factor (G-CSF), granulocyte-macrophage colony stimulating factor (GM-CSF), macrophage colony stimulating factor (M-CSF), stem cell factor (SCF), GDF9, HGF, HDGF, IGF, migration-stimulating factor, myostatin (GDF-8), NGF, neurotrophins, PDGF, thrombopoietin, TGF-α, TGF-β, TNF-α, VEGF, P1GF, gamma-IFN, IL-1, IL-2, IL-3, IL-4, IL-5, IL-6, IL-7, IL-12, IL-15, and IL-18.

In some embodiments, treatment with a non-mutated protein epitope therapeutic described herein can be accompanied by surgical removal of tumors, removal of cancer cells, or any other surgical therapy deemed necessary by a treating physician.

In certain embodiments, treatment involves the administration of a non-mutated protein epitope therapeutic described herein in combination with radiation therapy. Treatment with an agent can occur prior to, concurrently with, or subsequent to administration of radiation therapy. Dosing schedules for such radiation therapy can be determined by the skilled medical practitioner.

Combined administration can include co-administration, either in a single pharmaceutical formulation or using separate formulations, or consecutive administration in either order but generally within a time period such that all active agents can exert their biological activities simultaneously.

It will be appreciated that the combination of a non-mutated protein epitope therapeutic described herein and at least one additional therapeutic agent can be administered in any order or concurrently. In some embodiments, the agent will be administered to patients that have previously undergone treatment with a second therapeutic agent. In certain other embodiments, the non-mutated protein epitope therapeutic and a second therapeutic agent will be administered substantially simultaneously or concurrently. For example, a subject can be given an agent while undergoing a course of treatment with a second therapeutic agent (e.g., chemotherapy). In certain embodiments, a non-mutated protein epitope therapeutic will be administered within 1 year of the treatment with a second therapeutic agent. It will further be appreciated that the two (or more) agents or treatments can be administered to the subject within a matter of hours or minutes (i.e., substantially simultaneously).

For the treatment of a disease, the appropriate dosage of a non-mutated protein epitope therapeutic described herein depends on the type of disease to be treated, the severity and course of the disease, the responsiveness of the disease, whether the agent is administered for therapeutic or preventative purposes, previous therapy, the patient's clinical history, and so on, all at the discretion of the treating physician. The non-mutated protein epitope therapeutic can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual agent. The administering physician can determine optimum dosages, dosing methodologies, and repetition rates.

In some embodiments, a non-mutated protein epitope therapeutic can be administered at an initial higher "loading" dose, followed by one or more lower doses. In some embodiments, the frequency of administration can also change. In some embodiments, a dosing regimen can comprise administering an initial dose, followed by additional doses (or "maintenance" doses) once a week, once every two weeks, once every three weeks, or once every month. For example, a dosing regimen can comprise administering an initial loading dose, followed by a weekly maintenance dose of, for example, one-half of the initial dose. Or a dosing regimen can comprise administering an initial loading dose, followed by maintenance doses of, for example one-half of the initial dose every other week. Or a dosing regimen can comprise administering three initial doses for 3 weeks, followed by maintenance doses of, for example, the same amount every other week.

As is known to those of skill in the art, administration of any therapeutic agent can lead to side effects and/or toxicities. In some cases, the side effects and/or toxicities are so severe as to preclude administration of the particular agent at a therapeutically effective dose. In some cases, therapy must be discontinued, and other agents can be tried. However, many agents in the same therapeutic class display similar side effects and/or toxicities, meaning that the patient either has to stop therapy, or if possible, suffer from the unpleasant side effects associated with the therapeutic agent.

In some embodiments, the dosing schedule can be limited to a specific number of administrations or "cycles". In some embodiments, the agent is administered for 3, 4, 5, 6, 7, 8, or more cycles. For example, the agent is administered every 2 weeks for 6 cycles, the agent is administered every 3 weeks for 6 cycles, the agent is administered every 2 weeks for 4 cycles, the agent is administered every 3 weeks for 4 cycles, etc. Dosing schedules can be decided upon and subsequently modified by those skilled in the art.

The present invention provides methods of administering to a subject a non-mutated protein epitope therapeutic described herein comprising using an intermittent dosing strategy for administering one or more agents, which can reduce side effects and/or toxicities associated with administration of an agent, chemotherapeutic agent, etc. In some embodiments, a method for treating cancer in a human subject comprises administering to the subject a therapeutically effective dose of a non-mutated protein epitope therapeutic in combination with a therapeutically effective dose of a chemotherapeutic agent, wherein one or both of the agents are administered according to an intermittent dosing strategy. In some embodiments, a method for treating cancer in a human subject comprises administering to the subject a therapeutically effective dose of a non-mutated protein epitope therapeutic in combination with a therapeutically effective dose of a second immunotherapeutic agent, wherein one or both of the agents are administered according to an intermittent dosing strategy. In some embodiments, the intermittent dosing strategy comprises administering an initial dose of a non-mutated protein epitope therapeutic to the subject, and administering subsequent doses of the agent about once every 2 weeks. In some embodiments, the intermittent dosing strategy comprises administering an initial dose of a non-mutated protein epitope therapeutic to the subject, and administering subsequent doses of the agent about once every 3 weeks. In some embodiments, the intermittent dosing strategy comprises administering an initial dose of a non-mutated protein epitope therapeutic to the subject, and administering subsequent doses of the agent about once every 4 weeks. In some embodiments, the agent is administered using an intermittent dosing strategy and the additional therapeutic agent is administered weekly.

The present invention provides compositions comprising the non-mutated protein epitope therapeutic described herein. The present invention also provides pharmaceutical compositions comprising a non-mutated protein epitope therapeutic described herein and a pharmaceutically acceptable vehicle. In some embodiments, the pharmaceutical compositions find use in immunotherapy. In some embodiments, the compositions find use in inhibiting tumor growth. In some embodiments, the pharmaceutical compositions find use in inhibiting tumor growth in a subject (e.g., a human patient). In some embodiments, the compositions find use in treating cancer. In some embodiments, the pharmaceutical compositions find use in treating cancer in a subject (e.g., a human patient).

Formulations are prepared for storage and use by combining an antigen therapeutic of the present invention with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition. Exemplary formulations are listed in WO 2015/095811.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (Remington: The Science and Practice of Pharmacy, 22st Edition, 2012, Pharmaceutical Press, London). In one embodiment, the vehicle is 5% dextrose in water.

The pharmaceutical compositions described herein can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

The therapeutic formulation can be in unit dosage form. Such formulations include tablets, pills, capsules, powders, granules, solutions or suspensions in water or non-aqueous media, or suppositories.

The non-mutated protein epitope peptides described herein can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in Remington: The Science and Practice of Pharmacy, 22st Edition, 2012, Pharmaceutical Press, London.

In certain embodiments, pharmaceutical formulations include a non-mutated protein epitope therapeutic described herein complexed with liposomes. Methods to produce liposomes are known to those of skill in the art. For example, some liposomes can be generated by reverse phase evaporation with a lipid composition comprising phosphatidyl-choline, cholesterol, and PEG-derivatized phosphatidylethanolamine (PEG-PE). Liposomes can be extruded through filters of defined pore size to yield liposomes with the desired diameter.

In certain embodiments, sustained-release preparations comprising the non-mutated protein epitope peptides described herein can be produced. Suitable examples of sustained-release preparations include semi-permeable matrices of solid hydrophobic polymers containing an agent, where the matrices are in the form of shaped articles (e.g., films or microcapsules). Examples of sustained-release matrices include polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

VIII. Kits

The non-mutated protein epitope therapeutic described herein can be provided in kit form together with instructions for administration. Typically the kit would include the desired antigen therapeutic in a container, in unit dosage form and instructions for administration. Additional therapeutics, for example, cytokines, lymphokines, checkpoint inhibitors, antibodies, can also be included in the kit. Other kit components that can also be desirable include, for example, a sterile syringe, booster dosages, and other desired excipients.

The invention will be described in greater detail by way of specific examples. The following examples are offered for illustrative purposes, and are not intended to limit the invention in any manner. Those of skill in the art will readily recognize a variety of non-critical parameters that can be changed or modified to yield alternative embodiments according to the invention. All patents, patent applications, and printed publications listed herein are incorporated herein by reference in their entirety.

EXAMPLES

Example 1: Identification of Mutant Sequences with Immunogenic Potential

Applicants have discovered that the following epitopes are recurrent in cancer patients.

TABLE 1

| ERV element (nomenclature see: ncbi.nlm.nih.gov/ pmc/articles/ PMC3113919/) | Translated Sequence | SEQ ID NO: |
|---|---|---|
| ERVH-2: retroviral matrix | MGNLPPSIPPSPLACVLKNLKPLQLTPDLKPKCLIFFCNTAWPQYKLDN GSKWPENGTFDFSILQDLNNSCRKMGKWSEVPDVQAFFYTSVPS | 5 |
| ERVH48-1: coat protein | MPNRAIRLQAVLEIITNQTASALEMLAQQQNQMRAAIYQNRLALDYLL AEEGAGCGKFNISNCCLNIGNNGEEVLEIASNIRKVARVPVQTWEGWD PANLLGGWFSNLGGFKMLVGTVIFITGVLLFLPCGIPLKLLLKLQLTS | 6 |
| ERVH48-1: syncytin | MACIYPTTFYTSLPTKSLNMGISLTTILILSVAVLLSTAAPPSCRE-CYQSL HYRGEMQQYFTYHTHIERSCYGNLIEECVESGKSYYKVKNLGVCGSRN GAICPRGKQWLCFTKIGQWGVNTQVLEDIKREQIIAKAKASKPTTPPEN RPRHFHSFIQKL | 7 |
| ERVH-2: gag | MARSAATLRRFTALDPKRSKGRLILNIHFITQSAPDIK | 8 |
| ERVE-4: reverse transcriptase | RLFLTKPGKEIGPALAQWWPKVCAEDNPPGLAVNQAPVLREVKPEAQ PVRQNQYPVPREALEGIQVHLKHLRTFGIIVPCQSPWNTPLLPVPKPGT KDYRPVQDLRLVNQATVTFHPTVPNPYTLLGLLPAKDSWFTCLDLKD AFFSIRLAPESQKLFAFQWEDPGSGVTTHYTWTRLPQGFKNFPHHLWG GTGSRPPKVSCQRPRLRVVPVHRQPPAGTPHGSRVRQRNRRPASAPGG LWV | 9 |
| ERVE-4: reverse transcriptase | MAVGCVKGTDALLQHLEDYGYKVSKKKAQICRQQVRYLGFTIRQREC SLGSERKQVICNLLEPKTRRQLRELLGAVGFCRLWIPNFAVLAKPLVPS YKGG | 10 |
| ERVE-4: protease | NADLLAAAIRGVPLKGQGNGGSRKNTQSDRPRLQRNQCAYCKETGH WKDKCPQLKEKQGGSEQKTPDKDEGALFNLAEGLLDRRGPGSRAPKE PMVRMTVGGKDIKFLVNTGAEHSVVTTPVAPLSKKAIDIIGATGVLTK QAFCLPRTCSVGGHEVIHQFLYIPDCPLPLLGRDLLSKLRAIFLYQARLF TTEVAWNRSYHGPDSSPRGRVATLPNQTRQRDRASSGPVVAKSMRRR QPSWIGSQSSSCTQGS | 11 |

TABLE 1-continued

| ERV element (nomenclature see: ncbi.nlm.nih.gov/ pmc/articles/ PMC3113919/) | Translated Sequence | SEQ ID NO: |
|---|---|---|
| ERVE-4: unknown | SLFLHKTSVREVLSATIPATFLGSLTWKRGD | 12 |
| ERVK-5: gag, env, pol | MQNEAIEQVRAICLRAWGKIQDPGTAFPINSIRQGSKEPYPDFVARLQD AAQKSITDDNARKVIVELMAYENANPECQSAIKPLKGKVPAGVDVITE YVKACDGIGGAMHKAMLMAQAMRGLTLGGQVRTFGKKCYNCGQIG HLKRSCPVLNKQNIINQAITAKNKKPSGLCPKCGKGKHWANQCHSKFD KDGQPLSGNRKRGQPQAPQQTGAFPVQLFVPQGFQGQQPLQKIPPLQG VSQLQQSNSCPAPQQAAPQ | 13 |
| ERVI-1: envelope | MEWIKYSICTLNKSNCYACAHGRPEAQIVPFPLRWSSSRPSMGCMVAL FQDSTAWGNISCQALSLLYPEVQHPAGQPPRAIQLPSPNVSFISCLS | 14 |

For each epitope, the full-length amino acid sequence of the non-mutated protein epitope was derived. Any constituent 9mer or 10mer not found in the germline protein sequence was flagged and scored for binding potential on six common HLA alleles (HLA-A01:01, HLA-A02:01. HLA-A03:01, HLA-A24:02, HLA-1B07:02, and HLA-1B08:01) using available algorithms. Any peptide scoring better than 1000 nM was nominated.

TABLE 2

| ERV element (nomenclature see: http://www.ncbi.nlm. nih.gov/pmc/articles/ PMC3113919/) | Translated Sequence | SEQ ID NO: |
|---|---|---|
| ERVH-2: retroviral matrix | MGNLPPSIPPSPLACVLKNLKPLQLTPDLKPKCLIFFCNTAWPQYKLD NGSKWPENGTFDFSILQDLNNSCRKMGKWSEVPDVQAFFYTSVPS | 5 |
| ERVH48-1: coat protein | MPNRAIRLQAVLEIITNQTASALEMLAQQQNQMRAAIYQNRLALDY LLAEEGAGCGKFNISNCCLNIGNNGEEVLEIASNIRKVARVPVQTWE GWDPANLLGGWFSNLGGFKMLVGTVIFITGVLLFLPCGIPLKLLLKL QLTS | 6 |
| ERVH48-1: syncytin | MACIYPTTFYTSLPTKSLNMGISLTTILILSVAVLLSTAAPPSCRECYQS LHYRGEMQQYFTYHTHIERSCYGNLIEECVESGKSYYKVKNLGVCG SRNGAICPRGKQWLCFTKIGQWGVNTQVLEDIKREQIIAKAKASKPT TPPENRPRHFHSFIQKL | 7 |
| ERVH-2: gag | MARSAATLRRFTALDPKRSKGRLILNIHFITQSAPDIK | 8 |
| ERVE-4: reverse transcriptase | RLFLTKPGKEIGPALAQWWPKVCAEDNPPGLAVNQAPVLREVKPEA QPVRQNQYPVPREALEGIQVHLKHLRTFGIIVPCQSPWNTPLLPVPKP GTKDYRPVQDLRLVNQATVTFHPTVPNPYTLLGLLPAKDSWFTCLD LKDAFFSIRLAPESQKLFAFQWEDPGSGVTTHYTWTRLPQGFKNFPH HLWGGTGSRPPKVSCQRPRLRVVPVHRQPPAGTPHGSRVRQRNRRP ASAPGGLWV | 9 |
| ERVE-4: reverse transcriptase | MAVGCVKGTDALLQHLEDYGYKVSKKKAQICRQQVRYLGFTIRQR ECSLGSERKQVICNLLEPKTRRQLRELLGAVGFCRLWIPNFAVLAKPL VPSYKGG | 10 |
| ERVE-4: protease | NADLLAAAIRGVPLKGQGNGGSRKNTQSDRPRLQRNQCAYCKETGH WKDKCPQLKEKQGGSEQKTPDKDEGALFNLAEGLLDRRGPGSRAPK EPMVRMTVGGKDIKFLVNTGAEHSVVTTPVAPLSKKAIDIIGATGVL TKQAFCLPRTCSVGGHEVIHQFLYIPDCPLPLLGRDLLSKLRAIFLYQ ARLFTTEVAWNRSYHGPDSSPRGRVATLPNQTRQRDRASSGPVVAK SMRRRQPSWIGSQSSSCTQGS | 11 |
| ERVE-4: unknown | SLFLHKTSVREVLSATIPATFLGSLTWKRGD | 12 |
| ERVK-5: gag, env, pol | MQNEAIEQVRAICLRAWGKIQDPGTAFPINSIRQGSKEPYPDFVARLQ DAAQKSITDDNARKVIVELMAYENANPECQSAIKPLKGKVPAGVDVI TEYVKACDGIGGAMHKAMLMAQAMRGLTLGGQVRTFGKKCYNCG QIGHLKRSCPVLNKQNIINQAITAKNKKPSGLCPKCGKGKHWANQC HSKFDKDGQPLSGNRKRGQPQAPQQTGAFPVQLFVPQGFQGQQPLQ KIPPLQGVSQLQQSNSCPAPQQAAPQ | 13 |
| ERVI-1: envelope | MEWIKYSICTLNKSNCYACAHGRPEAQIVPFPLRWSSSRPSMGCMVA LFQDSTAWGNISCQALSLLYPEVQHPAGQPPRAIQLPSPNVSFISCLS | 14 |

TABLE 3

| Over-expressed gene | UCSC ID | Full Sequence | SEQ ID NO: |
|---|---|---|---|
| TYR | uc001pcs.3 | MLLAVLYCLLWSFQTSAGHFPRACVSSKNLMEKECCPPWSGDRSP CGQLSGRGSCQNILLSNAPLGPQFPFTGVDDRESWPSVFYNRTCQC SGNFMGFNCGNCKFGFWGPNCTERRLLVRRNIFDLSAPEKDKFFAY LTLAKHTISSDYVIPIGTYGQMKNGSTPMFNDINIYDLFVWMHYYV SMDALLGGSEIWRDIDFAHEAPAFLPWHRLFLLRWEQEIQKLTGDE NFTIPYWDWRDAEKCDICTDEYMGGQHPTNPNLLSPASFFSSWQIV CSRLEEYNSHQSLCNGTPEGPLRRNPGNHDKSRTPRLPSSADVEFCL SLTQYESGSMDKAANFSFRNTLEGFASPLTGIADASQSSMHNALHI YMNGTMSQVQGSANDPIFLLHHAFVDSIFEQWLRRHRPLQEVYPE ANAPIGHNRESYMVPFIPLYRNGDFFISSKDLGYDYSYLQDSDPDSF QDYIKSYLEQASRIWSWLLGAAMVGAVLTALLAGLVSLLCRHKRK QLPEEKQPLLMEKEDYHSLYQSHL | 15 |
| MAGEC1 | uc004fbt.3 | MGDKDMPTAGMPSLLQSSSESPQSCPEGEDSQSLPQIPQSSPESDDT LYPLQSPQSRSEGEDSSDPLQRPPEGKDSQSLPQIPQSSPEGDDTQSP LQNSQSSPEGKDSLSPLEISQSPPEGEDVQSPLQNPASSFFSSALLSIF QSSPESTQSPFEGFPQSVLQIPVSAASSSTLVSIFQSSPESTQSPFEGFP QSSPLQIPVSRSFSSTLLSIFQSSPERTQST-FEGFAQSPLQIPVSPSSSSTL LSLFQSFSERTQSTFEGFAQSSLQIPVSPSFSSTLVSLFQSSPERTQSTF EGFPQSPLQIPVSSSSSSTLLSLFQSSPERTHSTFEGFPQSLLQIPMTSS FSSTLLSIFQSSPESAQST-FEGFPQSSPLQIPGSPSFSSTLLSLFQSSPERT HSTFEGFPQSPLQIPMTSSFSSTLLSILQSSPESAQSAFEGFPQSPLQIP VSSSFSYTLLSLFQSSPERTHSTFEGFPQSPLQIPVSSSSSSSTLLSLFQ SSPECTQSTFEGFPQSPLQIPQSPPEGENTHSPLQIVPSLPEWEDSLSP HYFPQSPPQGEDSLSPHYFPQSPPQGEDSLSPHYFPQSPQGEDSLSPH YFPQSPPQGEDSMSPLYFPQSPLQGEEFQSSLQSPVSICSSSTPSSLPQ SFPESSQSSPPEGPVQSPLHSPQSPPEGMHSQSPLQSPESAPEGEDSLSP LQIPQSPLEGEDSLSSLHFPQSPPEWEDSLSPLHFPQFPPQGEDFQSSL QSPVSICSSSTSLSLPQSFPESPQSPPEGPAQSPLQRPVSSFFSYTLASL LQSSHESPQSPPEGPAQSPLQSPVSSFPSSTSSSLSQSSPVSSFPSSTSS SLSKSSPESPLQSPVISFSSSTSLSPF-SEEESSSPVDEYTSSSDTLLESDSL TDSESLIESEPLFTYTLDEKVDELARFLLLKYQVKQPITKAEMLTNVI SRYTGYFPVIFRKAREFIEILFGISLREVDPDDSYVFVNTLDLTSEGCL SDEQGMSQNRLLILILSIIFIKGTYASEEVIWDVLSGIGVRAGREHFA FGEPRELLTKVWVQEHYLEYREVPNSSPPRYEFLWGPRAHSEVIKR KVVEFLAMLKNTVPITFPSSYKDALKDVEERAQAIIDTTDDSTATES ASSSVMSPSFSSE | 16 |
| MAGEA10 | uc022cgz.1 | MPRAPKRQRCMPEEDLQSQSETQGLEGAQAPLAVEEDASSSTSTSS SFPSSFPSSSSSSSSSSCYPLIPSTPEEVSADDETPNPPQSAQIACSSPSV VASLPLDQSDEGSSSQKEESPSTLQVLPDSESLPRSEIDEKVTDLVQF LLFKYQMKEPITKAEILESVIRNYEDHFPLLFSEASECMLLVFGIDVK EVDPTGHSFVLVTSLGLTYDGMLSDVQSMPKTGILILILSIVFIEGYC TPEEVIWEALNMMGLYDGMEHLIYGEPRKLLTQDWVQENYLEYR QVPGSDPARYEFLWGPRAHAEIRKMSLLKFLAKVNGSDPRSFPLW YEEALKDEEERAQDRIATTDDTTAMASASSSATGSFSYPE | 17 |
| MAGEB17 | uc031tgu.1 | MPRGQASKRRAREKRRQARGEDQCLGGAQATAAEKEKLPSSSSPA CQSPPQSFPNAGIPQESQRASYPSSPASAVSLTSSDEGAKGQKGESP NSFHGPSSSESTGRDLLNTKTGELVQFLLNKYIRKEPITREAMLKVI NRKYQHFPEILRRSTENVEVVFGLYLKEMDPSRQSYVLVGKLDFP NQGSLSDGGGFPPLSGLLMVLLSTIFMHGNRATEEEMWECLNALGM YKGRKHFIYGEPQELVTKDLVREGYLEYQQVPSSDPPRYEFLWGPR ARAETSKMKVLEFVAKLNDTVASTYKSRYEEALREEEEQARARAV ARDSARARASRSFQP | 18 |
| MAGEA4 | uc022cgu.1 | MLPLSVGLWVPIAQLLPALLPAALTRVIMSSEQKSQHCKPEEGVEA QEEALGLVGAQAPTTEEQEAAVSSSSPLVPGTLEEVPAAESAGPPQS PQGASALPTTISFTCWRQPNEGSSSQEEEGPSTSPDAESLFREALSNK VDELAHFLLRKYRAKELVTKAEMLERVIKNYKRCFPVIFGKASESL KMIFGIDVKEVDPASNTYTLVTCLGLSYDGLLGNNQIFPKTGLLIIVL GTIAMEGDSASEEEIWEELGVMGVYDGREHTVYGEPRKLLTQDWV QENYLEYRQVPGSNPARYEFLWGPRALAETSYVKVLEHVVRVNAR VRIAYPSLREAALLEEEGV | 19 |
| MABEB16 | uc022bus.1 | MSQDQESPRCTHDQHLQTFSETQSLEVAQVSKALEKTLLSSSHPLV PGKLKEAPAAKAESPLEVPQSFCSSSIAVTTTSSSESDEASSNQEEED SPSSSEDTSDPRNVPADALDQKVAFLVNFMLHKCQMKKPITKADM LKIIIKDDESHFSEILLRASEHLEMIFGLDVVEVDPTTHCYGLFIKLGL TYDGMLSGEKGVPKTGLLIIVLGVIFMKGNRATEEEVWEVLNLTGV YSGKKHFIFGEPRMLITKDFVKEKYLEYQQVANSDPARYEFLWGPR AKAETSKMKVLEFVAKVHGSYPHSFPSQYAEALKEEEERARARI | 20 |

TABLE 3-continued

| Over-expressed gene | UCSC ID | Full Sequence | SEQ ID NO: |
|---|---|---|---|
| MAGEA1 | uc022chs.1 | MSLEQRSLHCKPEEALEAQQEALGLVCVQAATSSSSPLVLGTLEEV PTAGSTDPPQSPQGASAFPTTINFTRQRQPSEGSSSREEEGPSTSCILE SLFRAVITKKVADLVGFLLLKYRAREPVTKAEMLESVIKNYKHCFP EIFGKASESLQLVFGIDVKEADPTGHSYVLVTCLGLSYDGLLGDNQI MPKTGFLIIVLVMIAMEGGHAPEEEIWEELSVMEVYDGREHSAYGE PRKLLTQDLVQEKYLEYRQVPDSDPARYEFLWGPRALAETSYVKV LEYVIKVSARVRFFFPSLREAALREEEEGV | 21 |
| MAGEA8 | uc022cgo.1 | MLLGQKSQRYKAEEGLQAQGEAPGLMDVQIPTAEEQKAASSSSTLI MGTLEEVTDSGSPSPPQSPEGASSSLTVTDSTLWSQSDEGSSSNEEE GPSTSPDPAHLESLFREALDEKVAELVRFLLRKYQIKEPVTKAEMLE SVIKNYKNHFPDIFSKASECMQVIFGIDVKEVDPAGHSYILVTCLGL SYDGLLGDDQSTPKTGLLIIVLGMILMEGSRAPEEAIWEALSVMGL YDGREHSVYWKLRKLLTQEWVQENYLEYRQAPGSDPVRYEFLWG PRALAETSYVKVLEHVVRVNARVRISYPSLHEEALGEEKGV | 22 |
| MAGEB4 | uc004dcb.3 | MPRGQKSKLRAREKRQRTRGQTQDLKVGQPTAAEKEESPSSSSSVL RDTASSSLAFGIPQEPQREPPTTSAAAAMSCTGSDKGDESQDEENAS SSQASTSTERSLKDSLTRKTKMLVQFLLYKYKMKEPTTKAEMLKIIS KKYKEHFPEIFRKVSQRTELVFGLALKEVNPTTHSYILVSMLGPNDG NQSSAWTLPRNGLLMPLLSVIFLNGNCAREEEIWEFLNMLGIYDGK RHLIFGEPRKLITQDLVQEKYLEYQQVPNSDPPRYQFLWGPRAHAE TSKMKVLEFLAKVNDTTPNNFPLLYEEALRDEEERAGARPRVAAR RGTTAMTSAYSRATSSSSSQPM | 23 |
| CT45A5 | uc011mvu.2 | MTDKTEKVAVDPETVFKRPRECDSPSYQKRQRMALLARKQGAGD SLIAGSAMSKEKKLMTGHAIPPSQLDSQIDDFTGFSKDGMMQKPGS NAPVGGNVTSNFSGDDLECRGIASSPKSQQEINADIKCQVVKEIRCL GRKYEKIFEMLEGVQGPTAVRKRFFESIIKEAARCMRRDFVKHLKK KLKRMI | 24 |
| ALPPL2 | uc002vss.4 | MQGPWVLLLLGLRLQLSLGIIPVEEENPDFWNRQAAEALGAAKKL QPAQTAAKNLIIFLGDGMGVSTVTAARILKGQKKDKLGPETFLAMD RFPYVALSKTYSVDKHVPDSGATATAYLCGVKGNFQTIGLSAAARF NQCNTTRGNEVISVMNRAKKAGKSVGVVTTTRVQHASPAGAYAH TVNRNWYSDADVPASARQEGCQDIATQLISNMDIDVILGGGRKYM FPMGTPDPEYPDDYSQGGTRLDGKNLVQEWLAKHQGARYVWNRT ELLQASLDPSVTHLMGLFEPGDMKYEIHRDSTLDPSLMEMTEAALL LLSRNPRGFFLFVEGGRIDHGHHESRAYRALTETIMFDDAIERAGQL TSEEDTLSLVTADHSHVFSFGGYPLRGSSIFGLAPGKARDRKAYTVL LYGNGPGYVLKDGARPDVTESESGSPEYRQQSAVPLDGETHAGED VAVFARGPQAHLVHGVQEQTFIAHVMAFAACLEPYTACDLAPRAG TTDAAHPGPSVVPALLPLLAGTLLLLGTATAP | 25 |
| MMP13 | uc001ph1.3 | MHPGVLAAFLFLSWTHCRALPLPSGGDEDDLSEEDLQFAERYLRSY YHPTNLAGILKENAASSMTERLREMQSFFGLEVTGKLDDNTLDVM KKPRCGVPDVGEYNVFPRTLKWSKMNLTYRIVNYTPDMTHSEVEK AFKKAFKVWSDVTPLNFTRLHDGIADIMISFGIKEHGDFYPFDGPSG LLAHAFPPGPNYGGDAHFDDDETWTSSSKGYNLFLVAAHEFGHSL GLDHSKDPGALMFPIYTYTGKSHFMLPDDDVQGIQSLYGPGDEDPN PKHPKTPDKCDPSLSLDAITSLRGETMIFKDRFFWRLHPQQVDAELF LTKSFWPELPNRIDAAYEHPSHDLIFIFRGRKFWALNGYDILEGYPK KISELGLPKEVKKISAAVHFEDTGKTLLFSGNQVWRYDDTNHIMDK DYPRLIEEDFPGIGDKVDAVYEKNGYIYFFNGPIQFEYSIWSNRIVRV MPANSILWC | 26 |
| CTAG1B | uc004fmf.1 | MQAEGRGTGGSTGDADGPGGPGIPDGPGGNAGGPGEAGATGGRG PRGAGAARASGPGGGAPRGPHGGAASGLNGCRCGARGPESRLLE FYLAMPFATPMEAELARRSLAQDAPPLPVPGVLLKEFTVSGNILTIR LTAADHRQLQLSISSCLQQLSLLMWITQCFLPVFLAQPPSGQRR | 27 |
| DCT | uc010afh.3 | MSPLWWGFLLSCLGCKILPGAQGQFPRVCMTVDSLVNKECCPRLG AESANVCGSQQGRGQCTEVRADTRPWSGPYILRNQDDRELWPRKF FHRTCKCTGNFAGYNCGDCKFGWTGPNCERKKPPVIRQNIHSLSPQ EREQFLGALDLAKKRVHPDYVITTQHWLGLLGPNGTQPQPFANCSV YDFFVWLHYYSVRDTLLGPGRPYRAIDFSHQGPAFVTWHRYHLLC LERDLQRLIGNESFALPYWNFATGRNECDVCTDQLFGAARPDDPTL ISRNSRFSSWETVCDSLDDYNHLVTLCNGTYEGLLRRNQMGRNSM KLPTLKDIRDCLSLQKFDNPPFFQNSTFSFRNALEGFDKADGTLDSQ VMSLHNLVHSFLNGTNALPHSAANDPIFVVISNRLLYNATTNILEHV RKEKATKELPSLHVLVLHSFTDAIFDEWMKRFNPPADAWPQELAPI GHNRMYNMVPFFPPVTNEELFLTSDQLGYSYAIDLPVSVEETPGWP TTLLVVMGTLVALVGLFVLLAFLQYRRLRKGYTPLMETHLSSKRY TEEA | 28 |

TABLE 3-continued

| Over-expressed gene | UCSC ID | Full Sequence | SEQ ID NO: |
|---|---|---|---|
| CLDN6 | uc021tbb.1 | MASAGMQILGVVLTLLGWVNGLVSCALPMWKVTAFIGNSIVVAQ VVWEGLWMSCVVQSTGQMQCKVYDSLLALPQDLQAARALCVIAL LVALFGLLVYLAGAKCTTCVEEKDSKARLVLTSGIVFVISGVLTLIP VCWTAHAIIRDFYNPLVAEAQKRELGASLYLGWAASGLLLLGGGL LCCTCPSGGSQGPSHYMARYSTSAPAISRGPSEYPTKNYV | 29 |
| MLANA | uc003zjo.1 | MPREDAHFIYGYPKKGHGHSYTTAEEAAGIGILTVILGVLLLIGCWY CRRRNGYRALMDKSLHVGTQCALTRRCPQEGFDHRDSKVSLQEK NCEPVVPNAPPAYEKLSAEQSPPPYSP | 30 |
| AFP | uc003hgz.1 | MKWVESIFLIFLLNFTESRTLHRNEYGIASILDSYQCTAEISLADLATI FFAQFVQEATYKEVSKMVKDALTAIEKPTGDEQSSGCLENQLPAFL EELCHEKEILEKYGHSDCCSQSEEGRHNCFLAHKKPTPASIPLFQVP EPVTSCEAYEEDRETFMNKFIYEIARRHPFLYAPTILLWAARYDKIIP SCCKAENAVECFQTKAATVTKELRESSLLNQHACAVMKNFGTRTF QAITVTKLSQKFTKVNFTEIQKLVLDVAHVHEHCCRGDVLDCLQD GEKIMSYICSQQDTLSNKITECCKLTTLERGQCIIHAENDEKPEGLSP NLNRFLGDRDFNQFSSGEKNIFLASFVHEYSRRHPQLAVSVILRVAK GYQELLEKCFQTENPLECQDKGEEELQKYIQESQALAKRSCGLFQK LGEYYLQNAFLVAYTKKAPQLTSSELMAITRKMAATAATCCQLSE DKLLACGEGAADIIIGHLCIRHEMTPVNPGVGQCCTSSYANRRPCFS SLVVDETYVPPAFSDDKFIFHKDLCQAQGVALQTMKQEFLINLVKQ KPQITEEQLEAVIADFSGLLEKCCQGQEQEVCFAEEGQKLISKTRAA LGV | 31 |
| DKK4 | uc003xpb.3 | MVAAVLLGLSWLCSPLGALVLDFNNIRSSADLHGARKGSQCLSDT DCNTRKFCLQPRDEKPFCATCRGLRRRCQRDAMCCPGTLCVNDVC TTMEDATPILERQLDEQDGTHAEGTTGHPVQENQPKRKPSIKKSQG RKGQEGESCLRTFDCGPGLCCARHFWTKICKPVLLEGQVCSRRGH KDTAQAPEIFQRCDCGPGLLCRSQLTSNRQHARLRVCQKIEKL | 32 |
| ASCL2 | uc021qcf.1 | MDGGTLPRSAPPAPPVPVGCAARRRPASPELLRCSRRRRPATAETG GGAAAVARRNERERNRVKLVNLGFQALRQHVPHGGASKKLSKVE TLRSAVEYIRALQRLLAEHDAVRNALAGGLRPQAVRPSAPRGPPGT TPVAASPSRASSSPGRGGSSEPGSPRSAYSSDDSGCEGALSPAERELL DFSSWLGGY | 33 |
| GAGE1 | uc004dok.2 | MSWRGRSTYYWPRPRRYVQPPEMIGPMRPEQFSDEVEPATPEEGEP ATQRQDPAAAQEGEDEGASAGQGPKPEADSQEQGHPQTGCECEDG PDGQEMDPPNPEEVKTPEEEMRSHYVAQTGILWLLMNNCFLNLSP RKP | 34 |
| GAGE10 | uc010nir.1 | MSWRGRSTYRSRPRLYVEPPEMIGPMLPEQFSDEVEPATPEEGEPA TQRQDPAAAQEGEDEGASAGQGPKPEADSQEQVHPKTGCECGDGP DGQEMGLPNPEEVKRPEEGEKQSQC | 35 |
| SLC45A2 | uc003jid.3 | MGSNSGQAGRHIYKSLADDGPFDSVEPPKRPTSRLIMHSMAMFGRE FCYAVEAAYVTPVLLSVGLPSSLYSIVWFLSPILGFLLQPVVGSASD HCRSRWGRRRPYILTLGVMMLVGMALYLNGATVVAALIANPRRK LVWAISVTMIGVVLFDFAADFIDGPIKAYLFDVCSHQDKEKGLHYH ALFTGFGGALGYLLGAIDWAHLELGRLLGTEFQVMFFFSALVLTLC FTVHLCSISEAPLTEVAKGIPPQQTPQDPPLSSDGMYEYGSIEKVKN GYVNPELAMQGAKNKNHAEQTRRAMTLKSLLRALVNMPPHYRYL CISHLIGWTAFLSNMLFFTDFMGQIVYRGDPYSAHNSTEFLIYERGV EVGCWGFCINSVFSSLYSYFQKVLVSYIGLKGLYFTGYLLFGLGTGF IGLFPNVYSTLVLCSLFGVMSSTLYTVPFNLITEYHREEEKERQQAP GGDPDNSVRGKGMDCATLTCMVQLAQILVGGGLGFLVNTAGTVV VVVITASAVALIGCCFVALFVRYVD | 36 |
| PAGE5 | uc004duj.3 | MQAPWAGNRGWAGTREEVRDMSEHVTRSQSSERGNDQESSQPVG PVIVQQPTEEKRQEEEPPTDNQGIAPSGEIKNEGAPAVQGTDVEAFQ QELALLKIEDAPGDGPDVREGTLPTFDPTKVLEAGEGQL | 37 |
| PAGE2 | uc004duf.1 | MSELLRARSQSSERGNDQESSQPVGSIVQEPTEEKRQEEEPPTDNQ GIAPSGEIENQAVPAFQGPDMEAFQQELALLKIEDEPGDGPDVREGI MPTFDLTKVLEAGDAQP | 38 |
| PMEL | uc001siq.3 | MDLVLKRCLLHLAVIGALLAVGATKVPRNQDWLGVSRQLRTKAW NRQLYPEWTEAQRLDCWRGGQVSLKVSNDGPTLIGANASFSIALNF PGSQKVLPDGQVIWVNNTIINGSQVWGGQPVYPQETDDACIFPDG PCPSGSWSQKRSFVYVWKTWGQYWQVLGGPVSGLSIGTGRAMLG THTMEVTVYHRRGSRSYVPLAHSSSAFTITDQVPFSVSVSQLRALD GGNKHFLRNQPLTFALQLHDPSGYLAEADLSYTWDFGDSSGTLISR ALVVTHTYLEPGPVTAQVVLQAAIPLTSCGSSPVPGTTDGHRPTAE APNTTAGQVPTTEVVGTTPGQAPTAEPSGTTSVQVPTTEVISTAPVQ | 39 |

TABLE 3-continued

| Over-expressed gene | UCSC ID | Full Sequence | SEQ ID NO: |
|---|---|---|---|
| | | MPTAESTGMTPEKVPVSEVMGTTLAEMSTPEATGMTPAEVSIVVLS GTTAAQVTTTEWVETTARELPIPEPEGPDASSIMSTESITGSLGPLLD GTATLRLVKRQVPLDCVLYRYGSFSVTLDIVQGIESAEILQAVPSGE GDAFELTVSCQGGLPKEACMEISSPGCQPPAQRLCQPVLPSPACQL VLHQILKGGSGTYCLNVSLADTNSLAVVSTQLIMPVPGILLTGQEA GLGQVPLIVGILLVLMAVVLASLIYRRRLMKQDFSVPQLPHSSSHW LRLPRIFCSCPIGENSPLLSGQQV | |

For each epitope, the full-length amino acid sequence of the non-mutated protein epitope was derived. Any constituent 9mer or 10mer not found in the germline protein sequence was flagged and scored for binding potential on six common HLA alleles (HLA-A01:01, HLA-A02:01. HLA-A03:01, HLA-A24:02, HLA-1B07:02, and HLA-1B08:01) using available algorithms. Any peptide scoring better than 1000 nM was nominated.

TABLE 4

| Over-expressed gene | UCSC ID | Full Sequence | SEQ ID NO: |
|---|---|---|---|
| TYR | uc001pcs.3 | MLLAVLYCLLWSFQTSAGHFPRACVSSKNLMEKECCPPWSGDRS PCGQLSGRGSCQNILLSNAPLGPQFPFTGVDDRESWPSVFYNRTC QCSGNFMGFNCGNCKFGFWGPNCTERRLLVRRNIFDLSAPEKDK FFAYLTLAKHTISSDYVIPIGTYGQMKNGSTPMFNDINIYDLFVW MHYYVSMDALLGGSEIWRDIDFAHEAPAFLPWHRLFLLRWEQEI QKLTGDENFTIPYWDWRDAEKCDICTDEYMGGQHPTNPNLLSPA SFFSSWQIVCSRLEEYNSHQSLCNGTPEGPLRRNPGNHDKSRTPRL PSSADVEFCLSLTQYESGSMDKAANFSFRNTLEGFASPLTGIADAS QSSMHNALHIYMNGTMSQVQGSANDPIFLLHHAFVDSIFEQWLR RHRPLQEVYPEANAPIGHNRESYMVPFIPLYRNGDFFISSKDLGYD YSYLQDSDPDSFQDYIKSYLEQASRIWSWLLGAAMVGAVLTALL AGLVSLLCRHKRKQLPEEKQPLLMEKEDYHSLYQSHL | 15 |
| MAGEC1 | uc004fbt.3 | MGDKDMPTAGMPSLLQSSSESPQSCPEGEDSQSPLQIPQSSPESDD TLYPLQSPQSRSEGEDSSDPLQRPPEGKDSQSPLQIPQSSPEGDDTQ SPLQNSQSSPEGKDSLSPLEISQSPPEGEDVQSPLQNPASSFFSSALL SIFQSSPESTQSPFEGFPQSVLQIPVSAASSSTLVSIFQSSPESTQSPFE GFPQSPLQIPVSRSFSSTLLSIFQSSPERTQSTFEGFAQSPLQIPVSPS SSSTLLSLFQSFSERTQSTFEGFAQSSLQIPVSPSFSSTLVSLFQSSPE RTQSTFEGFPQSPLQIPVSSSSSSTLLSLFQSSPERTHSTFEGFPQSLL QIPMTSSFSSTLLSIFQSSPESAQSTFEGFPQSPLQIPGSPSFSSTLLSL FQSSPERTHSTFEGFPQSPLQIPMTSSFSSTLLSILQSSPESAQSAFEG FPQSPLQIPVSSSFSYTLLSLFQSSPERTHSTFEGFPQSPLQIPVSSSS SSSTLLSLFQSSPECTQSTFEGFPQSPLQIPQSPPEGENTHSPLQIVPS LPEWEDSLSPHYFPQSPPQGEDSLSPHYFPQSPPQGEDSLSPHYFPQ SPQGEDSLSPHYFPQSPPQGEDSMSPLYFPQSPLQGEEFQSSLQSPV SICSSSTPSSLPQSFPESSQSPPEGPVQSPLHSPQSPPEGMHSQSPLQ SPESAPEGEDSLSPLQIPQSPLEGEDSLSSLHFPQSPPEWEDSLSPLH FPQFPPQGEDFQSSLQSPVSICSSSTSLSLPQSFPESPQSPPEGPAQSP LQRPVSSFFSYTLASLLQSSHESPQSPPEGPAQSPLQSPVSSFPSSTS SSLSQSSPVSSFPSSTSSSLSKSSPESPLQSPVISFSSSTSLSPF- SEESSS PVDEYTSSSDTLLESDSLTDSESLIESEPLFTYTLDEKVDELARFLL LKYQVKQPITKAEMLTNVISRYTGYFPVIFRKAREFIEILFGISLRE VDPDDSYVFVNTLDLTSEGCLSDEQGMSQNRLLILILSIIFIKGTYA SEEVIWDVLSGIGVRAGREHFAFGEPRELLTKVWVQEHYLEYRE VPNSSPPRYEFLWGPRAHSEVIKRKVVEFLAMLKNTVPITFPSSYK DALKDVEERAQAIIDTTDDSTATESASSSVMSPSFSSE | 16 |
| MAGEA10 | uc022cgz.1 | MPRAPKRQRCMPEEDLQSQSETQGLEGAQAPLAVEEDASSSTSTS SSFPSSFPSSSSSSSSCYPLIPSTPEEVSADDETPNPPQSAQIACSSPS VVASLPLDQSDEGSSSQKEESPSTLQVLPDSESLPRSEIDEKVTDLV QFLLFKYQMKEPITKAEILESVIRNYEDHFPLLFSEASECMLLVFGI DVKEVDPTGHSFVLVTSLGLTYDGMLSDVQSMPKTGILILILSIVFI EGYCTPEEVIWEALNMMGLYDGMEHLIYGEPRKLLTQDWVQEN YLEYRQVPGSDPARYEFLWGPRAHAEIRKMSLLKFLAKVNGSDP RSFPLWYEEALKDEEERAQDRIATTDDTTAMASASSSATGSFSYP E | 17 |
| MAGEB17 | uc031tgu.1 | MPRGQASKRRAREKRRQARGEDQCLGGAQATAAEKEKLPSSSSP ACQSPPQSFPNAGIPQESQRASYPSSPASAVSLTSSDEGAKGQKGE SPNSFHGPSSSESTGRDLLNTKTGELVQFLLNKYIRKEPITREAML KVINRKYKQHFPEILRRSTENVEVVFGLYLKEMDPSRQSYVLVGK LDFPNQGSLSDGGGFPLSGLLMVLLSTIFMHGNRATEEEMWECL | 18 |

TABLE 4-continued

| Over-expressed gene | UCSC ID | Full Sequence | SEQ ID NO: |
|---|---|---|---|
| | | NALGMYKGRKHFIYGEPQELVTKDLVREGYLEYQQVPSSDPPRY EFLWGPRARAETSKMKVLEFVAKLNDTVASTYKSRYEEALREEE EQARARAVARDSARARASRSFQP | |
| MAGEA4 | uc022cgu.1 | MLPLSVGLWVPIAQLLPALLPAALTRVIMSSEQKSQHCKPEEGVE AQEEALGLVGAQAPTTEEQEAAVSSSSPLVPGTLEEVPAAESAGP PQSPQGASALPTTISFTCWRQPNEGSSSQEEEGPSTSPDAESLFREA LSNKVDELAHFLLRKYRAKELVTKAEMLERVIKNYKRCFPVIFGK ASESLKMIFGIDVKEVDPASNTYTLVTCLGLSYDGLLGNNQIFPKT GLLIIVLGTIAMEGDSASEEEIWEELGVMGVYDGREHTVYGEPRK LLTQDWVQENYLEYRQVPGSNPARYEFLWGPRALAETSYVKVLE HVVRVNARVRIAYPSLREAALLEEEEGV | 19 |
| MABEB16 | uc022bus.1 | MSQDQESPRCTHDQHLQTFSETQSLEVAQVSKALEKTLLSSSHPL VPGKLKEAPAAKAESPLEVPQSFCSSSIAVTTTSSSESDEASSNQEE EDSPSSSEDTSDPRNVPADALDQKVAFLVNFMLHKCQMKKPITK ADMLKIIIKDDESHFSEILLRASEHLEMIFGLDVVEVDPTTHCYGLF IKLGLTYDGMLSGEKGVPKTGLLIIVLGVIFMKGNRATEEEVWEV LNLTGVYSGKKHFIFGEPRMLITKDFVKEKYLEYQQVANSDPARY EFLWGPRAKAETSKMKVLEFVAKVHGSYPHSFPSQYAEALKEEE ERARARI | 20 |
| MAGEA1 | uc022chs.1 | MSLEQRSLHCKPEEALEAQQEALGLVCVQAATSSSSPLVLGTLEE VPTAGSTDPPQSPQGASAFPTTINFTRQRQPSEGSSSREEEGPSTSCI LESLFRAVITKKVADLVGFLLLKYRAREPVTKAEMLESVIKNYKH CFPEIFGKASESLQLVFGIDVKEADPTGHSYVLVTCLGLSYDGLLG DNQIMPKTGFLIIVLVMIAMEGGHAPEEEIWEELSVMEVYDGREH SAYGEPRKLLTQDLVQEKYLEYRQVPDSDPARYEFLWGPRALAE TSYVKVLEYVIKVSARVRFFFPSLREAALREEEEGV | 21 |
| MAGEA8 | uc022cgo.1 | MLLGQKSQRYKAEEGLQAQGEAPGLMDVQIPTAEEQKAASSSST LIMGTLEEVTDSGSPSPPQSPEGASSSLTVTDSTLWSQSDEGSSSNE EEGPSTSPDPAHLESLFREALDEKVAELVRFLLRKYQIKEPVTKAE MLESVIKNYKNHFPDIFSKASECMQVIFGIDVKEVDPAGHSYILVT CLGLSYDGLLGDDQSTPKTGLLIIVLGMILMEGSRAPEEAIWEALS VMGLYDGREHSVYWKLRKLLTQEWVQENYLEYRQAPGSDPVR YEFLWGPRALAETSYVKVLEHVVRVNARVRISYPSLHEEALGEE KGV | 22 |
| MAGEB4 | uc004dcb.3 | MPRGQKSKLRAREKRQRTRGQTQDLKVGQPTAAEKEESPSSSSS VLRDTASSSLAFGIPQEPQREPPTTSAAAAMSCTGSDKGDESQDEE NASSSQASTSTERSLKDSLTRKTKMLVQFLLYKYKMKEPTTKAE MLKIISKKYKEHFPEIFRKVSQRTELVFGLALKEVNPTTHSYILVS MLGPNDGNQSSAWTLPRNGLLMPLLSVIFLNGNCAREEEIWEFLN MLGIYDGKRHLIFGEPRKLITQDLVQEKYLEYQQVPNSDPPRYQF LWGPRAHAETSKMKVLEFLAKVNDTTPNNFPLLYEEALRDEEER AGARPRVAARRGTTAMTSAYSRATSSSSSQPM | 23 |
| CT45A5 | uc011mvu.2 | MTDKTEKVAVDPETVFKRPRECDSPSYQKRQRMALLARKQGAG DSLIAGSAMSKEKKLMTGHAIPPSQLDSQIDDFTGFSKDGMMQKP GSNAPVGGNVTSNFSGDDLECRGIASSPKSQQEINADIKCQVVKEI RCLGRKYEKIFEMLEGVQGPTAVRKRFFESIIKEAARCMRRDFVK HLKKKLKRMI | 24 |
| ALPPL2 | uc002vss.4 | MQGPWVLLLLGLRLQLSLGIIPVEEENPDFWNRQAAEALGAAKK LQPAQTAAKNLIIFLGDGMGVSTVTAARILKGQKKDKLGPETFLA MDRFPYVALSKTYSVDKHVPDSGATATAYLCGVKGNFQTIGLSA AARFNQCNTTRGNEVISVMNRAKKAGKSVGVVTTTRVQHASPA GAYAHTVNRNWYSDADVPASARQEGCQDIATQLISNMDIDVILG GGRKYMFPMGTPDPEYPDDYSQGGTRLDGKNLVQEWLAKHQG ARYVWNRTELLQASLDPSVTHLMGLFEPGDMKYEIHRDSTLDPS LMEMTEAALLLLSRNPRGFFLFVEGGRIDHGHHESRAYRALTETI MFDDAIERAGQLTSEEDTLSLVTADHSHVFSFGGYPLRGSSIFGLA PGKARDRKAYTVLLYGNGPGYVLKDGARPDVTESESGSPEYRQQ SAVPLDGETHAGEDVAVFARGPQAHLVHGVQEQTFIAHVMAFA ACLEPYTACDLAPRAGTTDAAHPGPSVVPALLPLLAGTLLLLGTA TAP | 25 |
| MMP13 | uc001ph1.3 | MHPGVLAAFLFLSWTHCRALPLPSGGDEDDLSEEDLQFAERYLRS YYHPTNLAGILKENAASSMTERLREMQSFFGLEVTGKLDDNTLD VMKKPRCGVPDVGEYNVFPRTLKWSKMNLTYRIVNYTPDMTHS EVEKAFKKAFKVWSDVTPLNFTRLHDGIADIMISFGIKEHGDFYPF DGPSGLLAHAFPPGPNYGGDAHFDDDETWTSSSKGYNLFLVAAH EFGHSLGLDHSKDPGALMFPIYTYTGKSHFMLPDDDVQGIQSLYG PGDEDPNPKHPKTPDKCDPSLSLDAITSLRGETMIFKDRFFWRLHP QQVDAELFLTKSFWPELPNRIDAAYEHPSHDLIFIFRGRKFWALN | 26 |

TABLE 4-continued

| Over-expressed gene | UCSC ID | Full Sequence | SEQ ID NO: |
|---|---|---|---|
| | | GYDILEGYPKKISELGLPKEVKKISAAVHFEDTGKTLLFSGNQVW RYDDTNHIMDKDYPRLIEEDFPGIGDKVDAVYEKNGYIYFFNGPI QFEYSIWSNRIVRVMPANSILWC | |
| CTAG1B | uc004fmf.1 | MQAEGRGTGGSTGDADGPGGPGIPDGPGGNAGGPGEAGATGRG GPRGAGAARASGPGGGAPRGPHGGAASGLNGCCRCGARGPESRL LEFYLAMPFATPMEAELARRSLAQDAPPLPVPGVLLKEFTVSGNI LTIRLTAADHRQLQLSISSCLQQLSLLMWITQCFLPVFLAQPPSGQ RR | 27 |
| DCT | uc010afh.3 | MSPLWWGFLLSCLGCKILPGAQGQFPRVCMTVDSLVNKECCPRL GAESANVCGSQQGRGQCTEVRADTRPWSGPYILRNQDDRELWPR KFFHRTCKCTGNFAGYNCGDCKFGWTGPNCERKKPPVIRQNIHSL SPQEREQFLGALDLAKKRVHPDYVITTQHWLGLLGPNGTQPQFA NCSVYDFFVWLHYYSVRDTLLGPGRPYRAIDFSHQGPAFVTWHR YHLLCLERDLQRLIGNESFALPYWNFATGRNECDVCTDQLFGAA RPDDPTLISRNSRFSSWETVCDSLDDYNHLVTLCNGTYEGLLRRN QMGRNSMKLPTLKDIRDCLSLQKFDNPPFFQNSTFSFRNALEGFD KADGTLDSQVMSLHNLVHSFLNGTNALPHSAANDPIFVVISNRLL YNATTNILEHVRKEKATKELPSLHVLVLHSFTDAIFDEWMKRFNP PADAWPQELAPIGHNRMYNMVPFFPPVTNEELFLTSDQLGYSYAI DLPVSVEETPGWPTTLLVVMGTLVALVGLFVLLAFLQYRRLRKG YTPLMETHLSSKRYTEEA | 28 |
| CLDN6 | uc021tbb.1 | MASAGMQILGVVLTLLGWVNGLVSCALPMWKVTAFIGNSIVVA QVVWEGLWMSCVVQSTGQMQCKVYDSLLALPQDLQAARALCV IALLVALFGLLVYLAGAKCTTCVEEKDSKARLVLTSGIVFVISGVL TLIPVCWTAHAIIRDFYNPLVAEAQKRELGASLYLGWAASGLLLL GGGLLCCTCPSGGSQGPSHYMARYSTSAPAISRGPSEYPTKNYV | 29 |
| MLANA | uc003zjo.1 | MPREDAHFIYGYPKKGHGHSYTTAEEAAGIGILTVILGVLLLIGC WYCRRRNGYRALMDKSLHVGTQCALTRRCPQEGFDHRDSKVSL QEKNCEPVVPNAPPAYEKLSAEQSPPPYSP | 30 |
| AFP | uc003hgz.1 | MKWVESIFLIFLLNFTESRTLHRNEYGIASILDSYQCTAEISLADLA TIFFAQFVQEATYKEVSKMVKDALTAIEKPTGDEQSSGCLENQLP AFLEELCHEKEILEKYGHSDCCSQSEEGRHNCFLAHKKPTPASIPL FQVPEPVTSCEAYEEDRETFMNKFIYEIARRHPFLYAPTILLWAAR YDKIIPSCCKAENAVECFQTKAATVTKELRESSLLNQHACAVMK NFGTRTFQAITVTKLSQKFTKVNFTEIQKLVLDVAHVHEHCCRGD VLDCLQDGEKIMSYICSQQDTLSNKITECCKLTTLERGQCIIHAEN DEKPEGLSPNLRFLGDRDFNQFSSGEKNIFLASFVHEYSRRHPQL AVSVILRVAKGYQELLEKCFQTENPLECQDKGEEELQKYIQESQA LAKRSCGLFQKLGEYYLQNAFLVAYTKKAPQLTSSELMAITRKM AATAATCCQLSEDKLLACGEGAADIIIGHLCIRHEMTPVNPGVGQ CCTSSYANRRPCFSSLVVDETYVPPAFSDDKFIFHKDLCQAQGVA LQTMKQEFLINLVKQKPQITEEQLEAVIADFSGLLEKCCQGQEQE VCFAEEGQKLISKTRAALGV | 31 |
| DKK4 | uc003xpb.3 | MVAAVLLGLSWLCSPLGALVLDFNNIRSSADLHGARKGSQCLSD TDCNTRKFCLQPRDEKPFCATCRGLRRRCQRDAMCCPGTLCVND VCTTMEDATPILERQLDEQDGTHAEGTTGHPVQENQPKRKPSIKK SQGRKGQEGESCLRTFDCGPGLCCARHFWTKICKPVLLEGQVCSR RGHKDTAQAPEIFQRCDCGPGLLCRSQLTSNRQHARLRVCQKIEK L | 32 |
| ASCL2 | uc021qcf.1 | MDGGTLPRSAPPAPPVPVGCAARRRPASPELLRCSRRRRPATAET GGGAAAVARRNERERNRVKLVNLGFQALRQHVPHGGASKKLSK VETLRSAVEYIRALQRLLAEHDAVRNALAGGLRPQAVRPSAPRGP PGTTPVAASPSRASSSPGRGGSSEPGSPRSAYSSDDSGCEGALSPA ERELLDFSSWLGGY | 33 |
| GAGE1 | uc004dok.2 | MSWRGRSTYYWPRPRRYVQPPEMIGPMRPEQFSDEVEPATPEEG EPATQRQDPAAAQEGEDEGASAGQGPKPEADSQEQGHPQTGCEC EDGPDGQEMDPPNPEEVKTPEEEMRSHYVAQTGILWLLMNNCFL NLSPRKP | 34 |
| GAGE10 | uc010nir.1 | MSWRGRSTYRSRPRLYVEPPEMIGPMLPEQFSDEVEPATPEEGEP ATQRQDPAAAQEGEDEGASAGQGPKPEADSQEQVHPKTGCECG DGPDGQEMGLPNPEEVKRPEEGEKQSQC | 35 |
| SLC45A2 | uc003jid.3 | MGSNSGQAGRHIYKSLADDGPFDSVEPPKRPTSRLIMHSMAMFG REFCYAVEEAAYVTPVLLSVGLPSSLYSIVWFLSPILGFLLQPVVGS ASDHCRSRWGRRRPYILTLGVMMLVGMALYLNGATVVAALIAN PRRKLVWAISVTMIGVVLFDFAADFIDGPIKAYLFDVCSHQDKEK GLHYHALFTGFGGALGYLLGAIDWAHLELGRLLGTEFQVMFFFS | 36 |

TABLE 4-continued

| Over-expressed gene | UCSC ID | Full Sequence | SEQ ID NO: |
|---|---|---|---|
| | | ALVLTLCFTVHLCSISEAPLTEVAKGIPPQQTPQDPPLSSDGMYEY GSIEKVKNGYVNPELAMQGAKNKNHAEQTRRAMTLKSLLRALV NMPPHYRYLCISHLIGWTAFLSNMLFFTDFMGQIVYRGDPYSAHN STEFLIYERGVEVGCWGFCINSVFSSLYSYFQKVLVSYIGLKGLYF TGYLLFGLGTGFIGLFPNVYSTLVLCSLFGVMSSTLYTVPFNLITE YHREEEKERQQAPGGDPDNSVRGKGMDCATLTCMVQLAQILVG GGLGFLVNTAGTVVVVVITASAVALIGCCFVALFVRYVD | |
| PAGE5 | uc004duj.3 | MQAPWAGNRGWAGTREEVRDMSEHVTRSQSSERGNDQESSQPV GPVIVQQPTEEKRQEEEPPTDNQGIAPSGEIKNEGAPAVQGTDVEA FQQELALLKIEDAPGDGPDVREGTLPTFDPTKVLEAGEGQL | 37 |
| PAGE2 | uc004duf.1 | MSELLRARSQSSERGNDQESSQPVGSVIVQEPTEEKRQEEEPPTDN QGIAPSGEIENQAVPAFQGPDMEAFQQELALLKIEDEPGDGPDVR EGIMPTFDLTKVLEAGDAQP | 38 |
| PMEL | uc001siq.3 | MDLVLKRCLLHLAVIGALLAVGATKVPRNQDWLGVSRQLRTKA WNRQLYPEWTEAQRLDCWRGGQVSLKVSNDGPTLIGANASFSIA LNFPGSQKVLPDGQVIWVNNTIINGSQVWGGQPVYPQETDDACIF PDGGPCPSGSWSQKRSFVYVWKTWGQYWQVLGGPVSGLSIGTG RAMLGTHTMEVTVYHRRGSRSYVPLAHSSSAFTITDQVPFSVSVS QLRALDGGNKHFLRNQPLTFALQLHDPSGYLAEADLSYTWDFGD SSGTLISRALVVTHTYLEPGPVTAQVVLQAAIPLTSCGSSPVPGTT DGHRPTAEAPNTTAGQVPTTEVVGTTPGQAPTAEPSGTTSVQVPT TEVISTAPVQMPTAESTGMTPEKVPVSEVMGTTLAEMSTPEATG MTPAEVSIVVLSGTTAAQVTTTEWVETTARELPIPEPEGPDASSIM STESITGSLGPLLDGTATLRLVKRQVPLDCVLYRYGSFSVTLDIVQ GIESAEILQAVPSGEGDAFELTVSCQGGLPKEACMEISSPGCQPPA QRLCQPVLPSPACQLVLHQILKGGSGTYCLNVSLADTNSLAVVST QLIMPVPGILLTGQEAGLGQVPLIVGILLVLMAVVLASLIYRRRLM KQDFSVPQLPHSSSHWLRLPRIFCSCPIGENSPLLSGQQV | 39 |

TABLE 5

| Virus, Gene | Genbank Accession | Sequence | SEQ ID NO: |
|---|---|---|---|
| HPV-16, E6 | NC_001526 | MHQKRTAMFQDPQERPRKLPQLCTELQTTIHDIILECVYCKQQLL RREVYDFAFRDLCIVYRDGNPYAVCDKCLKFYSKISEYRHYCYS LYGTTLEQQYNKPLCDLLIRCINCQKPLCPEEKQRHLDKKQRFH NIRGRWTGRCMSCCRSSRTRRETQL | 40 |
| HPV-16, E7 | NC_001526 | MHGDTPTLHEYMLDLQPETTDLYCYEQLNDSSEEEDEIDGPAGQ AEPDRAHYNIVTFCCKCDSTLRLCVQSTHVDIRTLEDLLMGTLGI VCPICSQKP | 41 |
| EBV, LF2 | KC207813 | MAEAYPGGAHAALASRRSSFRNSLRRLRPTEKPDTSFMRGVWK YEIFPSYVRVTNKQVLQLDAQCQELPPCPSVGQILSFKLPSFSFNT TTYGSRYFTVAFLFFGAEDNEVFLKPFFVMHSDQDIVLSVLNPRS LFIEKGKFTWYIVPIRLVKNPYLYLQILPGQSDIQLTRSCTQSGDK LNTSEPQIFLSGSPVTSQDECLPYLLAQHTPPFLKSYARIHTFPGK VCPVNAIRRGKGYVRVSVDTPDLKREGPLNVKVGMTLLDDVIIA FRYNPYPKSHWRWDGESTDIRYFGSPVIIPPNFITELEYNNTYEAP LSSKITAIVVSHSSNPVFYVYPQEWKPGQTLKLTVRNISNNPITIV TGQSMAQAFFIYAGDPSISTIMRRYIQRQGCALTLPGNIVVESSSL PTFERINKTFNGNIVASEGTL | 42 |
| EBV, BALF5 | KC207813 | MSGGLFYNPFLRPNKGLLKKPDKEYLRLIPKCFQTPGAAGVVDV RGPQPPLCFYQDSLTVVGGDEDGKGMWWRQRAQEGTARPEAD THGGSPLDFHVYDILETVYTHEKCAVIPSDKQGYVVPCGIVIKLLG RRKADGASVCVNVFGQQAYFYASAPQGLDVEFAVLSALKASTF DRRTPCRVSVEKVTRRSIMGYGNHAGDYHKITLSHPNSVCHVAT WLQDKHGCRIFEANVDATRRFVLDNDFVTFGWYSCRRAIPRLQ HRDSYAELEYDCEVGDLSVRREDSSWPSYQALAFDIECLGEEGF PTATNEADLILQISCVLWSTGEEAGRYRRILLTLGTCEDIEGVEVY EFPSELDMLYAFFQLIRDLSVEIVTGYNVANFDWPYILDRARHIY SINPASLGKIRAGGVCEVRRPHDAGKGFLRANTKVRITGLIPIDM YAVCRDKLSLSDYKLDTVARHLLGAKKEDVHYKEIPRLFAAGPE GRRRLGMYCVQDSALVMDLLNHFVIHVEVAEIAKIAHIPCRRVL DDGQQIRVFSCLLAAAQKENFILPMPSASDRDGYQGATVIQPLSG FYNSPVLVVDFASLYPSIIQAHNLCYSTMITPGEEHRLAGLRPGED YESFRLTGGVYHFVKKHVHESFLASLLTSWLAKRKAIKKLLAAC EDPRQRTILDKQQLAIKCTCNAVYGFTGVANGLFPCLSIAETVTL | 43 |

TABLE 5-continued

| Virus, Gene | Genbank Accession | Sequence | SEQ ID NO: |
|---|---|---|---|
| | | QGRTMLERAKAFVEALSPANLQALAPSPDAWAPLNPEGQLRVIY GDTDSLFIECRGFSESETLRFAEALAAHTTRSLFVAPISLE- AEKTFS CLMLITKKRYVGVLTDGKTLMKGVELVRKTACKFVQTRCRRVL DLVLADARVKEAASLLSHRPFQESFTQGLPVGFLPVIDILNQAYT DLREGRVPMGELCFSTELSRKLSAYKSTQMPHLAVYQKFVERNE ELPQIHDRIQYVFVEPKGGVKGARKTEMAEDPAYAERHGVPVA VDHYFDKLLQGAANILQCLFDNNSGAALSVLQNFTARPPF | |
| EBV, RPMS1 | KC207813 | MAGARRRARCPASAGCAYSARPPPLSTRGRRISAGSGQPRWWP WGSPPPLDTRYRRPGPGRRARSCLHAGPRGRPPHSRTRARRTSPG AGGGGWRGGSCTSQR | 44 |
| EBV, A73 | KC207813 | MSMPPKGFLKKEMKPETRLLNKPPTVLTRPAMFCAWKLYSRKM PSRSKTLEARCSSRPPCDSPACQTRDTGCPRRSGTGRRGWRARRL GKESWFADAWRMARYWGCAVKAAAQSAFSASTASPEEL | 45 |
| EBV, BALF4 | KC207813 | MTRRRVLSVVVLLAALACRLGAQTPEQPAPPATTVQPTATRQQT SFPFRVCELSSHGDLFRFSSDIQCPSFGTRENHTEGLLMVFKD-NIIP YSFKVRSYTKIVTNILIYNGWYADSVTNRHEEKFSVDSYETDQM DTIYQCYNAVKMTKDGLTRVYVDRDGVNITVNLKPTGGLANGV RRYASQTELYDAPGWLIWTYRTRTTVNCLITDMMAKSNSPFDFF VTTTGQTVEMSPFYDGKNKETFHERADSFHVRTNYKIVDYDNR GTNPQGERRAFLDKGTYTLSWKLENRTAYCPLQHWQTFDSTIAT ETGKSIHFVTDEGTSSFVTNTTVGIELPDAFKCIEEQVNKTMHEK YEAVQDRYTKGQEAITYFITSGGLLLAWLPLTPRSLATVKNLTEL TTPTSSPPSSPSPPAPPAARGSTSAAVLRRRRRDAGNATTPVPPAA PGKSLGTLNNPATVQIQFAYDSLRRQINRMLGDLARAWCLEQKR QNMVLRELTKINPTTVMSSIYGKAVAAKRLGDVISVSQCVPVNQ ATVTLRKSMRVPGSETMCYSRPLVSFSFINDTKTYEGQLGTDNEI FLTKKMTEVCQATSQYYFQSGNEIHVYNDYHHFKTIELDGIATL QTFISLNTSLIENIDFASLELYSRDEQRASNVFDLEGI-FREYNFQAQ NIAGLRKDLDNAVSNGRNQFVDGLGELMDSLGSVGQSITNLVST VGGLFSSLVSGFISFFKNPFGGMLILVLVAGVVILVISLTRRTRQM SQQPVQMLYPGIDELAQQHASGEGPGINPISKTELQAIMLALHEQ NQEQKRAAQRAAGPSVASRALQAARDRFPGLRRRRYHDPETAA ALLGEAETEF | 46 |
| EBV, BALF3 | KC207813 | MSGLLAAAYSQVYALAVELSVCARLDPRSLDVAAVVRNAGLLA ELEAILLPRLRRQNDRACSALSLELVHLLENSREASAALLAPGRK GTRVPPLRTPSVAYSVEFYGGHKVDVSLCLINDIEILMKRINSVFY CMSHTMGLESLERALDLLGRFRGVSPIPDPRLYITSVPCWRCVGE LMVLPNHGNPSTAEGTHVSCNHLAVPVNPEPVSGLFENEVRQAG LGHLLEAEEKARPGGPEEGAVPGPGRPEAEGATRALDTYNVFST VPPEVAELSELLYWNSGGHAIGATGQGEGGGHSRLSALFARERR LALVRRACEEALAGARLTHLFDAVAPGATERLFCGGVYSSSGDA VEALKADCAAAFTAHPQYRAILQKRNELYTRLNRAMQRLGRGE EEASRESPEVPRPAGAREPGPSGALSDALKRKEQYLRQVATEGL AKLQSCLAQQSETLTETLCLRVWGDVVYWELARMRNHFLYRR AFVSGPWEDRRAGEGAAFENSKYIKTHLFTQTLSSEHLHALTHSL YTFITGPLAEESGLFPPPSNVALARCCDAAGTLPHQKAFLTSLIWP GIEPSDWIETSFNSFYSVPGGSLASSQQILCRALREAVLTVSLYNK TWGRSLILRRADAVSPGQALPPDGLYLTYDSDRPLILLYKGRGW VFKDLYALLYLHLQMRDDSA | 47 |
| EBV, BARF0 | KC207813 | APGYAVEAVEGGLYPVARLDAWPYQGSQERLLVRQRTCGVTA ASQGHVAGWGKEPALLRQGPRDEGVQAVRQRVQVLRAQGLGK QVCFDVLGILKGGTLAGAPVLPGTRDEGPSVEEVVAHAGQLPVD HVPPDAQAQGLGQGLALLRQAGLQLGQTLGGHLAQVLLLALER VREGAGRAGLSCPSRPGHLRALPGRLLLASAQPLHGSVEPRVEL VPLLQDGPVLGVRREGGGAVRLQRLHRVARGAVDPAAEEPLCG PGSHGIKQVSQPCPRQRLLAGPPHQGQATLPGKQGREAGMSATL PLPRCTDSMAARVPIEELREFRHLRGHCREDVVGVQRSGRPLCL RPPRARDRALLWAARPRLLLSLQQVPEPSLPDFILKQSRDRLRIH RHRQVVTGDVGPLCRGRVAVVGQNHQLAHTAPAGHRGDVEAR VWDGTYAPKAAQQIQGPFQALQPHGVRHAIKHAIDSLH | 48 |

For each epitope, the full-length amino acid sequence of the non-mutated protein epitope was derived. Any constituent 9mer or 10mer not found in the germline protein sequence was flagged and scored for binding potential on six common HLA alleles (HLA-A01:01, HLA-A02:01. HLA-A03:01, HLA-A24:02, HLA-1B07:02, and HLA-1B08:01) using available algorithms. Any peptide scoring better than 1000 nM was nominated.

TABLE 6

| Peptide | SEQ ID NO: | Virus, Gene | Affinity |
|---|---|---|---|
| CMSCCRSSR | 49 | HPV-16, E6 | A03.01 = 610 |
| CPEEKQRHL | 50 | HPV-16, E6 | B07.02 = 720 |
| CVYCKQQLL | 51 | HPV-16, E6 | B08.01 = 880 |
| CVYCKQQLLR | 52 | HPV-16, E6 | A03.01 = 250 |
| CYSLYGTTL | 53 | HPV-16, E6 | A24.02 = 290 |
| DKKQRFHNI | 54 | HPV-16, E6 | B08.01 = 200 |
| EYRHYCYSL | 55 | HPV-16, E6 | A24.02 = 350; B08.01 = 360 |
| FAFRDLCIV | 56 | HPV-16, E6 | A02.01 = 150 |
| IILECVYCK | 57 | HPV-16, E6 | A03.01 = 150 |
| ISEYRHYCY | 58 | HPV-16, E6 | A01.01 = 81 |
| IVYRDGNPY | 59 | HPV-16, E6 | A03.01 = 700 |
| IVYRDGNPYA | 60 | HPV-16, E6 | A02.01 = 760 |
| KFYSKISEY | 61 | HPV-16, E6 | A03.01 = 670 |
| KISEYRHYCY | 62 | HPV-16, E6 | A03.01 = 570 |
| KLPQLCTEL | 63 | HPV-16, E6 | A02.01 = 130 |
| LIRCINCQK | 64 | HPV-16, E6 | A03.01 = 230 |
| LLIRCINCQK | 65 | HPV-16, E6 | A03.01 = 130 |
| MHQKRTAMF | 66 | HPV-16, E6 | A24.02 = 980; B08.01 = 580 |
| NPYAVCDKCL | 67 | HPV-16, E6 | B07.02 = 550 |
| QYNKPLCDLL | 68 | HPV-16, E6 | A24.02 = 520 |
| RFHNIRGRW | 69 | HPV-16, E6 | A24.02 = 620 |
| RGRWTGRCM | 70 | HPV-16, E6 | B07.02 = 720 |
| RPRKLPQLC | 71 | HPV-16, E6 | B07.02 = 310 |
| RPRKLPQLCT | 72 | HPV-16, E6 | B07.02 = 79 |
| SEYRHYCYSL | 73 | HPV-16, E6 | B08.01 = 390 |
| SSRTRRETQL | 74 | HPV-16, E6 | B08.01 = 230 |
| TIHDIILECV | 75 | HPV-16, E6 | A02.01 = 140 |
| TTLEQQYNK | 76 | HPV-16, E6 | A03.01 = 520 |
| VYDFAFRDL | 77 | HPV-16, E6 | A24.02 = 600 |
| GIVCPICSQK | 78 | HPV-16, E7 | A03.01 = 200 |
| GTLGIVCPI | 79 | HPV-16, E7 | A02.01 = 120 |
| HGDTPTLHEY | 80 | HPV-16, E7 | A01.01 = 270 |
| IVCPICSQK | 81 | HPV-16, E7 | A03.01 = 200 |
| LLMGTLGIV | 82 | HPV-16, E7 | A02.01 = 20 |
| RAHYNIVTF | 83 | HPV-16, E7 | A24.02 = 330 |
| RLCVQSTHV | 84 | HPV-16, E7 | A02.01 = 770 |
| TLEDLLMGTL | 85 | HPV-16, E7 | A02.01 = 480 |
| TLHEYMLDL | 86 | HPV-16, E7 | A02.01 = 95 |

TABLE 6-continued

| Peptide | SEQ ID NO: | Virus, Gene | Affinity |
|---|---|---|---|
| TPTLHEYML | 87 | HPV-16, E7 | B07.02 = 490 |
| YMLDLQPET | 88 | HPV-16, E7 | A02.01 = 7 |
| YMLDLQPETT | 89 | HPV-16, E7 | A02.01 = 25 |
| AALASRRSSF | 90 | EBV, LF2 | B07.02 = 160 |
| ALASRRSSF | 91 | EBV, LF2 | B07.02 = 290; B08.01 = 41 |
| ALASRRSSFR | 92 | EBV, LF2 | A03.01 = 160 |
| ALTLPGNIVV | 93 | EBV, LF2 | A02.01 = 470 |
| APLSSKITA | 94 | EBV, LF2 | B07.02 = 490 |
| APLSSKITAI | 95 | EBV, LF2 | B07.02 = 31 |
| AQHTPPFLK | 96 | EBV, LF2 | A03.01 = 140 |
| AYPGGAHAAL | 97 | EBV, LF2 | A24.02 = 470 |
| CPSVGQILSF | 98 | EBV, LF2 | B07.02 = 190 |
| EVFLKPFFV | 99 | EBV, LF2 | A02.01 = 210 |
| FFGAEDNEVF | 100 | EBV, LF2 | A24.02 = 910 |
| FIEKGKFTWY | 101 | EBV, LF2 | A01.01 = 450 |
| FIYAGDPSI | 102 | EBV, LF2 | A02.01 = 13 |
| FLSGSPVTS | 103 | EBV, LF2 | A02.01 = 630 |
| FMRGVWKYEI | 104 | EBV, LF2 | A02.01 = 140; B08.01 = 340 |
| FTVAFLFFGA | 105 | EBV, LF2 | A02.01 = 17 |
| FTWYIVPIRL | 106 | EBV, LF2 | A02.01 = 63 |
| FVMHSDQDIV | 107 | EBV, LF2 | A02.01 = 130 |
| GPLNVKVGM | 108 | EBV, LF2 | B07.02 = 610 |
| GQSMAQAFFI | 109 | EBV, LF2 | A02.01 = 510 |
| HSDQDIVLSV | 110 | EBV, LF2 | A01.01 = 860 |
| HSSNPVFYV | 111 | EBV, LF2 | A02.01 = 800 |
| HSSNPVFYVY | 112 | EBV, LF2 | A01.01 = 170 |
| HTFPGKVCPV | 113 | EBV, LF2 | A02.01 = 200 |
| IAFRYNPYPK | 114 | EBV, LF2 | A03.01 = 58 |
| IIPPNFITEL | 115 | EBV, LF2 | A02.01 = 350 |
| ILPGQSDIQL | 116 | EBV, LF2 | A02.01 = 350 |
| IPPNFITEL | 117 | EBV, LF2 | B07.02 = 200 |
| ITELEYNNTY | 118 | EBV, LF2 | A01.01 = 61 |
| IVVSHSSNPV | 119 | EBV, LF2 | A02.01 = 160 |
| KFTWYIVPI | 120 | EBV, LF2 | A24.02 = 200 |
| KLNTSEPQI | 121 | EBV, LF2 | A02.01 = 270 |
| KLPSFSFNT | 122 | EBV, LF2 | A02.01 = 63 |
| KLPSFSFNTT | 123 | EBV, LF2 | A02.01 = 520 |
| KNPYLYLQI | 124 | EBV, LF2 | A24.02 = 900 |

TABLE 6-continued

| Peptide | SEQ ID NO: | Virus, Gene | Affinity |
|---|---|---|---|
| KPDTSFMRGV | 125 | EBV, LF2 | B07.02 = 920 |
| KPGQTLKLTV | 126 | EBV, LF2 | B07.02 = 320 |
| KSYARIHTF | 127 | EBV, LF2 | A24.02 = 210 |
| KVCPVNAIRR | 128 | EBV, LF2 | A03.01 = 850 |
| KYEIFPSYV | 129 | EBV, LF2 | A24.02 = 740 |
| LAQHTPPFLK | 130 | EBV, LF2 | A03.01 = 440 |
| LDDVIIAFRY | 131 | EBV, LF2 | A01.01 = 860 |
| LFIEKGKFTW | 132 | EBV, LF2 | A24.02 = 230 |
| LLAQHTPPF | 133 | EBV, LF2 | A02.01 = 540; B07.02 = 750; B08.01 = 190 |
| LLAQHTPPFL | 134 | EBV, LF2 | A02.01 = 9.6; B08.01 = 480 |
| LLDDVIIAF | 135 | EBV, LF2 | A02.01 = 120 |
| LPGQSDIQL | 136 | EBV, LF2 | B07.02 = 470 |
| LPPCPSVGQI | 137 | EBV, LF2 | B07.02 = 930 |
| LPSFSFNTT | 138 | EBV, LF2 | B07.02 = 490 |
| LPSFSFNTTT | 139 | EBV, LF2 | B07.02 = 560 |
| LQLDAQCQEL | 140 | EBV, LF2 | A02.01 = 220 |
| LTLPGNIVV | 141 | EBV, LF2 | A02.01 = 880 |
| MAQAFFIYA | 142 | EBV, LF2 | A02.01 = 450 |
| NPYLYLQIL | 143 | EBV, LF2 | B07.02 = 170; B08.01 = 150 |
| NSLRRLRPT | 144 | EBV, LF2 | B08.01 = 370 |
| NTTTYGSRY | 145 | EBV, LF2 | A01.01 = 210 |
| NTYEAPLSSK | 146 | EBV, LF2 | A03.01 = 120 |
| PFLKSYARI | 147 | EBV, LF2 | A24.02 = 390 |
| PSYVRVTNK | 148 | EBV, LF2 | A03.01 = 620 |
| PYPKSHWRW | 149 | EBV, LF2 | A24.02 = 100 |
| QIFLSGSPV | 150 | EBV, LF2 | A02.01 = 380 |
| QLDAQCQEL | 151 | EBV, LF2 | A02.01 = 370 |
| QSMAQAFFI | 152 | EBV, LF2 | A02.01 = 890 |
| QSMAQAFFIY | 153 | EBV, LF2 | A01.01 = 190 |
| RLVKNPYLY | 154 | EBV, LF2 | A03.01 = 410 |
| RLVKNPYLYL | 155 | EBV, LF2 | A02.01 = 120 |
| RPTEKPDTSF | 156 | EBV, LF2 | B07.02 = 39 |
| RSLFIEKGK | 157 | EBV, LF2 | A03.01 = 430 |
| RSSFRNSLR | 158 | EBV, LF2 | A03.01 = 230 |
| RSSFRNSLRR | 159 | EBV, LF2 | A03.01 = 490 |
| RVSVDTPDLK | 160 | EBV, LF2 | A03.01 = 600 |
| RYFGSPVII | 161 | EBV, LF2 | A24.02 = 25 |
| RYFTVAFLF | 162 | EBV, LF2 | A24.02 = 3.7 |

TABLE 6-continued

| Peptide | SEQ ID NO: | Virus, Gene | Affinity |
|---|---|---|---|
| RYFTVAFLFF | 163 | EBV, LF2 | A24.02 = 5.2 |
| RYIQRQGCAL | 164 | EBV, LF2 | A24.02 = 450 |
| RYNPYPKSHW | 165 | EBV, LF2 | A24.02 = 530 |
| SFKLPSFSF | 166 | EBV, LF2 | A24.02 = 98 |
| SFMRGVWKY | 167 | EBV, LF2 | A24.02 = 460 |
| SLPTFERINK | 168 | EBV, LF2 | A03.01 = 420 |
| SLRRLRPTEK | 169 | EBV, LF2 | A03.01 = 120 |
| SMAQAFFIY | 170 | EBV, LF2 | A01.01 = 870; A03.01 = 340 |
| SMAQAFFIYA | 171 | EBV, LF2 | A02.01 = 18 |
| SPVTSQDECL | 172 | EBV, LF2 | B07.02 = 540 |
| SQDECLPYL | 173 | EBV, LF2 | A02.01 = 18 |
| SQDECLPYLL | 174 | EBV, LF2 | A02.01 = 45 |
| SRRSSFRNSL | 175 | EBV, LF2 | B07.02 = 620; B08.01 = 150 |
| SSFRNSLRR | 176 | EBV, LF2 | A03.01 = 350 |
| SSNPVFYVY | 177 | EBV, LF2 | A01.01 = 110 |
| SVGQILSFK | 178 | EBV, LF2 | A03.01 = 73 |
| TFERINKTF | 179 | EBV, LF2 | A24.02 = 540 |
| TIMRRYIQR | 180 | EBV, LF2 | A03.01 = 280 |
| TLLDDVIIA | 181 | EBV, LF2 | A02.01 = 51 |
| TLLDDVIIAF | 182 | EBV, LF2 | A02.01 = 650 |
| TPDLKREGPL | 183 | EBV, LF2 | B07.02 = 100 |
| TSFMRGVWK | 184 | EBV, LF2 | A03.01 = 83 |
| TSFMRGVWKY | 185 | EBV, LF2 | A01.01 = 730 |
| TSQDECLPY | 186 | EBV, LF2 | A01.01 = 74 |
| TTYGSRYFTV | 187 | EBV, LF2 | A02.01 = 130 |
| TVAFLFFGA | 188 | EBV, LF2 | A02.01 = 290 |
| TVRNISNNPI | 189 | EBV, LF2 | B07.02 = 450 |
| TWYIVPIRL | 190 | EBV, LF2 | A24.02 = 680 |
| TYEAPLSSKI | 191 | EBV, LF2 | A24.02 = 420 |
| TYGSRYFTV | 192 | EBV, LF2 | A24.02 = 19 |
| VFLKPFFVM | 193 | EBV, LF2 | A24.02 = 600 |
| VFYVYPQEW | 194 | EBV, LF2 | A24.02 = 110 |
| VFYVYPQEWK | 195 | EBV, LF2 | A03.01 = 650 |
| VLNPRSLFI | 196 | EBV, LF2 | A02.01 = 110 |
| VLSVLNPRSL | 197 | EBV, LF2 | A02.01 = 680 |
| VMHSDQDIV | 198 | EBV, LF2 | A02.01 = 440 |
| VMHSDQDIVL | 199 | EBV, LF2 | A02.01 = 910 |
| VSHSSNPVFY | 200 | EBV, LF2 | A01.01 = 330 |

TABLE 6-continued

| Peptide | SEQ ID NO: | Virus, Gene | Affinity |
|---|---|---|---|
| VTSQDECLPY | 201 | EBV, LF2 | A01.01 = 26 |
| VVSHSSNPV | 202 | EBV, LF2 | A02.01 = 690 |
| WYIVPIRLV | 203 | EBV, LF2 | A24.02 = 700 |
| YARIHTFPG | 204 | EBV, LF2 | B08.01 = 430 |
| YARIHTFPGK | 205 | EBV, LF2 | A03.01 = 660 |
| YFTVAFLFF | 206 | EBV, LF2 | A24.02 = 62 |
| YIQRQGCAL | 207 | EBV, LF2 | B07.02 = 500; B08.01 = 890 |
| YIVPIRLVK | 208 | EBV, LF2 | A03.01 = 300 |
| YLLAQHTPPF | 209 | EBV, LF2 | A02.01 = 69; A24.02 = 550; B08.01 = 310 |
| YLYLQILPG | 210 | EBV, LF2 | A02.01 = 320 |
| YLYLQILPGQ | 211 | EBV, LF2 | A02.01 = 800 |
| YPGGAHAAL | 212 | EBV, LF2 | B07.02 = 7; B08.01 = 700 |
| YPGGAHAALA | 213 | EBV, LF2 | B07.02 = 410 |
| YVRVTNKQVL | 214 | EBV, LF2 | B07.02 = 70; B08.01 = 470 |
| AGRYRRILL | 215 | EBV, BALF5 | B08.01 = 810 |
| AIKCTCNAV | 216 | EBV, BALF5 | B08.01 = 760 |
| ALAAHTTRSL | 217 | EBV, BALF5 | A02.01 = 93; B07.02 = 200; B08.01 = 340 |
| ALAFDIECL | 218 | EBV, BALF5 | A02.01 = 70 |
| ALAPSPDAWA | 219 | EBV, BALF5 | A02.01 = 280 |
| ALKASTFDR | 220 | EBV, BALF5 | A03.01 = 1000 |
| ALSPANLQA | 221 | EBV, BALF5 | A02.01 = 530 |
| ALSPANLQAL | 222 | EBV, BALF5 | A02.01 = 65 |
| ALSVLQNFTA | 223 | EBV, BALF5 | A02.01 = 260 |
| APLNPEGQL | 224 | EBV, BALF5 | B07.02 = 85 |
| APQGLDVEF | 225 | EBV, BALF5 | B07.02 = 280 |
| APSPDAWAPL | 226 | EBV, BALF5 | B07.02 = 18 |
| ASLLTSWLAK | 227 | EBV, BALF5 | A03.01 = 140 |
| AVYGFTGVA | 228 | EBV, BALF5 | A02.01 = 830 |
| AVYQKFVER | 229 | EBV, BALF5 | A03.01 = 340 |
| AYKSTQMPHL | 230 | EBV, BALF5 | A24.02 = 770 |
| CLFDNNSGA | 231 | EBV, BALF5 | A02.01 = 130 |
| CLFDNNSGAA | 232 | EBV, BALF5 | A02.01 = 390 |
| CLGEEGFPT | 233 | EBV, BALF5 | A02.01 = 680 |
| CLGEEGFPTA | 234 | EBV, BALF5 | A02.01 = 120 |
| CLSIAETVTL | 235 | EBV, BALF5 | A02.01 = 580 |
| CVNVFGQQAY | 236 | EBV, BALF5 | A01.01 = 750 |
| DARVKEAASL | 237 | EBV, BALF5 | B08.01 = 330 |
| DLLNHFVIHV | 238 | EBV, BALF5 | A02.01 = 290 |

TABLE 6-continued

| Peptide | SEQ ID NO: | Virus, Gene | Affinity |
|---|---|---|---|
| DLREGRVPM | 239 | EBV, BALF5 | B07.02 = 690; B08.01 = 600 |
| DMLYAFFQL | 240 | EBV, BALF5 | A02.01 = 340 |
| DNDFVTFGWY | 241 | EBV, BALF5 | A01.01 = 820 |
| DRARHIYSI | 242 | EBV, BALF5 | B08.01 = 350 |
| DVRGPQPPL | 243 | EBV, BALF5 | B07.02 = 870 |
| EAGRYRRIL | 244 | EBV, BALF5 | B08.01 = 770 |
| ELSRKLSAYK | 245 | EBV, BALF5 | A03.01 = 450 |
| EMAEDPAYA | 246 | EBV, BALF5 | A02.01 = 480 |
| EYLRLIPKCF | 247 | EBV, BALF5 | A24.02 = 310 |
| FLASLLTSW | 248 | EBV, BALF5 | A02.01 = 150 |
| FLASLLTSWL | 249 | EBV, BALF5 | A02.01 = 4.1 |
| FLRANTKVRI | 250 | EBV, BALF5 | B08.01 = 260 |
| FLRPNKGLL | 251 | EBV, BALF5 | B08.01 = 250 |
| FLRPNKGLLK | 252 | EBV, BALF5 | A03.01 = 96 |
| FPTATNEADL | 253 | EBV, BALF5 | B07.02 = 180 |
| FQESFTQGL | 254 | EBV, BALF5 | A02.01 = 920 |
| FQLIRDLSV | 255 | EBV, BALF5 | A02.01 = 210; B08.01 = 390 |
| FQTPGAAGV | 256 | EBV, BALF5 | A02.01 = 48 |
| FQTPGAAGVV | 257 | EBV, BALF5 | A02.01 = 640 |
| FSESETLRF | 258 | EBV, BALF5 | A01.01 = 180 |
| FTQGLPVGFL | 259 | EBV, BALF5 | A02.01 = 960 |
| FVAPISLEA | 260 | EBV, BALF5 | A02.01 = 26 |
| FVEALSPANL | 261 | EBV, BALF5 | A02.01 = 860 |
| FVIHVEVAEI | 262 | EBV, BALF5 | A02.01 = 64 |
| FVKKHVHESF | 263 | EBV, BALF5 | B08.01 = 130 |
| FVLDNDFVT | 264 | EBV, BALF5 | A02.01 = 650 |
| FVLDNDFVTF | 265 | EBV, BALF5 | A24.02 = 750 |
| FVQTRCRRV | 266 | EBV, BALF5 | B08.01 = 340 |
| FVQTRCRRVL | 267 | EBV, BALF5 | B07.02 = 330; B08.01 = 100 |
| FYASAPQGL | 268 | EBV, BALF5 | A24.02 = 100 |
| GLDVEFAVL | 269 | EBV, BALF5 | A02.01 = 640 |
| GLFPCLSIA | 270 | EBV, BALF5 | A02.01 = 33 |
| GLFYNPFLR | 271 | EBV, BALF5 | A03.01 = 100 |
| GLIPIDMYA | 272 | EBV, BALF5 | A02.01 = 28 |
| GLIPIDMYAV | 273 | EBV, BALF5 | A02.01 = 5.9 |
| GLPVGFLPV | 274 | EBV, BALF5 | A02.01 = 68 |
| GLPVGFLPVI | 275 | EBV, BALF5 | A02.01 = 330 |
| GMYCVQDSA | 276 | EBV, BALF5 | A02.01 = 100 |

TABLE 6-continued

| Peptide | SEQ ID NO: | Virus, Gene | Affinity |
|---|---|---|---|
| GMYCVQDSAL | 277 | EBV, BALF5 | A02.01 = 64 |
| GPEGRRRLGM | 278 | EBV, BALF5 | B07.02 = 47 |
| GQQAYFYASA | 279 | EBV, BALF5 | A02.01 = 800 |
| GVANGLFPCL | 280 | EBV, BALF5 | A02.01 = 340 |
| GVYHFVKKH | 281 | EBV, BALF5 | A03.01 = 990 |
| GYNVANFDW | 282 | EBV, BALF5 | A24.02 = 270 |
| HIYSINPASL | 283 | EBV, BALF5 | A02.01 = 360 |
| HLAVYQKFV | 284 | EBV, BALF5 | A02.01 = 140 |
| HPNSVCHVA | 285 | EBV, BALF5 | B07.02 = 530 |
| HPNSVCHVAT | 286 | EBV, BALF5 | B07.02 = 380 |
| HVATWLQDK | 287 | EBV, BALF5 | A03.01 = 380 |
| HVHESFLASL | 288 | EBV, BALF5 | A02.01 = 670; B07.02 = 260; B08.01 = 990 |
| HVYDILETV | 289 | EBV, BALF5 | A02.01 = 12 |
| HVYDILETVY | 290 | EBV, BALF5 | A03.01 = 990 |
| HYKEIPRLF | 291 | EBV, BALF5 | A24.02 = 71 |
| IAHIPCRRVL | 292 | EBV, BALF5 | B07.02 = 620 |
| IIQAHNLCY | 293 | EBV, BALF5 | A01.01 = 600; A03.01 = 790 |
| ILDKQQLAI | 294 | EBV, BALF5 | A02.01 = 180 |
| ILDKQQLAIK | 295 | EBV, BALF5 | A03.01 = 310 |
| ILDRARHIY | 296 | EBV, BALF5 | A01.01 = 160 |
| ILETVYTHEK | 297 | EBV, BALF5 | A03.01 = 290 |
| ILNQAYTDL | 298 | EBV, BALF5 | A02.01 = 750 |
| ILQISCVLW | 299 | EBV, BALF5 | A24.02 = 990 |
| IPRLFAAGPE | 300 | EBV, BALF5 | B07.02 = 640 |
| IPRLQHRDSY | 301 | EBV, BALF5 | B07.02 = 360 |
| IPSDKQGYV | 302 | EBV, BALF5 | B07.02 = 610 |
| IPSDKQGYVV | 303 | EBV, BALF5 | B07.02 = 150 |
| IQYVFVEPK | 304 | EBV, BALF5 | A03.01 = 78 |
| ITGLIPIDMY | 305 | EBV, BALF5 | A01.01 = 340 |
| ITKKRYVGV | 306 | EBV, BALF5 | B08.01 = 520 |
| ITKKRYVGVL | 307 | EBV, BALF5 | B08.01 = 240 |
| ITLSHPNSV | 308 | EBV, BALF5 | A02.01 = 610 |
| IVIKLLGRRK | 309 | EBV, BALF5 | A03.01 = 350 |
| IYGDTDSLF | 310 | EBV, BALF5 | A24.02 = 37 |
| IYGDTDSLFI | 311 | EBV, BALF5 | A24.02 = 95 |
| IYSINPASL | 312 | EBV, BALF5 | A24.02 = 110 |
| KAIKKLLAA | 313 | EBV, BALF5 | B08.01 = 790 |
| KEYLRLIPK | 314 | EBV, BALF5 | A03.01 = 810 |

TABLE 6-continued

| Peptide | SEQ ID NO: | Virus, Gene | Affinity |
|---|---|---|---|
| KGFLRANTK | 315 | EBV, BALF5 | A03.01 = 170 |
| KIAHIPCRR | 316 | EBV, BALF5 | A03.01 = 340 |
| KITLSHPNSV | 317 | EBV, BALF5 | A02.01 = 920 |
| KLDTVARHL | 318 | EBV, BALF5 | A02.01 = 900 |
| KLDTVARHLL | 319 | EBV, BALF5 | A02.01 = 170 |
| KLLQGAANI | 320 | EBV, BALF5 | A02.01 = 25 |
| KLLQGAANIL | 321 | EBV, BALF5 | A02.01 = 63 |
| KLSAYKSTQM | 322 | EBV, BALF5 | A02.01 = 620 |
| KLSLSDYKL | 323 | EBV, BALF5 | A02.01 = 160 |
| KPDKEYLRL | 324 | EBV, BALF5 | B07.02 = 810 |
| KTACKFVQTR | 325 | EBV, BALF5 | A03.01 = 740 |
| KTEMAEDPAY | 326 | EBV, BALF5 | A01.01 = 200 |
| KTFSCLMLI | 327 | EBV, BALF5 | A02.01 = 46; A24.02 = 400 |
| KTLMKGVELV | 328 | EBV, BALF5 | A02.01 = 730 |
| KVRITGLIPI | 329 | EBV, BALF5 | B07.02 = 260 |
| KVTRRSIMGY | 330 | EBV, BALF5 | A03.01 = 140 |
| LAAHTTRSL | 331 | EBV, BALF5 | B07.02 = 76 |
| LAKRKAIKKL | 332 | EBV, BALF5 | B08.01 = 180 |
| LDRARHIYSI | 333 | EBV, BALF5 | B08.01 = 410 |
| LILQISCVL | 334 | EBV, BALF5 | A02.01 = 810 |
| LIPIDMYAV | 335 | EBV, BALF5 | A02.01 = 150 |
| LITKKRYVGV | 336 | EBV, BALF5 | B08.01 = 860 |
| LLNHFVIHV | 337 | EBV, BALF5 | A02.01 = 7.3 |
| LLQGAANIL | 338 | EBV, BALF5 | A02.01 = 360 |
| LLTSWLAKRK | 339 | EBV, BALF5 | A03.01 = 240 |
| LMKGVELVRK | 340 | EBV, BALF5 | A03.01 = 130 |
| LMLITKKRYV | 341 | EBV, BALF5 | A02.01 = 910 |
| LPVGFLPVI | 342 | EBV, BALF5 | B07.02 = 530 |
| LQISCVLWST | 343 | EBV, BALF5 | A02.01 = 220 |
| LSRKLSAYK | 344 | EBV, BALF5 | A03.01 = 94 |
| LTDGKTLMK | 345 | EBV, BALF5 | A01.01 = 410; A03.01 = 610 |
| LTGGVYHFV | 346 | EBV, BALF5 | A02.01 = 200 |
| LTGGVYHFVK | 347 | EBV, BALF5 | A03.01 = 330 |
| LTSWLAKRK | 348 | EBV, BALF5 | A03.01 = 560 |
| LVMDLLNHFV | 349 | EBV, BALF5 | A02.01 = 5.3 |
| LVVDFASLY | 350 | EBV, BALF5 | A01.01 = 460 |
| MLERAKAFV | 351 | EBV, BALF5 | A02.01 = 400 |
| MLITKKRYV | 352 | EBV, BALF5 | A02.01 = 190; B08.01 = 130 |

TABLE 6-continued

| Peptide | SEQ ID NO: | Virus, Gene | Affinity |
|---|---|---|---|
| MLITKKRYVG | 353 | EBV, BALF5 | B08.01 = 560 |
| MLYAFFQLI | 354 | EBV, BALF5 | A02.01 = 6.6; A24.02 = 800; B08.01 = 640 |
| MLYAFFQLIR | 355 | EBV, BALF5 | A03.01 = 40 |
| MPHLAVYQKF | 356 | EBV, BALF5 | B07.02 = 150 |
| MSGGLFYNPF | 357 | EBV, BALF5 | A24.02 = 490 |
| MYAVCRDKL | 358 | EBV, BALF5 | A24.02 = 210 |
| NPEGQLRVI | 359 | EBV, BALF5 | B07.02 = 650 |
| NPFLRPNKGL | 360 | EBV, BALF5 | B07.02 = 140; B08.01 = 630 |
| NTKVRITGL | 361 | EBV, BALF5 | B08.01 = 120 |
| NTKVRITGLI | 362 | EBV, BALF5 | B08.01 = 940 |
| NVANFDWPY | 363 | EBV, BALF5 | A01.01 = 300 |
| NVANFDWPYI | 364 | EBV, BALF5 | A02.01 = 320 |
| PLSGFYNSPV | 365 | EBV, BALF5 | A02.01 = 520 |
| QIHDRIQYV | 366 | EBV, BALF5 | A02.01 = 180 |
| QIRVFSCLL | 367 | EBV, BALF5 | B08.01 = 960 |
| QLIRDLSVEI | 368 | EBV, BALF5 | A02.01 = 94 |
| QMPHLAVYQK | 369 | EBV, BALF5 | A03.01 = 900 |
| QQIRVFSCLL | 370 | EBV, BALF5 | A02.01 = 980 |
| QTRCRRVLDL | 371 | EBV, BALF5 | B08.01 = 200 |
| RAKAFVEAL | 372 | EBV, BALF5 | B07.02 = 270; B08.01 = 990 |
| RIFEANVDA | 373 | EBV, BALF5 | A02.01 = 870 |
| RIQYVFVEPK | 374 | EBV, BALF5 | A03.01 = 85 |
| RLFAAGPEGR | 375 | EBV, BALF5 | A03.01 = 260 |
| RLIPKCFQT | 376 | EBV, BALF5 | A02.01 = 130 |
| RLTGGVYHF | 377 | EBV, BALF5 | A24.02 = 340 |
| RLTGGVYHFV | 378 | EBV, BALF5 | A02.01 = 8.1 |
| RPGEDYESF | 379 | EBV, BALF5 | B07.02 = 630 |
| RPHDAGKGF | 380 | EBV, BALF5 | B07.02 = 21 |
| RPHDAGKGFL | 381 | EBV, BALF5 | B07.02 = 9.1 |
| RTMLERAKAF | 382 | EBV, BALF5 | B07.02 = 920 |
| RTPCRVSVEK | 383 | EBV, BALF5 | A03.01 = 430 |
| RVFSCLLAA | 384 | EBV, BALF5 | A02.01 = 69; A03.01 = 810 |
| RVFSCLLAAA | 385 | EBV, BALF5 | A02.01 = 58 |
| RVIYGDTDSL | 386 | EBV, BALF5 | B07.02 = 560 |
| RVKEAASLL | 387 | EBV, BALF5 | B07.02 = 380 |
| RVLDLVLADA | 388 | EBV, BALF5 | A02.01 = 670 |
| RYRRILLTL | 389 | EBV, BALF5 | A24.02 = 23 |
| SFLASLLTSW | 390 | EBV, BALF5 | A24.02 = 56 |

TABLE 6-continued

| Peptide | SEQ ID NO: | Virus, Gene | Affinity |
|---|---|---|---|
| SFTQGLPVGF | 391 | EBV, BALF5 | A24.02 = 350 |
| SIMGYGNHA | 392 | EBV, BALF5 | A02.01 = 760 |
| SINPASLGK | 393 | EBV, BALF5 | A03.01 = 63 |
| SLFVAPISL | 394 | EBV, BALF5 | A02.01 = 30 |
| SLLTSWLAK | 395 | EBV, BALF5 | A03.01 = 23 |
| SLLTSWLAKR | 396 | EBV, BALF5 | A03.01 = 490 |
| SLSDYKLDTV | 397 | EBV, BALF5 | A02.01 = 22 |
| SLYPSIIQA | 398 | EBV, BALF5 | A02.01 = 23 |
| SLYPSIIQAH | 399 | EBV, BALF5 | A03.01 = 240 |
| SPANLQALA | 400 | EBV, BALF5 | B07.02 = 500 |
| SPLDFHVYDI | 401 | EBV, BALF5 | B07.02 = 570 |
| STFDRRTPCR | 402 | EBV, BALF5 | A03.01 = 600 |
| STGEEAGRY | 403 | EBV, BALF5 | A01.01 = 130 |
| STQMPHLAVY | 404 | EBV, BALF5 | A01.01 = 130 |
| SWLAKRKAI | 405 | EBV, BALF5 | B08.01 = 340 |
| SWPSYQALAF | 406 | EBV, BALF5 | A24.02 = 49 |
| SYQALAFDI | 407 | EBV, BALF5 | A24.02 = 13 |
| TKKRYVGVL | 408 | EBV, BALF5 | B08.01 = 460 |
| TLMKGVELV | 409 | EBV, BALF5 | A02.01 = 7.9 |
| TMLERAKAF | 410 | EBV, BALF5 | B08.01 = 100 |
| TMLERAKAFV | 411 | EBV, BALF5 | A02.01 = 33; B08.01 = 840 |
| TVARHLLGAK | 412 | EBV, BALF5 | A03.01 = 90 |
| VARHLLGAK | 413 | EBV, BALF5 | A03.01 = 600 |
| VARHLLGAKK | 414 | EBV, BALF5 | A03.01 = 820 |
| VIDILNQAY | 415 | EBV, BALF5 | A01.01 = 34 |
| VIKLLGRRK | 416 | EBV, BALF5 | A03.01 = 720 |
| VIQPLSGFY | 417 | EBV, BALF5 | A01.01 = 990; A03.01 = 920 |
| VIYGDTDSL | 418 | EBV, BALF5 | A02.01 = 680 |
| VLADARVKEA | 419 | EBV, BALF5 | A02.01 = 450 |
| VLDDGQQIRV | 420 | EBV, BALF5 | A02.01 = 17 |
| VLDLVLADA | 421 | EBV, BALF5 | A02.01 = 540 |
| VLTDGKTLMK | 422 | EBV, BALF5 | A03.01 = 200 |
| VLVVDFASL | 423 | EBV, BALF5 | A02.01 = 190 |
| VLWSTGEEA | 424 | EBV, BALF5 | A02.01 = 210 |
| VMDLLNHFV | 425 | EBV, BALF5 | A01.01 = 780; A02.01 = 9.7 |
| VMDLLNHFVI | 426 | EBV, BALF5 | A02.01 = 79 |
| VTFGWYSCR | 427 | EBV, BALF5 | A03.01 = 290 |
| VTFGWYSCRR | 428 | EBV, BALF5 | A03.01 = 230 |

TABLE 6-continued

| Peptide | SEQ ID NO: | Virus, Gene | Affinity |
|---|---|---|---|
| VTRRSIMGY | 429 | EBV, BALF5 | A03.01 = 250 |
| VYTHEKCAVI | 430 | EBV, BALF5 | A24.02 = 490 |
| WLAKRKAIK | 431 | EBV, BALF5 | A03.01 = 470 |
| WLAKRKAIKK | 432 | EBV, BALF5 | A03.01 = 190 |
| WLQDKHGCRI | 433 | EBV, BALF5 | A02.01 = 790; B08.01 = 810 |
| WPSYQALAF | 434 | EBV, BALF5 | B07.02 = 31 |
| WSTGEEAGRY | 435 | EBV, BALF5 | A01.01 = 370 |
| YAERHGVPV | 436 | EBV, BALF5 | B08.01 = 700 |
| YAVCRDKLSL | 437 | EBV, BALF5 | B08.01 = 330 |
| YFYASAPQGL | 438 | EBV, BALF5 | A24.02 = 650 |
| YILDRARHI | 439 | EBV, BALF5 | A02.01 = 740; B08.01 = 770 |
| YLRLIPKCF | 440 | EBV, BALF5 | B08.01 = 330 |
| YPSIIQAHNL | 441 | EBV, BALF5 | B07.02 = 76 |
| YQGATVIQPL | 442 | EBV, BALF5 | A02.01 = 62 |
| YSINPASLGK | 443 | EBV, BALF5 | A03.01 = 230 |
| YTDLREGRV | 444 | EBV, BALF5 | A01.01 = 510 |
| YVFVEPKGGV | 445 | EBV, BALF5 | A02.01 = 650 |
| AYSARPPPL | 446 | EBV, RPMS1 | A24.02 = 550 |
| CAYSARPPPL | 447 | EBV, RPMS1 | B07.02 = 420; B08.01 = 770 |
| GARRRARCPA | 448 | EBV, RPMS1 | B08.01 = 240 |
| GPGRRARSCL | 449 | EBV, RPMS1 | B07.02 = 52; B08.01 = 650 |
| MAGARRRARC | 450 | EBV, RPMS1 | B08.01 = 460 |
| RPGPGRRARS | 451 | EBV, RPMS1 | B07.02 = 520 |
| RPPHSRTRA | 452 | EBV, RPMS1 | B07.02 = 93 |
| RRRARCPASA | 453 | EBV, RPMS1 | B08.01 = 610 |
| SGQPRWWPW | 454 | EBV, RPMS1 | A24.02 = 350 |
| STRGRRISA | 455 | EBV, RPMS1 | B07.02 = 990; B08.01 = 240 |
| WPWGSPPPL | 456 | EBV, RPMS1 | B07.02 = 7.8 |
| WWPWGSPPPL | 457 | EBV, RPMS1 | A24.02 = 650 |
| AMFCAWKLY | 458 | EBV, A73 | A03.01 = 120 |
| AMFCAWKLYS | 459 | EBV, A73 | A02.01 = 700 |
| AVKAAAQSAF | 460 | EBV, A73 | B07.02 = 750 |
| CAWKLYSRK | 461 | EBV, A73 | A03.01 = 350 |
| FADAWRMARY | 462 | EBV, A73 | A01.01 = 11 |
| KLYSRKMPS | 463 | EBV, A73 | A03.01 = 400 |
| KLYSRKMPSR | 464 | EBV, A73 | A03.01 = 19 |
| KPPTVLTRPA | 465 | EBV, A73 | B07.02 = 540 |
| KTLEARCSSR | 466 | EBV, A73 | A03.01 = 770 |

TABLE 6-continued

| Peptide | SEQ ID NO: | Virus, Gene | Affinity |
|---|---|---|---|
| MARYWGCAV | 467 | EBV, A73 | B07.02 = 37; B08.01 = 51 |
| MARYWGCAVK | 468 | EBV, A73 | A03.01 = 420 |
| MPSRSKTLEA | 469 | EBV, A73 | B07.02 = 92; B08.01 = 910 |
| MSMPPKGFLK | 470 | EBV, A73 | A03.01 = 29 |
| PPTVLTRPAM | 471 | EBV, A73 | B07.02 = 350 |
| RGWRARRLGK | 472 | EBV, A73 | A03.01 = 290 |
| RKMPSRSKTL | 473 | EBV, A73 | B07.02 = 580 |
| RLGKESWFA | 474 | EBV, A73 | A02.01 = 56 |
| RLLNKPPTV | 475 | EBV, A73 | A02.01 = 21 |
| RLLNKPPTVL | 476 | EBV, A73 | A02.01 = 290 |
| RMARYWGCAV | 477 | EBV, A73 | A02.01 = 41; B08.01 = 740 |
| RPAMFCAWKL | 478 | EBV, A73 | B07.02 = 40 |
| SMPPKGFLK | 479 | EBV, A73 | A03.01 = 200 |
| SMPPKGFLKK | 480 | EBV, A73 | A03.01 = 230 |
| SPACQTRDT | 481 | EBV, A73 | B07.02 = 440 |
| SWFADAWRM | 482 | EBV, A73 | A24.02 = 530 |
| VLTRPAMFCA | 483 | EBV, A73 | A02.01 = 650 |
| WRMARYWGC | 484 | EBV, A73 | B08.01 = 880 |
| WRMARYWGCA | 485 | EBV, A73 | B08.01 = 190 |
| YSRKMPSRSK | 486 | EBV, A73 | A03.01 = 680 |
| AARDRFPGL | 487 | EBV, BALF4 | B07.02 = 720; B08.01 = 270 |
| AARGSTSAA | 488 | EBV, BALF4 | B07.02 = 110 |
| AARGSTSAAV | 489 | EBV, BALF4 | B07.02 = 61 |
| AFLDKGTYTL | 490 | EBV, BALF4 | A24.02 = 960 |
| ALHEQNQEQK | 491 | EBV, BALF4 | A03.01 = 730 |
| APGKSLGTL | 492 | EBV, BALF4 | B07.02 = 16 |
| APPAARGST | 493 | EBV, BALF4 | B07.02 = 170 |
| AQNIAGLRK | 494 | EBV, BALF4 | A03.01 = 570 |
| ATLQTFISL | 495 | EBV, BALF4 | A02.01 = 980 |
| ATRQQTSFPF | 496 | EBV, BALF4 | B07.02 = 720 |
| ATVQIQFAY | 497 | EBV, BALF4 | A01.01 = 170 |
| CLEQKRQNM | 498 | EBV, BALF4 | B08.01 = 650 |
| CLITDMMAK | 499 | EBV, BALF4 | A03.01 = 74 |
| CPLQHWQTF | 500 | EBV, BALF4 | B07.02 = 88; B08.01 = 630 |
| CQATSQYYF | 501 | EBV, BALF4 | A24.02 = 620 |
| CYSRPLVSF | 502 | EBV, BALF4 | A24.02 = 12 |
| DMMAKSNSPF | 503 | EBV, BALF4 | B08.01 = 190 |
| DSFHVRTNYK | 504 | EBV, BALF4 | A03.01 = 850 |

TABLE 6-continued

| Peptide | SEQ ID NO: | Virus, Gene | Affinity |
|---|---|---|---|
| ELMDSLGSV | 505 | EBV, BALF4 | A02.01 = 21 |
| ELYDAPGWLI | 506 | EBV, BALF4 | A02.01 = 400 |
| ENRTAYCPL | 507 | EBV, BALF4 | B08.01 = 680 |
| EQKRQNMVL | 508 | EBV, BALF4 | B08.01 = 470 |
| ETDQMDTIY | 509 | EBV, BALF4 | A01.01 = 13 |
| ETMCYSRPL | 510 | EBV, BALF4 | B08.01 = 160 |
| FFKNPFGGML | 511 | EBV, BALF4 | B08.01 = 980 |
| FISLNTSLI | 512 | EBV, BALF4 | A02.01 = 140 |
| FITSGGLLL | 513 | EBV, BALF4 | A02.01 = 350 |
| FITSGGLLLA | 514 | EBV, BALF4 | A02.01 = 330 |
| FLDKGTYTL | 515 | EBV, BALF4 | A02.01 = 3 |
| FLDKGTYTLS | 516 | EBV, BALF4 | A02.01 = 200 |
| FLTKKMTEV | 517 | EBV, BALF4 | A02.01 = 10; B08.01 = 980 |
| FPGLRRRRY | 518 | EBV, BALF4 | B07.02 = 850 |
| FQAQNIAGL | 519 | EBV, BALF4 | A02.01 = 25 |
| FQSGNEIHV | 520 | EBV, BALF4 | A02.01 = 79 |
| FSFINDTKTY | 521 | EBV, BALF4 | A01.01 = 740 |
| FVDGLGELM | 522 | EBV, BALF4 | A01.01 = 760 |
| FVTNTTVGI | 523 | EBV, BALF4 | A02.01 = 340 |
| FYDGKNKETF | 524 | EBV, BALF4 | A24.02 = 190 |
| GFISFFKNPF | 525 | EBV, BALF4 | A24.02 = 160 |
| GIATLQTFI | 526 | EBV, BALF4 | A02.01 = 490 |
| GIFREYNFQA | 527 | EBV, BALF4 | A02.01 = 310 |
| GLFSSLVSG | 528 | EBV, BALF4 | A02.01 = 870 |
| GLFSSLVSGF | 529 | EBV, BALF4 | A02.01 = 850 |
| GLGELMDSL | 530 | EBV, BALF4 | A02.01 = 73 |
| GLLLAWLPL | 531 | EBV, BALF4 | A02.01 = 85 |
| GLLLAWLPLT | 532 | EBV, BALF4 | A02.01 = 280 |
| GLLMVFKDNI | 533 | EBV, BALF4 | A02.01 = 610 |
| GLRKDLDNAV | 534 | EBV, BALF4 | A02.01 = 680 |
| GMLILVLVA | 535 | EBV, BALF4 | A02.01 = 570 |
| GPSVASRAL | 536 | EBV, BALF4 | B07.02 = 7.9 |
| GQEAITYFI | 537 | EBV, BALF4 | A02.01 = 430 |
| GTDNEIFLTK | 538 | EBV, BALF4 | A03.01 = 690 |
| GTLNNPATV | 539 | EBV, BALF4 | A02.01 = 940 |
| GTYTLSWKL | 540 | EBV, BALF4 | A02.01 = 410 |
| GVNITVNLK | 541 | EBV, BALF4 | A03.01 = 120 |
| HTEGLLMVFK | 542 | EBV, BALF4 | A03.01 = 450 |

TABLE 6-continued

| Peptide | SEQ ID NO: | Virus, Gene | Affinity |
|---|---|---|---|
| HVYNDYHHFK | 543 | EBV, BALF4 | A03.01 = 22 |
| HWQTFDSTI | 544 | EBV, BALF4 | A24.02 = 490 |
| ILIYNGWYA | 545 | EBV, BALF4 | A02.01 = 15 |
| IQFAYDSLR | 546 | EBV, BALF4 | A03.01 = 920 |
| IQFAYDSLRR | 547 | EBV, BALF4 | A03.01 = 610 |
| IYNGWYADSV | 548 | EBV, BALF4 | A24.02 = 290 |
| IYQCYNAVKM | 549 | EBV, BALF4 | A24.02 = 140 |
| KGTYTLSWK | 550 | EBV, BALF4 | A03.01 = 570 |
| KIVTNILIY | 551 | EBV, BALF4 | A03.01 = 460 |
| KMTEVCQAT | 552 | EBV, BALF4 | A02.01 = 400 |
| KMTKDGLTRV | 553 | EBV, BALF4 | A02.01 = 96 |
| KPTGGLANGV | 554 | EBV, BALF4 | B07.02 = 580 |
| KSNSPFDFFV | 555 | EBV, BALF4 | A02.01 = 570 |
| KTMHEKYEAV | 556 | EBV, BALF4 | A02.01 = 250 |
| LARAWCLEQK | 557 | EBV, BALF4 | A03.01 = 920 |
| LFSSLVSGF | 558 | EBV, BALF4 | A24.02 = 490 |
| LILVLVAGV | 559 | EBV, BALF4 | A02.01 = 58 |
| LILVLVAGVV | 560 | EBV, BALF4 | A02.01 = 940 |
| LLAALACRL | 561 | EBV, BALF4 | A02.01 = 37 |
| LLAWLPLTPR | 562 | EBV, BALF4 | A03.01 = 440 |
| LLLAWLPLT | 563 | EBV, BALF4 | A02.01 = 21 |
| LLMVFKDNI | 564 | EBV, BALF4 | A02.01 = 130 |
| LLMVFKDNII | 565 | EBV, BALF4 | A02.01 = 320; B08.01 = 700 |
| LPLTPRSLA | 566 | EBV, BALF4 | B07.02 = 250 |
| LPLTPRSLAT | 567 | EBV, BALF4 | B07.02 = 110 |
| LRRQINRML | 568 | EBV, BALF4 | B08.01 = 770 |
| LTPRSLATV | 569 | EBV, BALF4 | A02.01 = 900 |
| LVAGVVILV | 570 | EBV, BALF4 | A02.01 = 46 |
| LVSGFISFFK | 571 | EBV, BALF4 | A03.01 = 27 |
| LYDAPGWLI | 572 | EBV, BALF4 | A24.02 = 110 |
| LYDAPGWLIW | 573 | EBV, BALF4 | A24.02 = 170 |
| MCYSRPLVSF | 574 | EBV, BALF4 | B08.01 = 760 |
| MLILVLVAGV | 575 | EBV, BALF4 | A02.01 = 7.6 |
| MLYPGIDEL | 576 | EBV, BALF4 | A02.01 = 4.2 |
| MLYPGIDELA | 577 | EBV, BALF4 | A02.01 = 16 |
| MMAKSNSPF | 578 | EBV, BALF4 | A02.01 = 920; A24.02 = 240; B07.02 = 290; B08.01 = 630 |
| MSQQPVQMLY | 579 | EBV, BALF4 | A01.01 = 67 |
| MTRRRVLSV | 580 | EBV, BALF4 | B07.02 = 200; B08.01 = 7.4 |

TABLE 6-continued

| Peptide | SEQ ID NO: | Virus, Gene | Affinity |
|---|---|---|---|
| MTRRRVLSVV | 581 | EBV, BALF4 | B07.02 = 490; B08.01 = 39 |
| MVFKDNIIPY | 582 | EBV, BALF4 | A03.01 = 360 |
| MVLRELTKI | 583 | EBV, BALF4 | A02.01 = 580 |
| NIDFASLELY | 584 | EBV, BALF4 | A01.01 = 24 |
| NIIPYSFKV | 585 | EBV, BALF4 | A02.01 = 11 |
| NILIYNGWYA | 586 | EBV, BALF4 | A02.01 = 470 |
| NLTELTTPT | 587 | EBV, BALF4 | A02.01 = 1000 |
| NMVLRELTK | 588 | EBV, BALF4 | A03.01 = 840 |
| NPATVQIQF | 589 | EBV, BALF4 | B07.02 = 810 |
| NPFGGMLIL | 590 | EBV, BALF4 | B07.02 = 110 |
| NPQGERRAF | 591 | EBV, BALF4 | B07.02 = 48 |
| NPQGERRAFL | 592 | EBV, BALF4 | B07.02 = 73 |
| NPTTVMSSI | 593 | EBV, BALF4 | B07.02 = 240 |
| PPAAPGKSL | 594 | EBV, BALF4 | B07.02 = 84 |
| PPAARGSTSA | 595 | EBV, BALF4 | B07.02 = 800 |
| QMDTIYQCY | 596 | EBV, BALF4 | A01.01 = 75 |
| QMLYPGIDEL | 597 | EBV, BALF4 | A02.01 = 210 |
| QPAPPATTV | 598 | EBV, BALF4 | B07.02 = 95 |
| QQTSFPFRV | 599 | EBV, BALF4 | A02.01 = 400 |
| QTVEMSPFY | 600 | EBV, BALF4 | A01.01 = 320 |
| QVNKTMHEK | 601 | EBV, BALF4 | A03.01 = 520 |
| QYYFQSGNEI | 602 | EBV, BALF4 | A24.02 = 320 |
| RMLGDLARA | 603 | EBV, BALF4 | A02.01 = 47 |
| RMLGDLARAW | 604 | EBV, BALF4 | A24.02 = 1000 |
| RPLVSFSFI | 605 | EBV, BALF4 | B07.02 = 87 |
| RQQTSFPFR | 606 | EBV, BALF4 | A03.01 = 790 |
| RQQTSFPFRV | 607 | EBV, BALF4 | A02.01 = 250 |
| RTAYCPLQH | 608 | EBV, BALF4 | A03.01 = 420 |
| RTNYKIVDY | 609 | EBV, BALF4 | A03.01 = 890 |
| RTRQMSQQPV | 610 | EBV, BALF4 | B07.02 = 160 |
| RTRTTVNCL | 611 | EBV, BALF4 | B07.02 = 220 |
| RVLSVVVLL | 612 | EBV, BALF4 | A02.01 = 150 |
| RVLSVVVLLA | 613 | EBV, BALF4 | A02.01 = 500 |
| RYASQTELY | 614 | EBV, BALF4 | A24.02 = 870 |
| RYTKGQEAI | 615 | EBV, BALF4 | A24.02 = 350 |
| SFHVRTNYK | 616 | EBV, BALF4 | A03.01 = 1000 |
| SFHVRTNYKI | 617 | EBV, BALF4 | A24.02 = 580 |
| SFKVRSYTKI | 618 | EBV, BALF4 | B08.01 = 410 |

TABLE 6-continued

| Peptide | SEQ ID NO: | Virus, Gene | Affinity |
|---|---|---|---|
| SFPFRVCEL | 619 | EBV, BALF4 | A24.02 = 670; B08.01 = 970 |
| SITNLVSTV | 620 | EBV, BALF4 | A02.01 = 370 |
| SIYGKAVAA | 621 | EBV, BALF4 | A02.01 = 490 |
| SIYGKAVAAK | 622 | EBV, BALF4 | A03.01 = 17 |
| SLGSVGQSI | 623 | EBV, BALF4 | A02.01 = 790 |
| SLIENIDFA | 624 | EBV, BALF4 | A02.01 = 7.7 |
| SLIENIDFAS | 625 | EBV, BALF4 | A02.01 = 320 |
| SLNTSLIENI | 626 | EBV, BALF4 | A02.01 = 76 |
| SLRRQINRM | 627 | EBV, BALF4 | B08.01 = 77 |
| SLRRQINRML | 628 | EBV, BALF4 | B07.02 = 560; B08.01 = 80 |
| SLTRRTRQM | 629 | EBV, BALF4 | B08.01 = 55 |
| SLVSGFISF | 630 | EBV, BALF4 | A02.01 = 990 |
| SLVSGFISFF | 631 | EBV, BALF4 | A02.01 = 770 |
| SMRVPGSETM | 632 | EBV, BALF4 | B07.02 = 270; B08.01 = 780 |
| SPPSSPSPPA | 633 | EBV, BALF4 | B07.02 = 260 |
| SPSPPAPPA | 634 | EBV, BALF4 | B07.02 = 55 |
| SPSPPAPPAA | 635 | EBV, BALF4 | B07.02 = 58 |
| STIATETGK | 636 | EBV, BALF4 | A03.01 = 320 |
| STVGGLFSSL | 637 | EBV, BALF4 | A02.01 = 490 |
| SVGQSITNLV | 638 | EBV, BALF4 | A02.01 = 810 |
| SVVVLLAAL | 639 | EBV, BALF4 | A02.01 = 980 |
| SYTKIVTNI | 640 | EBV, BALF4 | A24.02 = 62 |
| SYTKIVTNIL | 641 | EBV, BALF4 | A24.02 = 120 |
| TFHERADSF | 642 | EBV, BALF4 | A24.02 = 860 |
| TFISLNTSLI | 643 | EBV, BALF4 | A24.02 = 200 |
| TIYQCYNAV | 644 | EBV, BALF4 | A02.01 = 160 |
| TIYQCYNAVK | 645 | EBV, BALF4 | A03.01 = 43 |
| TMCYSRPLV | 646 | EBV, BALF4 | A02.01 = 630 |
| TMHEKYEAV | 647 | EBV, BALF4 | A02.01 = 61; B08.01 = 300 |
| TTVMSSIYGK | 648 | EBV, BALF4 | A03.01 = 220 |
| TVGGLFSSLV | 649 | EBV, BALF4 | A02.01 = 690 |
| TVMSSIYGK | 650 | EBV, BALF4 | A03.01 = 44 |
| TYFITSGGLL | 651 | EBV, BALF4 | A24.02 = 480 |
| VILVISLTR | 652 | EBV, BALF4 | A03.01 = 750 |
| VILVISLTRR | 653 | EBV, BALF4 | A03.01 = 850 |
| VISVSQCVPV | 654 | EBV, BALF4 | A02.01 = 510 |
| VLLAALACR | 655 | EBV, BALF4 | A03.01 = 980 |
| VLLAALACRL | 656 | EBV, BALF4 | A02.01 = 31 |

TABLE 6-continued

| Peptide | SEQ ID NO: | Virus, Gene | Affinity |
|---|---|---|---|
| VLRRRRRDA | 657 | EBV, BALF4 | B08.01 = 190 |
| VLRRRRRDAG | 658 | EBV, BALF4 | B08.01 = 490 |
| VLSVVVLLA | 659 | EBV, BALF4 | A02.01 = 340 |
| VLSVVVLLAA | 660 | EBV, BALF4 | A02.01 = 250 |
| VLVAGVVIL | 661 | EBV, BALF4 | A02.01 = 150 |
| VLVAGVVILV | 662 | EBV, BALF4 | A02.01 = 21 |
| VMSSIYGKA | 663 | EBV, BALF4 | A02.01 = 910 |
| VMSSIYGKAV | 664 | EBV, BALF4 | A02.01 = 140 |
| VPPAAPGKSL | 665 | EBV, BALF4 | B07.02 = 82 |
| VPVNQATVTL | 666 | EBV, BALF4 | B07.02 = 42 |
| VSFSFINDTK | 667 | EBV, BALF4 | A03.01 = 220 |
| VSGFISFFK | 668 | EBV, BALF4 | A03.01 = 65 |
| VTDEGTSSF | 669 | EBV, BALF4 | A01.01 = 110 |
| VTDEGTSSFV | 670 | EBV, BALF4 | A01.01 = 220; A02.01 = 150 |
| VYVDRDGVNI | 671 | EBV, BALF4 | A24.02 = 690 |
| YADSVTNRH | 672 | EBV, BALF4 | A01.01 = 950 |
| YCPLQHWQTF | 673 | EBV, BALF4 | A24.02 = 690 |
| YFITSGGLLL | 674 | EBV, BALF4 | A24.02 = 630 |
| YSFKVRSYTK | 675 | EBV, BALF4 | A03.01 = 52 |
| YSRPLVSFSF | 676 | EBV, BALF4 | A24.02 = 900 |
| YTKGQEAITY | 677 | EBV, BALF4 | A01.01 = 940 |
| YYFQSGNEI | 678 | EBV, BALF4 | A24.02 = 38 |
| AAAYSQVYAL | 679 | EBV, BALF3 | B07.02 = 440 |
| AAFENSKYIK | 680 | EBV, BALF3 | A03.01 = 430 |
| AAFTAHPQYR | 681 | EBV, BALF3 | A03.01 = 790 |
| AAYSQVYAL | 682 | EBV, BALF3 | A02.01 = 610; B07.02 = 490; B08.01 = 980 |
| AGARLTHLF | 683 | EBV, BALF3 | A24.02 = 640 |
| AILLPRLRR | 684 | EBV, BALF3 | A03.01 = 490 |
| AILQKRNEL | 685 | EBV, BALF3 | B08.01 = 250 |
| ALAGARLTH | 686 | EBV, BALF3 | A03.01 = 800 |
| ALAGARLTHL | 687 | EBV, BALF3 | A02.01 = 120 |
| ALARCCDAA | 688 | EBV, BALF3 | A02.01 = 570 |
| ALAVELSVCA | 689 | EBV, BALF3 | A02.01 = 170 |
| ALDTYNVFST | 690 | EBV, BALF3 | A02.01 = 150 |
| ALFARERRL | 691 | EBV, BALF3 | B08.01 = 800 |
| ALKRKEQYL | 692 | EBV, BALF3 | B08.01 = 100 |
| ALLYLHLQM | 693 | EBV, BALF3 | A02.01 = 540 |
| ALPPDGLYL | 694 | EBV, BALF3 | A02.01 = 330 |

TABLE 6-continued

| Peptide | SEQ ID NO: | Virus, Gene | Affinity |
|---|---|---|---|
| ALPPDGLYLT | 695 | EBV, BALF3 | A02.01 = 940 |
| ALREAVLTV | 696 | EBV, BALF3 | A02.01 = 40 |
| ALSDALKRK | 697 | EBV, BALF3 | A03.01 = 320 |
| ALSLELVHL | 698 | EBV, BALF3 | A02.01 = 130 |
| ALSLELVHLL | 699 | EBV, BALF3 | A02.01 = 50 |
| ALTHSLYTF | 700 | EBV, BALF3 | A24.02 = 540 |
| ALTHSLYTFI | 701 | EBV, BALF3 | A02.01 = 35 |
| APGATERLF | 702 | EBV, BALF3 | B07.02 = 990 |
| APGRKGTRV | 703 | EBV, BALF3 | B07.02 = 210 |
| AVLTVSLYNK | 704 | EBV, BALF3 | A03.01 = 60 |
| AYSQVYALA | 705 | EBV, BALF3 | A24.02 = 540 |
| AYSQVYALAV | 706 | EBV, BALF3 | A24.02 = 330 |
| CARLDPRSL | 707 | EBV, BALF3 | B07.02 = 530; B08.01 = 940 |
| CLAQQSETL | 708 | EBV, BALF3 | A02.01 = 570 |
| CLINDIEIL | 709 | EBV, BALF3 | A02.01 = 220 |
| CLINDIEILM | 710 | EBV, BALF3 | A02.01 = 540 |
| DLLGRFRGV | 711 | EBV, BALF3 | B08.01 = 620 |
| DLYALLYLHL | 712 | EBV, BALF3 | A02.01 = 620 |
| DPRLYITSV | 713 | EBV, BALF3 | B07.02 = 430; B08.01 = 220 |
| DPRSLDVAAV | 714 | EBV, BALF3 | B07.02 = 580 |
| DSDRPLILLY | 715 | EBV, BALF3 | A01.01 = 10 |
| DWIETSFNSF | 716 | EBV, BALF3 | A24.02 = 810 |
| EILMKRINSV | 717 | EBV, BALF3 | B08.01 = 120 |
| ELARMRNHFL | 718 | EBV, BALF3 | B08.01 = 350 |
| ELYTRLNRA | 719 | EBV, BALF3 | B08.01 = 550 |
| ELYTRLNRAM | 720 | EBV, BALF3 | B08.01 = 130 |
| EVAELSELLY | 721 | EBV, BALF3 | A01.01 = 220 |
| FARERRLAL | 722 | EBV, BALF3 | B07.02 = 8.5; B08.01 = 3.6 |
| FARERRLALV | 723 | EBV, BALF3 | B07.02 = 910; B08.01 = 20 |
| FKDLYALLY | 724 | EBV, BALF3 | A01.01 = 480 |
| FLTSLIWPG | 725 | EBV, BALF3 | A02.01 = 30 |
| FLTSLIWPGI | 726 | EBV, BALF3 | A02.01 = 6.6 |
| FLYRRAFVS | 727 | EBV, BALF3 | A02.01 = 230; B08.01 = 600 |
| FLYRRAFVSG | 728 | EBV, BALF3 | A02.01 = 610; B08.01 = 380 |
| FPPPSNVAL | 729 | EBV, BALF3 | B07.02 = 44 |
| FYCMSHTMGL | 730 | EBV, BALF3 | A24.02 = 660 |
| GGHSRLSAL | 731 | EBV, BALF3 | B08.01 = 800 |
| GLAKLQSCL | 732 | EBV, BALF3 | A02.01 = 350 |

TABLE 6-continued

| Peptide | SEQ ID NO: | Virus, Gene | Affinity |
|---|---|---|---|
| GLAKLQSCLA | 733 | EBV, BALF3 | A02.01 = 390 |
| GLFENEVRQA | 734 | EBV, BALF3 | A02.01 = 140 |
| GLFPPPSNV | 735 | EBV, BALF3 | A02.01 = 25 |
| GLFPPPSNVA | 736 | EBV, BALF3 | A02.01 = 430 |
| GLLAAAYSQV | 737 | EBV, BALF3 | A02.01 = 10 |
| GLLAELEAI | 738 | EBV, BALF3 | A02.01 = 25 |
| GLLAELEAIL | 739 | EBV, BALF3 | A02.01 = 100 |
| GPSGALSDAL | 740 | EBV, BALF3 | B07.02 = 47 |
| HALTHSLYTF | 741 | EBV, BALF3 | A24.02 = 630 |
| HFLYRRAFV | 742 | EBV, BALF3 | B08.01 = 350 |
| HLFDAVAPG | 743 | EBV, BALF3 | A02.01 = 420 |
| HLFDAVAPGA | 744 | EBV, BALF3 | A02.01 = 12 |
| HLHALTHSL | 745 | EBV, BALF3 | A02.01 = 78; B07.02 = 450; B08.01 = 160 |
| HLHALTHSLY | 746 | EBV, BALF3 | A03.01 = 120 |
| HLLEAEEKA | 747 | EBV, BALF3 | A02.01 = 810 |
| HLLENSREA | 748 | EBV, BALF3 | A02.01 = 350 |
| HLQMRDDSA | 749 | EBV, BALF3 | B08.01 = 870 |
| HQKAFLTSL | 750 | EBV, BALF3 | B08.01 = 450 |
| HVSCNHLAV | 751 | EBV, BALF3 | A02.01 = 960; B07.02 = 950 |
| ILCRALREAV | 752 | EBV, BALF3 | A02.01 = 390 |
| ILLYKGRGWV | 753 | EBV, BALF3 | A02.01 = 930 |
| ILMKRINSV | 754 | EBV, BALF3 | A02.01 = 6.7; B08.01 = 9.4 |
| ILMKRINSVF | 755 | EBV, BALF3 | A24.02 = 660; B08.01 = 75 |
| IWPGIEPSDW | 756 | EBV, BALF3 | A24.02 = 350 |
| KTWGRSLIL | 757 | EBV, BALF3 | A02.01 = 650 |
| KTWGRSLILR | 758 | EBV, BALF3 | A03.01 = 120 |
| KVDVSLCLI | 759 | EBV, BALF3 | A02.01 = 900 |
| LAAAYSQVY | 760 | EBV, BALF3 | A01.01 = 800 |
| LAGARLTHL | 761 | EBV, BALF3 | B08.01 = 320 |
| LARMRNHFL | 762 | EBV, BALF3 | B07.02 = 350; B08.01 = 22 |
| LFARERRLAL | 763 | EBV, BALF3 | B08.01 = 280 |
| LGRFRGVSPI | 764 | EBV, BALF3 | B08.01 = 300 |
| LILRRADAV | 765 | EBV, BALF3 | B08.01 = 350 |
| LINDIEILM | 766 | EBV, BALF3 | A02.01 = 880 |
| LINDIEILMK | 767 | EBV, BALF3 | A03.01 = 190 |
| LLAAAYSQV | 768 | EBV, BALF3 | A02.01 = 12 |
| LLAAAYSQVY | 769 | EBV, BALF3 | A03.01 = 850 |
| LLAELEAIL | 770 | EBV, BALF3 | A02.01 = 28 |

TABLE 6-continued

| Peptide | SEQ ID NO: | Virus, Gene | Affinity |
|---|---|---|---|
| LLAELEAILL | 771 | EBV, BALF3 | A02.01 = 17 |
| LLYKGRGWV | 772 | EBV, BALF3 | A02.01 = 460 |
| LLYKGRGWVF | 773 | EBV, BALF3 | B08.01 = 720 |
| LLYLHLQMR | 774 | EBV, BALF3 | A03.01 = 410 |
| LLYWNSGGH | 775 | EBV, BALF3 | A03.01 = 610 |
| LLYWNSGGHA | 776 | EBV, BALF3 | A02.01 = 750 |
| LMKRINSVF | 777 | EBV, BALF3 | B08.01 = 130 |
| LMKRINSVFY | 778 | EBV, BALF3 | A03.01 = 450 |
| LPNHGNPST | 779 | EBV, BALF3 | B07.02 = 400 |
| LPNHGNPSTA | 780 | EBV, BALF3 | B07.02 = 240 |
| LSLELVHLL | 781 | EBV, BALF3 | A02.01 = 630 |
| LVRRACEEAL | 782 | EBV, BALF3 | B07.02 = 370 |
| LYALLYLHL | 783 | EBV, BALF3 | A24.02 = 64 |
| LYITSVPCW | 784 | EBV, BALF3 | A24.02 = 60 |
| LYKGRGWVF | 785 | EBV, BALF3 | A24.02 = 68 |
| LYNKTWGRSL | 786 | EBV, BALF3 | A24.02 = 630 |
| LYTFITGPL | 787 | EBV, BALF3 | A24.02 = 350 |
| LYWNSGGHAI | 788 | EBV, BALF3 | A24.02 = 150 |
| MSGLLAAAY | 789 | EBV, BALF3 | A01.01 = 91 |
| NSREASAAL | 790 | EBV, BALF3 | B07.02 = 230 |
| NVFSTVPPEV | 791 | EBV, BALF3 | A02.01 = 46 |
| PQYRAILQK | 792 | EBV, BALF3 | A03.01 = 850 |
| QVYALAVEL | 793 | EBV, BALF3 | A02.01 = 520 |
| RAILQKRNEL | 794 | EBV, BALF3 | B07.02 = 260 |
| RLDPRSLDV | 795 | EBV, BALF3 | A02.01 = 500 |
| RLFCGGVYS | 796 | EBV, BALF3 | A02.01 = 390 |
| RLFCGGVYSS | 797 | EBV, BALF3 | A02.01 = 150 |
| RLNRAMQRL | 798 | EBV, BALF3 | A02.01 = 810 |
| RLSALFARER | 799 | EBV, BALF3 | A03.01 = 400 |
| RLTHLFDAV | 800 | EBV, BALF3 | A02.01 = 90 |
| RMRNHFLYR | 801 | EBV, BALF3 | A03.01 = 17 |
| RMRNHFLYRR | 802 | EBV, BALF3 | A03.01 = 61 |
| RPAGAREPG | 803 | EBV, BALF3 | B07.02 = 200 |
| RPGGPEEGAV | 804 | EBV, BALF3 | B07.02 = 180 |
| RQAGLGHLL | 805 | EBV, BALF3 | A02.01 = 460 |
| RQVATEGLAK | 806 | EBV, BALF3 | A03.01 = 780 |
| RTPSVAYSV | 807 | EBV, BALF3 | A02.01 = 430 |
| SAALLAPGRK | 808 | EBV, BALF3 | A03.01 = 1000 |

TABLE 6-continued

| Peptide | SEQ ID NO: | Virus, Gene | Affinity |
|---|---|---|---|
| SLASSQQIL | 809 | EBV, BALF3 | A02.01 = 600 |
| SLCLINDIEI | 810 | EBV, BALF3 | A02.01 = 690 |
| SLILRRADA | 811 | EBV, BALF3 | B08.01 = 330 |
| SLILRRADAV | 812 | EBV, BALF3 | A02.01 = 490; B08.01 = 190 |
| SLYNKTWGR | 813 | EBV, BALF3 | A03.01 = 170 |
| SLYTFITGPL | 814 | EBV, BALF3 | A02.01 = 31; B08.01 = 790 |
| SPEVPRPAGA | 815 | EBV, BALF3 | B07.02 = 630 |
| SPIPDPRLYI | 816 | EBV, BALF3 | B07.02 = 150 |
| SQVYALAVEL | 817 | EBV, BALF3 | A02.01 = 340 |
| SVAYSVEFY | 818 | EBV, BALF3 | A01.01 = 690 |
| SVEFYGGHK | 819 | EBV, BALF3 | A03.01 = 900 |
| SVFYCMSHTM | 820 | EBV, BALF3 | A02.01 = 900 |
| TLSSEHLHAL | 821 | EBV, BALF3 | A02.01 = 99 |
| TLTETLCLRV | 822 | EBV, BALF3 | A02.01 = 45 |
| TPSVAYSVEF | 823 | EBV, BALF3 | B07.02 = 180 |
| TSFNSFYSV | 824 | EBV, BALF3 | A02.01 = 210 |
| TYDSDRPLI | 825 | EBV, BALF3 | A24.02 = 990 |
| VAELSELLY | 826 | EBV, BALF3 | A01.01 = 74 |
| VFKDLYALL | 827 | EBV, BALF3 | A24.02 = 390 |
| VFYCMSHTM | 828 | EBV, BALF3 | A24.02 = 350 |
| VLTVSLYNK | 829 | EBV, BALF3 | A03.01 = 88 |
| VPCWRCVGEL | 830 | EBV, BALF3 | B07.02 = 170 |
| VPGPGRPEA | 831 | EBV, BALF3 | B07.02 = 260 |
| VPPLRTPSV | 832 | EBV, BALF3 | B07.02 = 250; B08.01 = 470 |
| VPPLRTPSVA | 833 | EBV, BALF3 | B07.02 = 850 |
| VPRPAGARE | 834 | EBV, BALF3 | B07.02 = 720 |
| VPRPAGAREP | 835 | EBV, BALF3 | B07.02 = 620 |
| VVYWELARMR | 836 | EBV, BALF3 | A03.01 = 660 |
| VWGDVVYWEL | 837 | EBV, BALF3 | A24.02 = 97 |
| VYALAVELSV | 838 | EBV, BALF3 | A24.02 = 340 |
| WIETSFNSFY | 839 | EBV, BALF3 | A01.01 = 120 |
| WVFKDLYAL | 840 | EBV, BALF3 | A02.01 = 46 |
| WVFKDLYALL | 841 | EBV, BALF3 | A02.01 = 130 |
| YALAVELSV | 842 | EBV, BALF3 | A02.01 = 110 |
| YALLYLHLQM | 843 | EBV, BALF3 | B08.01 = 690 |
| YCMSHTMGL | 844 | EBV, BALF3 | A02.01 = 940; B08.01 = 420 |
| YLRQVATEGL | 845 | EBV, BALF3 | A02.01 = 180; B07.02 = 860; B08.01 = 570 |
| YLTYDSDRPL | 846 | EBV, BALF3 | A02.01 = 98 |

TABLE 6-continued

| Peptide | SEQ ID NO: | Virus, Gene | Affinity |
|---|---|---|---|
| YNKTWGRSL | 847 | EBV, BALF3 | B08.01 = 240 |
| YTFITGPLA | 848 | EBV, BALF3 | A02.01 = 960 |
| YWNSGGHAI | 849 | EBV, BALF3 | A24.02 = 770 |
| AARPRLLLSL | 850 | EBV, BARF0 | B07.02 = 58; B08.01 = 70 |
| AARVPIEEL | 851 | EBV, BARF0 | B07.02 = 950 |
| AGMSATLPL | 852 | EBV, BARF0 | B07.02 = 550 |
| ALLRQAGLQL | 853 | EBV, BARF0 | A02.01 = 450 |
| ALLWAARPR | 854 | EBV, BARF0 | A03.01 = 590 |
| ALLWAARPRL | 855 | EBV, BARF0 | A02.01 = 130 |
| ALPGRLLLA | 856 | EBV, BARF0 | A02.01 = 620 |
| APAGHRGDV | 857 | EBV, BARF0 | B07.02 = 23 |
| APAGHRGDVE | 858 | EBV, BARF0 | B07.02 = 840 |
| APGYAVEAV | 859 | EBV, BARF0 | B07.02 = 130 |
| AVEAVEGGLY | 860 | EBV, BARF0 | A01.01 = 540 |
| AVEGGLYPV | 861 | EBV, BARF0 | A02.01 = 63 |
| AVRLQRLHRV | 862 | EBV, BARF0 | B08.01 = 730 |
| AVRQRVQVL | 863 | EBV, BARF0 | B07.02 = 37; B08.01 = 47 |
| CPRQRLLAG | 864 | EBV, BARF0 | B07.02 = 190; B08.01 = 180 |
| CPSRPGHLRA | 865 | EBV, BARF0 | B07.02 = 680 |
| CTDSMAARV | 866 | EBV, BARF0 | A01.01 = 220 |
| EPRVELVPL | 867 | EBV, BARF0 | B07.02 = 64; B08.01 = 410 |
| EPRVELVPLL | 868 | EBV, BARF0 | B07.02 = 430 |
| FQALQPHGV | 869 | EBV, BARF0 | A02.01 = 44 |
| GLALLRQAGL | 870 | EBV, BARF0 | A02.01 = 910 |
| GLGKQVCFDV | 871 | EBV, BARF0 | A02.01 = 99 |
| GLGQGLALL | 872 | EBV, BARF0 | A02.01 = 96 |
| GMSATLPLR | 873 | EBV, BARF0 | A03.01 = 410 |
| GPLCRGRVA | 874 | EBV, BARF0 | B07.02 = 150 |
| GPLCRGRVAV | 875 | EBV, BARF0 | B07.02 = 23; B08.01 = 360 |
| GPPHQGQATL | 876 | EBV, BARF0 | B07.02 = 180 |
| GPRDEGVQA | 877 | EBV, BARF0 | B07.02 = 670 |
| GPRDEGVQAV | 878 | EBV, BARF0 | B07.02 = 35 |
| GVQRSGRPL | 879 | EBV, BARF0 | B07.02 = 330 |
| GVRREGGGAV | 880 | EBV, BARF0 | B07.02 = 860 |
| HAIKHAIDSL | 881 | EBV, BARF0 | B07.02 = 700 |
| HLAQVLLLA | 882 | EBV, BARF0 | A02.01 = 99 |
| HLAQVLLLAL | 883 | EBV, BARF0 | A02.01 = 42 |
| HLRALPGRL | 884 | EBV, BARF0 | B07.02 = 970; B08.01 = 700 |

TABLE 6-continued

| Peptide | SEQ ID NO: | Virus, Gene | Affinity |
|---|---|---|---|
| HLRALPGRLL | 885 | EBV, BARF0 | B07.02 = 370; B08.01 = 700 |
| HLRGHCREDV | 886 | EBV, BARF0 | B08.01 = 680 |
| HQLAHTAPA | 887 | EBV, BARF0 | A02.01 = 360; B08.01 = 880 |
| ILKGGTLAGA | 888 | EBV, BARF0 | A02.01 = 860 |
| KQVCFDVLGI | 889 | EBV, BARF0 | A02.01 = 140 |
| LALLRQAGL | 890 | EBV, BARF0 | B08.01 = 170 |
| LCRGRVAVV | 891 | EBV, BARF0 | B08.01 = 400 |
| LLASAQPLH | 892 | EBV, BARF0 | A03.01 = 950 |
| LLLASAQPL | 893 | EBV, BARF0 | A02.01 = 20; B08.01 = 790 |
| LLQDGPVLGV | 894 | EBV, BARF0 | A02.01 = 18 |
| LLRQAGLQL | 895 | EBV, BARF0 | B07.02 = 110; B08.01 = 280 |
| LLVRQRTCGV | 896 | EBV, BARF0 | A02.01 = 300 |
| LLWAARPRL | 897 | EBV, BARF0 | A02.01 = 39 |
| LLWAARPRLL | 898 | EBV, BARF0 | A02.01 = 73; B08.01 = 860 |
| LPGKQGREA | 899 | EBV, BARF0 | B07.02 = 280 |
| LPGRLLLASA | 900 | EBV, BARF0 | B07.02 = 560 |
| LPLPRCTDSM | 901 | EBV, BARF0 | B07.02 = 40; B08.01 = 600 |
| LPRCTDSMA | 902 | EBV, BARF0 | B07.02 = 140 |
| LPRCTDSMAA | 903 | EBV, BARF0 | B07.02 = 44; B08.01 = 860 |
| LQDGPVLGV | 904 | EBV, BARF0 | A02.01 = 200 |
| LRIHRHRQV | 905 | EBV, BARF0 | B08.01 = 840 |
| LRIHRHRQVV | 906 | EBV, BARF0 | B08.01 = 490 |
| LVRQRTCGV | 907 | EBV, BARF0 | B07.02 = 690; B08.01 = 72 |
| LWAARPRLLL | 908 | EBV, BARF0 | A24.02 = 770 |
| LYPVARLDAW | 909 | EBV, BARF0 | A24.02 = 85 |
| MSATLPLPR | 910 | EBV, BARF0 | A03.01 = 760 |
| PPHQGQATL | 911 | EBV, BARF0 | B07.02 = 320 |
| PPRARDRAL | 912 | EBV, BARF0 | B07.02 = 44; B08.01 = 760 |
| PPRARDRALL | 913 | EBV, BARF0 | B07.02 = 230 |
| QPCPRQRLL | 914 | EBV, BARF0 | B07.02 = 540 |
| QPHGVRHAI | 915 | EBV, BARF0 | B07.02 = 22 |
| QTLGGHLAQV | 916 | EBV, BARF0 | A02.01 = 600 |
| QVLRAQGLGK | 917 | EBV, BARF0 | A03.01 = 430 |
| RALLWAARPR | 918 | EBV, BARF0 | A03.01 = 960 |
| RALPGRLLL | 919 | EBV, BARF0 | B07.02 = 230 |
| RARDRALLWA | 920 | EBV, BARF0 | B07.02 = 1000 |
| RIHRHRQVV | 921 | EBV, BARF0 | B07.02 = 340; B08.01 = 130 |
| RLLLASAQPL | 922 | EBV, BARF0 | A02.01 = 54 |

TABLE 6-continued

| Peptide | SEQ ID NO: | Virus, Gene | Affinity |
|---|---|---|---|
| RLLLSLQQV | 923 | EBV, BARF0 | A02.01 = 22 |
| RLRIHRHRQV | 924 | EBV, BARF0 | B07.02 = 530; B08.01 = 58 |
| RPGHLRALPG | 925 | EBV, BARF0 | B07.02 = 410 |
| RPLCLRPPRA | 926 | EBV, BARF0 | B07.02 = 320 |
| RPPRARDRA | 927 | EBV, BARF0 | B07.02 = 640 |
| RPPRARDRAL | 928 | EBV, BARF0 | B07.02 = 9.5 |
| RPRLLLSLQQ | 929 | EBV, BARF0 | B07.02 = 630 |
| RVQVLRAQGL | 930 | EBV, BARF0 | B07.02 = 700 |
| RVREGAGRA | 931 | EBV, BARF0 | B07.02 = 990 |
| RVREGAGRAG | 932 | EBV, BARF0 | B07.02 = 970 |
| RVWDGTYAPK | 933 | EBV, BARF0 | A03.01 = 52 |
| SLQQVPEPSL | 934 | EBV, BARF0 | A02.01 = 230 |
| SQGHVAGWGK | 935 | EBV, BARF0 | A03.01 = 950 |
| TLGGHLAQV | 936 | EBV, BARF0 | A02.01 = 18 |
| TLGGHLAQVL | 937 | EBV, BARF0 | A02.01 = 760 |
| TYAPKAAQQI | 938 | EBV, BARF0 | A24.02 = 61 |
| VLLLALERV | 939 | EBV, BARF0 | A02.01 = 31 |
| VLRAQGLGK | 940 | EBV, BARF0 | A03.01 = 33 |
| VPIEELREF | 941 | EBV, BARF0 | B07.02 = 790 |
| VPLLQDGPV | 942 | EBV, BARF0 | B07.02 = 170 |
| VPLLQDGPVL | 943 | EBV, BARF0 | B07.02 = 68 |
| VVAHAGQLPV | 944 | EBV, BARF0 | A02.01 = 530 |
| WAARPRLLL | 945 | EBV, BARF0 | B07.02 = 260 |
| WPYQGSQERL | 946 | EBV, BARF0 | B07.02 = 35 |
| YPVARLDAW | 947 | EBV, BARF0 | B07.02 = 250 |

Example 2: HLA Class I and Class II Binding Assays

The following example of peptide binding to HLA molecules demonstrates quantification of binding affinities of HLA class I and class II peptides. Binding assays can be performed with peptides that are either motif-bearing or not motif-bearing.

Epstein-Barr virus (EBV)-transformed homozygous cell lines, fibroblasts, CIR, or 721.22 transfectants are used as sources of HLA class I molecules. Cell lysates are prepared and HLA molecules purified in accordance with disclosed protocols (Sidney et al., Current Protocols in Immunology 18.3.1 (1998); Sidney, et al., J. Immunol. 154:247 (1995); Sette, et al., Mol. Immunol. 31:813 (1994)). HLA molecules are purified from lysates by affinity chromatography. The lysates are passed over a column of Sepharose CL-4B beads coupled to an appropriate antibody. The anti-HLA column is then washed with 10 mM Tris-HCL, pH 8.0, in 1% NP-40, PBS, and PBS containing 0.4% n-octylglucoside and HLA molecules are eluted with 50 mM diethylamine in 0.15M NaCl containing 0.4% n-octylglucoside, pH 11.5. A 1/25 volume of 2.0 M Tris, pH 6.8, is added to the eluate to reduce the pH to ~8.0. Eluates are then concentrated by centrifugation in Centriprep 30 concentrators (Amicon, Beverly, MA). Protein content is evaluated by a BCA protein assay (Pierce Chemical Co., Rockford, IL) and confirmed by SDS-PAGE.

A detailed description of the protocol utilized to measure the binding of peptides to Class I and Class II MHC has been published (Sette et al., Mol. Immunol. 31:813, 1994; Sidney et al., in Current Protocols in Immunology, Margulies, Ed., John Wiley & Sons, New York, Section 18.3, 1998). Briefly, purified MHC molecules (5 to 500 nM) are incubated with various unlabeled peptide inhibitors and 1-10 nM 125I-radiolabeled probe peptides for 48 h in PBS containing 0.05% Nonidet P-40 (NP40) (or 20% w/v digitonin for H-2 IA assays) in the presence of a protease inhibitor cocktail. All assays are at pH 7.0 with the exception of DRB1*0301, which was performed at pH 4.5, and DRB1*1601 (DR2w21β1) and DRB4*0101 (DRw53), which were performed at pH 5.0.

Following incubation, MHC-peptide complexes are separated from free peptide by gel filtration on 7.8 mm×15 cm TSK200 columns (TosoHaas 16215, Montgomeryville, PA). Because the large size of the radiolabeled peptide used for the DRB1*1501 (DR2w2β1) assay makes separation of bound from unbound peaks more difficult under these conditions, all DRB1*1501 (DR2w2β1) assays were performed using a 7.8 mm×30 cm TSK2000 column eluted at 0.6 mLs/min. The eluate from the TSK columns is passed through a Beckman 170 radioisotope detector, and radioactivity is plotted and integrated using a Hewlett-Packard 3396A integrator, and the fraction of peptide bound is determined.

Radiolabeled peptides are iodinated using the chloramine-T method. Typically, in preliminary experiments, each MHC preparation is titered in the presence of fixed amounts of radiolabeled peptides to determine the concentration of HLA molecules necessary to bind 10-20% of the total radioactivity. All subsequent inhibition and direct binding assays are performed using these HLA concentrations.

Since under these conditions [label]<[HLA] and $IC_{50} \geq$ [HLA], the measured $IC_{50}$ values are reasonable approximations of the true $K_D$ values. Peptide inhibitors are typically tested at concentrations ranging from 120 µg/ml to 1.2 ng/ml, and are tested in two to four completely independent experiments. To allow comparison of the data obtained in different experiments, a relative binding figure is calculated for each peptide by dividing the $IC_{50}$ of a positive control for inhibition by the $IC_{50}$ for each tested peptide (typically unlabeled versions of the radiolabeled probe peptide). For database purposes, and inter-experiment comparisons, relative binding values are compiled. These values can subsequently be converted back into $IC_{50}$ nM values by dividing the $IC_{50}$ nM of the positive controls for inhibition by the relative binding of the peptide of interest. This method of data compilation has proven to be the most accurate and consistent for comparing peptides that have been tested on different days, or with different lots of purified MHC.

Because the antibody used for HLA-DR purification (LB3.1) is α-chain specific, β1 molecules are not separated from β3 (and/or β4 and β35) molecules. The β1 specificity of the binding assay is obvious in the cases of DRB1*0101 (DR1), DRB1*0802 (DR8w2), and DRB1*0803 (DR8w3), where no β3 is expressed. It has also been demonstrated for DRB1*0301 (DR3) and DRB3*0101 (DR52a), DRB1*0401 (DR4w4), DRB1*0404 (DR4w14), DRB1*0405 (DR4w15), DRB1*1101 (DR5), DRB1*1201 (DR5w12), DRB1*1302 (DR6w19) and DRB1*0701 (DR7). The problem of p chain specificity for DRB1*1501 (DR2w2β1), DRB5*0101 (DR2w2p2), DRB1*1601 (DR2w21β1), DRB5*0201 (DR51Dw21), and DRB4*0101 (DRw53) assays is circumvented by the use of fibroblasts. Development and validation of assays with regard to DRβ molecule specificity have been described previously (see, e.g., Southwood et al., J. Immunol. 160:3363-3373, 1998).

The live cell/flow cytometry-based assays can also be used. This is a well-established assay utilizing the TAP-deficient hybridoma cell line T2 (American Type Culture Collection (ATCC) Accession No. CRL-1992), Manassas, Va.). The TAP deficiency in this cell line leads to inefficient loading of MHCI in the ER and an excess of empty MHCIs. Salter and Cresswell, EMBO J. 5:943-49 (1986); Salter, Immunogenetics 21:235-46 (1985). Empty MHCIs are highly unstable, and are therefore short-lived. When T2 cells are cultured at reduced temperatures, empty MHCIs appear transiently on the cell surface, where they can be stabilized by the exogenous addition of MHCI-binding peptides. To perform this binding assay, peptide-receptive MHCIs were induced by culturing aliquots of $10^7$ T2 cells overnight at 26° C. in serum free AIM-V medium alone, or in medium containing escalating concentrations (0.1 to 100 µM) of peptide. Cells were then washed twice with PBS, and subsequently incubated with a fluorescent tagged HLA-A0201-specific monoclonal antibody, BB7.2, to quantify cell surface expression. Samples were acquired on a FACS Calibur instrument (Becton Dickinson) and the mean fluorescence intensity (MFI) determined using the accompanying Cellquest software.

Example 3: Confirmation of Immunogenicity

In vitro education (IVE) assays are used to test the ability of each test peptide to expand CD8+ T-cells. Mature professional APCs are prepared for these assays in the following way. 80-90×10⁶ PBMCs isolated from a healthy human donor are plated in 20 ml of RPMI media containing 2% human AB serum, and incubated at 37° C. for 2 hours to allow for plastic adherence by monocytes. Non-adherent cells are removed and the adherent cells are cultured in RPMI, 2% human AB serum, 800 IU/ml of GM-CSF and 500 IU/ml of IL-4. After 6 days, TNF-alpha is added to a final concentration of 10 ng/ml. On day 7, the dendritic cells (DC) are matured either by the addition of 12.5 µg/ml poly I:C or 0.3 µg/ml of CD40L. The mature dendritic cells (mDC) are harvested on day 8, washed, and either used directly or cryopreserved for future use.

For the IVE of CD8+ T-cells, aliquots of 2×10⁵ mDCs are pulsed with each peptide at a final concentration of 100 µM, incubated for 4 hours at 37° C., and then irradiated (2500 rads). The peptide-pulsed mDCs are washed twice in RPMI containing 2% human AB serum. 2×10⁵ mDCs and 2×10⁶ autologous CD8+ cells are plated per well of a 24-well plate in 2 ml of RPMI containing 2% human AB, 20 ng/ml IL-7 and 100 µg/ml of IL-12, and incubated for 12 days. The CD8+ T-cells are then re-stimulated with peptide-pulsed, irradiated mDCs. Two to three days later, 20 IU/ml IL-2 and 20 ng/IL7 are added. Expanding CD8+ T-cells are re-stimulated every 8-10 days, and are maintained in media containing IL-2 and IL-7. Cultures are monitored for peptide-specific T-cells using a combination of functional assays and/or tetramer staining. Parallel IVEs with the modified and parent peptides allowed for comparisons of the relative efficiency with which the peptides expanded peptide-specific T-cells.

Quantitative and Functional Assessment of CD8+ T-Cells
Tetramer Staining

MHC tetramers are purchased or manufactured on-site, and are used to measure peptide-specific T-cell expansion in the IVE assays. For the assessment, tetramer is added to 1×10⁵ cells in PBS containing 1% FCS and 0.1% sodium azide (FACS buffer) according to manufacturer's instructions. Cells are incubated in the dark for 20 minutes at room temperature. Antibodies specific for T-cell markers, such as CD8, are then added to a final concentration suggested by the manufacturer, and the cells are incubated in the dark at 4° C. for 20 minutes. Cells are washed with cold FACS buffer and resuspended in buffer containing 1% formaldehyde. Cells are acquired on a FACS Calibur (Becton Dickinson) instrument, and are analyzed by use of Cellquest software (Becton Dickinson). For analysis of tetramer positive cells, the lymphocyte gate is taken from the forward and side-scatter plots. Data are reported as the percentage of cells that were CD8+/Tetramer+.

ELISPOT

Peptide-specific T-cells are functionally enumerated using the ELISPOT assay (BD Biosciences), which measures the release of IFNgamma from T-cells on a single cell basis. Target cells (T2 or HLA-A0201 transfected C1Rs) were pulsed with 10 μM peptide for 1 hour at 37° C., and washed three times. $1 \times 10^5$ peptide-pulsed targets are co-cultured in the ELISPOT plate wells with varying concentrations of T-cells ($5 \times 10^2$ to $2 \times 103$) taken from the IVE culture. Plates are developed according to the manufacturer's protocol, and analyzed on an ELISPOT reader (Cellular Technology Ltd.) with accompanying software. Spots corresponding to the number of IFNgamma-producing T-cells are reported as the absolute number of spots per number of T-cells plated. T-cells expanded on modified peptides are tested not only for their ability to recognize targets pulsed with the modified peptide, but also for their ability to recognize targets pulsed with the parent peptide.

CD107 Staining

CD107a and b are expressed on the cell surface of CD8+ T-cells following activation with cognate peptide. The lytic granules of T-cells have a lipid bilayer that contains lysosomal-associated membrane glycoproteins ("LAMPs"), which include the molecules CD107a and b. When cytotoxic T-cells are activated through the T-cell receptor, the membranes of these lytic granules mobilize and fuse with the plasma membrane of the T-cell. The granule contents are released, and this leads to the death of the target cell. As the granule membrane fuses with the plasma membrane, C107a and b are exposed on the cell surface, and therefore are markers of degranulation. Because degranulation as measured by CD107 a and b staining is reported on a single cell basis, the assay is used to functionally enumerate peptide-specific T-cells. To perform the assay, peptide is added to HLA-A0201-transfected cells CIR to a final concentration of 20 μM, the cells were incubated for 1 hour at 37° C., and washed three times. $1 \times 10^5$ of the peptide-pulsed C1R cells were aliquoted into tubes, and antibodies specific for CD107 a and b are added to a final concentration suggested by the manufacturer (Becton Dickinson). Antibodies are added prior to the addition of T-cells in order to "capture" the CD107 molecules as they transiently appear on the surface during the course of the assay. $1 \times 10^5$ T-cells from the IVE culture are added next, and the samples were incubated for 4 hours at 37° C. The T-cells are further stained for additional cell surface molecules such as CD8 and acquired on a FACS Calibur instrument (Becton Dickinson). Data is analyzed using the accompanying Cellquest software, and results were reported as the percentage of CD8+CD107 a and b+ cells.

CTL Lysis

Cytotoxic activity is measured using a chromium release assay. Target T2 cells are labeled for 1 hour at 37° C. with $Na^{51}Cr$ and washed $5 \times 10^3$ target T2 cells were then added to varying numbers of T-cells from the IVE culture. Chromium release is measured in supernatant harvested after 4 hours of incubation at 37° C. The percentage of specific lysis is calculated as: Experimental release-spontaneous release/ Total release-spontaneous release×100

Example 4: Selection of CTL and HTL Epitopes for Inclusion in an Tumor-Specific Vaccine This example illustrates the procedure for the selection of peptide epitopes for vaccine compositions of the invention. The peptides in the composition can be in the form of a nucleic acid sequence, either single or one or more sequences (i.e., minigene) that encodes peptide(s), or may be single and/or polyepitopic peptides.

Epitopes are selected which, upon administration, mimic immune responses that have been observed to be correlated with tumor clearance. For example, vaccine can include 1-2 epitopes that come from at least one tumor antigen region. Epitopes from one region can be used in combination with epitopes from one or more additional tumor antigen regions.

Epitopes can be selected that have a binding affinity of an $IC_{50}$ of 500 nM or less for an HLA class I molecule, or for class II, an $IC_{50}$ of 1000 nM or less.

When creating a polyepitopic compositions, e.g. a minigene, it is typically desirable to generate the smallest peptide possible that encompasses the epitopes of interest. The principles employed are similar, if not the same, as those employed when selecting a peptide comprising nested epitopes. Additionally, however, upon determination of the nucleic acid sequence to be provided as a minigene, the peptide sequence encoded thereby is analyzed to determine whether any "junctional epitopes" have been created. A junctional epitope is a potential HLA binding epitope, as predicted, e.g., by motif analysis. Junctional epitopes are generally to be avoided because the recipient may bind to an HLA molecule and generate an immune response to that epitope, which is not present in a native protein sequence.

Peptide epitopes for inclusion in vaccine compositions are, for example, selected from those listed in the Tables. A vaccine composition comprised of selected peptides, when administered, is safe, efficacious, and elicits an immune response similar in magnitude of an immune response that inhibits tumor growth.

Example 5: Peptide Composition for Prophylactic or Therapeutic Uses

Immunogenic or vaccine compositions of the invention are used to inhibit tumor growth. For example, a polyepitopic composition (or a nucleic acid comprising the same) containing multiple CTL and HTL epitopes is administered to individuals having tumors. The composition is provided as a single lipidated polypeptide that encompasses multiple epitopes. The composition is administered in an aqueous carrier comprised of alum. The dose of peptide for the initial immunization is from about 1 to about 50,000 μg, generally 100-5,000 μg, for a 70 kg patient. The initial administration is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious to inhibit tumor growth.

Alternatively, the polyepitopic composition can be administered as a nucleic acid, for example as RNA, in accordance with methodologies known in the art and disclosed herein.

Non-mutated protein epitope binding agents, such as TCR or CARs can be can be administered in accordance with methodologies known in the art and disclosed herein. The binding agents can be administered as polypeptides or polynucleotides, for example RNA, encoding the binding agents, or as a cellular therapy, by administering cells expressing the binding agents.

Non-mutated protein epitope peptides, polynucleotides, binding agents, or cells expressing these molecules can be delivered to the same patient via multiple methodologies known in the art, and can further be combined with other cancer therapies (e.g., chemotherapy, surgery, radiation, checkpoint inhibitors, etc.).

Example 6. Administration of Compositions Using Dendritic Cells

Vaccines comprising epitopes of the invention may be administered using dendritic cells. In this example, the peptide-pulsed dendritic cells can be administered to a patient to stimulate a CTL response in vivo. In this method dendritic cells are isolated, expanded, and pulsed with a vaccine comprising peptide CTL and HTL epitopes of the invention. The dendritic cells are infused back into the patient to elicit CTL and HTL responses in vivo. The induced CTL and HTL then destroy (CTL) or facilitate destruction (HTL) of the specific target tumor cells that bear the proteins from which the epitopes in the vaccine are derived.

Alternatively, ex vivo CTL or HTL responses to a particular tumor-associated antigen can be induced by incubating in tissue culture the patient's, or genetically compatible, CTL or HTL precursor cells together with a source of antigen-presenting cells, such as dendritic cells, and the appropriate immunogenic peptides.

After an appropriate incubation time (typically about 7-28 days), in which the precursor cells are activated and expanded into effector cells, the cells are infused back into the patient, where they will destroy (CTL) or facilitate destruction (HTL) of their specific target cells, i.e., tumor cells.

Embodiments

Embodiment 1. An isolated antigenic peptide comprising an epitope from a sequence in Table 1 or 2.

Embodiment 2. An isolated antigenic peptide 100 amino acids or less in length which comprises an epitope from a sequence in Table 1 or 2.

Embodiment 3. An isolated antigenic peptide comprising an epitope from a sequence in Table 3 or 4.

Embodiment 4. An isolated antigenic peptide 100 amino acids or less in length which comprises an epitope from a sequence in Table 3 or 4.

Embodiment 5. An isolated antigenic peptide comprising an epitope from a sequence in Table 5 or 6.

Embodiment 6. An isolated antigenic peptide 100 amino acids or less in length which comprises an epitope from a sequence in Table 5 or 6.

Embodiment 7. The isolated antigenic peptide of embodiment 1 or 2, wherein the isolated antigenic peptide is a retroviral antigen.

Embodiment 8. The isolated antigenic peptide of embodiment 3 or 4, wherein the isolated antigenic peptide is a non-mutated overexpressed antigen.

Embodiment 9. The isolated antigenic peptide of embodiment 5 or 6, wherein the isolated antigenic peptide is a viral antigen.

Embodiment 10. The isolated antigenic peptide of any of embodiments 1-9, which is between about 5 to about 50 amino acids in length.

Embodiment 11. The isolated antigenic peptide of any of embodiments 1-10, which is between about 15 to about 35 amino acids in length.

Embodiment 12. The isolated antigenic peptide of embodiment 11, which is about 15 amino acids or less in length.

Embodiment 13. The isolated antigenic peptide of embodiment 12, which is between about 8 and about 11 amino acids in length.

Embodiment 14. The isolated antigenic peptide of embodiment 13, which is 9 or 10 amino acids in length.

Embodiment 15. The isolated antigenic peptide of any of embodiments 1-14, which binds major histocompatibility complex (MHC) class I.

Embodiment 16. The isolated antigenic peptide of embodiment 15, which binds MHC class I with a binding affinity of less than about 500 nM.

Embodiment 17. The isolated antigenic peptide of any of embodiments 1-6, which is about 30 amino acids or less in length.

Embodiment 18. The isolated antigenic peptide of embodiment 17, which is between about 6 and about 25 amino acids in length.

Embodiment 19. The isolated antigenic peptide of embodiment 18, which is between about 15 and about 24 amino acids in length.

Embodiment 20. The isolated antigenic peptide of embodiment 18, which is between about 9 and about 15 amino acids in length.

Embodiment 21. The isolated antigenic peptide of any of embodiments 1-6 and 17-20, which binds MHC class II.

Embodiment 22. The isolated antigenic peptide of embodiment 21, which binds MHC class II with a binding affinity of less than about 1000 nM.

Embodiment 23. The isolated antigenic peptide of any of embodiments 1-22, further comprising flanking amino acids.

Embodiment 24. The isolated antigenic peptide of embodiment 23, wherein the flanking amino acids are not native flanking amino acids.

Embodiment 25. The isolated antigenic peptide of any of embodiments 1-24, which is linked to at least a second antigenic peptide.

Embodiment 26. The isolated antigenic peptide of embodiment 25, wherein peptides are linked using a polyglycine or poly-serine linker.

Embodiment 27. The isolated antigenic peptide of embodiment 25 or 26, wherein the second antigenic peptide binds MHC class I or class II with a binding affinity of less than about 1000 nM.

Embodiment 28. The isolated antigenic peptide of embodiment 27, wherein the second antigenic peptide binds MHC class I or class II with a binding affinity of less than about 500 nM.

Embodiment 29. The isolated antigenic peptide of embodiment 27 or 28, wherein both of the epitopes bind to human leukocyte antigen (HLA)-A, -B, -C, -DP, -DQ, or -DR.

Embodiment 30. The isolated antigenic peptide of any of embodiments 27-29, wherein the isolated antigenic peptide binds a class I HLA and the second antigenic peptide binds a class II HLA.

Embodiment 31. The isolated antigenic peptide of any of embodiments 27-29, wherein the isolated antigenic peptide binds a class II HLA and the second antigenic peptide binds a class I HLA.

Embodiment 32. The isolated antigenic peptide of any of embodiments 1-31, further comprising modifications which increase in vivo half-life, cellular targeting, antigen uptake, antigen processing, MHC affinity, MHC stability, or antigen presentation.

Embodiment 33. The isolated antigenic peptide of embodiment 32, wherein the modification is conjugation to a carrier protein, conjugation to a ligand, conjugation to an antibody, PEGylation, polysialylation HESylation, recombinant PEG mimetics, Fc fusion, albumin fusion, nanoparticle attachment, nanoparticulate encapsulation, cholesterol fusion, iron fusion, acylation, amidation, glycosylation, side chain oxidation, phosphorylation, biotinylation, the addition of a surface active material, the addition of amino acid mimetics, or the addition of unnatural amino acids.

Embodiment 34. The isolated antigenic peptide of embodiment 32, wherein the cells that are targeted are antigen presenting cells.

Embodiment 35. The isolated antigenic peptide of embodiment 34, wherein the antigen presenting cells are dendritic cells.

Embodiment 36. The isolated antigenic peptide of embodiment 35, wherein the dendritic cells are targeted using DEC205, XCR1, CD197, CD80, CD86, CD123, CD209, CD273, CD283, CD289, CD184, CD85h, CD85j, CD85k, CD85d, CD85g, CD85a, CD141, CD11c, CD83, TSLP receptor, or CD1a marker.

Embodiment 37. The isolated antigenic peptide of embodiment 36, wherein the dendritic cells are targeted using the CD141, DEC205, or XCR1 marker.

Embodiment 38. An in vivo delivery system comprising the isolated antigenic peptide of any of embodiments 1-37.

Embodiment 39. The delivery system of embodiment 38, wherein the delivery system includes cell-penetrating peptides, nanoparticulate encapsulation, virus like particles, or liposomes.

Embodiment 40. The delivery system of embodiment 38, wherein the cell-penetrating peptide is TAT peptide, herpes simplex virus VP22, transportan, or Antp.

Embodiment 41. A cell comprising the isolated antigenic peptide of any of embodiments 1-37.

Embodiment 42. The cell of embodiment 41, which is an antigen presenting cell.

Embodiment 43. The cell of embodiment 42, which is a dendritic cell.

Embodiment 44. A composition comprising the isolated antigenic peptide of any of embodiments 1-37.

Embodiment 45. The composition of embodiment 44, wherein the composition comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 of the isolated antigenic peptides comprising a tumor-specific epitope defined in Table 1 or 2.

Embodiment 46. The composition of embodiment 44, wherein the composition comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 of the isolated antigenic peptides comprising a tumor-specific epitope defined in Table 3 or 4.

Embodiment 47. The composition of embodiment 44, wherein the composition comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 of the isolated antigenic peptides comprising a tumor-specific epitope defined in Table 5 or 6.

Embodiment 48. The composition of any of embodiments 45-47, wherein the composition comprises between 2 and 20 antigenic peptides.

Embodiment 49. The composition of any one of embodiments 45-48, wherein the composition further comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25, at least 26, at least 27, at least 28, at least 29, or at least 30 additional antigenic peptides.

Embodiment 50. The composition of embodiment 49, wherein the composition comprises between about 4 and about 20 additional antigenic peptides.

Embodiment 51. The composition of any of embodiments 44-50, wherein the additional antigenic peptide is specific for an individual patient's tumor.

Embodiment 52. The composition of embodiment 51, wherein the patient specific antigenic peptide is selected by identifying sequence differences between the genome, exome, and/or transcriptome of the patient's tumor sample and the genome, exome, and/or transcriptome of a non-tumor sample.

Embodiment 53. The composition of embodiment 47, wherein the samples are fresh or formalin-fixed paraffin embedded tumor tissues, freshly isolated cells, or circulating tumor cells.

Embodiment 54. The composition of embodiment 52 or 53, wherein the sequence differences are determined by Next Generation Sequencing.

Embodiment 55. An isolated polynucleotide encoding the isolated antigenic peptide of any of embodiments 1-10.

Embodiment 56. The isolated polynucleotide embodiment 55, which is RNA, optionally a self-amplifying RNA.

Embodiment 57. The isolated polynucleotide of embodiment 56, wherein the RNA is modified to increase stability, increase cellular targeting, increase translation efficiency, adjuvanticity, cytosol accessibility, and/or decrease cytotoxicity.

Embodiment 58. The isolated polynucleotide of embodiment 57, wherein the modification is conjugation to a carrier protein, conjugation to a ligand, conjugation to an antibody, codon optimization, increased GC-content, incorporation of modified nucleosides, incorporation of 5'-cap or cap analog, and/or incorporation of an unmasked poly-A sequence.

Embodiment 59. A cell comprising the polynucleotide of any of embodiments 55-58.

Embodiment 60. A vector comprising the polynucleotide of any one of embodiments 55-58.

Embodiment 61. The vector of embodiment 60, in which the polynucleotide is operably linked to a promoter.

Embodiment 62. The vector of embodiments 60 or 61, which is a self-amplifying RNA replicon, plasmid, phage, transposon, cosmid, virus, or virion.

Embodiment 63. The vector of embodiment 62, which is an adeno-associated virus, herpesvirus, lentivirus, or pseudotypes thereof.

Embodiment 64. An in vivo delivery system comprising the isolated polynucleotide of any of embodiments 55-58.

Embodiment 65. The delivery system of embodiment 60, wherein the delivery system includes spherical nucleic acids, viruses, virus-like particles, plasmids, bacterial plasmids, or nanoparticles.

Embodiment 66. A cell comprising the vector or delivery system of any of embodiments 60-65.

Embodiment 67. The cell of embodiment 66, which is an antigen presenting cell.

Embodiment 68. The cell of embodiment 67, which is a dendritic cell.

Embodiment 69. The cell of embodiment 68, which is an immature dendritic cell.

Embodiment 70. A composition comprising at least one polynucleotide of any of embodiments 55-58.

Embodiment 71. The composition of embodiment 70, wherein the composition comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 of the isolated polynucleotides.

Embodiment 72. The composition of embodiment 71, wherein the composition comprises between about 2 and about 20 polynucleotides.

Embodiment 73. The composition of any one of embodiments 70-72, wherein the composition further comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 additional antigenic polynucleotides encoding for additional antigenic peptides.

Embodiment 74. The composition of embodiment 73, wherein the composition comprises between about 4 and about 20 additional antigenic polynucleotides.

Embodiment 75. The composition of embodiment 73, wherein the isolated polynucleotides and the additional antigenic polynucleotides are linked.

Embodiment 76. The composition of embodiment 75, wherein the polynucleotides are linked using nucleic acids that encode a poly-glycine or poly-serine linker.

Embodiment 77. The composition of any of embodiments 70-76, wherein at least one of the additional antigenic peptide is specific for an individual patient's tumor.

Embodiment 78. The composition of embodiment 77, wherein the patient specific antigenic peptide is selected by identifying sequence differences between the genome, exome, and/or transcriptome of the patient's tumor sample and the genome, exome, and/or transcriptome of a non-tumor sample.

Embodiment 79. The composition of embodiment 78, wherein the samples are fresh or formalin-fixed paraffin embedded tumor tissues, freshly isolated cells, or circulating tumor cells.

Embodiment 80. The composition of embodiments 78 or 79, wherein the sequence differences are determined by Next Generation Sequencing.

Embodiment 81. A T cell receptor (TCR) capable of binding at least one antigenic peptide listed in any of embodiments 1-34.

Embodiment 82. The TCR of embodiment 81, which is capable of binding the isolated antigenic peptide in the context of MHC class I or class II.

Embodiment 83. A chimeric antigen receptor comprising: (i) a T cell activation molecule; (ii) a transmembrane region; and (iii) an antigen recognition moiety capable of binding an isolated antigenic peptide of any one of embodiments 1-34.

Embodiment 84. The chimeric antigen receptor of embodiment 83, wherein CD3-zeta is the T cell activation molecule.

Embodiment 85. The chimeric antigen receptor of embodiment 83 or 84, further comprising at least one costimulatory signaling domain.

Embodiment 86. The chimeric antigen receptor of any of embodiments 83-85, wherein the signaling domain is CD28, 4-1BB, ICOS, OX40, ITAM, or Fc epsilon RI-gamma.

Embodiment 87. The chimeric antigen receptor of any of embodiments 83-86, wherein the antigen recognition moiety is capable of binding the isolated antigenic peptide in the context of MHC class I or class II.

Embodiment 88. The chimeric antigen receptor of any of embodiments 83-87, comprising the CD3-zeta, CD28, CTLA-4, ICOS, BTLA, KIR, LAG3, CD137, OX40, CD27, CD40L, Tim-3, A2aR, or PD-1 transmembrane region.

Embodiment 89. The chimeric antigen receptor of any of embodiments 83-88, wherein the tumor-specific epitope is located in the extracellular domain of a tumor associated polypeptide.

Embodiment 90. A T cell comprising the T cell receptor or chimeric antigen receptor of any of embodiments 83-88.

Embodiment 91. The T cell of embodiment 90, which is a helper or cytotoxic T cell.

Embodiment 92. A nucleic acid comprising a promoter operably linked to a polynucleotide encoding the T cell receptor of embodiment 81 or 82.

Embodiment 93. The nucleic acid of embodiment 92, wherein the TCR is capable of binding the at least one antigenic peptide in the context of major histocompatibility complex (MHC) class I or class IL.

Embodiment 94. A nucleic acid comprising a promoter operably linked to a polynucleotide encoding the chimeric antigen receptor of any of embodiments 83-89.

Embodiment 95. The nucleic acid of embodiment 94, wherein the antigen recognition moiety is capable of binding the at least one antigenic peptide in the context of major histocompatibility complex (MHC) class I or class II.

Embodiment 96. The nucleic acid of embodiment 94 or 95, wherein the tumor-specific epitope is located in the extracellular domain of a tumor associated polypeptide.

Embodiment 97. The nucleic acid of any of embodiments 94-96, comprising the CD3-zeta, CD28, CTLA-4, ICOS, BTLA, KIR, LAG3, CD137, OX40, CD27, CD40L, Tim-3, A2aR, or PD-1 transmembrane region.

Embodiment 98. An antibody capable of binding at least one antigenic peptide listed in Table 1 or 2.

Embodiment 99. An antibody capable of binding at least one antigenic peptide listed in Table 3 or 4.

Embodiment 100. An antibody capable of binding at least one antigenic peptide listed in Table 5 or 6.

Embodiment 101. An antibody of embodiment 98, wherein the at least one antigenic peptide listed in Table 1 or 2 is a retroviral antigenic peptide.

Embodiment 102. An antibody of embodiment 99, wherein the at least one antigenic peptide listed in Table 3 or 4 is a non-mutated overexpressed antigenic peptide.

Embodiment 103. An antibody of embodiment 100, wherein the at least one antigenic peptide listed in Table 5 or 6 is a viral antigenic peptide.

Embodiment 104. A modified cell transfected or transduced with the nucleic acid of any one of embodiments 92-97.

Embodiment 105. The modified cell of embodiment 104, wherein the modified cell is a T cell, tumor infiltrating lymphocyte, NK-T cell, TCR-expressing cell, CD4+ T cell, CD8+ T cell, or NK cell.

Embodiment 106. A composition comprising the T cell receptor or chimeric antigen receptor of any of embodiments 81-89.

Embodiment 107. A composition comprising autologous patient T cells containing the T cell receptor or chimeric antigen receptor of any of embodiments 81-89.

Embodiment 108. The composition of embodiment 105 or 106, further comprising an immune checkpoint inhibitor.

Embodiment 109. The composition of embodiment 106 or 107, further comprising at least two immune checkpoint inhibitors.

Embodiment 110. The composition of embodiment 108 or 109, wherein each of the immune checkpoint inhibitors inhibits a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands or a combination thereof.

Embodiment 111. The composition of embodiment 108 or 109, wherein each of the immune checkpoint inhibitors interacts with a ligand of a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands or a combination thereof.

Embodiment 112. The composition of any of embodiments 44-54, 70-79, and 106-111, further comprising an immune modulator or adjuvant.

Embodiment 113. The composition of embodiment 112, wherein the immune modulator is a co-stimulatory ligand, a TNF ligand, an Ig superfamily ligand, CD28, CD80, CD86, ICOS, CD40L, OX40, CD27, GITR, CD30, DR3, CD69, or 4-1BB.

Embodiment 114. The composition of embodiment 112, wherein the immune modulator is at least one cancer cell or cancer cell extract.

Embodiment 115. The composition of embodiment 114, wherein the cancer cell is autologous to the subject in need of the composition.

Embodiment 116. The composition of embodiment 115, wherein the cancer cell has undergone lysis or been exposed to UV radiation.

Embodiment 117. The composition of embodiment 112, wherein the composition further comprises an adjuvant.

Embodiment 118. The composition of embodiment 117, wherein the adjuvant is selected from the group consisting of: Poly(I:C), Poly-ICLC, STING agonist, 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312 VG, Montanide ISA 206 VG, Montanide ISA 50 V2, Montanide ISA 51 VG, OK-432, OM-174, OM-197-MP-EC, ISA-TLR2 agonist, ONTAK, PepTel®. vector system, PLG microparticles, resiquimod, SRL172, virosomes and other virus-like particles, YF-17D, VEGF trap, R848, beta-glucan, Pam3Cys, Pam3CSK4, acrylic or methacrylic polymers, copolymers of maleic anhydride, and QS21 stimulon.

Embodiment 119. The composition of embodiment 118 or 118, wherein the adjuvant induces a humoral when administered to a subject.

Embodiment 120. The composition of embodiment 119, wherein the adjuvant induces a T helper cell type 1 when administered to a subject.

Embodiment 121. A method of inhibiting growth of a tumor cell expressing a tumor-specific epitope defined in Table 1 or 2, comprising contacting the tumor cell with the peptide, polynucleotide, delivery system, vector, composition, antibody, or cells of any of embodiments 1-120.

Embodiment 122. A method of inhibiting growth of a tumor cell expressing a tumor-specific epitope defined in Table 3 or 4, comprising contacting the tumor cell with the peptide, polynucleotide, delivery system, vector, composition, antibody, or cells of any of embodiments 1-120.

Embodiment 123. A method of inhibiting growth of a tumor cell expressing a tumor-specific epitope defined in Table 5 or 6, comprising contacting the tumor cell with the peptide, polynucleotide, delivery system, vector, composition, antibody, or cells of any of embodiments 1-120.

Embodiment 124. A method of treating cancer or initiating, enhancing, or prolonging an anti-tumor response in a subject in need thereof comprising administering to the subject the peptide, polynucleotide, vector, composition, antibody, or cells of any of embodiments 1-120.

Embodiment 125. The method of any of embodiments 121-124, wherein the subject is a human.

Embodiment 126. The method of embodiment 125, wherein the subject has cancer.

Embodiment 127. The method of embodiment 126, wherein the cancer is selected from the group consisting of urogenital, renal, gynecological, lung, gastrointestinal, head and neck cancer, malignant glioblastoma, malignant mesothelioma, non-metastatic or metastatic breast cancer, malignant melanoma, Merkel Cell Carcinoma or bone and soft tissue sarcomas, hematologic neoplasias, multiple myeloma, acute myelogenous leukemia, chronic myelogenous leukemia, myelodysplastic syndrome and acute lymphoblastic leukemia, non-small cell lung cancer (NSCLC), triple-negative breast cancer (TNBC), smoldering myeloma (SMM), breast cancer, metastatic colorectal cancers, hormone sensitive or hormone refractory prostate cancer, colorectal cancer, ovarian cancer, hepatocellular cancer, renal cell cancer, pancreatic cancer, gastric cancer, esophageal cancers, hepatocellular cancers, cholangiocellular cancers, head and neck squamous cell cancer soft tissue sarcoma, and small cell lung cancer.

Embodiment 128. The method of any of embodiments 121-127, wherein the subject has undergone surgical removal of the tumor.

Embodiment 129. The method of any of embodiments 121-128, wherein the peptide, polynucleotide, vector, composition, or cells is administered via intravenous, intraperitoneal, intratumoral, intradermal, or subcutaneous administration.

Embodiment 130. The method of embodiment 129, wherein the peptide, polynucleotide, vector, composition, or cells is administered into an anatomic site that drains into a lymph node basin.

Embodiment 131. The method of embodiment 130, wherein administration is into multiple lymph node basins.

Embodiment 132. The method of any one of embodiments 121-131, wherein administration is by a subcutaneous or intradermal route.

Embodiment 133. The method of embodiment 129, wherein peptide is administered.

Embodiment 134. The method of embodiment 133, wherein administration is intratumorally.

Embodiment 135. The method of embodiment 129, wherein polynucleotide, optionally RNA, is administered.

Embodiment 136. The method of embodiment 129 or 135, wherein the polynucleotide is administered intravenously.

Embodiment 137. The method of embodiment 129, wherein the cell is a T cell or dendritic cell.

Embodiment 138. The method of embodiment 129 or 137, wherein the peptide or polynucleotide comprises an antigen presenting cell targeting moiety.

Embodiment 139. The method of any of embodiments 121-138, further comprising administering at least one immune checkpoint inhibitor to the subject.

Embodiment 140. The method of embodiment 139, wherein the checkpoint inhibitor is a biologic therapeutic or a small molecule.

Embodiment 141. The method of embodiment 139 or 140, wherein the checkpoint inhibitor is selected from the group consisting of a monoclonal antibody, a humanized antibody, a fully human antibody and a fusion protein or a combination thereof.

Embodiment 142. The method of any of embodiments 139-141, wherein the checkpoint inhibitor inhibits a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands or a combination thereof.

Embodiment 143. The method of any of embodiments 139-142, wherein the checkpoint inhibitor interacts with a ligand of a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands or a combination thereof.

Embodiment 144. The method of any of embodiments 139-143, wherein two or more checkpoint inhibitors are administered.

Embodiment 145. The method of embodiment 144, wherein the checkpoint inhibitors are: (i) ipilimumab or tremelimumab, and (ii) nivolumab.

Embodiment 146. The method of any of embodiments 139-145, wherein the checkpoint inhibitor and the composition are administered simultaneously or sequentially in any order.

Embodiment 147. The method of embodiment 146, wherein the peptide, polynucleotide, vector, composition, or cells is administered prior to the checkpoint inhibitor.

Embodiment 148. The method of embodiment 146, wherein the peptide, polynucleotide, vector, composition, or cells is administered after the checkpoint inhibitor.

Embodiment 149. The method of embodiment 146, wherein administration of the checkpoint inhibitor is continued throughout antigen peptide, polynucleotide, vector, composition, or cell therapy.

Embodiment 150. The method of any of embodiments 139-149, wherein the antigen peptide, polynucleotide, vector, composition, or cell therapy is administered to subjects that only partially respond or do not respond to checkpoint inhibitor therapy.

Embodiment 151. The method of any one of embodiments 121-138, wherein the composition is administered intravenously or subcutaneously.

Embodiment 152. The method of any one of embodiments 139-150, wherein the checkpoint inhibitor is administered intravenously or subcutaneously.

Embodiment 153. The method of any one of embodiments 139-151, wherein the checkpoint inhibitor is administered subcutaneously within about 2 cm of the site of administration of the composition.

Embodiment 154. The method of embodiment 153, wherein the composition is administered into the same draining lymph node as the checkpoint inhibitor.

Embodiment 155. The method of any of embodiments 121-154, further comprising administering an additional therapeutic agent to the subject either prior to, simultaneously with, or after treatment with the peptide, polynucleotide, vector, composition, or cells.

Embodiment 156. The method of embodiment 155, wherein the additional agent is a chemotherapeutic agent, an immunomodulatory drug, an immune metabolism modifying drug, a targeted therapy, radiation an anti-angiogenesis agent, or an agent that reduces immune-suppression.

Embodiment 157. The method of embodiment 156, wherein the chemotherapeutic agent is an alkylating agent, a topoisomerase inhibitor, an anti-metabolite, or an anti-mitotic agent.

Embodiment 158. The method of embodiment 155, wherein the additional agent is an anti-glucocorticoid induced tumor necrosis factor family receptor (GITR) agonistic antibody or antibody fragment, ibrutinib, docetaxel, cisplatin, or cyclophosphamide.

Embodiment 159. The method of any of embodiments 121-158, which elicits a CD4+ T cell immune response.

Embodiment 160. The method of any of embodiments 121-159, which elicits a CD4+ T cell immune response and a CD8+ T cell immune response.

Embodiment 161. A method for stimulating an immune response in a subject, comprising administering an effective amount of modified cells or composition of any of embodiments 104-120.

Embodiment 162. The method of embodiment 161, wherein the immune response is cytotoxic and/or humoral immune response.

Embodiment 163. The method of embodiment 161, wherein the method stimulates a T cell-mediated immune response in a subject.

Embodiment 164. The method of embodiment 163, wherein the T cell-mediated immune response is directed against a target cell.

Embodiment 165. The method of embodiment 164, wherein the target cell is a tumor cell.

Embodiment 166. The method of any of embodiments 161-165, wherein the modified cells are transfected or transduced in vivo.

Embodiment 167. The method of any of embodiments 161-166, wherein the modified cells are transfected or transduced ex vivo.

Embodiment 168. The method of any of embodiments 161-167, wherein the modified cells are autologous patient T cells.

Embodiment 169. The method of embodiment 168, wherein the autologous patient T cells are obtained from a patient that has received an antigen peptide or nucleic acid vaccine.

Embodiment 170. The method of embodiment 169, wherein the antigen peptide or nucleic acid vaccine comprises at least one personalized antigen.

Embodiment 171. The method of embodiment 170, wherein the antigen peptide or nucleic acid vaccine comprises at least one additional antigenic peptide listed in Table 1 or 2.

Embodiment 172. The method of embodiment 170, wherein the antigen peptide or nucleic acid vaccine comprises at least one additional antigenic peptide listed in Table 3 or 4.

Embodiment 173. The method of embodiment 170, wherein the antigen peptide or nucleic acid vaccine comprises at least one additional antigenic peptide listed in Table 5 or 6.

Embodiment 174. The method of embodiment 171, wherein the at least one additional antigenic peptide listed in Table 1 or 2 is a retroviral antigenic peptide.

Embodiment 175. The method of embodiment 172, wherein the at least one additional antigenic peptide listed in Table 3 or 4 is a non-mutated overexpressed antigenic peptide.

Embodiment 176. The method of embodiment 173, wherein the at least one additional antigenic peptide listed in Table 5 or 6 is a viral antigenic peptide.

Embodiment 177. The method of any of embodiments 171-176, wherein the patient received a chemotherapeutic agent, an immunomodulatory drug, an immune metabolism modifying drug, targeted therapy or radiation prior to and/or during receipt of the antigen peptide or nucleic acid vaccine.

Embodiment 178. The method of any of embodiments 169-177, wherein the patient receives treatment with at least one checkpoint inhibitor.

Embodiment 179. The method of any of embodiments 169-178, wherein the autologous T cells are obtained from a patient that has already received at least one round of T cell therapy containing an antigen.

Embodiment 180. The method of any of embodiments 169-179, wherein the method further comprises adoptive T cell therapy.

Embodiment 181. The method of embodiment 180, wherein the adoptive T cell therapy comprises autologous T-cells.

Embodiment 182. The method of embodiment 181, wherein the autologous T-cells are targeted against tumor antigens.

Embodiment 183. The method of embodiment 180 or 181, wherein the adoptive T cell therapy further comprises allogenic T-cells.

Embodiment 184. The method of embodiment 183, wherein the allogenic T-cells are targeted against tumor antigens.

Embodiment 185. The method of any of embodiments 180-184, wherein the adoptive T cell therapy is administered before the checkpoint inhibitor.

Embodiment 186. A method for evaluating the efficacy of any of embodiments 121-185, comprising: (i) measuring the number or concentration of target cells in a first sample obtained from the subject before administering the modified cell, (ii) measuring the number concentration of target cells in a second sample obtained from the subject after administration of the modified cell, and (iii) determining an increase or decrease of the number or concentration of target cells in the second sample compared to the number or concentration of target cells in the first sample.

Embodiment 187. The method of embodiment 186, wherein treatment efficacy is determined by monitoring a clinical outcome; an increase, enhancement or prolongation of anti-tumor activity by T cells; an increase in the number of anti-tumor T cells or activated T cells as compared with the number prior to treatment; B cell activity; CD4 T cell activity; or a combination thereof.

Embodiment 188. The method of embodiment 187, wherein treatment efficacy is determined by monitoring a biomarker.

Embodiment 189. The method of embodiment 188, wherein the biomarker is selected from the group consisting of CEA, Her-2/neu, bladder tumor antigen, thyroglobulin, alpha-fetoprotein, PSA, CA 125, CA19.9, CA 15.3, leptin, prolactin, osteopontin, IGF-II, CD98, fascin, sPIgR, 14-3-3 eta, troponin I, and b-type natriuretic peptide.

Embodiment 190. The method of embodiment 187, wherein clinical outcome is selected from the group consisting of tumor regression; tumor shrinkage; tumor necrosis; anti-tumor response by the immune system; tumor expansion, recurrence or spread; or a combination thereof.

Embodiment 191. The method of embodiment 187, wherein the treatment effect is predicted by presence of T cells or by presence of a gene signature indicating T cell inflammation or a combination thereof.

Embodiment 192. A method of treating cancer or initiating, enhancing, or prolonging an anti-tumor response in a subject in need thereof comprising administering to the subject: the peptide, polynucleotide, vector, composition, antibody, or cells of any of embodiments 1-120; and at least one checkpoint inhibitor.

Embodiment 193. The method of embodiment 192, further comprising administration of an immunomodulator or adjuvant.

Embodiment 194. The method of embodiment 192, wherein the immunomodulator or adjuvant is selected from the group consisting of Poly(I:C), Poly-ICLC, STING agonist, 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312 VG, Montanide ISA 206 VG, Montanide ISA 50 V2, Montanide ISA 51 VG, OK-432, OM-174, OM-197-MP-EC, ISA-TLR2 agonist, ONTAK, PepTel® vector system, PLG microparticles, resiquimod, SRL172, virosomes and other virus-like particles, YF-17D, VEGF trap, R848, beta-glucan, Pam3Cys, Pam3CSK4, acrylic or methacrylic polymers, copolymers of maleic anhydride, and QS21 stimulon. a co-stimulatory ligand, a TNF ligand, an Ig superfamily ligand, CD28, CD80, CD86, ICOS, CD40L, OX40, CD27, GITR, CD30, DR3, CD69, or 4-1BB.

Embodiment 195. The method of embodiment 192, wherein the immunomodulator or adjuvant is Poly-ICLC.

Embodiment 196. The method of any one of embodiments 192-193, wherein the checkpoint inhibitor is an anti-PD1 antibody or antibody fragment.

Embodiment 197. The method of embodiment 194, wherein the inhibitor of the PD-1 pathway is nivolumab.

Embodiment 198. The method of any one of embodiments 192-193, wherein the checkpoint inhibitor is an anti-CTLA4 antibody or antibody fragment.

Embodiment 199. The method of embodiment 196, wherein the anti-CTLA4 antibody is ipilimumab or tremelimumab.

Embodiment 200. The method of any one of embodiments 192-197, wherein the method comprises administering both an anti-PD1 antibody and an anti-CTLA4 antibody.

Embodiment 201. The method of any one of embodiments 192-197, wherein administration of the checkpoint inhibitor is initiated before initiation of administration of the peptide, polynucleotide, vector, composition, antibody, or cell.

Embodiment 202. The method of any one of embodiments 192-197, wherein administration of the checkpoint inhibitor is initiated after initiation of administration of the peptide, polynucleotide, vector, composition, antibody, or cell.

Embodiment 203. The method of any one of embodiments 192-197, wherein administration of the checkpoint inhibitor is initiated simultaneously with the initiation of administration of the peptide, polynucleotide, vector, composition, antibody, or cell.

Embodiment 204. The method of any one of embodiments 192-201, wherein the peptide, polynucleotide, vector, composition, antibody, or cell is administered intravenously or subcutaneously.

Embodiment 205. The method of any one of embodiments 192-201, wherein the checkpoint inhibitor is administered intravenously or subcutaneously.

Embodiment 206. The method of any one of embodiments 192-203, wherein the checkpoint inhibitor is administered subcutaneously within about 2 cm of the site of administration of the peptide, polynucleotide, vector, composition, antibody, or cell.

Embodiment 207. The method of embodiment 204, wherein the peptide, polynucleotide, vector, composition, antibody, or cell is administered into the same draining lymph node as the checkpoint inhibitor.

Embodiment 208. A kit comprising an antigen therapeutic of any of embodiments 1-120.

Embodiment 209. The method of embodiment 124, wherein the cancer is selected from the group consisting of: CRC, head and neck, stomach, lung squamous, lung adeno., prostate, bladder, stomach, renal cell carcinoma, and uterine.

Embodiment 210. The method of embodiment 124, wherein the cancer is selected from the group consisting of: melanoma, lung squamous, DLBCL, uterine, head and neck, uterine, liver, and CRC.

Embodiment 211. The method of embodiment 124, wherein the cancer is selected from the group consisting of: cervical, head and neck, anal, stomach, Burkitt's lymphoma, and nasopharyngeal carcinoma.

Provided herein is an immunogenic vaccine composition comprising a peptide comprising at least 8 contiguous amino acids of a sequence in any one of Tables 1-6. In some embodiments, the peptide is a synthetic peptide. In some embodiments, the peptide is a recombinant peptide. In some embodiments, the peptide comprises a sequence from an endogenous retroviral protein. In some embodiments, the peptide comprises a sequence from an exogenous viral protein. In some embodiments, the peptide comprises a sequence of a protein expressed by a cancer cell of a subject with cancer, wherein the protein is expressed by the cancer cell at a level that is higher than a level expressed by a non-cancer cell of the subject. In some embodiments, the peptide is 100 amino acids or less in length. In some embodiments, the peptide is from about 5 to about 50 amino acids in length or from about 15 to about 35 amino acids in length. In some embodiments, the peptide is about 30 amino acids or less in length or about 15 amino acids or less in length. In some embodiments, the peptide comprises a sequence which binds a major histocompatibility complex (MHC) class I with a binding affinity of less than about 500 nM. In some embodiments, the peptide comprises a sequence which binds a major histocompatibility complex (MHC) class II with a binding affinity of less than about 1000 nM. In some embodiments, the peptide further comprises non-native amino acids flanking the at least 8 contiguous amino acids. In some embodiments, the composition further comprises a second peptide comprising at least 8 contiguous amino acids of a sequence in any one of Tables 1-6, wherein the second antigenic peptide binds MHC class I or class II with a binding affinity of less than about 1000 nM. In some embodiments, the peptides are linked using a poly-glycine or poly-serine linker. In some embodiments, the second antigenic peptide binds MHC class I or class II with a binding affinity of less than about 1000 nM or less than about 500 nM. In some embodiments, the peptide further comprises a modification which increases in vivo half-life, cellular targeting, antigen uptake, antigen processing, MHC affinity, MHC stability, or antigen presentation. In some embodiments, the modification is conjugation to a carrier protein, conjugation to a ligand, conjugation to an antibody, PEGylation, polysialylation HESylation, recombinant PEG mimetics, Fc fusion, albumin fusion, nanoparticle attachment, nanoparticulate encapsulation, cholesterol fusion, iron fusion, acylation, amidation, glycosylation, side chain oxidation, phosphorylation, biotinylation, the addition of a surface active material, the addition of amino acid mimetics, or the addition of unnatural amino acids. In some embodiments, the peptide comprises a modification which increases targeting by antigen presenting cells. In some embodiments, the antigen presenting cells are dendritic cells. In some embodiments, the modification which increases targeting by the dendritic cells is a DEC205, XCR1, CD197, CD80, CD86, CD123, CD209, CD273, CD283, CD289, CD184, CD85h, CD85j, CD85k, CD85d, CD85g, CD85a, CD141, CD11c, CD83, TSLP receptor, or CD1a marker. In some embodiments, the composition comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 of peptides each comprising at least 8 contiguous amino acids of a sequence in any one of Tables 1-6. In some embodiments, the composition comprises from 2 to 20 peptides each comprising at least 8 contiguous amino acids of a sequence in any one of Tables 1-6. In some embodiments, the composition further comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25, at least 26, at least 27, at least 28, at least 29, or at least 30 additional antigenic peptides. In some embodiments, the additional antigenic peptides are specific for an individual patient's tumor. In some embodiments, the additional antigenic peptides are selected by identifying sequence differences between the genome, exome, and/or transcriptome of the patient's tumor sample and the genome, exome, and/or transcriptome of a non-tumor sample. In some embodiments, identifying sequence differences comprises performing Next Generation Sequencing. Provided herein is a composition comprising an antigen presenting cell comprising a peptide comprising at least 8 contiguous amino acids of a sequence in any one of Tables 1-6. In some embodiments, the antigen presenting cell is a dendritic cell.

Provided herein is an in vivo delivery system comprising a composition described herein. In some embodiments, the delivery system includes a cell-penetrating peptide, nanoparticulate encapsulation, a virus like particle, or a liposome. In some embodiments, the cell-penetrating peptide is a TAT peptide, herpes simplex virus VP22, transportan, or Antp.

Provided herein is an immunogenic vaccine composition comprising a recombinant polynucleotide encoding a peptide comprising at least 8 contiguous amino acids of a sequence in any one of Tables 1-6. In some embodiments, the recombinant polynucleotide is RNA, optionally a self-amplifying RNA. In some embodiments, the RNA is modified to increase stability, increase cellular targeting, increase translation efficiency, adjuvanticity, cytosol accessibility, and/or decrease cytotoxicity. In some embodiments, the modification is conjugation to a carrier protein, conjugation to a ligand, conjugation to an antibody, codon optimization, increased GC-content, incorporation of modified nucleosides, incorporation of 5'-cap or cap analog, and/or incorporation of an unmasked poly-A sequence.

Provided herein is a composition comprising a cell comprising a recombinant polynucleotide encoding a peptide comprising at least 8 contiguous amino acids of a sequence in any one of Tables 1-6.

Provided herein is a composition comprising a vector comprising a polynucleotide comprising a sequence encoding a peptide comprising at least 8 contiguous amino acids of a sequence in any one of Tables 1-6. In some embodiments, the polynucleotide is operably linked to a promoter. In some embodiments, the polynucleotide is a self-amplifying RNA replicon, plasmid, phage, transposon, cosmid, virus, or virion. In some embodiments, the virus is an adeno-associated virus, herpesvirus, lentivirus, or pseudotypes thereof.

Provided herein is an in vivo delivery system comprising a composition described herein. In some embodiments, the delivery system includes spherical nucleic acids, viruses, virus-like particles, plasmids, bacterial plasmids, or nanoparticle.

Provided herein is a T cell receptor (TCR) that specifically binds to a peptide:MHC complex, wherein the peptide of the peptide of the peptide:MHC complex is a peptide comprising at least 8 contiguous amino acids of a sequence in any one of Tables 1-6.

Provided herein is a T cell comprising a T cell receptor (TCR) that specifically binds to a peptide:MHC complex, wherein the peptide of the peptide of the peptide:MHC complex is a peptide comprising at least 8 contiguous amino acids of a sequence in any one of Tables 1-6. In some embodiments, the T cell is a helper or cytotoxic T cell. In some embodiments, the T cell is an autologous patient T cell.

Provided herein is a method of treating cancer in a subject in need thereof comprising administering to the subject a composition described herein; wherein the subject comprises cancer cells expressing a protein comprising at least 8 contiguous amino acids of a sequence in any one of Tables 1-6. In some embodiments, the subject is a human. In some embodiments, the cancer is selected from the group consisting of urogenital, gynecological, lung, gastrointestinal, head and neck cancer, malignant glioblastoma, malignant mesothelioma, non-metastatic or metastatic breast cancer, triple-negative breast cancer (TNBC), malignant melanoma, Merkel Cell Carcinoma or bone and soft tissue sarcomas, hematologic neoplasias, multiple myeloma, smoldering myeloma (SMM), acute myelogenous leukemia, chronic myelogenous leukemia, myelodysplastic syndrome and acute lymphoblastic leukemia, non-small cell lung cancer (NSCLC), breast cancer, metastatic colorectal cancers, hormone sensitive or hormone refractory prostate cancer, colorectal cancer, ovarian cancer, hepatocellular cancer, renal cell cancer, pancreatic cancer, gastric cancer, esophageal cancers, hepatocellular cancers, cholangiocellular cancers, head and neck squamous cell cancer soft tissue sarcoma, and small cell lung cancer. In some embodiments, the method further comprises administering at least one immune checkpoint inhibitor to the subject. In some embodiments, the checkpoint inhibitor inhibits a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands or a combination thereof.

What is claimed is:

1. A method of treating a cancer in a subject in need thereof, the method comprising administering to the subject a polypeptide or a polynucleotide encoding the polypeptide, wherein the polypeptide comprises an amino acid sequence comprising at least 8 contiguous amino acids of a viral protein epitope sequence encoded by (I) an E6 gene of Human papillomavirus type 16 (HPV-16) or (II) an E7 gene of HPV-16, wherein:

(a) the subject expresses an MHC encoded by an HLA B07:02 allele and wherein the amino acid sequence is encoded by the E6 gene of HPV-16 and comprises a sequence of RGRWTGRCM (SEQ ID NO: 70);

(b) the subject expresses an MHC encoded by an HLA B08:01 allele and wherein the amino acid sequence is encoded by the E6 gene of HPV-16; or (c) the subject expresses an MHC encoded by an HLA A24:02 allele and (i) the amino acid sequence is encoded by the E7 gene of HPV-16 and comprises the sequence of RAHYNIVTF (SEQ ID NO: 83), or (ii) the amino acid sequence is encoded by the E6 gene of HPV-16 and comprises a sequence of MHQKRTAMF (SEQ ID NO: 66);

wherein the cancer is a cancer expressing an antigen encoded by the E6 gene of HPV-16 or the E7 gene of HPV-16; and wherein the subject is a human.

2. The method of claim 1, wherein the amino acid sequence comprises a first amino acid sequence comprising at least 8 contiguous amino acids of the viral protein epitope sequence encoded by the E6 gene of HPV-16, and a second amino acid sequence comprising at least 8 contiguous amino acids of the viral protein epitope sequence encoded by the E7 gene of HPV-16.

3. The method of claim 2, wherein the polypeptide comprises a first polypeptide comprising the first amino acid sequence and a second polypeptide comprising the second amino acid sequence.

4. The method of claim 1, wherein the method comprises administering to the subject the polynucleotide encoding the polypeptide, and wherein the polynucleotide is a messenger-RNA (mRNA).

5. The method of claim 4, wherein the mRNA is a part of a lipid nanoparticle.

6. The method of claim 1, wherein the viral protein epitope sequence binds an MHC class I with a binding affinity of 500 nM or less.

7. The method of claim 3, wherein the first polypeptide or the second polypeptide is less than or equal to 600 amino acids in length.

8. The method of claim 1, wherein the polypeptide further comprises a modification which increases in vivo half-life, cellular targeting, antigen uptake, antigen processing, MHC affinity, MHC stability, or antigen presentation.

9. The method of claim 1, wherein the polypeptide further comprises a poly-glycine or poly-serine linker.

10. The method of claim 1, wherein the polypeptide further comprises a peptide sequence of QYIKANSKFIGITE (SEQ ID NO: 1).

11. The method of claim 1, wherein the cancer is selected from the group consisting of cervical cancer, head and neck cancer, anal cancer, urogenital cancer, and gynecological cancer.

12. The method of claim 1, further comprising administering an additional therapeutic agent to the subject for a combination therapy, wherein the additional therapeutic agent comprises a chemotherapeutic agent, an immunotherapeutic agent, or an immune checkpoint inhibitor.

13. The method of claim 1, wherein the subject expresses the MHC encoded by the HLA B07:02 allele.

14. The method of claim 13, wherein the amino acid sequence is encoded by the E6 gene of HPV-16 and comprises a sequence of RGRWTGRCM (SEQ ID NO: 70).

15. The method of claim 1, wherein the subject expresses the MHC encoded by the HLA B08:01 allele and the amino acid sequence is encoded by the E6 gene of HPV-16.

16. The method of claim 15, wherein the amino acid sequence comprises a sequence selected from the group consisting of CVYCKQQLL (SEQ ID NO: 51), DKKQRFHNI (SEQ ID NO: 54), EYRHYCYSL (SEQ ID NO: 55), MHQKRTAMF (SEQ ID NO: 66), SEYRHYCYSL (SEQ ID NO: 73), and SSRTRRETQL (SEQ ID NO: 74).

17. The method of claim 1, wherein the subject expresses the MHC encoded by the HLA A24:02 allele, and wherein the amino acid sequence is encoded by the E7 gene of HPV-16 and comprises the sequence of RAHYNIVTF (SEQ ID NO: 83).

18. The method of claim 1, wherein the subject expresses the MHC encoded by the HLA A24:02 allele, and wherein the amino acid sequence is encoded by the E6 gene of HPV-16 and comprises the sequence of MHQKRTAMF (SEQ ID NO: 66).

19. The method of claim 15, wherein the amino acid sequence comprises a sequence of CVYCKQQLL (SEQ ID NO: 51).

20. The method of claim 15, wherein the amino acid sequence comprises a sequence of DKKQRFHNI (SEQ ID NO: 54).

21. The method of claim 15, wherein the amino acid sequence comprises a sequence of EYRHYCYSL (SEQ ID NO: 55).

22. The method of claim 15, wherein the amino acid sequence comprises a sequence of MHQKRTAMF (SEQ ID NO: 66).

23. The method of claim 15, wherein the amino acid sequence comprises a sequence of SEYRHYCYSL (SEQ ID NO: 73).

24. The method of claim 15, wherein the amino acid sequence comprises a sequence of SSRTRRETQL (SEQ ID NO: 74).

* * * * *

UNITED STATES PATENT AND TRADEMARK OFFICE
CERTIFICATE OF CORRECTION

| | | Page 1 of 1 |
|---|---|---|
| PATENT NO. | : 12,303,561 B2 | |
| APPLICATION NO. | : 16/500707 | |
| DATED | : May 20, 2025 | |
| INVENTOR(S) | : Michael Steven Rooney | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 379 days.

Signed and Sealed this
Sixteenth Day of December, 2025

John A. Squires
*Director of the United States Patent and Trademark Office*

SEQUENCE LISTING

```
<160> NUMBER OF SEQ ID NOS: 947

<210> SEQ ID NO 1
<211> LENGTH: 14
<212> TYPE: PRT
<213> ORGANISM: Clostridium tetani

<400> SEQUENCE: 1

Gln Tyr Ile Lys Ala Asn Ser Lys Phe Ile Gly Ile Thr Glu
1               5                   10

<210> SEQ ID NO 2
<211> LENGTH: 21
<212> TYPE: PRT
<213> ORGANISM: Plasmodium falciparum

<400> SEQUENCE: 2

Asp Ile Glu Lys Lys Ile Ala Lys Met Glu Lys Ala Ser Ser Val Phe
1               5                   10                  15

Asn Val Val Asn Ser
            20

<210> SEQ ID NO 3
<211> LENGTH: 16
<212> TYPE: PRT
<213> ORGANISM: Streptococcus sp.

<400> SEQUENCE: 3

Gly Ala Val Asp Ser Ile Leu Gly Gly Val Ala Thr Tyr Gly Ala Ala
1               5                   10                  15
```

-continued

```
<210> SEQ ID NO 4
<211> LENGTH: 13
<212> TYPE: PRT
<213> ORGANISM: Unknown
<220> FEATURE:
<221> NAME/KEY: source
<223> OTHER INFORMATION: /note="Description of Unknown:
      PADRE sequence"
<220> FEATURE:
<221> NAME/KEY: VARIANT
<222> LOCATION: (1)..(1)
<223> OTHER INFORMATION: /replace="D-Ala"
<220> FEATURE:
<221> NAME/KEY: VARIANT
<222> LOCATION: (3)..(3)
<223> OTHER INFORMATION: /replace="Cyclohexylalanine" or "Phenylalanine"
<220> FEATURE:
<221> NAME/KEY: VARIANT
<222> LOCATION: (13)..(13)
<223> OTHER INFORMATION: /replace="D-Ala"
<220> FEATURE:
<221> NAME/KEY: MISC_FEATURE
<222> LOCATION: (1)..(13)
<223> OTHER INFORMATION: /note="Variant residues given in the sequence
      have no preference with respect to those in the annotations
      for variant positions"

<400> SEQUENCE: 4

Ala Lys Tyr Val Trp Ala Asn Thr Leu Lys Ala Ala Ala
1               5                   10

<210> SEQ ID NO 5
<211> LENGTH: 93
<212> TYPE: PRT
<213> ORGANISM: Homo sapiens

<400> SEQUENCE: 5

Met Gly Asn Leu Pro Pro Ser Ile Pro Pro Ser Leu Ala Cys Val
1               5                   10                  15

Leu Lys Asn Leu Lys Pro Leu Gln Leu Thr Pro Asp Leu Lys Pro Lys
            20                  25                  30

Cys Leu Ile Phe Phe Cys Asn Thr Ala Trp Pro Gln Tyr Lys Leu Asp
        35                  40                  45

Asn Gly Ser Lys Trp Pro Glu Asn Gly Thr Phe Asp Phe Ser Ile Leu
    50                  55                  60

Gln Asp Leu Asn Asn Ser Cys Arg Lys Met Gly Lys Trp Ser Glu Val
65                  70                  75                  80

Pro Asp Val Gln Ala Phe Phe Tyr Thr Ser Val Pro Ser
                85                  90

<210> SEQ ID NO 6
<211> LENGTH: 144
<212> TYPE: PRT
<213> ORGANISM: Homo sapiens

<400> SEQUENCE: 6

Met Pro Asn Arg Ala Ile Arg Leu Gln Ala Val Leu Glu Ile Ile Thr
1               5                   10                  15

Asn Gln Thr Ala Ser Ala Leu Glu Met Leu Ala Gln Gln Asn Gln
            20                  25                  30

Met Arg Ala Ala Ile Tyr Gln Asn Arg Leu Ala Leu Asp Tyr Leu Leu
        35                  40                  45

Ala Glu Glu Gly Ala Gly Cys Gly Lys Phe Asn Ile Ser Asn Cys Cys
    50                  55                  60
```

Leu Asn Ile Gly Asn Asn Gly Glu Glu Val Leu Glu Ile Ala Ser Asn
65                  70                  75                  80

Ile Arg Lys Val Ala Arg Val Pro Val Gln Thr Trp Glu Gly Trp Asp
                85                  90                  95

Pro Ala Asn Leu Leu Gly Gly Trp Phe Ser Asn Leu Gly Gly Phe Lys
            100                 105                 110

Met Leu Val Gly Thr Val Ile Phe Ile Thr Gly Val Leu Leu Phe Leu
        115                 120                 125

Pro Cys Gly Ile Pro Leu Lys Leu Leu Lys Leu Gln Leu Thr Ser
    130                 135                 140

<210> SEQ ID NO 7
<211> LENGTH: 160
<212> TYPE: PRT
<213> ORGANISM: Homo sapiens

<400> SEQUENCE: 7

Met Ala Cys Ile Tyr Pro Thr Thr Phe Tyr Thr Ser Leu Pro Thr Lys
1               5                   10                  15

Ser Leu Asn Met Gly Ile Ser Leu Thr Thr Ile Leu Ile Leu Ser Val
            20                  25                  30

Ala Val Leu Leu Ser Thr Ala Ala Pro Pro Ser Cys Arg Glu Cys Tyr
        35                  40                  45

Gln Ser Leu His Tyr Arg Gly Glu Met Gln Gln Tyr Phe Thr Tyr His
    50                  55                  60

Thr His Ile Glu Arg Ser Cys Tyr Gly Asn Leu Ile Glu Glu Cys Val
65                  70                  75                  80

Glu Ser Gly Lys Ser Tyr Tyr Lys Val Lys Asn Leu Gly Val Cys Gly
                85                  90                  95

Ser Arg Asn Gly Ala Ile Cys Pro Arg Gly Lys Gln Trp Leu Cys Phe
            100                 105                 110

Thr Lys Ile Gly Gln Trp Gly Val Asn Thr Gln Val Leu Glu Asp Ile
        115                 120                 125

Lys Arg Glu Gln Ile Ile Ala Lys Ala Lys Ala Ser Lys Pro Thr Thr
    130                 135                 140

Pro Pro Glu Asn Arg Pro Arg His Phe His Ser Phe Ile Gln Lys Leu
145                 150                 155                 160

<210> SEQ ID NO 8
<211> LENGTH: 38
<212> TYPE: PRT
<213> ORGANISM: Homo sapiens

<400> SEQUENCE: 8

Met Ala Arg Ser Ala Ala Thr Leu Arg Arg Phe Thr Ala Leu Asp Pro
1               5                   10                  15

Lys Arg Ser Lys Gly Arg Leu Ile Leu Asn Ile His Phe Ile Thr Gln
            20                  25                  30

Ser Ala Pro Asp Ile Lys
        35

<210> SEQ ID NO 9
<211> LENGTH: 242
<212> TYPE: PRT
<213> ORGANISM: Homo sapiens

<400> SEQUENCE: 9

```
Arg Leu Phe Leu Thr Lys Pro Gly Lys Glu Ile Gly Pro Ala Leu Ala
1               5                   10                  15

Gln Trp Trp Pro Lys Val Cys Ala Glu Asp Asn Pro Gly Leu Ala
            20                  25                  30

Val Asn Gln Ala Pro Val Leu Arg Glu Val Lys Pro Glu Ala Gln Pro
        35                  40                  45

Val Arg Gln Asn Gln Tyr Pro Val Pro Arg Glu Ala Leu Glu Gly Ile
    50                  55                  60

Gln Val His Leu Lys His Leu Arg Thr Phe Gly Ile Ile Val Pro Cys
65              70                  75                  80

Gln Ser Pro Trp Asn Thr Pro Leu Leu Pro Val Pro Lys Pro Gly Thr
            85                  90                  95

Lys Asp Tyr Arg Pro Val Gln Asp Leu Arg Leu Val Asn Gln Ala Thr
            100                 105                 110

Val Thr Phe His Pro Thr Val Pro Asn Pro Tyr Thr Leu Leu Gly Leu
            115                 120                 125

Leu Pro Ala Lys Asp Ser Trp Phe Thr Cys Leu Asp Leu Lys Asp Ala
    130                 135                 140

Phe Phe Ser Ile Arg Leu Ala Pro Glu Ser Gln Lys Leu Phe Ala Phe
145                 150                 155                 160

Gln Trp Glu Asp Pro Gly Ser Gly Val Thr Thr His Tyr Thr Trp Thr
            165                 170                 175

Arg Leu Pro Gln Gly Phe Lys Asn Phe Pro His His Leu Trp Gly Gly
            180                 185                 190

Thr Gly Ser Arg Pro Pro Lys Val Ser Cys Gln Arg Pro Arg Leu Arg
            195                 200                 205

Val Val Pro Val His Arg Gln Pro Pro Ala Gly Thr Pro His Gly Ser
    210                 215                 220

Arg Val Arg Gln Arg Asn Arg Arg Pro Ala Ser Ala Pro Gly Gly Leu
225                 230                 235                 240

Trp Val

<210> SEQ ID NO 10
<211> LENGTH: 100
<212> TYPE: PRT
<213> ORGANISM: Homo sapiens

<400> SEQUENCE: 10

Met Ala Val Gly Cys Val Lys Gly Thr Asp Ala Leu Leu Gln His Leu
1               5                   10                  15

Glu Asp Tyr Gly Tyr Lys Val Ser Lys Lys Ala Gln Ile Cys Arg
            20                  25                  30

Gln Gln Val Arg Tyr Leu Gly Phe Thr Ile Arg Gln Arg Glu Cys Ser
        35                  40                  45

Leu Gly Ser Glu Arg Lys Gln Val Ile Cys Asn Leu Leu Glu Pro Lys
    50                  55                  60

Thr Arg Arg Gln Leu Arg Glu Leu Leu Gly Ala Val Gly Phe Cys Arg
65              70                  75                  80

Leu Trp Ile Pro Asn Phe Ala Val Leu Ala Lys Pro Leu Val Pro Ser
            85                  90                  95

Tyr Lys Gly Gly
            100

<210> SEQ ID NO 11
<211> LENGTH: 254
```

```
<212> TYPE: PRT
<213> ORGANISM: Homo sapiens

<400> SEQUENCE: 11

Asn Ala Asp Leu Leu Ala Ala Ile Arg Gly Val Pro Leu Lys Gly
1               5                   10                  15

Gln Gly Asn Gly Gly Ser Arg Lys Asn Thr Gln Ser Asp Arg Pro Arg
            20                  25                  30

Leu Gln Arg Asn Gln Cys Ala Tyr Cys Lys Glu Thr Gly His Trp Lys
        35                  40                  45

Asp Lys Cys Pro Gln Leu Lys Glu Lys Gln Gly Ser Glu Gln Lys
    50                  55                  60

Thr Pro Asp Lys Asp Glu Gly Ala Leu Phe Asn Leu Ala Glu Gly Leu
65                  70                  75                  80

Leu Asp Arg Arg Gly Pro Gly Ser Arg Ala Pro Lys Glu Pro Met Val
                85                  90                  95

Arg Met Thr Val Gly Gly Lys Asp Ile Lys Phe Leu Val Asn Thr Gly
                100                 105                 110

Ala Glu His Ser Val Val Thr Thr Pro Val Ala Pro Leu Ser Lys Lys
            115                 120                 125

Ala Ile Asp Ile Ile Gly Ala Thr Gly Val Leu Thr Lys Gln Ala Phe
    130                 135                 140

Cys Leu Pro Arg Thr Cys Ser Val Gly Gly His Glu Val Ile His Gln
145                 150                 155                 160

Phe Leu Tyr Ile Pro Asp Cys Pro Leu Pro Leu Leu Gly Arg Asp Leu
                165                 170                 175

Leu Ser Lys Leu Arg Ala Ile Phe Leu Tyr Gln Ala Arg Leu Phe Thr
            180                 185                 190

Thr Glu Val Ala Trp Asn Arg Ser Tyr His Gly Pro Asp Ser Ser Pro
        195                 200                 205

Arg Gly Arg Val Ala Thr Leu Pro Asn Gln Thr Arg Gln Arg Asp Arg
    210                 215                 220

Ala Ser Ser Gly Pro Val Val Ala Lys Ser Met Arg Arg Arg Gln Pro
225                 230                 235                 240

Ser Trp Ile Gly Ser Gln Ser Ser Ser Cys Thr Gln Gly Ser
                245                 250

<210> SEQ ID NO 12
<211> LENGTH: 31
<212> TYPE: PRT
<213> ORGANISM: Homo sapiens

<400> SEQUENCE: 12

Ser Leu Phe Leu His Lys Thr Ser Val Arg Glu Val Leu Ser Ala Thr
1               5                   10                  15

Ile Pro Ala Thr Phe Leu Gly Ser Leu Thr Trp Lys Arg Gly Asp
            20                  25                  30

<210> SEQ ID NO 13
<211> LENGTH: 257
<212> TYPE: PRT
<213> ORGANISM: Homo sapiens

<400> SEQUENCE: 13

Met Gln Asn Glu Ala Ile Glu Gln Val Arg Ala Ile Cys Leu Arg Ala
1               5                   10                  15

Trp Gly Lys Ile Gln Asp Pro Gly Thr Ala Phe Pro Ile Asn Ser Ile
```

```
                20                  25                  30
Arg Gln Gly Ser Lys Glu Pro Tyr Pro Asp Phe Val Ala Arg Leu Gln
            35                  40                  45
Asp Ala Ala Gln Lys Ser Ile Thr Asp Asp Asn Ala Arg Lys Val Ile
        50                  55                  60
Val Glu Leu Met Ala Tyr Glu Asn Ala Asn Pro Glu Cys Gln Ser Ala
 65                  70                  75                  80
Ile Lys Pro Leu Lys Gly Lys Val Pro Ala Gly Val Asp Val Ile Thr
                85                  90                  95
Glu Tyr Val Lys Ala Cys Asp Gly Ile Gly Gly Ala Met His Lys Ala
            100                 105                 110
Met Leu Met Ala Gln Ala Met Arg Gly Leu Thr Leu Gly Gly Gln Val
            115                 120                 125
Arg Thr Phe Gly Lys Lys Cys Tyr Asn Cys Gly Gln Ile Gly His Leu
            130                 135                 140
Lys Arg Ser Cys Pro Val Leu Asn Lys Gln Asn Ile Ile Asn Gln Ala
145                 150                 155                 160
Ile Thr Ala Lys Asn Lys Lys Pro Ser Gly Leu Cys Pro Lys Cys Gly
                165                 170                 175
Lys Gly Lys His Trp Ala Asn Gln Cys His Ser Lys Phe Asp Lys Asp
            180                 185                 190
Gly Gln Pro Leu Ser Gly Asn Arg Lys Arg Gly Gln Pro Gln Ala Pro
            195                 200                 205
Gln Gln Thr Gly Ala Phe Pro Val Gln Leu Phe Val Pro Gln Gly Phe
            210                 215                 220
Gln Gly Gln Gln Pro Leu Gln Lys Ile Pro Pro Leu Gln Gly Val Ser
225                 230                 235                 240
Gln Leu Gln Gln Ser Asn Ser Cys Pro Ala Pro Gln Gln Ala Ala Pro
                245                 250                 255
Gln

<210> SEQ ID NO 14
<211> LENGTH: 95
<212> TYPE: PRT
<213> ORGANISM: Homo sapiens

<400> SEQUENCE: 14

Met Glu Trp Ile Lys Tyr Ser Ile Cys Thr Leu Asn Lys Ser Asn Cys
 1               5                  10                  15
Tyr Ala Cys Ala His Gly Arg Pro Glu Ala Gln Ile Val Pro Phe Pro
            20                  25                  30
Leu Arg Trp Ser Ser Ser Arg Pro Ser Met Gly Cys Met Val Ala Leu
            35                  40                  45
Phe Gln Asp Ser Thr Ala Trp Gly Asn Ile Ser Cys Gln Ala Leu Ser
        50                  55                  60
Leu Leu Tyr Pro Glu Val Gln His Pro Ala Gly Gln Pro Pro Arg Ala
 65                  70                  75                  80
Ile Gln Leu Pro Ser Pro Asn Val Ser Phe Ile Ser Cys Leu Ser
                85                  90                  95

<210> SEQ ID NO 15
<211> LENGTH: 529
<212> TYPE: PRT
<213> ORGANISM: Homo sapiens

<400> SEQUENCE: 15
```

```
Met Leu Leu Ala Val Leu Tyr Cys Leu Leu Trp Ser Phe Gln Thr Ser
1               5                   10                  15

Ala Gly His Phe Pro Arg Ala Cys Val Ser Ser Lys Asn Leu Met Glu
                20                  25                  30

Lys Glu Cys Cys Pro Pro Trp Ser Gly Asp Arg Ser Pro Cys Gly Gln
            35                  40                  45

Leu Ser Gly Arg Gly Ser Cys Gln Asn Ile Leu Leu Ser Asn Ala Pro
    50                  55                  60

Leu Gly Pro Gln Phe Pro Phe Thr Gly Val Asp Asp Arg Glu Ser Trp
65                  70                  75                  80

Pro Ser Val Phe Tyr Asn Arg Thr Cys Gln Cys Ser Gly Asn Phe Met
                85                  90                  95

Gly Phe Asn Cys Gly Asn Cys Lys Phe Gly Phe Trp Gly Pro Asn Cys
                100                 105                 110

Thr Glu Arg Arg Leu Leu Val Arg Arg Asn Ile Phe Asp Leu Ser Ala
            115                 120                 125

Pro Glu Lys Asp Lys Phe Phe Ala Tyr Leu Thr Leu Ala Lys His Thr
    130                 135                 140

Ile Ser Ser Asp Tyr Val Ile Pro Ile Gly Thr Tyr Gly Gln Met Lys
145                 150                 155                 160

Asn Gly Ser Thr Pro Met Phe Asn Asp Ile Asn Ile Tyr Asp Leu Phe
                165                 170                 175

Val Trp Met His Tyr Tyr Val Ser Met Asp Ala Leu Leu Gly Gly Ser
                180                 185                 190

Glu Ile Trp Arg Asp Ile Asp Phe Ala His Glu Ala Pro Ala Phe Leu
    195                 200                 205

Pro Trp His Arg Leu Phe Leu Leu Arg Trp Glu Gln Glu Ile Gln Lys
    210                 215                 220

Leu Thr Gly Asp Glu Asn Phe Thr Ile Pro Tyr Trp Asp Trp Arg Asp
225                 230                 235                 240

Ala Glu Lys Cys Asp Ile Cys Thr Asp Glu Tyr Met Gly Gly Gln His
            245                 250                 255

Pro Thr Asn Pro Asn Leu Leu Ser Pro Ala Ser Phe Phe Ser Ser Trp
                260                 265                 270

Gln Ile Val Cys Ser Arg Leu Glu Glu Tyr Asn Ser His Gln Ser Leu
    275                 280                 285

Cys Asn Gly Thr Pro Glu Gly Pro Leu Arg Arg Asn Pro Gly Asn His
    290                 295                 300

Asp Lys Ser Arg Thr Pro Arg Leu Pro Ser Ser Ala Asp Val Glu Phe
305                 310                 315                 320

Cys Leu Ser Leu Thr Gln Tyr Glu Ser Gly Ser Met Asp Lys Ala Ala
            325                 330                 335

Asn Phe Ser Phe Arg Asn Thr Leu Glu Gly Phe Ala Ser Pro Leu Thr
                340                 345                 350

Gly Ile Ala Asp Ala Ser Gln Ser Ser Met His Asn Ala Leu His Ile
    355                 360                 365

Tyr Met Asn Gly Thr Met Ser Gln Val Gln Gly Ser Ala Asn Asp Pro
370                 375                 380

Ile Phe Leu Leu His His Ala Phe Val Asp Ser Ile Phe Glu Gln Trp
385                 390                 395                 400

Leu Arg Arg His Arg Pro Leu Gln Glu Val Tyr Pro Glu Ala Asn Ala
                405                 410                 415
```

```
Pro Ile Gly His Asn Arg Glu Ser Tyr Met Val Pro Phe Ile Pro Leu
                420                 425                 430

Tyr Arg Asn Gly Asp Phe Phe Ile Ser Ser Lys Asp Leu Gly Tyr Asp
            435                 440                 445

Tyr Ser Tyr Leu Gln Asp Ser Asp Pro Asp Ser Phe Gln Asp Tyr Ile
450                 455                 460

Lys Ser Tyr Leu Glu Gln Ala Ser Arg Ile Trp Ser Trp Leu Leu Gly
465                 470                 475                 480

Ala Ala Met Val Gly Ala Val Leu Thr Ala Leu Leu Ala Gly Leu Val
                485                 490                 495

Ser Leu Leu Cys Arg His Lys Arg Lys Gln Leu Pro Glu Glu Lys Gln
                500                 505                 510

Pro Leu Leu Met Glu Lys Glu Asp Tyr His Ser Leu Tyr Gln Ser His
            515                 520                 525

Leu

<210> SEQ ID NO 16
<211> LENGTH: 1142
<212> TYPE: PRT
<213> ORGANISM: Homo sapiens

<400> SEQUENCE: 16

Met Gly Asp Lys Asp Met Pro Thr Ala Gly Met Pro Ser Leu Leu Gln
1               5                   10                  15

Ser Ser Ser Glu Ser Pro Gln Ser Cys Pro Glu Gly Glu Asp Ser Gln
                20                  25                  30

Ser Pro Leu Gln Ile Pro Gln Ser Pro Glu Ser Asp Asp Thr Leu
            35                  40                  45

Tyr Pro Leu Gln Ser Pro Gln Ser Arg Ser Gly Glu Asp Ser Ser
50                  55                  60

Asp Pro Leu Gln Arg Pro Pro Glu Gly Lys Asp Ser Gln Ser Pro Leu
65                  70                  75                  80

Gln Ile Pro Gln Ser Ser Pro Glu Gly Asp Asp Thr Gln Ser Pro Leu
                85                  90                  95

Gln Asn Ser Gln Ser Ser Pro Glu Gly Lys Asp Ser Leu Ser Pro Leu
                100                 105                 110

Glu Ile Ser Gln Ser Pro Pro Glu Gly Glu Asp Val Gln Ser Pro Leu
                115                 120                 125

Gln Asn Pro Ala Ser Ser Phe Phe Ser Ser Ala Leu Leu Ser Ile Phe
130                 135                 140

Gln Ser Ser Pro Glu Ser Thr Gln Ser Pro Phe Glu Gly Phe Pro Gln
145                 150                 155                 160

Ser Val Leu Gln Ile Pro Val Ser Ala Ala Ser Ser Ser Thr Leu Val
                165                 170                 175

Ser Ile Phe Gln Ser Ser Pro Glu Ser Thr Gln Ser Pro Phe Glu Gly
                180                 185                 190

Phe Pro Gln Ser Pro Leu Gln Ile Pro Val Ser Arg Ser Phe Ser Ser
            195                 200                 205

Thr Leu Leu Ser Ile Phe Gln Ser Ser Pro Glu Arg Thr Gln Ser Thr
210                 215                 220

Phe Glu Gly Phe Ala Gln Ser Pro Leu Gln Ile Pro Val Ser Pro Ser
225                 230                 235                 240

Ser Ser Thr Leu Leu Ser Leu Phe Gln Ser Phe Ser Glu Arg Thr
                245                 250                 255
```

-continued

```
Gln Ser Thr Phe Glu Gly Phe Ala Gln Ser Ser Leu Gln Ile Pro Val
            260                 265                 270

Ser Pro Ser Phe Ser Ser Thr Leu Val Ser Leu Phe Gln Ser Ser Pro
        275                 280                 285

Glu Arg Thr Gln Ser Thr Phe Glu Gly Phe Pro Gln Ser Pro Leu Gln
    290                 295                 300

Ile Pro Val Ser Ser Ser Ser Ser Thr Leu Leu Ser Leu Phe Gln
305                 310                 315                 320

Ser Ser Pro Glu Arg Thr His Ser Thr Phe Glu Gly Phe Pro Gln Ser
                325                 330                 335

Leu Leu Gln Ile Pro Met Thr Ser Ser Phe Ser Ser Thr Leu Leu Ser
            340                 345                 350

Ile Phe Gln Ser Ser Pro Glu Ser Ala Gln Ser Thr Phe Glu Gly Phe
355                 360                 365

Pro Gln Ser Pro Leu Gln Ile Pro Gly Ser Pro Ser Phe Ser Ser Thr
        370                 375                 380

Leu Leu Ser Leu Phe Gln Ser Ser Pro Glu Arg Thr His Ser Thr Phe
385                 390                 395                 400

Glu Gly Phe Pro Gln Ser Pro Leu Gln Ile Pro Met Thr Ser Ser Phe
                405                 410                 415

Ser Ser Thr Leu Leu Ser Ile Leu Gln Ser Ser Pro Glu Ser Ala Gln
            420                 425                 430

Ser Ala Phe Glu Gly Phe Pro Gln Ser Pro Leu Gln Ile Pro Val Ser
        435                 440                 445

Ser Ser Phe Ser Tyr Thr Leu Leu Ser Leu Phe Gln Ser Ser Pro Glu
    450                 455                 460

Arg Thr His Ser Thr Phe Glu Gly Phe Pro Gln Ser Pro Leu Gln Ile
465                 470                 475                 480

Pro Val Ser Ser Ser Ser Ser Ser Thr Leu Leu Ser Leu Phe Gln
                485                 490                 495

Ser Ser Pro Glu Cys Thr Gln Ser Thr Phe Glu Gly Phe Pro Gln Ser
            500                 505                 510

Pro Leu Gln Ile Pro Gln Ser Pro Pro Glu Gly Glu Asn Thr His Ser
        515                 520                 525

Pro Leu Gln Ile Val Pro Ser Leu Pro Glu Trp Glu Asp Ser Leu Ser
    530                 535                 540

Pro His Tyr Phe Pro Gln Ser Pro Gln Gly Glu Asp Ser Leu Ser
545                 550                 555                 560

Pro His Tyr Phe Pro Gln Ser Pro Gln Gly Glu Asp Ser Leu Ser
                565                 570                 575

Pro His Tyr Phe Pro Gln Ser Pro Gln Gly Glu Asp Ser Leu Ser Pro
            580                 585                 590

His Tyr Phe Pro Gln Ser Pro Gln Gly Glu Asp Ser Met Ser Pro
        595                 600                 605

Leu Tyr Phe Pro Gln Ser Pro Leu Gln Gly Glu Phe Gln Ser Ser
    610                 615                 620

Leu Gln Ser Pro Val Ser Ile Cys Ser Ser Thr Pro Ser Ser Leu
625                 630                 635                 640

Pro Gln Ser Phe Pro Glu Ser Ser Gln Ser Pro Glu Gly Pro Val
                645                 650                 655

Gln Ser Pro Leu His Ser Pro Gln Ser Pro Glu Gly Met His Ser
            660                 665                 670

Gln Ser Pro Leu Gln Ser Pro Glu Ser Ala Pro Glu Gly Glu Asp Ser
```

```
                675                 680                 685
Leu Ser Pro Leu Gln Ile Pro Gln Ser Pro Leu Glu Gly Glu Asp Ser
    690                 695                 700

Leu Ser Ser Leu His Phe Pro Gln Ser Pro Glu Trp Glu Asp Ser
705                 710                 715                 720

Leu Ser Pro Leu His Phe Pro Gln Phe Pro Gln Gly Glu Asp Phe
                725                 730                 735

Gln Ser Ser Leu Gln Ser Pro Val Ser Ile Cys Ser Ser Ser Thr Ser
            740                 745                 750

Leu Ser Leu Pro Gln Ser Phe Pro Glu Ser Pro Gln Ser Pro Pro Glu
        755                 760                 765

Gly Pro Ala Gln Ser Pro Leu Gln Arg Pro Val Ser Ser Phe Phe Ser
    770                 775                 780

Tyr Thr Leu Ala Ser Leu Leu Gln Ser Ser His Glu Ser Pro Gln Ser
785                 790                 795                 800

Pro Pro Glu Gly Pro Ala Gln Ser Pro Leu Gln Ser Pro Val Ser Ser
                805                 810                 815

Phe Pro Ser Ser Thr Ser Ser Ser Leu Ser Gln Ser Ser Pro Val Ser
            820                 825                 830

Ser Phe Pro Ser Ser Thr Ser Ser Ser Leu Ser Lys Ser Ser Pro Glu
        835                 840                 845

Ser Pro Leu Gln Ser Pro Val Ile Ser Phe Ser Ser Thr Ser Leu
    850                 855                 860

Ser Pro Phe Ser Glu Glu Ser Ser Ser Pro Val Asp Glu Tyr Thr Ser
865                 870                 875                 880

Ser Ser Asp Thr Leu Leu Glu Ser Asp Ser Leu Thr Asp Ser Glu Ser
                885                 890                 895

Leu Ile Glu Ser Glu Pro Leu Phe Thr Tyr Thr Leu Asp Glu Lys Val
            900                 905                 910

Asp Glu Leu Ala Arg Phe Leu Leu Lys Tyr Gln Val Lys Gln Pro
        915                 920                 925

Ile Thr Lys Ala Glu Met Leu Thr Asn Val Ile Ser Arg Tyr Thr Gly
    930                 935                 940

Tyr Phe Pro Val Ile Phe Arg Lys Ala Arg Glu Phe Ile Glu Ile Leu
945                 950                 955                 960

Phe Gly Ile Ser Leu Arg Glu Val Asp Pro Asp Ser Tyr Val Phe
                965                 970                 975

Val Asn Thr Leu Asp Leu Thr Ser Glu Gly Cys Leu Ser Asp Glu Gln
            980                 985                 990

Gly Met Ser Gln Asn Arg Leu Leu Ile Leu Ile Leu Ser Ile Ile Phe
        995                 1000                1005

Ile Lys Gly Thr Tyr Ala Ser Glu Glu Val Ile Trp Asp Val Leu
    1010                1015                1020

Ser Gly Ile Gly Val Arg Ala Gly Arg Glu His Phe Ala Phe Gly
    1025                1030                1035

Glu Pro Arg Glu Leu Leu Thr Lys Val Trp Val Gln Glu His Tyr
    1040                1045                1050

Leu Glu Tyr Arg Glu Val Pro Asn Ser Ser Pro Pro Arg Tyr Glu
    1055                1060                1065

Phe Leu Trp Gly Pro Arg Ala His Ser Glu Val Ile Lys Arg Lys
    1070                1075                1080

Val Val Glu Phe Leu Ala Met Leu Lys Asn Thr Val Pro Ile Thr
    1085                1090                1095
```

Phe Pro Ser Ser Tyr Lys Asp Ala Leu Lys Asp Val Glu Glu Arg
    1100            1105                1110

Ala Gln Ala Ile Ile Asp Thr Thr Asp Asp Ser Thr Ala Thr Glu
    1115            1120                1125

Ser Ala Ser Ser Ser Val Met Ser Pro Ser Phe Ser Ser Glu
    1130            1135                1140

<210> SEQ ID NO 17
<211> LENGTH: 369
<212> TYPE: PRT
<213> ORGANISM: Homo sapiens

<400> SEQUENCE: 17

Met Pro Arg Ala Pro Lys Arg Gln Arg Cys Met Pro Glu Glu Asp Leu
1               5                   10                  15

Gln Ser Gln Ser Glu Thr Gln Gly Leu Glu Gly Ala Gln Ala Pro Leu
                20                  25                  30

Ala Val Glu Glu Asp Ala Ser Ser Thr Ser Thr Ser Ser Ser Ser Phe
            35                  40                  45

Pro Ser Ser Phe Pro Ser Ser Ser Ser Ser Ser Ser Ser Cys Tyr
50                  55                  60

Pro Leu Ile Pro Ser Thr Pro Glu Glu Val Ser Ala Asp Asp Glu Thr
65                  70                  75                  80

Pro Asn Pro Pro Gln Ser Ala Gln Ile Ala Cys Ser Ser Pro Ser Val
                85                  90                  95

Val Ala Ser Leu Pro Leu Asp Gln Ser Asp Glu Gly Ser Ser Ser Gln
            100                 105                 110

Lys Glu Glu Ser Pro Ser Thr Leu Gln Val Leu Pro Asp Ser Glu Ser
        115                 120                 125

Leu Pro Arg Ser Glu Ile Asp Glu Lys Val Thr Asp Leu Val Gln Phe
130                 135                 140

Leu Leu Phe Lys Tyr Gln Met Lys Glu Pro Ile Thr Lys Ala Glu Ile
145                 150                 155                 160

Leu Glu Ser Val Ile Arg Asn Tyr Glu Asp His Phe Pro Leu Leu Phe
                165                 170                 175

Ser Glu Ala Ser Glu Cys Met Leu Leu Val Phe Gly Ile Asp Val Lys
            180                 185                 190

Glu Val Asp Pro Thr Gly His Ser Phe Val Leu Val Thr Ser Leu Gly
        195                 200                 205

Leu Thr Tyr Asp Gly Met Leu Ser Asp Val Gln Ser Met Pro Lys Thr
210                 215                 220

Gly Ile Leu Ile Leu Ile Leu Ser Ile Val Phe Ile Glu Gly Tyr Cys
225                 230                 235                 240

Thr Pro Glu Glu Val Ile Trp Glu Ala Leu Asn Met Met Gly Leu Tyr
                245                 250                 255

Asp Gly Met Glu His Leu Ile Tyr Gly Glu Pro Arg Lys Leu Leu Thr
            260                 265                 270

Gln Asp Trp Val Gln Glu Asn Tyr Leu Glu Tyr Arg Gln Val Pro Gly
        275                 280                 285

Ser Asp Pro Ala Arg Tyr Glu Phe Leu Trp Gly Pro Arg Ala His Ala
290                 295                 300

Glu Ile Arg Lys Met Ser Leu Leu Lys Phe Leu Ala Lys Val Asn Gly
305                 310                 315                 320

Ser Asp Pro Arg Ser Phe Pro Leu Trp Tyr Glu Glu Ala Leu Lys Asp

```
                325                 330                 335
Glu Glu Glu Arg Ala Gln Asp Arg Ile Ala Thr Thr Asp Asp Thr Thr
            340                 345                 350

Ala Met Ala Ser Ala Ser Ser Ala Thr Gly Ser Phe Ser Tyr Pro
        355                 360                 365

Glu

<210> SEQ ID NO 18
<211> LENGTH: 336
<212> TYPE: PRT
<213> ORGANISM: Homo sapiens

<400> SEQUENCE: 18

Met Pro Arg Gly Gln Ala Ser Lys Arg Ala Arg Glu Lys Arg Arg
1               5                   10                  15

Gln Ala Arg Gly Glu Asp Gln Cys Leu Gly Gly Ala Gln Ala Thr Ala
                20                  25                  30

Ala Glu Lys Glu Lys Leu Pro Ser Ser Ser Pro Ala Cys Gln Ser
        35                  40                  45

Pro Pro Gln Ser Phe Pro Asn Ala Gly Ile Pro Gln Glu Ser Gln Arg
    50                  55                  60

Ala Ser Tyr Pro Ser Pro Ala Ser Ala Val Ser Leu Thr Ser Ser
65              70                  75                  80

Asp Glu Gly Ala Lys Gly Gln Lys Gly Glu Ser Pro Asn Ser Phe His
                85                  90                  95

Gly Pro Ser Ser Glu Ser Thr Gly Arg Asp Leu Leu Asn Thr Lys
        100                 105                 110

Thr Gly Glu Leu Val Gln Phe Leu Leu Asn Lys Tyr Ile Arg Lys Glu
        115                 120                 125

Pro Ile Thr Arg Glu Ala Met Leu Lys Val Ile Asn Arg Lys Tyr Lys
130                 135                 140

Gln His Phe Pro Glu Ile Leu Arg Arg Ser Thr Glu Asn Val Glu Val
145                 150                 155                 160

Val Phe Gly Leu Tyr Leu Lys Glu Met Asp Pro Ser Arg Gln Ser Tyr
                165                 170                 175

Val Leu Val Gly Lys Leu Asp Phe Pro Asn Gln Gly Ser Leu Ser Asp
                180                 185                 190

Gly Gly Gly Phe Pro Leu Ser Gly Leu Leu Met Val Leu Leu Ser Thr
        195                 200                 205

Ile Phe Met His Gly Asn Arg Ala Thr Glu Glu Met Trp Glu Cys
210                 215                 220

Leu Asn Ala Leu Gly Met Tyr Lys Gly Arg Lys His Phe Ile Tyr Gly
225                 230                 235                 240

Glu Pro Gln Glu Leu Val Thr Lys Asp Leu Val Arg Glu Gly Tyr Leu
                245                 250                 255

Glu Tyr Gln Gln Val Pro Ser Ser Asp Pro Pro Arg Tyr Glu Phe Leu
            260                 265                 270

Trp Gly Pro Arg Ala Arg Ala Glu Thr Ser Lys Met Lys Val Leu Glu
        275                 280                 285

Phe Val Ala Lys Leu Asn Asp Thr Val Ala Ser Thr Tyr Lys Ser Arg
    290                 295                 300

Tyr Glu Glu Ala Leu Arg Glu Glu Glu Gln Ala Arg Ala Arg Ala
305                 310                 315                 320

Val Ala Arg Asp Ser Ala Arg Ala Arg Ala Ser Arg Ser Phe Gln Pro
```

<210> SEQ ID NO 19
<211> LENGTH: 345
<212> TYPE: PRT
<213> ORGANISM: Homo sapiens

<400> SEQUENCE: 19

```
Met Leu Pro Leu Ser Val Gly Leu Trp Val Pro Ile Ala Gln Leu Leu
1               5                   10                  15

Pro Ala Leu Leu Pro Ala Ala Leu Thr Arg Val Ile Met Ser Ser Glu
            20                  25                  30

Gln Lys Ser Gln His Cys Lys Pro Glu Glu Gly Val Glu Ala Gln Glu
        35                  40                  45

Glu Ala Leu Gly Leu Val Gly Ala Gln Ala Pro Thr Thr Glu Glu Gln
    50                  55                  60

Glu Ala Ala Val Ser Ser Ser Pro Leu Val Pro Gly Thr Leu Glu
65                  70                  75                  80

Glu Val Pro Ala Ala Glu Ser Ala Gly Pro Pro Gln Ser Pro Gln Gly
                85                  90                  95

Ala Ser Ala Leu Pro Thr Thr Ile Ser Phe Thr Cys Trp Arg Gln Pro
            100                 105                 110

Asn Glu Gly Ser Ser Ser Gln Glu Glu Glu Gly Pro Ser Thr Ser Pro
        115                 120                 125

Asp Ala Glu Ser Leu Phe Arg Glu Ala Leu Ser Asn Lys Val Asp Glu
    130                 135                 140

Leu Ala His Phe Leu Leu Arg Lys Tyr Arg Ala Lys Glu Leu Val Thr
145                 150                 155                 160

Lys Ala Glu Met Leu Glu Arg Val Ile Lys Asn Tyr Lys Arg Cys Phe
                165                 170                 175

Pro Val Ile Phe Gly Lys Ala Ser Glu Ser Leu Lys Met Ile Phe Gly
            180                 185                 190

Ile Asp Val Lys Glu Val Asp Pro Ala Ser Asn Thr Tyr Thr Leu Val
        195                 200                 205

Thr Cys Leu Gly Leu Ser Tyr Asp Gly Leu Leu Gly Asn Asn Gln Ile
    210                 215                 220

Phe Pro Lys Thr Gly Leu Leu Ile Ile Val Leu Gly Thr Ile Ala Met
225                 230                 235                 240

Glu Gly Asp Ser Ala Ser Glu Glu Ile Trp Glu Leu Gly Val
                245                 250                 255

Met Gly Val Tyr Asp Gly Arg Glu His Thr Val Tyr Gly Glu Pro Arg
            260                 265                 270

Lys Leu Leu Thr Gln Asp Trp Val Gln Glu Asn Tyr Leu Glu Tyr Arg
        275                 280                 285

Gln Val Pro Gly Ser Asn Pro Ala Arg Tyr Glu Phe Leu Trp Gly Pro
    290                 295                 300

Arg Ala Leu Ala Glu Thr Ser Tyr Val Lys Val Leu Glu His Val Val
305                 310                 315                 320

Arg Val Asn Ala Arg Val Arg Ile Ala Tyr Pro Ser Leu Arg Glu Ala
                325                 330                 335

Ala Leu Leu Glu Glu Glu Glu Gly Val
            340                 345
```

<210> SEQ ID NO 20
<211> LENGTH: 324

```
<212> TYPE: PRT
<213> ORGANISM: Homo sapiens

<400> SEQUENCE: 20

Met Ser Gln Asp Gln Glu Ser Pro Arg Cys Thr His Asp Gln His Leu
1               5                   10                  15

Gln Thr Phe Ser Glu Thr Gln Ser Leu Glu Val Ala Gln Val Ser Lys
            20                  25                  30

Ala Leu Glu Lys Thr Leu Leu Ser Ser His Pro Leu Val Pro Gly
        35                  40                  45

Lys Leu Lys Glu Ala Pro Ala Ala Lys Ala Glu Ser Pro Leu Glu Val
    50                  55                  60

Pro Gln Ser Phe Cys Ser Ser Ile Ala Val Thr Thr Thr Ser Ser
65                  70                  75                  80

Ser Glu Ser Asp Glu Ala Ser Ser Asn Gln Glu Glu Asp Ser Pro
                85                  90                  95

Ser Ser Ser Glu Asp Thr Ser Asp Pro Arg Asn Val Pro Ala Asp Ala
                100                 105                 110

Leu Asp Gln Lys Val Ala Phe Leu Val Asn Phe Met Leu His Lys Cys
            115                 120                 125

Gln Met Lys Lys Pro Ile Thr Lys Ala Asp Met Leu Lys Ile Ile Ile
130                 135                 140

Lys Asp Asp Glu Ser His Phe Ser Glu Ile Leu Leu Arg Ala Ser Glu
145                 150                 155                 160

His Leu Glu Met Ile Phe Gly Leu Asp Val Val Glu Val Asp Pro Thr
                165                 170                 175

Thr His Cys Tyr Gly Leu Phe Ile Lys Leu Gly Leu Thr Tyr Asp Gly
            180                 185                 190

Met Leu Ser Gly Glu Lys Gly Val Pro Lys Thr Gly Leu Leu Ile Ile
        195                 200                 205

Val Leu Gly Val Ile Phe Met Lys Gly Asn Arg Ala Thr Glu Glu
            210                 215                 220

Val Trp Glu Val Leu Asn Leu Thr Gly Val Tyr Ser Gly Lys Lys His
225                 230                 235                 240

Phe Ile Phe Gly Glu Pro Arg Met Leu Ile Thr Lys Asp Phe Val Lys
                245                 250                 255

Glu Lys Tyr Leu Glu Tyr Gln Gln Val Ala Asn Ser Asp Pro Ala Arg
            260                 265                 270

Tyr Glu Phe Leu Trp Gly Pro Arg Ala Lys Ala Glu Thr Ser Lys Met
        275                 280                 285

Lys Val Leu Glu Phe Val Ala Lys Val His Gly Ser Tyr Pro His Ser
    290                 295                 300

Phe Pro Ser Gln Tyr Ala Glu Ala Leu Lys Glu Glu Glu Arg Ala
305                 310                 315                 320

Arg Ala Arg Ile

<210> SEQ ID NO 21
<211> LENGTH: 309
<212> TYPE: PRT
<213> ORGANISM: Homo sapiens

<400> SEQUENCE: 21

Met Ser Leu Glu Gln Arg Ser Leu His Cys Lys Pro Glu Glu Ala Leu
1               5                   10                  15

Glu Ala Gln Gln Glu Ala Leu Gly Leu Val Cys Val Gln Ala Ala Thr
```

```
                20                  25                  30
Ser Ser Ser Ser Pro Leu Val Leu Gly Thr Leu Glu Glu Val Pro Thr
            35                  40                  45

Ala Gly Ser Thr Asp Pro Pro Gln Ser Pro Gln Gly Ala Ser Ala Phe
        50                  55                  60

Pro Thr Thr Ile Asn Phe Thr Arg Gln Arg Gln Pro Ser Glu Gly Ser
 65                  70                  75                  80

Ser Ser Arg Glu Glu Glu Gly Pro Ser Thr Ser Cys Ile Leu Glu Ser
                85                  90                  95

Leu Phe Arg Ala Val Ile Thr Lys Lys Val Ala Asp Leu Val Gly Phe
            100                 105                 110

Leu Leu Leu Lys Tyr Arg Ala Arg Glu Pro Val Thr Lys Ala Glu Met
            115                 120                 125

Leu Glu Ser Val Ile Lys Asn Tyr Lys His Cys Phe Pro Glu Ile Phe
        130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Leu Val Thr Cys Leu Gly
                165                 170                 175

Leu Ser Tyr Asp Gly Leu Leu Gly Asp Asn Gln Ile Met Pro Lys Thr
            180                 185                 190

Gly Phe Leu Ile Ile Val Leu Val Met Ile Ala Met Glu Gly Gly His
        195                 200                 205

Ala Pro Glu Glu Glu Ile Trp Glu Glu Leu Ser Val Met Glu Val Tyr
    210                 215                 220

Asp Gly Arg Glu His Ser Ala Tyr Gly Glu Pro Arg Lys Leu Leu Thr
225                 230                 235                 240

Gln Asp Leu Val Gln Glu Lys Tyr Leu Glu Tyr Arg Gln Val Pro Asp
                245                 250                 255

Ser Asp Pro Ala Arg Tyr Glu Phe Leu Trp Gly Pro Arg Ala Leu Ala
            260                 265                 270

Glu Thr Ser Tyr Val Lys Val Leu Glu Tyr Val Ile Lys Val Ser Ala
        275                 280                 285

Arg Val Arg Phe Phe Phe Pro Ser Leu Arg Glu Ala Ala Leu Arg Glu
    290                 295                 300

Glu Glu Glu Gly Val
305

<210> SEQ ID NO 22
<211> LENGTH: 318
<212> TYPE: PRT
<213> ORGANISM: Homo sapiens

<400> SEQUENCE: 22

Met Leu Leu Gly Gln Lys Ser Gln Arg Tyr Lys Ala Glu Glu Gly Leu
 1               5                  10                  15

Gln Ala Gln Gly Glu Ala Pro Gly Leu Met Asp Val Gln Ile Pro Thr
            20                  25                  30

Ala Glu Glu Gln Lys Ala Ala Ser Ser Ser Thr Leu Ile Met Gly
            35                  40                  45

Thr Leu Glu Glu Val Thr Asp Ser Gly Ser Pro Ser Pro Gln Ser
        50                  55                  60

Pro Glu Gly Ala Ser Ser Ser Leu Thr Val Thr Asp Ser Thr Leu Trp
 65                  70                  75                  80
```

```
Ser Gln Ser Asp Glu Gly Ser Ser Ser Asn Glu Glu Gly Pro Ser
            85                  90                  95

Thr Ser Pro Asp Pro Ala His Leu Glu Ser Leu Phe Arg Glu Ala Leu
        100                 105                 110

Asp Glu Lys Val Ala Glu Leu Val Arg Phe Leu Leu Arg Lys Tyr Gln
        115                 120                 125

Ile Lys Glu Pro Val Thr Lys Ala Glu Met Leu Glu Ser Val Ile Lys
        130                 135                 140

Asn Tyr Lys Asn His Phe Pro Asp Ile Phe Lys Ala Ser Glu Cys
145                 150                 155                 160

Met Gln Val Ile Phe Gly Ile Asp Val Lys Glu Val Asp Pro Ala Gly
            165                 170                 175

His Ser Tyr Ile Leu Val Thr Cys Leu Gly Leu Ser Tyr Asp Gly Leu
            180                 185                 190

Leu Gly Asp Asp Gln Ser Thr Pro Lys Thr Gly Leu Leu Ile Ile Val
        195                 200                 205

Leu Gly Met Ile Leu Met Glu Gly Ser Arg Ala Pro Glu Glu Ala Ile
        210                 215                 220

Trp Glu Ala Leu Ser Val Met Gly Leu Tyr Asp Gly Arg Glu His Ser
225                 230                 235                 240

Val Tyr Trp Lys Leu Arg Lys Leu Leu Thr Gln Glu Trp Val Gln Glu
            245                 250                 255

Asn Tyr Leu Glu Tyr Arg Gln Ala Pro Gly Ser Asp Pro Val Arg Tyr
            260                 265                 270

Glu Phe Leu Trp Gly Pro Arg Ala Leu Ala Glu Thr Ser Tyr Val Lys
            275                 280                 285

Val Leu Glu His Val Val Arg Val Asn Ala Arg Val Arg Ile Ser Tyr
        290                 295                 300

Pro Ser Leu His Glu Glu Ala Leu Gly Glu Glu Lys Gly Val
305                 310                 315

<210> SEQ ID NO 23
<211> LENGTH: 346
<212> TYPE: PRT
<213> ORGANISM: Homo sapiens

<400> SEQUENCE: 23

Met Pro Arg Gly Gln Lys Ser Lys Leu Arg Ala Arg Glu Lys Arg Gln
1               5                   10                  15

Arg Thr Arg Gly Gln Thr Gln Asp Leu Lys Val Gly Gln Pro Thr Ala
            20                  25                  30

Ala Glu Lys Glu Glu Ser Pro Ser Ser Ser Ser Val Leu Arg Asp
        35                  40                  45

Thr Ala Ser Ser Ser Leu Ala Phe Gly Ile Pro Gln Glu Pro Gln Arg
    50                  55                  60

Glu Pro Pro Thr Thr Ser Ala Ala Ala Met Ser Cys Thr Gly Ser
65                  70                  75                  80

Asp Lys Gly Asp Glu Ser Gln Asp Glu Glu Asn Ala Ser Ser Gln
            85                  90                  95

Ala Ser Thr Ser Thr Glu Arg Ser Leu Lys Asp Ser Leu Thr Arg Lys
        100                 105                 110

Thr Lys Met Leu Val Gln Phe Leu Leu Tyr Lys Tyr Lys Met Lys Glu
        115                 120                 125

Pro Thr Thr Lys Ala Glu Met Leu Lys Ile Ile Ser Lys Lys Tyr Lys
        130                 135                 140
```

```
Glu His Phe Pro Glu Ile Phe Arg Lys Val Ser Gln Arg Thr Glu Leu
145                 150                 155                 160

Val Phe Gly Leu Ala Leu Lys Glu Val Asn Pro Thr Thr His Ser Tyr
                165                 170                 175

Ile Leu Val Ser Met Leu Gly Pro Asn Asp Gly Asn Gln Ser Ser Ala
                180                 185                 190

Trp Thr Leu Pro Arg Asn Gly Leu Leu Met Pro Leu Leu Ser Val Ile
                195                 200                 205

Phe Leu Asn Gly Asn Cys Ala Arg Glu Glu Ile Trp Glu Phe Leu
    210                 215                 220

Asn Met Leu Gly Ile Tyr Asp Gly Lys Arg His Leu Ile Phe Gly Glu
225                 230                 235                 240

Pro Arg Lys Leu Ile Thr Gln Asp Leu Val Gln Glu Lys Tyr Leu Glu
                245                 250                 255

Tyr Gln Gln Val Pro Asn Ser Asp Pro Pro Arg Tyr Gln Phe Leu Trp
                260                 265                 270

Gly Pro Arg Ala His Ala Glu Thr Ser Lys Met Lys Val Leu Glu Phe
                275                 280                 285

Leu Ala Lys Val Asn Asp Thr Thr Pro Asn Asn Phe Pro Leu Leu Tyr
                290                 295                 300

Glu Glu Ala Leu Arg Asp Glu Glu Arg Ala Gly Ala Arg Pro Arg
305                 310                 315                 320

Val Ala Ala Arg Arg Gly Thr Thr Ala Met Thr Ser Ala Tyr Ser Arg
                325                 330                 335

Ala Thr Ser Ser Ser Ser Ser Gln Pro Met
                340                 345

<210> SEQ ID NO 24
<211> LENGTH: 189
<212> TYPE: PRT
<213> ORGANISM: Homo sapiens

<400> SEQUENCE: 24

Met Thr Asp Lys Thr Glu Lys Val Ala Val Asp Pro Glu Thr Val Phe
1               5                   10                  15

Lys Arg Pro Arg Glu Cys Asp Ser Pro Ser Tyr Gln Lys Arg Gln Arg
                20                  25                  30

Met Ala Leu Leu Ala Arg Lys Gln Gly Ala Gly Asp Ser Leu Ile Ala
                35                  40                  45

Gly Ser Ala Met Ser Lys Glu Lys Lys Leu Met Thr Gly His Ala Ile
50                  55                  60

Pro Pro Ser Gln Leu Asp Ser Gln Ile Asp Asp Phe Thr Gly Phe Ser
65                  70                  75                  80

Lys Asp Gly Met Met Gln Lys Pro Gly Ser Asn Ala Pro Val Gly Gly
                85                  90                  95

Asn Val Thr Ser Asn Phe Ser Gly Asp Asp Leu Glu Cys Arg Gly Ile
                100                 105                 110

Ala Ser Ser Pro Lys Ser Gln Gln Glu Ile Asn Ala Asp Ile Lys Cys
                115                 120                 125

Gln Val Val Lys Glu Ile Arg Cys Leu Gly Arg Lys Tyr Glu Lys Ile
                130                 135                 140

Phe Glu Met Leu Glu Gly Val Gln Gly Pro Thr Ala Val Arg Lys Arg
145                 150                 155                 160

Phe Phe Glu Ser Ile Ile Lys Glu Ala Ala Arg Cys Met Arg Arg Asp
```

-continued

```
                165                 170                 175
Phe Val Lys His Leu Lys Lys Lys Leu Lys Arg Met Ile
            180                 185

<210> SEQ ID NO 25
<211> LENGTH: 532
<212> TYPE: PRT
<213> ORGANISM: Homo sapiens

<400> SEQUENCE: 25

Met Gln Gly Pro Trp Val Leu Leu Leu Leu Gly Arg Leu Gln Leu
1               5                   10                  15

Ser Leu Gly Ile Ile Pro Val Glu Glu Asn Pro Asp Phe Trp Asn
            20                  25                  30

Arg Gln Ala Ala Glu Ala Leu Gly Ala Ala Lys Lys Leu Gln Pro Ala
            35                  40                  45

Gln Thr Ala Ala Lys Asn Leu Ile Ile Phe Leu Gly Asp Gly Met Gly
        50                  55                  60

Val Ser Thr Val Thr Ala Ala Arg Ile Leu Lys Gly Gln Lys Lys Asp
65                  70                  75                  80

Lys Leu Gly Pro Glu Thr Phe Leu Ala Met Asp Arg Phe Pro Tyr Val
                85                  90                  95

Ala Leu Ser Lys Thr Tyr Ser Val Asp Lys His Val Pro Asp Ser Gly
            100                 105                 110

Ala Thr Ala Thr Ala Tyr Leu Cys Gly Val Lys Gly Asn Phe Gln Thr
        115                 120                 125

Ile Gly Leu Ser Ala Ala Ala Arg Phe Asn Gln Cys Asn Thr Thr Arg
        130                 135                 140

Gly Asn Glu Val Ile Ser Val Met Asn Arg Ala Lys Lys Ala Gly Lys
145                 150                 155                 160

Ser Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190

Val Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Gly Arg Lys
        210                 215                 220

Tyr Met Phe Pro Met Gly Thr Pro Asp Pro Glu Tyr Pro Asp Asp Tyr
225                 230                 235                 240

Ser Gln Gly Gly Thr Arg Leu Asp Gly Lys Asn Leu Val Gln Glu Trp
                245                 250                 255

Leu Ala Lys His Gln Gly Ala Arg Tyr Val Trp Asn Arg Thr Glu Leu
            260                 265                 270

Leu Gln Ala Ser Leu Asp Pro Ser Val Thr His Leu Met Gly Leu Phe
        275                 280                 285

Glu Pro Gly Asp Met Lys Tyr Glu Ile His Arg Asp Ser Thr Leu Asp
        290                 295                 300

Pro Ser Leu Met Glu Met Thr Glu Ala Ala Leu Leu Leu Leu Ser Arg
305                 310                 315                 320

Asn Pro Arg Gly Phe Phe Leu Phe Val Glu Gly Gly Arg Ile Asp His
                325                 330                 335

Gly His His Glu Ser Arg Ala Tyr Arg Ala Leu Thr Glu Thr Ile Met
            340                 345                 350
```

```
Phe Asp Asp Ala Ile Glu Arg Ala Gly Gln Leu Thr Ser Glu Glu Asp
            355                 360                 365

Thr Leu Ser Leu Val Thr Ala Asp His Ser His Val Phe Ser Phe Gly
    370                 375                 380

Gly Tyr Pro Leu Arg Gly Ser Ser Ile Phe Gly Leu Ala Pro Gly Lys
385                 390                 395                 400

Ala Arg Asp Arg Lys Ala Tyr Thr Val Leu Leu Tyr Gly Asn Gly Pro
                405                 410                 415

Gly Tyr Val Leu Lys Asp Gly Ala Arg Pro Asp Val Thr Glu Ser Glu
            420                 425                 430

Ser Gly Ser Pro Glu Tyr Arg Gln Gln Ser Ala Val Pro Leu Asp Gly
            435                 440                 445

Glu Thr His Ala Gly Glu Asp Val Ala Val Phe Ala Arg Gly Pro Gln
            450                 455                 460

Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
                485                 490                 495

Pro Arg Ala Gly Thr Thr Asp Ala Ala His Pro Gly Pro Ser Val Val
                500                 505                 510

Pro Ala Leu Leu Pro Leu Leu Ala Gly Thr Leu Leu Leu Leu Gly Thr
            515                 520                 525

Ala Thr Ala Pro
            530

<210> SEQ ID NO 26
<211> LENGTH: 471
<212> TYPE: PRT
<213> ORGANISM: Homo sapiens

<400> SEQUENCE: 26

Met His Pro Gly Val Leu Ala Ala Phe Leu Phe Leu Ser Trp Thr His
1               5                   10                  15

Cys Arg Ala Leu Pro Leu Pro Ser Gly Gly Asp Glu Asp Asp Leu Ser
            20                  25                  30

Glu Glu Asp Leu Gln Phe Ala Glu Arg Tyr Leu Arg Ser Tyr Tyr His
        35                  40                  45

Pro Thr Asn Leu Ala Gly Ile Leu Lys Glu Asn Ala Ala Ser Ser Met
    50                  55                  60

Thr Glu Arg Leu Arg Glu Met Gln Ser Phe Phe Gly Leu Glu Val Thr
65                  70                  75                  80

Gly Lys Leu Asp Asp Asn Thr Leu Asp Val Met Lys Lys Pro Arg Cys
                85                  90                  95

Gly Val Pro Asp Val Gly Glu Tyr Asn Val Phe Pro Arg Thr Leu Lys
            100                 105                 110

Trp Ser Lys Met Asn Leu Thr Tyr Arg Ile Val Asn Tyr Thr Pro Asp
        115                 120                 125

Met Thr His Ser Glu Val Glu Lys Ala Phe Lys Lys Ala Phe Lys Val
    130                 135                 140

Trp Ser Asp Val Thr Pro Leu Asn Phe Thr Arg Leu His Asp Gly Ile
145                 150                 155                 160

Ala Asp Ile Met Ile Ser Phe Gly Ile Lys Glu His Gly Asp Phe Tyr
                165                 170                 175

Pro Phe Asp Gly Pro Ser Gly Leu Leu Ala His Ala Phe Pro Pro Gly
            180                 185                 190
```

```
Pro Asn Tyr Gly Gly Asp Ala His Phe Asp Asp Glu Thr Trp Thr
            195                 200                 205

Ser Ser Ser Lys Gly Tyr Asn Leu Phe Leu Val Ala Ala His Glu Phe
210                 215                 220

Gly His Ser Leu Gly Leu Asp His Ser Lys Asp Pro Gly Ala Leu Met
225                 230                 235                 240

Phe Pro Ile Tyr Thr Tyr Thr Gly Lys Ser His Phe Met Leu Pro Asp
                245                 250                 255

Asp Asp Val Gln Gly Ile Gln Ser Leu Tyr Gly Pro Gly Asp Glu Asp
                260                 265                 270

Pro Asn Pro Lys His Pro Lys Thr Pro Asp Lys Cys Asp Pro Ser Leu
            275                 280                 285

Ser Leu Asp Ala Ile Thr Ser Leu Arg Gly Glu Thr Met Ile Phe Lys
290                 295                 300

Asp Arg Phe Phe Trp Arg Leu His Pro Gln Gln Val Asp Ala Glu Leu
305                 310                 315                 320

Phe Leu Thr Lys Ser Phe Trp Pro Glu Leu Pro Asn Arg Ile Asp Ala
                325                 330                 335

Ala Tyr Glu His Pro Ser His Asp Leu Ile Phe Ile Phe Arg Gly Arg
                340                 345                 350

Lys Phe Trp Ala Leu Asn Gly Tyr Asp Ile Leu Glu Gly Tyr Pro Lys
            355                 360                 365

Lys Ile Ser Glu Leu Gly Leu Pro Lys Glu Val Lys Lys Ile Ser Ala
370                 375                 380

Ala Val His Phe Glu Asp Thr Gly Lys Thr Leu Leu Phe Ser Gly Asn
385                 390                 395                 400

Gln Val Trp Arg Tyr Asp Asp Thr Asn His Ile Met Asp Lys Asp Tyr
                405                 410                 415

Pro Arg Leu Ile Glu Glu Asp Phe Pro Gly Ile Gly Asp Lys Val Asp
            420                 425                 430

Ala Val Tyr Glu Lys Asn Gly Tyr Ile Tyr Phe Phe Asn Gly Pro Ile
            435                 440                 445

Gln Phe Glu Tyr Ser Ile Trp Ser Asn Arg Ile Val Arg Val Met Pro
    450                 455                 460

Ala Asn Ser Ile Leu Trp Cys
465                 470

<210> SEQ ID NO 27
<211> LENGTH: 180
<212> TYPE: PRT
<213> ORGANISM: Homo sapiens

<400> SEQUENCE: 27

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
```

```
              85                  90                  95
Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
            115                 120                 125

Ser Gly Asn Ile Leu Thr Ile Arg Leu Thr Ala Ala Asp His Arg Gln
            130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 28
<211> LENGTH: 552
<212> TYPE: PRT
<213> ORGANISM: Homo sapiens

<400> SEQUENCE: 28

Met Ser Pro Leu Trp Trp Gly Phe Leu Leu Ser Cys Leu Gly Cys Lys
1               5                   10                  15

Ile Leu Pro Gly Ala Gln Gly Gln Phe Pro Arg Val Cys Met Thr Val
            20                  25                  30

Asp Ser Leu Val Asn Lys Glu Cys Cys Pro Arg Leu Gly Ala Glu Ser
            35                  40                  45

Ala Asn Val Cys Gly Ser Gln Gly Arg Gly Gln Cys Thr Glu Val
            50                  55                  60

Arg Ala Asp Thr Arg Pro Trp Ser Gly Pro Tyr Ile Leu Arg Asn Gln
65                  70                  75                  80

Asp Asp Arg Glu Leu Trp Pro Arg Lys Phe Phe His Arg Thr Cys Lys
                85                  90                  95

Cys Thr Gly Asn Phe Ala Gly Tyr Asn Cys Gly Asp Cys Lys Phe Gly
            100                 105                 110

Trp Thr Gly Pro Asn Cys Glu Arg Lys Lys Pro Val Ile Arg Gln
            115                 120                 125

Asn Ile His Ser Leu Ser Pro Gln Glu Arg Glu Gln Phe Leu Gly Ala
            130                 135                 140

Leu Asp Leu Ala Lys Lys Arg Val His Pro Asp Tyr Val Ile Thr Thr
145                 150                 155                 160

Gln His Trp Leu Gly Leu Leu Gly Pro Asn Gly Thr Gln Pro Gln Phe
                165                 170                 175

Ala Asn Cys Ser Val Tyr Asp Phe Phe Val Trp Leu His Tyr Tyr Ser
            180                 185                 190

Val Arg Asp Thr Leu Leu Gly Pro Gly Arg Pro Tyr Arg Ala Ile Asp
            195                 200                 205

Phe Ser His Gln Gly Pro Ala Phe Val Thr Trp His Arg Tyr His Leu
            210                 215                 220

Leu Cys Leu Glu Arg Asp Leu Gln Arg Leu Ile Gly Asn Glu Ser Phe
225                 230                 235                 240

Ala Leu Pro Tyr Trp Asn Phe Ala Thr Gly Arg Asn Glu Cys Asp Val
                245                 250                 255

Cys Thr Asp Gln Leu Phe Gly Ala Ala Arg Pro Asp Asp Pro Thr Leu
            260                 265                 270
```

```
Ile Ser Arg Asn Ser Arg Phe Ser Trp Glu Thr Val Cys Asp Ser
            275                 280                 285

Leu Asp Asp Tyr Asn His Leu Val Thr Leu Cys Asn Gly Thr Tyr Glu
290                 295                 300

Gly Leu Leu Arg Arg Asn Gln Met Gly Arg Asn Ser Met Lys Leu Pro
305                 310                 315                 320

Thr Leu Lys Asp Ile Arg Asp Cys Leu Ser Leu Gln Lys Phe Asp Asn
                325                 330                 335

Pro Pro Phe Phe Gln Asn Ser Thr Phe Ser Phe Arg Asn Ala Leu Glu
                340                 345                 350

Gly Phe Asp Lys Ala Asp Gly Thr Leu Asp Ser Gln Val Met Ser Leu
                355                 360                 365

His Asn Leu Val His Ser Phe Leu Asn Gly Thr Asn Ala Leu Pro His
            370                 375                 380

Ser Ala Ala Asn Asp Pro Ile Phe Val Val Ile Ser Asn Arg Leu Leu
385                 390                 395                 400

Tyr Asn Ala Thr Thr Asn Ile Leu Glu His Val Arg Lys Glu Lys Ala
                405                 410                 415

Thr Lys Glu Leu Pro Ser Leu His Val Leu Val Leu His Ser Phe Thr
                420                 425                 430

Asp Ala Ile Phe Asp Glu Trp Met Lys Arg Phe Asn Pro Pro Ala Asp
            435                 440                 445

Ala Trp Pro Gln Glu Leu Ala Pro Ile Gly His Asn Arg Met Tyr Asn
            450                 455                 460

Met Val Pro Phe Phe Pro Pro Val Thr Asn Glu Glu Leu Phe Leu Thr
465                 470                 475                 480

Ser Asp Gln Leu Gly Tyr Ser Tyr Ala Ile Asp Leu Pro Val Ser Val
                485                 490                 495

Glu Glu Thr Pro Gly Trp Pro Thr Thr Leu Leu Val Val Met Gly Thr
                500                 505                 510

Leu Val Ala Leu Val Gly Leu Phe Val Leu Leu Ala Phe Leu Gln Tyr
            515                 520                 525

Arg Arg Leu Arg Lys Gly Tyr Thr Pro Leu Met Glu Thr His Leu Ser
530                 535                 540

Ser Lys Arg Tyr Thr Glu Glu Ala
545                 550

<210> SEQ ID NO 29
<211> LENGTH: 220
<212> TYPE: PRT
<213> ORGANISM: Homo sapiens

<400> SEQUENCE: 29

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
                20                  25                  30

Thr Ala Phe Ile Gly Asn Ser Ile Val Val Ala Gln Val Val Trp Glu
            35                  40                  45

Gly Leu Trp Met Ser Cys Val Gln Ser Thr Gly Gln Met Gln Cys
            50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95
```

```
Val Tyr Leu Ala Gly Ala Lys Cys Thr Thr Cys Val Glu Glu Lys Asp
                100                 105                 110

Ser Lys Ala Arg Leu Val Leu Thr Ser Gly Ile Val Phe Val Ile Ser
                115                 120                 125

Gly Val Leu Thr Leu Ile Pro Val Cys Trp Thr Ala His Ala Ile Ile
    130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                    165                 170                 175

Gly Gly Gly Leu Leu Cys Cys Thr Cys Pro Ser Gly Ser Gln Gly
                180                 185                 190

Pro Ser His Tyr Met Ala Arg Tyr Ser Thr Ser Ala Pro Ala Ile Ser
                195                 200                 205

Arg Gly Pro Ser Glu Tyr Pro Thr Lys Asn Tyr Val
    210                 215                 220

<210> SEQ ID NO 30
<211> LENGTH: 118
<212> TYPE: PRT
<213> ORGANISM: Homo sapiens

<400> SEQUENCE: 30

Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
                20                  25                  30

Leu Thr Val Ile Leu Gly Val Leu Leu Leu Ile Gly Cys Trp Tyr Cys
            35                  40                  45

Arg Arg Arg Asn Gly Tyr Arg Ala Leu Met Asp Lys Ser Leu His Val
50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
                100                 105                 110

Pro Pro Pro Tyr Ser Pro
            115

<210> SEQ ID NO 31
<211> LENGTH: 609
<212> TYPE: PRT
<213> ORGANISM: Homo sapiens

<400> SEQUENCE: 31

Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
                20                  25                  30

Asp Ser Tyr Gln Cys Thr Ala Glu Ile Ser Leu Ala Asp Leu Ala Thr
            35                  40                  45

Ile Phe Phe Ala Gln Phe Val Gln Glu Ala Thr Tyr Lys Glu Val Ser
        50                  55                  60

Lys Met Val Lys Asp Ala Leu Thr Ala Ile Glu Lys Pro Thr Gly Asp
65                  70                  75                  80
```

-continued

```
Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
            115                 120                 125

Lys Lys Pro Thr Pro Ala Ser Ile Pro Leu Phe Gln Val Pro Glu Pro
130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
            195                 200                 205

Val Thr Lys Glu Leu Arg Glu Ser Ser Leu Leu Asn Gln His Ala Cys
            210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
            260                 265                 270

Asp Val Leu Asp Cys Leu Gln Asp Gly Glu Lys Ile Met Ser Tyr Ile
            275                 280                 285

Cys Ser Gln Gln Asp Thr Leu Ser Asn Lys Ile Thr Glu Cys Cys Lys
            290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
            340                 345                 350

Ser Phe Val His Glu Tyr Ser Arg Arg His Pro Gln Leu Ala Val Ser
            355                 360                 365

Val Ile Leu Arg Val Ala Lys Gly Tyr Gln Glu Leu Leu Glu Lys Cys
            370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
            420                 425                 430

Val Ala Tyr Thr Lys Lys Ala Pro Gln Leu Thr Ser Ser Glu Leu Met
            435                 440                 445

Ala Ile Thr Arg Lys Met Ala Ala Thr Ala Thr Cys Cys Gln Leu
            450                 455                 460

Ser Glu Asp Lys Leu Leu Ala Cys Gly Glu Gly Ala Ala Asp Ile Ile
465                 470                 475                 480

Ile Gly His Leu Cys Ile Arg His Glu Met Thr Pro Val Asn Pro Gly
                485                 490                 495
```

```
Val Gly Gln Cys Cys Thr Ser Ser Tyr Ala Asn Arg Arg Pro Cys Phe
            500                 505                 510

Ser Ser Leu Val Val Asp Glu Thr Tyr Val Pro Pro Ala Phe Ser Asp
        515                 520                 525

Asp Lys Phe Ile Phe His Lys Asp Leu Cys Gln Ala Gln Gly Val Ala
    530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
                565                 570                 575

Gly Leu Leu Glu Lys Cys Cys Gln Gly Gln Glu Gln Glu Val Cys Phe
            580                 585                 590

Ala Glu Glu Gly Gln Lys Leu Ile Ser Lys Thr Arg Ala Ala Leu Gly
            595                 600                 605

Val

<210> SEQ ID NO 32
<211> LENGTH: 224
<212> TYPE: PRT
<213> ORGANISM: Homo sapiens

<400> SEQUENCE: 32

Met Val Ala Ala Val Leu Leu Gly Leu Ser Trp Leu Cys Ser Pro Leu
1               5                   10                  15

Gly Ala Leu Val Leu Asp Phe Asn Asn Ile Arg Ser Ser Ala Asp Leu
                20                  25                  30

His Gly Ala Arg Lys Gly Ser Gln Cys Leu Ser Asp Thr Asp Cys Asn
            35                  40                  45

Thr Arg Lys Phe Cys Leu Gln Pro Arg Asp Glu Lys Pro Phe Cys Ala
    50                  55                  60

Thr Cys Arg Gly Leu Arg Arg Arg Cys Gln Arg Asp Ala Met Cys Cys
65                  70                  75                  80

Pro Gly Thr Leu Cys Val Asn Asp Val Cys Thr Thr Met Glu Asp Ala
                85                  90                  95

Thr Pro Ile Leu Glu Arg Gln Leu Asp Glu Gln Asp Gly Thr His Ala
                100                 105                 110

Glu Gly Thr Thr Gly His Pro Val Gln Glu Asn Gln Pro Lys Arg Lys
            115                 120                 125

Pro Ser Ile Lys Lys Ser Gln Gly Arg Lys Gly Gln Glu Gly Glu Ser
    130                 135                 140

Cys Leu Arg Thr Phe Asp Cys Gly Pro Gly Leu Cys Cys Ala Arg His
145                 150                 155                 160

Phe Trp Thr Lys Ile Cys Lys Pro Val Leu Leu Glu Gly Gln Val Cys
                165                 170                 175

Ser Arg Arg Gly His Lys Asp Thr Ala Gln Ala Pro Glu Ile Phe Gln
            180                 185                 190

Arg Cys Asp Cys Gly Pro Gly Leu Leu Cys Arg Ser Gln Leu Thr Ser
        195                 200                 205

Asn Arg Gln His Ala Arg Leu Arg Val Cys Gln Lys Ile Glu Lys Leu
    210                 215                 220

<210> SEQ ID NO 33
<211> LENGTH: 193
<212> TYPE: PRT
<213> ORGANISM: Homo sapiens
```

```
<400> SEQUENCE: 33

Met Asp Gly Gly Thr Leu Pro Arg Ser Ala Pro Pro Ala Pro Pro Val
1               5                   10                  15

Pro Val Gly Cys Ala Ala Arg Arg Arg Pro Ala Ser Pro Glu Leu Leu
                20                  25                  30

Arg Cys Ser Arg Arg Arg Arg Pro Ala Thr Ala Glu Thr Gly Gly Gly
            35                  40                  45

Ala Ala Ala Val Ala Arg Arg Asn Glu Arg Glu Arg Asn Arg Val Lys
            50                  55                  60

Leu Val Asn Leu Gly Phe Gln Ala Leu Arg Gln His Val Pro His Gly
65                  70                  75                  80

Gly Ala Ser Lys Lys Leu Ser Lys Val Glu Thr Leu Arg Ser Ala Val
                85                  90                  95

Glu Tyr Ile Arg Ala Leu Gln Arg Leu Leu Ala Glu His Asp Ala Val
            100                 105                 110

Arg Asn Ala Leu Ala Gly Gly Leu Arg Pro Gln Ala Val Arg Pro Ser
            115                 120                 125

Ala Pro Arg Gly Pro Gly Thr Thr Pro Val Ala Ala Ser Pro Ser
            130                 135                 140

Arg Ala Ser Ser Ser Pro Gly Arg Gly Gly Ser Ser Glu Pro Gly Ser
145                 150                 155                 160

Pro Arg Ser Ala Tyr Ser Ser Asp Asp Ser Gly Cys Glu Gly Ala Leu
                165                 170                 175

Ser Pro Ala Glu Arg Glu Leu Leu Asp Phe Ser Ser Trp Leu Gly Gly
            180                 185                 190

Tyr

<210> SEQ ID NO 34
<211> LENGTH: 139
<212> TYPE: PRT
<213> ORGANISM: Homo sapiens

<400> SEQUENCE: 34

Met Ser Trp Arg Gly Arg Ser Thr Tyr Tyr Trp Pro Arg Pro Arg Arg
1               5                   10                  15

Tyr Val Gln Pro Pro Glu Met Ile Gly Pro Met Arg Pro Glu Gln Phe
                20                  25                  30

Ser Asp Glu Val Glu Pro Ala Thr Pro Glu Glu Gly Glu Pro Ala Thr
            35                  40                  45

Gln Arg Gln Asp Pro Ala Ala Ala Gln Glu Gly Glu Asp Glu Gly Ala
            50                  55                  60

Ser Ala Gly Gln Gly Pro Lys Pro Glu Ala Asp Ser Gln Glu Gln Gly
65                  70                  75                  80

His Pro Gln Thr Gly Cys Glu Cys Glu Asp Gly Pro Asp Gly Gln Glu
                85                  90                  95

Met Asp Pro Pro Asn Pro Glu Glu Val Lys Thr Pro Glu Glu Glu Met
            100                 105                 110

Arg Ser His Tyr Val Ala Gln Thr Gly Ile Leu Trp Leu Leu Met Asn
            115                 120                 125

Asn Cys Phe Leu Asn Leu Ser Pro Arg Lys Pro
            130                 135

<210> SEQ ID NO 35
<211> LENGTH: 116
<212> TYPE: PRT
```

<213> ORGANISM: Homo sapiens

<400> SEQUENCE: 35

Met Ser Trp Arg Gly Arg Ser Thr Tyr Arg Ser Arg Pro Arg Leu Tyr
1               5                   10                  15

Val Glu Pro Pro Glu Met Ile Gly Pro Met Leu Pro Glu Gln Phe Ser
            20                  25                  30

Asp Glu Val Glu Pro Ala Thr Pro Glu Glu Gly Glu Pro Ala Thr Gln
        35                  40                  45

Arg Gln Asp Pro Ala Ala Gln Glu Gly Glu Asp Glu Gly Ala Ser
    50                  55                  60

Ala Gly Gln Gly Pro Lys Pro Glu Ala Asp Ser Gln Glu Gln Val His
65                  70                  75                  80

Pro Lys Thr Gly Cys Glu Cys Gly Asp Gly Pro Asp Gly Gln Glu Met
                85                  90                  95

Gly Leu Pro Asn Pro Glu Glu Val Lys Arg Pro Glu Glu Gly Glu Lys
            100                 105                 110

Gln Ser Gln Cys
        115

<210> SEQ ID NO 36
<211> LENGTH: 530
<212> TYPE: PRT
<213> ORGANISM: Homo sapiens

<400> SEQUENCE: 36

Met Gly Ser Asn Ser Gly Gln Ala Gly Arg His Ile Tyr Lys Ser Leu
1               5                   10                  15

Ala Asp Asp Gly Pro Phe Asp Ser Val Glu Pro Pro Lys Arg Pro Thr
            20                  25                  30

Ser Arg Leu Ile Met His Ser Met Ala Met Phe Gly Arg Glu Phe Cys
        35                  40                  45

Tyr Ala Val Glu Ala Ala Tyr Val Thr Pro Val Leu Leu Ser Val Gly
    50                  55                  60

Leu Pro Ser Ser Leu Tyr Ser Ile Val Trp Phe Leu Ser Pro Ile Leu
65                  70                  75                  80

Gly Phe Leu Leu Gln Pro Val Val Gly Ser Ala Ser Asp His Cys Arg
                85                  90                  95

Ser Arg Trp Gly Arg Arg Arg Pro Tyr Ile Leu Thr Leu Gly Val Met
            100                 105                 110

Met Leu Val Gly Met Ala Leu Tyr Leu Asn Gly Ala Thr Val Val Ala
        115                 120                 125

Ala Leu Ile Ala Asn Pro Arg Arg Lys Leu Val Trp Ala Ile Ser Val
    130                 135                 140

Thr Met Ile Gly Val Val Leu Phe Asp Phe Ala Ala Asp Phe Ile Asp
145                 150                 155                 160

Gly Pro Ile Lys Ala Tyr Leu Phe Asp Val Cys Ser His Gln Asp Lys
                165                 170                 175

Glu Lys Gly Leu His Tyr His Ala Leu Phe Thr Gly Phe Gly Ala
            180                 185                 190

Leu Gly Tyr Leu Leu Gly Ala Ile Asp Trp Ala His Leu Glu Leu Gly
        195                 200                 205

Arg Leu Leu Gly Thr Glu Phe Gln Val Met Phe Phe Ser Ala Leu
    210                 215                 220

Val Leu Thr Leu Cys Phe Thr Val His Leu Cys Ser Ile Ser Glu Ala

```
            225                 230                 235                 240
        Pro Leu Thr Glu Val Ala Lys Gly Ile Pro Pro Gln Thr Pro Gln
                        245                 250                 255

Asp Pro Pro Leu Ser Ser Asp Gly Met Tyr Glu Tyr Gly Ser Ile Glu
                        260                 265                 270

Lys Val Lys Asn Gly Tyr Val Asn Pro Glu Leu Ala Met Gln Gly Ala
                        275                 280                 285

Lys Asn Lys Asn His Ala Glu Gln Thr Arg Arg Ala Met Thr Leu Lys
                        290                 295                 300

Ser Leu Leu Arg Ala Leu Val Asn Met Pro Pro His Tyr Arg Tyr Leu
        305                 310                 315                 320

Cys Ile Ser His Leu Ile Gly Trp Thr Ala Phe Leu Ser Asn Met Leu
                        325                 330                 335

Phe Phe Thr Asp Phe Met Gly Gln Ile Val Tyr Arg Gly Asp Pro Tyr
                        340                 345                 350

Ser Ala His Asn Ser Thr Glu Phe Leu Ile Tyr Glu Arg Gly Val Glu
                        355                 360                 365

Val Gly Cys Trp Gly Phe Cys Ile Asn Ser Val Phe Ser Ser Leu Tyr
                        370                 375                 380

Ser Tyr Phe Gln Lys Val Leu Val Ser Tyr Ile Gly Leu Lys Gly Leu
        385                 390                 395                 400

Tyr Phe Thr Gly Tyr Leu Leu Phe Gly Leu Gly Thr Gly Phe Ile Gly
                        405                 410                 415

Leu Phe Pro Asn Val Tyr Ser Thr Leu Val Leu Cys Ser Leu Phe Gly
                        420                 425                 430

Val Met Ser Ser Thr Leu Tyr Thr Val Pro Phe Asn Leu Ile Thr Glu
                        435                 440                 445

Tyr His Arg Glu Glu Lys Glu Arg Gln Gln Ala Pro Gly Gly Asp
                        450                 455                 460

Pro Asp Asn Ser Val Arg Gly Lys Gly Met Asp Cys Ala Thr Leu Thr
        465                 470                 475                 480

Cys Met Val Gln Leu Ala Gln Ile Leu Val Gly Gly Leu Gly Phe
                        485                 490                 495

Leu Val Asn Thr Ala Gly Thr Val Val Val Val Ile Thr Ala Ser
                        500                 505                 510

Ala Val Ala Leu Ile Gly Cys Cys Phe Val Ala Leu Phe Val Arg Tyr
                        515                 520                 525

Val Asp
            530

<210> SEQ ID NO 37
<211> LENGTH: 130
<212> TYPE: PRT
<213> ORGANISM: Homo sapiens

<400> SEQUENCE: 37

Met Gln Ala Pro Trp Ala Gly Asn Arg Gly Trp Ala Gly Thr Arg Glu
1               5                   10                  15

Glu Val Arg Asp Met Ser Glu His Val Thr Arg Ser Gln Ser Ser Glu
                20                  25                  30

Arg Gly Asn Asp Gln Glu Ser Ser Gln Pro Val Gly Pro Val Ile Val
                35                  40                  45

Gln Gln Pro Thr Glu Glu Lys Arg Gln Glu Glu Pro Pro Thr Asp
            50                  55                  60
```

-continued

```
Asn Gln Gly Ile Ala Pro Ser Gly Glu Ile Lys Asn Glu Gly Ala Pro
 65                  70                  75                  80

Ala Val Gln Gly Thr Asp Val Glu Ala Phe Gln Gln Glu Leu Ala Leu
                 85                  90                  95

Leu Lys Ile Glu Asp Ala Pro Gly Asp Gly Pro Asp Val Arg Glu Gly
            100                 105                 110

Thr Leu Pro Thr Phe Asp Pro Thr Lys Val Leu Glu Ala Gly Glu Gly
        115                 120                 125

Gln Leu
    130

<210> SEQ ID NO 38
<211> LENGTH: 111
<212> TYPE: PRT
<213> ORGANISM: Homo sapiens

<400> SEQUENCE: 38

Met Ser Glu Leu Leu Arg Ala Arg Ser Gln Ser Ser Glu Arg Gly Asn
  1               5                  10                  15

Asp Gln Glu Ser Ser Gln Pro Val Gly Ser Val Ile Val Gln Glu Pro
             20                  25                  30

Thr Glu Glu Lys Arg Gln Glu Glu Pro Pro Thr Asp Asn Gln Gly
         35                  40                  45

Ile Ala Pro Ser Gly Glu Ile Glu Asn Gln Ala Val Pro Ala Phe Gln
     50                  55                  60

Gly Pro Asp Met Glu Ala Phe Gln Gln Glu Leu Ala Leu Leu Lys Ile
 65                  70                  75                  80

Glu Asp Glu Pro Gly Asp Gly Pro Asp Val Arg Glu Gly Ile Met Pro
                 85                  90                  95

Thr Phe Asp Leu Thr Lys Val Leu Glu Ala Gly Asp Ala Gln Pro
            100                 105                 110

<210> SEQ ID NO 39
<211> LENGTH: 668
<212> TYPE: PRT
<213> ORGANISM: Homo sapiens

<400> SEQUENCE: 39

Met Asp Leu Val Leu Lys Arg Cys Leu Leu His Leu Ala Val Ile Gly
  1               5                  10                  15

Ala Leu Leu Ala Val Gly Ala Thr Lys Val Pro Arg Asn Gln Asp Trp
             20                  25                  30

Leu Gly Val Ser Arg Gln Leu Arg Thr Lys Ala Trp Asn Arg Gln Leu
         35                  40                  45

Tyr Pro Glu Trp Thr Glu Ala Gln Arg Leu Asp Cys Trp Arg Gly Gly
     50                  55                  60

Gln Val Ser Leu Lys Val Ser Asn Asp Gly Pro Thr Leu Ile Gly Ala
 65                  70                  75                  80

Asn Ala Ser Phe Ser Ile Ala Leu Asn Phe Pro Gly Ser Gln Lys Val
                 85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140
```

-continued

```
Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
            165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ala Phe Thr
        195                 200                 205

Ile Thr Asp Gln Val Pro Phe Ser Val Ser Val Gln Leu Arg Ala
    210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
            245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Ala
            275                 280                 285

Gln Val Val Leu Gln Ala Ala Ile Pro Leu Thr Ser Cys Gly Ser Ser
    290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
            325                 330                 335

Pro Gly Gln Ala Pro Thr Ala Glu Pro Ser Gly Thr Thr Ser Val Gln
        340                 345                 350

Val Pro Thr Thr Glu Val Ile Ser Thr Ala Pro Val Gln Met Pro Thr
        355                 360                 365

Ala Glu Ser Thr Gly Met Thr Pro Glu Lys Val Pro Val Ser Glu Val
    370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
            405                 410                 415

Gln Val Thr Thr Thr Glu Trp Val Glu Thr Thr Ala Arg Glu Leu Pro
            420                 425                 430

Ile Pro Glu Pro Glu Gly Pro Asp Ala Ser Ser Ile Met Ser Thr Glu
        435                 440                 445

Ser Ile Thr Gly Ser Leu Gly Pro Leu Leu Asp Gly Thr Ala Thr Leu
    450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
            485                 490                 495

Glu Ile Leu Gln Ala Val Pro Ser Gly Glu Gly Asp Ala Phe Glu Leu
        500                 505                 510

Thr Val Ser Cys Gln Gly Gly Leu Pro Lys Glu Ala Cys Met Glu Ile
    515                 520                 525

Ser Ser Pro Gly Cys Gln Pro Ala Gln Arg Leu Cys Gln Pro Val
    530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
```

```
                        565                 570                 575
Leu Ala Val Val Ser Thr Gln Leu Ile Met Pro Val Pro Gly Ile Leu
                580                 585                 590

Leu Thr Gly Gln Glu Ala Gly Leu Gly Gln Val Pro Leu Ile Val Gly
            595                 600                 605

Ile Leu Leu Val Leu Met Ala Val Val Leu Ala Ser Leu Ile Tyr Arg
        610                 615                 620

Arg Arg Leu Met Lys Gln Asp Phe Ser Val Pro Gln Leu Pro His Ser
625                 630                 635                 640

Ser Ser His Trp Leu Arg Leu Pro Arg Ile Phe Cys Ser Cys Pro Ile
                645                 650                 655

Gly Glu Asn Ser Pro Leu Leu Ser Gly Gln Gln Val
                660                 665

<210> SEQ ID NO 40
<211> LENGTH: 158
<212> TYPE: PRT
<213> ORGANISM: Human papillomavirus type 16

<400> SEQUENCE: 40

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 41
<211> LENGTH: 98
<212> TYPE: PRT
<213> ORGANISM: Human papillomavirus type 16

<400> SEQUENCE: 41

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
```

-continued

```
                65                  70                  75                  80
Asp Leu Leu Met Gly Thr Leu Gly Ile Val Cys Pro Ile Cys Ser Gln
                    85                  90                  95
Lys Pro

<210> SEQ ID NO 42
<211> LENGTH: 429
<212> TYPE: PRT
<213> ORGANISM: Epstein-Barr virus

<400> SEQUENCE: 42

Met Ala Glu Ala Tyr Pro Gly Gly Ala His Ala Ala Leu Ala Ser Arg
1               5                   10                  15
Arg Ser Ser Phe Arg Asn Ser Leu Arg Arg Leu Arg Pro Thr Glu Lys
                    20                  25                  30
Pro Asp Thr Ser Phe Met Arg Gly Val Trp Lys Tyr Glu Ile Phe Pro
                35                  40                  45
Ser Tyr Val Arg Val Thr Asn Lys Gln Val Leu Gln Leu Asp Ala Gln
            50                  55                  60
Cys Gln Glu Leu Pro Pro Cys Pro Ser Val Gly Gln Ile Leu Ser Phe
65                  70                  75                  80
Lys Leu Pro Ser Phe Ser Phe Asn Thr Thr Thr Tyr Gly Ser Arg Tyr
                    85                  90                  95
Phe Thr Val Ala Phe Leu Phe Phe Gly Ala Glu Asp Asn Glu Val Phe
                100                 105                 110
Leu Lys Pro Phe Phe Val Met His Ser Asp Gln Asp Ile Val Leu Ser
                115                 120                 125
Val Leu Asn Pro Arg Ser Leu Phe Ile Glu Lys Gly Lys Phe Thr Trp
            130                 135                 140
Tyr Ile Val Pro Ile Arg Leu Val Lys Asn Pro Tyr Leu Tyr Leu Gln
145                 150                 155                 160
Ile Leu Pro Gly Gln Ser Asp Ile Gln Leu Thr Arg Ser Cys Thr Gln
                    165                 170                 175
Ser Gly Asp Lys Leu Asn Thr Ser Glu Pro Gln Ile Phe Leu Ser Gly
                180                 185                 190
Ser Pro Val Thr Ser Gln Asp Glu Cys Leu Pro Tyr Leu Leu Ala Gln
                195                 200                 205
His Thr Pro Pro Phe Leu Lys Ser Tyr Ala Arg Ile His Thr Phe Pro
            210                 215                 220
Gly Lys Val Cys Pro Val Asn Ala Ile Arg Arg Gly Lys Gly Tyr Val
225                 230                 235                 240
Arg Val Ser Val Asp Thr Pro Asp Leu Lys Arg Glu Gly Pro Leu Asn
                    245                 250                 255
Val Lys Val Gly Met Thr Leu Leu Asp Asp Val Ile Ile Ala Phe Arg
                260                 265                 270
Tyr Asn Pro Tyr Pro Lys Ser His Trp Arg Trp Asp Gly Glu Ser Thr
                275                 280                 285
Asp Ile Arg Tyr Phe Gly Ser Pro Val Ile Pro Pro Asn Phe Ile
            290                 295                 300
Thr Glu Leu Glu Tyr Asn Asn Thr Tyr Glu Ala Pro Leu Ser Ser Lys
305                 310                 315                 320
Ile Thr Ala Ile Val Val Ser His Ser Ser Asn Pro Val Phe Tyr Val
                    325                 330                 335
Tyr Pro Gln Glu Trp Lys Pro Gly Gln Thr Leu Lys Leu Thr Val Arg
```

```
              340                 345                 350
Asn Ile Ser Asn Asn Pro Ile Thr Ile Val Thr Gly Gln Ser Met Ala
            355                 360                 365

Gln Ala Phe Phe Ile Tyr Ala Gly Asp Pro Ser Ile Ser Thr Ile Met
        370                 375                 380

Arg Arg Tyr Ile Gln Arg Gln Gly Cys Ala Leu Thr Leu Pro Gly Asn
385                 390                 395                 400

Ile Val Val Glu Ser Ser Leu Pro Thr Phe Glu Arg Ile Asn Lys
                405                 410                 415

Thr Phe Asn Gly Asn Ile Val Ala Ser Glu Gly Thr Leu
            420                 425

<210> SEQ ID NO 43
<211> LENGTH: 1015
<212> TYPE: PRT
<213> ORGANISM: Epstein-Barr virus

<400> SEQUENCE: 43

Met Ser Gly Gly Leu Phe Tyr Asn Pro Phe Leu Arg Pro Asn Lys Gly
1               5                   10                  15

Leu Leu Lys Lys Pro Asp Lys Glu Tyr Leu Arg Leu Ile Pro Lys Cys
            20                  25                  30

Phe Gln Thr Pro Gly Ala Ala Gly Val Val Asp Val Arg Gly Pro Gln
        35                  40                  45

Pro Pro Leu Cys Phe Tyr Gln Asp Ser Leu Thr Val Gly Gly Asp
    50                  55                  60

Glu Asp Gly Lys Gly Met Trp Trp Arg Gln Ala Gln Glu Gly Thr
65                  70                  75                  80

Ala Arg Pro Glu Ala Asp Thr His Gly Ser Pro Leu Asp Phe His Val
            85                  90                  95

Tyr Asp Ile Leu Glu Thr Val Tyr Thr His Glu Lys Cys Ala Val Ile
        100                 105                 110

Pro Ser Asp Lys Gln Gly Tyr Val Val Pro Cys Gly Ile Val Ile Lys
    115                 120                 125

Leu Leu Gly Arg Arg Lys Ala Asp Gly Ala Ser Val Cys Val Asn Val
        130                 135                 140

Phe Gly Gln Gln Ala Tyr Phe Tyr Ala Ser Ala Pro Gln Gly Leu Asp
145                 150                 155                 160

Val Glu Phe Ala Val Leu Ser Ala Leu Lys Ala Ser Thr Phe Asp Arg
                165                 170                 175

Arg Thr Pro Cys Arg Val Ser Val Glu Lys Val Thr Arg Arg Ser Ile
            180                 185                 190

Met Gly Tyr Gly Asn His Ala Gly Asp Tyr His Lys Ile Thr Leu Ser
        195                 200                 205

His Pro Asn Ser Val Cys His Val Ala Thr Trp Leu Gln Asp Lys His
    210                 215                 220

Gly Cys Arg Ile Phe Glu Ala Asn Val Asp Ala Thr Arg Arg Phe Val
225                 230                 235                 240

Leu Asp Asn Asp Phe Val Thr Phe Gly Trp Tyr Ser Cys Arg Arg Ala
                245                 250                 255

Ile Pro Arg Leu Gln His Arg Asp Ser Tyr Ala Glu Leu Glu Tyr Asp
            260                 265                 270

Cys Glu Val Gly Asp Leu Ser Val Arg Arg Glu Asp Ser Ser Trp Pro
        275                 280                 285
```

```
Ser Tyr Gln Ala Leu Ala Phe Asp Ile Glu Cys Leu Gly Glu Gly
    290                 295                 300

Phe Pro Thr Ala Thr Asn Glu Ala Asp Leu Ile Leu Gln Ile Ser Cys
305                 310                 315                 320

Val Leu Trp Ser Thr Gly Glu Glu Ala Gly Arg Tyr Arg Arg Ile Leu
                325                 330                 335

Leu Thr Leu Gly Thr Cys Glu Asp Ile Glu Gly Val Glu Val Tyr Glu
                340                 345                 350

Phe Pro Ser Glu Leu Asp Met Leu Tyr Ala Phe Phe Gln Leu Ile Arg
            355                 360                 365

Asp Leu Ser Val Glu Ile Val Thr Gly Tyr Asn Val Ala Asn Phe Asp
370                 375                 380

Trp Pro Tyr Ile Leu Asp Arg Ala Arg His Ile Tyr Ser Ile Asn Pro
385                 390                 395                 400

Ala Ser Leu Gly Lys Ile Arg Ala Gly Val Cys Glu Val Arg Arg
                405                 410                 415

Pro His Asp Ala Gly Lys Gly Phe Leu Arg Ala Asn Thr Lys Val Arg
            420                 425                 430

Ile Thr Gly Leu Ile Pro Ile Asp Met Tyr Ala Val Cys Arg Asp Lys
            435                 440                 445

Leu Ser Leu Ser Asp Tyr Lys Leu Asp Thr Val Ala Arg His Leu Leu
450                 455                 460

Gly Ala Lys Lys Glu Asp Val His Tyr Lys Glu Ile Pro Arg Leu Phe
465                 470                 475                 480

Ala Ala Gly Pro Glu Gly Arg Arg Leu Gly Met Tyr Cys Val Gln
                485                 490                 495

Asp Ser Ala Leu Val Met Asp Leu Leu Asn His Phe Val Ile His Val
            500                 505                 510

Glu Val Ala Glu Ile Ala Lys Ile Ala His Ile Pro Cys Arg Arg Val
            515                 520                 525

Leu Asp Asp Gly Gln Gln Ile Arg Val Phe Ser Cys Leu Leu Ala Ala
    530                 535                 540

Ala Gln Lys Glu Asn Phe Ile Leu Pro Met Pro Ser Ala Ser Asp Arg
545                 550                 555                 560

Asp Gly Tyr Gln Gly Ala Thr Val Ile Gln Pro Leu Ser Gly Phe Tyr
                565                 570                 575

Asn Ser Pro Val Leu Val Asp Phe Ala Ser Leu Tyr Pro Ser Ile
                580                 585                 590

Ile Gln Ala His Asn Leu Cys Tyr Ser Thr Met Ile Thr Pro Gly Glu
            595                 600                 605

Glu His Arg Leu Ala Gly Leu Arg Pro Gly Glu Asp Tyr Glu Ser Phe
    610                 615                 620

Arg Leu Thr Gly Gly Val Tyr His Phe Val Lys Lys His Val His Glu
625                 630                 635                 640

Ser Phe Leu Ala Ser Leu Leu Thr Ser Trp Leu Ala Lys Arg Lys Ala
                645                 650                 655

Ile Lys Lys Leu Leu Ala Ala Cys Glu Asp Pro Arg Gln Arg Thr Ile
                660                 665                 670

Leu Asp Lys Gln Gln Leu Ala Ile Lys Cys Thr Cys Asn Ala Val Tyr
            675                 680                 685

Gly Phe Thr Gly Val Ala Asn Gly Leu Phe Pro Cys Leu Ser Ile Ala
690                 695                 700

Glu Thr Val Thr Leu Gln Gly Arg Thr Met Leu Glu Arg Ala Lys Ala
```

```
            705                 710                 715                 720

Phe Val Glu Ala Leu Ser Pro Ala Asn Leu Gln Ala Leu Ala Pro Ser
                      725                 730                 735

Pro Asp Ala Trp Ala Pro Leu Asn Pro Glu Gly Gln Leu Arg Val Ile
                      740                 745                 750

Tyr Gly Asp Thr Asp Ser Leu Phe Ile Glu Cys Arg Gly Phe Ser Glu
                      755                 760                 765

Ser Glu Thr Leu Arg Phe Ala Glu Ala Leu Ala Ala His Thr Thr Arg
                      770                 775                 780

Ser Leu Phe Val Ala Pro Ile Ser Leu Glu Ala Glu Lys Thr Phe Ser
      785                 790                 795                 800

Cys Leu Met Leu Ile Thr Lys Lys Arg Tyr Val Gly Val Leu Thr Asp
                      805                 810                 815

Gly Lys Thr Leu Met Lys Gly Val Glu Leu Val Arg Lys Thr Ala Cys
                      820                 825                 830

Lys Phe Val Gln Thr Arg Cys Arg Arg Val Leu Asp Leu Val Leu Ala
                      835                 840                 845

Asp Ala Arg Val Lys Glu Ala Ala Ser Leu Leu Ser His Arg Pro Phe
      850                 855                 860

Gln Glu Ser Phe Thr Gln Gly Leu Pro Val Gly Phe Leu Pro Val Ile
      865                 870                 875                 880

Asp Ile Leu Asn Gln Ala Tyr Thr Asp Leu Arg Glu Gly Arg Val Pro
                      885                 890                 895

Met Gly Glu Leu Cys Phe Ser Thr Glu Leu Ser Arg Lys Leu Ser Ala
                      900                 905                 910

Tyr Lys Ser Thr Gln Met Pro His Leu Ala Val Tyr Gln Lys Phe Val
                      915                 920                 925

Glu Arg Asn Glu Glu Leu Pro Gln Ile His Asp Arg Ile Gln Tyr Val
                      930                 935                 940

Phe Val Glu Pro Lys Gly Gly Val Lys Gly Ala Arg Lys Thr Glu Met
      945                 950                 955                 960

Ala Glu Asp Pro Ala Tyr Ala Glu Arg His Gly Val Pro Val Ala Val
                      965                 970                 975

Asp His Tyr Phe Asp Lys Leu Leu Gln Gly Ala Ala Asn Ile Leu Gln
                      980                 985                 990

Cys Leu Phe Asp Asn Asn Ser Gly Ala Ala Leu Ser Val Leu Gln Asn
                      995                 1000                1005

Phe Thr Ala Arg Pro Pro Phe
         1010                1015

<210> SEQ ID NO 44
<211> LENGTH: 103
<212> TYPE: PRT
<213> ORGANISM: Epstein-Barr virus

<400> SEQUENCE: 44

Met Ala Gly Ala Arg Arg Ala Arg Cys Pro Ala Ser Ala Gly Cys
      1               5                   10                  15

Ala Tyr Ser Ala Arg Pro Pro Leu Ser Thr Arg Gly Arg Arg Ile
                      20                  25                  30

Ser Ala Gly Ser Gly Gln Pro Arg Trp Trp Pro Trp Gly Ser Pro
                      35                  40                  45

Pro Leu Asp Thr Arg Tyr Arg Arg Pro Gly Pro Gly Arg Arg Ala Arg
                      50                  55                  60
```

```
Ser Cys Leu His Ala Gly Pro Arg Gly Arg Pro His Ser Arg Thr
 65                  70                  75                  80

Arg Ala Arg Arg Thr Ser Pro Gly Ala Gly Gly Gly Trp Arg Gly
                 85                  90                  95

Gly Ser Cys Thr Ser Gln Arg
            100

<210> SEQ ID NO 45
<211> LENGTH: 126
<212> TYPE: PRT
<213> ORGANISM: Epstein-Barr virus

<400> SEQUENCE: 45

Met Ser Met Pro Pro Lys Gly Phe Leu Lys Glu Met Lys Pro Glu
 1               5                  10                  15

Thr Arg Leu Leu Asn Lys Pro Pro Thr Val Leu Thr Arg Pro Ala Met
                 20                  25                  30

Phe Cys Ala Trp Lys Leu Tyr Ser Arg Lys Met Pro Ser Arg Ser Lys
                 35                  40                  45

Thr Leu Glu Ala Arg Cys Ser Ser Arg Pro Pro Cys Asp Ser Pro Ala
 50                  55                  60

Cys Gln Thr Arg Asp Thr Gly Cys Pro Arg Arg Ser Gly Thr Gly Arg
 65                  70                  75                  80

Arg Gly Trp Arg Ala Arg Arg Leu Gly Lys Glu Ser Trp Phe Ala Asp
                 85                  90                  95

Ala Trp Arg Met Ala Arg Tyr Trp Gly Cys Ala Val Lys Ala Ala Ala
                100                 105                 110

Gln Ser Ala Phe Ser Ala Ser Thr Ala Ser Pro Glu Glu Leu
                115                 120                 125

<210> SEQ ID NO 46
<211> LENGTH: 857
<212> TYPE: PRT
<213> ORGANISM: Epstein-Barr virus

<400> SEQUENCE: 46

Met Thr Arg Arg Arg Val Leu Ser Val Val Leu Leu Ala Ala Leu
 1               5                  10                  15

Ala Cys Arg Leu Gly Ala Gln Thr Pro Glu Gln Pro Ala Pro Ala
                 20                  25                  30

Thr Thr Val Gln Pro Thr Ala Thr Arg Gln Gln Thr Ser Phe Pro Phe
                 35                  40                  45

Arg Val Cys Glu Leu Ser Ser His Gly Asp Leu Phe Arg Phe Ser Ser
 50                  55                  60

Asp Ile Gln Cys Pro Ser Phe Gly Thr Arg Glu Asn His Thr Glu Gly
 65                  70                  75                  80

Leu Leu Met Val Phe Lys Asp Asn Ile Ile Pro Tyr Ser Phe Lys Val
                 85                  90                  95

Arg Ser Tyr Thr Lys Ile Val Thr Asn Ile Leu Ile Tyr Asn Gly Trp
                100                 105                 110

Tyr Ala Asp Ser Val Thr Asn Arg His Glu Glu Lys Phe Ser Val Asp
                115                 120                 125

Ser Tyr Glu Thr Asp Gln Met Asp Thr Ile Tyr Gln Cys Tyr Asn Ala
                130                 135                 140

Val Lys Met Thr Lys Asp Gly Leu Thr Arg Val Tyr Val Asp Arg Asp
145                 150                 155                 160
```

```
Gly Val Asn Ile Thr Val Asn Leu Lys Pro Thr Gly Gly Leu Ala Asn
            165                 170                 175
Gly Val Arg Arg Tyr Ala Ser Gln Thr Glu Leu Tyr Asp Ala Pro Gly
            180                 185                 190
Trp Leu Ile Trp Thr Tyr Arg Thr Arg Thr Thr Val Asn Cys Leu Ile
            195                 200                 205
Thr Asp Met Met Ala Lys Ser Asn Ser Pro Phe Asp Phe Val Thr
            210                 215                 220
Thr Thr Gly Gln Thr Val Glu Met Ser Pro Phe Tyr Asp Gly Lys Asn
225                 230                 235                 240
Lys Glu Thr Phe His Glu Arg Ala Asp Ser Phe His Val Arg Thr Asn
            245                 250                 255
Tyr Lys Ile Val Asp Tyr Asp Asn Arg Gly Thr Asn Pro Gln Gly Glu
            260                 265                 270
Arg Arg Ala Phe Leu Asp Lys Gly Thr Tyr Thr Leu Ser Trp Lys Leu
            275                 280                 285
Glu Asn Arg Thr Ala Tyr Cys Pro Leu Gln His Trp Gln Thr Phe Asp
            290                 295                 300
Ser Thr Ile Ala Thr Glu Thr Gly Lys Ser Ile His Phe Val Thr Asp
305                 310                 315                 320
Glu Gly Thr Ser Ser Phe Val Thr Asn Thr Thr Val Gly Ile Glu Leu
            325                 330                 335
Pro Asp Ala Phe Lys Cys Ile Glu Glu Gln Val Asn Lys Thr Met His
            340                 345                 350
Glu Lys Tyr Glu Ala Val Gln Asp Arg Tyr Thr Lys Gly Gln Glu Ala
            355                 360                 365
Ile Thr Tyr Phe Ile Thr Ser Gly Gly Leu Leu Leu Ala Trp Leu Pro
            370                 375                 380
Leu Thr Pro Arg Ser Leu Ala Thr Val Lys Asn Leu Thr Glu Leu Thr
385                 390                 395                 400
Thr Pro Thr Ser Ser Pro Ser Ser Pro Ser Pro Ala Pro Pro
            405                 410                 415
Ala Ala Arg Gly Ser Thr Ser Ala Ala Val Leu Arg Arg Arg Arg
            420                 425                 430
Asp Ala Gly Asn Ala Thr Thr Pro Val Pro Ala Ala Pro Gly Lys
            435                 440                 445
Ser Leu Gly Thr Leu Asn Asn Pro Ala Thr Val Gln Ile Gln Phe Ala
            450                 455                 460
Tyr Asp Ser Leu Arg Arg Gln Ile Asn Arg Met Leu Gly Asp Leu Ala
465                 470                 475                 480
Arg Ala Trp Cys Leu Glu Gln Lys Arg Gln Asn Met Val Leu Arg Glu
            485                 490                 495
Leu Thr Lys Ile Asn Pro Thr Thr Val Met Ser Ser Ile Tyr Gly Lys
            500                 505                 510
Ala Val Ala Ala Lys Arg Leu Gly Asp Val Ile Ser Val Ser Gln Cys
            515                 520                 525
Val Pro Val Asn Gln Ala Thr Val Thr Leu Arg Lys Ser Met Arg Val
            530                 535                 540
Pro Gly Ser Glu Thr Met Cys Tyr Ser Arg Pro Leu Val Ser Phe Ser
545                 550                 555                 560
Phe Ile Asn Asp Thr Lys Thr Tyr Glu Gly Gln Leu Gly Thr Asp Asn
            565                 570                 575
Glu Ile Phe Leu Thr Lys Lys Met Thr Glu Val Cys Gln Ala Thr Ser
```

```
            580                 585                 590

Gln Tyr Tyr Phe Gln Ser Gly Asn Glu Ile His Val Tyr Asn Asp Tyr
        595                 600                 605

His His Phe Lys Thr Ile Glu Leu Asp Gly Ile Ala Thr Leu Gln Thr
    610                 615                 620

Phe Ile Ser Leu Asn Thr Ser Leu Ile Glu Asn Ile Asp Phe Ala Ser
625                 630                 635                 640

Leu Glu Leu Tyr Ser Arg Asp Glu Gln Arg Ala Ser Asn Val Phe Asp
                645                 650                 655

Leu Glu Gly Ile Phe Arg Glu Tyr Asn Phe Gln Ala Gln Asn Ile Ala
            660                 665                 670

Gly Leu Arg Lys Asp Leu Asp Asn Ala Val Ser Asn Gly Arg Asn Gln
        675                 680                 685

Phe Val Asp Gly Leu Gly Glu Leu Met Asp Ser Leu Gly Ser Val Gly
    690                 695                 700

Gln Ser Ile Thr Asn Leu Val Ser Thr Val Gly Gly Leu Phe Ser Ser
705                 710                 715                 720

Leu Val Ser Gly Phe Ile Ser Phe Phe Lys Asn Pro Phe Gly Gly Met
                725                 730                 735

Leu Ile Leu Val Leu Val Ala Gly Val Val Ile Leu Val Ile Ser Leu
            740                 745                 750

Thr Arg Arg Thr Arg Gln Met Ser Gln Gln Pro Val Gln Met Leu Tyr
        755                 760                 765

Pro Gly Ile Asp Glu Leu Ala Gln Gln His Ala Ser Gly Glu Gly Pro
    770                 775                 780

Gly Ile Asn Pro Ile Ser Lys Thr Glu Leu Gln Ala Ile Met Leu Ala
785                 790                 795                 800

Leu His Glu Gln Asn Gln Glu Gln Lys Arg Ala Ala Gln Arg Ala Ala
                805                 810                 815

Gly Pro Ser Val Ala Ser Arg Ala Leu Gln Ala Ala Arg Asp Arg Phe
            820                 825                 830

Pro Gly Leu Arg Arg Arg Arg Tyr His Asp Pro Glu Thr Ala Ala Ala
        835                 840                 845

Leu Leu Gly Glu Ala Glu Thr Glu Phe
    850                 855

<210> SEQ ID NO 47
<211> LENGTH: 685
<212> TYPE: PRT
<213> ORGANISM: Epstein-Barr virus

<400> SEQUENCE: 47

Met Ser Gly Leu Leu Ala Ala Ala Tyr Ser Gln Val Tyr Ala Leu Ala
1               5                   10                  15

Val Glu Leu Ser Val Cys Ala Arg Leu Asp Pro Arg Ser Leu Asp Val
            20                  25                  30

Ala Ala Val Val Arg Asn Ala Gly Leu Leu Ala Glu Leu Glu Ala Ile
        35                  40                  45

Leu Leu Pro Arg Leu Arg Arg Gln Asn Asp Arg Ala Cys Ser Ala Leu
    50                  55                  60

Ser Leu Glu Leu Val His Leu Leu Glu Asn Ser Arg Glu Ala Ser Ala
65                  70                  75                  80

Ala Leu Leu Ala Pro Gly Arg Lys Gly Thr Arg Val Pro Pro Leu Arg
                85                  90                  95
```

-continued

```
Thr Pro Ser Val Ala Tyr Ser Val Glu Phe Tyr Gly Gly His Lys Val
            100                 105                 110

Asp Val Ser Leu Cys Leu Ile Asn Asp Ile Glu Ile Leu Met Lys Arg
            115                 120                 125

Ile Asn Ser Val Phe Tyr Cys Met Ser His Thr Met Gly Leu Glu Ser
        130                 135                 140

Leu Glu Arg Ala Leu Asp Leu Leu Gly Arg Phe Arg Gly Val Ser Pro
145                 150                 155                 160

Ile Pro Asp Pro Arg Leu Tyr Ile Thr Ser Val Pro Cys Trp Arg Cys
                165                 170                 175

Val Gly Glu Leu Met Val Leu Pro Asn His Gly Asn Pro Ser Thr Ala
            180                 185                 190

Glu Gly Thr His Val Ser Cys Asn His Leu Ala Val Pro Val Asn Pro
        195                 200                 205

Glu Pro Val Ser Gly Leu Phe Glu Asn Glu Val Arg Gln Ala Gly Leu
    210                 215                 220

Gly His Leu Leu Glu Ala Glu Lys Ala Arg Pro Gly Gly Pro Glu
225                 230                 235                 240

Glu Gly Ala Val Pro Gly Pro Gly Arg Pro Glu Ala Glu Gly Ala Thr
                245                 250                 255

Arg Ala Leu Asp Thr Tyr Asn Val Phe Ser Thr Val Pro Pro Glu Val
            260                 265                 270

Ala Glu Leu Ser Glu Leu Leu Tyr Trp Asn Ser Gly His Ala Ile
        275                 280                 285

Gly Ala Thr Gly Gln Gly Glu Gly Gly His Ser Arg Leu Ser Ala
290                 295                 300

Leu Phe Ala Arg Glu Arg Arg Leu Ala Leu Val Arg Arg Ala Cys Glu
305                 310                 315                 320

Glu Ala Leu Ala Gly Ala Arg Leu Thr His Leu Phe Asp Ala Val Ala
                325                 330                 335

Pro Gly Ala Thr Glu Arg Leu Phe Cys Gly Gly Val Tyr Ser Ser Ser
            340                 345                 350

Gly Asp Ala Val Glu Ala Leu Lys Ala Asp Cys Ala Ala Ala Phe Thr
        355                 360                 365

Ala His Pro Gln Tyr Arg Ala Ile Leu Gln Lys Arg Asn Glu Leu Tyr
    370                 375                 380

Thr Arg Leu Asn Arg Ala Met Gln Arg Leu Gly Arg Gly Glu Glu Glu
385                 390                 395                 400

Ala Ser Arg Glu Ser Pro Glu Val Pro Arg Pro Ala Gly Ala Arg Glu
                405                 410                 415

Pro Gly Pro Ser Gly Ala Leu Ser Asp Ala Leu Lys Arg Lys Glu Gln
            420                 425                 430

Tyr Leu Arg Gln Val Ala Thr Glu Gly Leu Ala Lys Leu Gln Ser Cys
        435                 440                 445

Leu Ala Gln Gln Ser Glu Thr Leu Thr Glu Thr Leu Cys Leu Arg Val
    450                 455                 460

Trp Gly Asp Val Val Tyr Trp Glu Leu Ala Arg Met Arg Asn His Phe
465                 470                 475                 480

Leu Tyr Arg Arg Ala Phe Val Ser Gly Pro Trp Glu Asp Arg Arg Ala
                485                 490                 495

Gly Glu Gly Ala Ala Phe Glu Asn Ser Lys Tyr Ile Lys Thr His Leu
            500                 505                 510

Phe Thr Gln Thr Leu Ser Ser Glu His Leu His Ala Leu Thr His Ser
```

```
                515                 520                 525
Leu Tyr Thr Phe Ile Thr Gly Pro Leu Ala Glu Glu Ser Gly Leu Phe
    530                 535                 540

Pro Pro Pro Ser Asn Val Ala Leu Ala Arg Cys Cys Asp Ala Ala Gly
545                 550                 555                 560

Thr Leu Pro His Gln Lys Ala Phe Leu Thr Ser Leu Ile Trp Pro Gly
                565                 570                 575

Ile Glu Pro Ser Asp Trp Ile Glu Thr Ser Phe Asn Ser Phe Tyr Ser
            580                 585                 590

Val Pro Gly Gly Ser Leu Ala Ser Ser Gln Gln Ile Leu Cys Arg Ala
        595                 600                 605

Leu Arg Glu Ala Val Leu Thr Val Ser Leu Tyr Asn Lys Thr Trp Gly
    610                 615                 620

Arg Ser Leu Ile Leu Arg Arg Ala Asp Ala Val Ser Pro Gly Gln Ala
625                 630                 635                 640

Leu Pro Pro Asp Gly Leu Tyr Leu Thr Tyr Asp Ser Asp Arg Pro Leu
                645                 650                 655

Ile Leu Leu Tyr Lys Gly Arg Gly Trp Val Phe Lys Asp Leu Tyr Ala
            660                 665                 670

Leu Leu Tyr Leu His Leu Gln Met Arg Asp Asp Ser Ala
        675                 680                 685

<210> SEQ ID NO 48
<211> LENGTH: 471
<212> TYPE: PRT
<213> ORGANISM: Epstein-Barr virus

<400> SEQUENCE: 48

Ala Pro Gly Tyr Ala Val Glu Ala Val Glu Gly Gly Leu Tyr Pro Val
1               5                   10                  15

Ala Arg Leu Asp Ala Trp Pro Tyr Gln Gly Ser Gln Glu Arg Leu Leu
            20                  25                  30

Val Arg Gln Arg Thr Cys Gly Val Thr Ala Ala Ser Gln Gly His Val
        35                  40                  45

Ala Gly Trp Gly Lys Glu Pro Ala Leu Leu Arg Gln Gly Pro Arg Asp
    50                  55                  60

Glu Gly Val Gln Ala Val Arg Gln Arg Val Gln Val Leu Arg Ala Gln
65                  70                  75                  80

Gly Leu Gly Lys Gln Val Cys Phe Asp Val Leu Gly Ile Leu Lys Gly
                85                  90                  95

Gly Thr Leu Ala Gly Ala Pro Val Leu Pro Gly Thr Arg Asp Glu Gly
            100                 105                 110

Pro Ser Val Glu Glu Val Val Ala His Ala Gly Gln Leu Pro Val Asp
        115                 120                 125

His Val Pro Pro Asp Ala Gln Ala Gln Gly Leu Gly Gln Gly Leu Ala
    130                 135                 140

Leu Leu Arg Gln Ala Gly Leu Gln Leu Gln Gly Gln Thr Leu Gly His
145                 150                 155                 160

Leu Ala Gln Val Leu Leu Leu Ala Leu Glu Arg Val Arg Glu Gly Ala
                165                 170                 175

Gly Arg Ala Gly Leu Ser Cys Pro Ser Arg Pro Gly His Leu Arg Ala
            180                 185                 190

Leu Pro Gly Arg Leu Leu Leu Ala Ser Ala Gln Pro Leu His Gly Ser
        195                 200                 205
```

```
Val Glu Pro Arg Val Glu Leu Val Pro Leu Leu Gln Asp Gly Pro Val
    210                 215                 220
Leu Gly Val Arg Glu Gly Gly Ala Val Arg Leu Gln Arg Leu
225                 230                 235                 240
His Arg Val Ala Arg Gly Ala Val Asp Pro Ala Ala Glu Glu Pro Leu
                245                 250                 255
Cys Gly Pro Gly Ser His Gly Ile Lys Gln Val Ser Gln Pro Cys Pro
                260                 265                 270
Arg Gln Arg Leu Leu Ala Gly Pro His Gln Gly Gln Ala Thr Leu
                275                 280                 285
Pro Gly Lys Gln Gly Arg Glu Ala Gly Met Ser Ala Thr Leu Pro Leu
    290                 295                 300
Pro Arg Cys Thr Asp Ser Met Ala Ala Arg Val Pro Ile Glu Glu Leu
305                 310                 315                 320
Arg Glu Phe Arg His Leu Arg Gly His Cys Arg Glu Asp Val Val Gly
                325                 330                 335
Val Gln Arg Ser Gly Arg Pro Leu Cys Leu Arg Pro Arg Ala Arg
                340                 345                 350
Asp Arg Ala Leu Leu Trp Ala Ala Arg Pro Arg Leu Leu Leu Ser Leu
                355                 360                 365
Gln Gln Val Pro Glu Pro Ser Leu Pro Asp Phe Ile Leu Lys Gln Ser
    370                 375                 380
Arg Asp Arg Leu Arg Ile His Arg His Arg Gln Val Val Thr Gly Asp
385                 390                 395                 400
Val Gly Pro Leu Cys Arg Gly Arg Val Ala Val Val Gly Gln Asn His
                405                 410                 415
Gln Leu Ala His Thr Ala Pro Ala Gly His Arg Gly Asp Val Glu Ala
                420                 425                 430
Arg Val Trp Asp Gly Thr Tyr Ala Pro Lys Ala Ala Gln Gln Ile Gln
                435                 440                 445
Gly Pro Phe Gln Ala Leu Gln Pro His Gly Val Arg His Ala Ile Lys
    450                 455                 460
His Ala Ile Asp Ser Leu His
465                 470

<210> SEQ ID NO 49
<211> LENGTH: 9
<212> TYPE: PRT
<213> ORGANISM: Human papillomavirus type 16

<400> SEQUENCE: 49

Cys Met Ser Cys Cys Arg Ser Ser Arg
1               5

<210> SEQ ID NO 50
<211> LENGTH: 9
<212> TYPE: PRT
<213> ORGANISM: Human papillomavirus type 17

<400> SEQUENCE: 50

Cys Pro Glu Glu Lys Gln Arg His Leu
1               5

<210> SEQ ID NO 51
<211> LENGTH: 9
<212> TYPE: PRT
<213> ORGANISM: Human papillomavirus type 18
```

```
<400> SEQUENCE: 51

Cys Val Tyr Cys Lys Gln Gln Leu Leu
1               5

<210> SEQ ID NO 52
<211> LENGTH: 10
<212> TYPE: PRT
<213> ORGANISM: Human papillomavirus type 19

<400> SEQUENCE: 52

Cys Val Tyr Cys Lys Gln Gln Leu Leu Arg
1               5                   10

<210> SEQ ID NO 53
<211> LENGTH: 9
<212> TYPE: PRT
<213> ORGANISM: Human papillomavirus type 20

<400> SEQUENCE: 53

Cys Tyr Ser Leu Tyr Gly Thr Thr Leu
1               5

<210> SEQ ID NO 54
<211> LENGTH: 9
<212> TYPE: PRT
<213> ORGANISM: Human papillomavirus type 21

<400> SEQUENCE: 54

Asp Lys Lys Gln Arg Phe His Asn Ile
1               5

<210> SEQ ID NO 55
<211> LENGTH: 9
<212> TYPE: PRT
<213> ORGANISM: Human papillomavirus type 22

<400> SEQUENCE: 55

Glu Tyr Arg His Tyr Cys Tyr Ser Leu
1               5

<210> SEQ ID NO 56
<211> LENGTH: 9
<212> TYPE: PRT
<213> ORGANISM: Human papillomavirus type 23

<400> SEQUENCE: 56

Phe Ala Phe Arg Asp Leu Cys Ile Val
1               5

<210> SEQ ID NO 57
<211> LENGTH: 9
<212> TYPE: PRT
<213> ORGANISM: Human papillomavirus type 24

<400> SEQUENCE: 57

Ile Ile Leu Glu Cys Val Tyr Cys Lys
1               5

<210> SEQ ID NO 58
<211> LENGTH: 9
<212> TYPE: PRT
<213> ORGANISM: Human papillomavirus type 25

<400> SEQUENCE: 58
```

```
Ile Ser Glu Tyr Arg His Tyr Cys Tyr
1               5
```

<210> SEQ ID NO 59
<211> LENGTH: 9
<212> TYPE: PRT
<213> ORGANISM: Human papillomavirus type 26

<400> SEQUENCE: 59

```
Ile Val Tyr Arg Asp Gly Asn Pro Tyr
1               5
```

<210> SEQ ID NO 60
<211> LENGTH: 10
<212> TYPE: PRT
<213> ORGANISM: Human papillomavirus type 27

<400> SEQUENCE: 60

```
Ile Val Tyr Arg Asp Gly Asn Pro Tyr Ala
1               5                   10
```

<210> SEQ ID NO 61
<211> LENGTH: 9
<212> TYPE: PRT
<213> ORGANISM: Human papillomavirus type 28

<400> SEQUENCE: 61

```
Lys Phe Tyr Ser Lys Ile Ser Glu Tyr
1               5
```

<210> SEQ ID NO 62
<211> LENGTH: 10
<212> TYPE: PRT
<213> ORGANISM: Human papillomavirus type 29

<400> SEQUENCE: 62

```
Lys Ile Ser Glu Tyr Arg His Tyr Cys Tyr
1               5                   10
```

<210> SEQ ID NO 63
<211> LENGTH: 9
<212> TYPE: PRT
<213> ORGANISM: Human papillomavirus type 30

<400> SEQUENCE: 63

```
Lys Leu Pro Gln Leu Cys Thr Glu Leu
1               5
```

<210> SEQ ID NO 64
<211> LENGTH: 9
<212> TYPE: PRT
<213> ORGANISM: Human papillomavirus type 31

<400> SEQUENCE: 64

```
Leu Ile Arg Cys Ile Asn Cys Gln Lys
1               5
```

<210> SEQ ID NO 65
<211> LENGTH: 10
<212> TYPE: PRT
<213> ORGANISM: Human papillomavirus type 32

<400> SEQUENCE: 65

```
Leu Leu Ile Arg Cys Ile Asn Cys Gln Lys
1               5                   10
```

```
<210> SEQ ID NO 66
<211> LENGTH: 9
<212> TYPE: PRT
<213> ORGANISM: Human papillomavirus type 33

<400> SEQUENCE: 66

Met His Gln Lys Arg Thr Ala Met Phe
1               5

<210> SEQ ID NO 67
<211> LENGTH: 10
<212> TYPE: PRT
<213> ORGANISM: Human papillomavirus type 34

<400> SEQUENCE: 67

Asn Pro Tyr Ala Val Cys Asp Lys Cys Leu
1               5                   10

<210> SEQ ID NO 68
<211> LENGTH: 10
<212> TYPE: PRT
<213> ORGANISM: Human papillomavirus type 35

<400> SEQUENCE: 68

Gln Tyr Asn Lys Pro Leu Cys Asp Leu Leu
1               5                   10

<210> SEQ ID NO 69
<211> LENGTH: 9
<212> TYPE: PRT
<213> ORGANISM: Human papillomavirus type 36

<400> SEQUENCE: 69

Arg Phe His Asn Ile Arg Gly Arg Trp
1               5

<210> SEQ ID NO 70
<211> LENGTH: 9
<212> TYPE: PRT
<213> ORGANISM: Human papillomavirus type 37

<400> SEQUENCE: 70

Arg Gly Arg Trp Thr Gly Arg Cys Met
1               5

<210> SEQ ID NO 71
<211> LENGTH: 9
<212> TYPE: PRT
<213> ORGANISM: Human papillomavirus type 38

<400> SEQUENCE: 71

Arg Pro Arg Lys Leu Pro Gln Leu Cys
1               5

<210> SEQ ID NO 72
<211> LENGTH: 10
<212> TYPE: PRT
<213> ORGANISM: Human papillomavirus type 39

<400> SEQUENCE: 72

Arg Pro Arg Lys Leu Pro Gln Leu Cys Thr
1               5                   10
```

-continued

```
<210> SEQ ID NO 73
<211> LENGTH: 10
<212> TYPE: PRT
<213> ORGANISM: Human papillomavirus type 40

<400> SEQUENCE: 73

Ser Glu Tyr Arg His Tyr Cys Tyr Ser Leu
1               5                   10

<210> SEQ ID NO 74
<211> LENGTH: 10
<212> TYPE: PRT
<213> ORGANISM: Human papillomavirus type 41

<400> SEQUENCE: 74

Ser Ser Arg Thr Arg Arg Glu Thr Gln Leu
1               5                   10

<210> SEQ ID NO 75
<211> LENGTH: 10
<212> TYPE: PRT
<213> ORGANISM: Human papillomavirus type 42

<400> SEQUENCE: 75

Thr Ile His Asp Ile Ile Leu Glu Cys Val
1               5                   10

<210> SEQ ID NO 76
<211> LENGTH: 9
<212> TYPE: PRT
<213> ORGANISM: Human papillomavirus type 43

<400> SEQUENCE: 76

Thr Thr Leu Glu Gln Gln Tyr Asn Lys
1               5

<210> SEQ ID NO 77
<211> LENGTH: 9
<212> TYPE: PRT
<213> ORGANISM: Human papillomavirus type 44

<400> SEQUENCE: 77

Val Tyr Asp Phe Ala Phe Arg Asp Leu
1               5

<210> SEQ ID NO 78
<211> LENGTH: 10
<212> TYPE: PRT
<213> ORGANISM: Human papillomavirus type 45

<400> SEQUENCE: 78

Gly Ile Val Cys Pro Ile Cys Ser Gln Lys
1               5                   10

<210> SEQ ID NO 79
<211> LENGTH: 9
<212> TYPE: PRT
<213> ORGANISM: Human papillomavirus type 46

<400> SEQUENCE: 79

Gly Thr Leu Gly Ile Val Cys Pro Ile
1               5

<210> SEQ ID NO 80
<211> LENGTH: 10
```

```
<212> TYPE: PRT
<213> ORGANISM: Human papillomavirus type 47

<400> SEQUENCE: 80

His Gly Asp Thr Pro Thr Leu His Glu Tyr
1               5                   10

<210> SEQ ID NO 81
<211> LENGTH: 9
<212> TYPE: PRT
<213> ORGANISM: Human papillomavirus type 48

<400> SEQUENCE: 81

Ile Val Cys Pro Ile Cys Ser Gln Lys
1               5

<210> SEQ ID NO 82
<211> LENGTH: 9
<212> TYPE: PRT
<213> ORGANISM: Human papillomavirus type 49

<400> SEQUENCE: 82

Leu Leu Met Gly Thr Leu Gly Ile Val
1               5

<210> SEQ ID NO 83
<211> LENGTH: 9
<212> TYPE: PRT
<213> ORGANISM: Human papillomavirus type 50

<400> SEQUENCE: 83

Arg Ala His Tyr Asn Ile Val Thr Phe
1               5

<210> SEQ ID NO 84
<211> LENGTH: 9
<212> TYPE: PRT
<213> ORGANISM: Human papillomavirus type 51

<400> SEQUENCE: 84

Arg Leu Cys Val Gln Ser Thr His Val
1               5

<210> SEQ ID NO 85
<211> LENGTH: 10
<212> TYPE: PRT
<213> ORGANISM: Human papillomavirus type 52

<400> SEQUENCE: 85

Thr Leu Glu Asp Leu Leu Met Gly Thr Leu
1               5                   10

<210> SEQ ID NO 86
<211> LENGTH: 9
<212> TYPE: PRT
<213> ORGANISM: Human papillomavirus type 53

<400> SEQUENCE: 86

Thr Leu His Glu Tyr Met Leu Asp Leu
1               5

<210> SEQ ID NO 87
<211> LENGTH: 9
<212> TYPE: PRT
<213> ORGANISM: Human papillomavirus type 54
```

<400> SEQUENCE: 87

Thr Pro Thr Leu His Glu Tyr Met Leu
1               5

<210> SEQ ID NO 88
<211> LENGTH: 9
<212> TYPE: PRT
<213> ORGANISM: Human papillomavirus type 55

<400> SEQUENCE: 88

Tyr Met Leu Asp Leu Gln Pro Glu Thr
1               5

<210> SEQ ID NO 89
<211> LENGTH: 10
<212> TYPE: PRT
<213> ORGANISM: Human papillomavirus type 56

<400> SEQUENCE: 89

Tyr Met Leu Asp Leu Gln Pro Glu Thr Thr
1               5                   10

<210> SEQ ID NO 90
<211> LENGTH: 10
<212> TYPE: PRT
<213> ORGANISM: Epstein-Barr virus

<400> SEQUENCE: 90

Ala Ala Leu Ala Ser Arg Arg Ser Ser Phe
1               5                   10

<210> SEQ ID NO 91
<211> LENGTH: 9
<212> TYPE: PRT
<213> ORGANISM: Epstein-Barr virus

<400> SEQUENCE: 91

Ala Leu Ala Ser Arg Arg Ser Ser Phe
1               5

<210> SEQ ID NO 92
<211> LENGTH: 10
<212> TYPE: PRT
<213> ORGANISM: Epstein-Barr virus

<400> SEQUENCE: 92

Ala Leu Ala Ser Arg Arg Ser Ser Phe Arg
1               5                   10

<210> SEQ ID NO 93
<211> LENGTH: 10
<212> TYPE: PRT
<213> ORGANISM: Epstein-Barr virus

<400> SEQUENCE: 93

Ala Leu Thr Leu Pro Gly Asn Ile Val Val
1               5                   10

<210> SEQ ID NO 94
<211> LENGTH: 9
<212> TYPE: PRT
<213> ORGANISM: Epstein-Barr virus

<400> SEQUENCE: 94

```
Ala Pro Leu Ser Ser Lys Ile Thr Ala
1               5

<210> SEQ ID NO 95
<211> LENGTH: 10
<212> TYPE: PRT
<213> ORGANISM: Epstein-Barr virus

<400> SEQUENCE: 95

Ala Pro Leu Ser Ser Lys Ile Thr Ala Ile
1               5                   10

<210> SEQ ID NO 96
<211> LENGTH: 9
<212> TYPE: PRT
<213> ORGANISM: Epstein-Barr virus

<400> SEQUENCE: 96

Ala Gln His Thr Pro Pro Phe Leu Lys
1               5

<210> SEQ ID NO 97
<211> LENGTH: 10
<212> TYPE: PRT
<213> ORGANISM: Epstein-Barr virus

<400> SEQUENCE: 97

Ala Tyr Pro Gly Gly Ala His Ala Ala Leu
1               5                   10

<210> SEQ ID NO 98
<211> LENGTH: 10
<212> TYPE: PRT
<213> ORGANISM: Epstein-Barr virus

<400> SEQUENCE: 98

Cys Pro Ser Val Gly Gln Ile Leu Ser Phe
1               5                   10

<210> SEQ ID NO 99
<211> LENGTH: 9
<212> TYPE: PRT
<213> ORGANISM: Epstein-Barr virus

<400> SEQUENCE: 99

Glu Val Phe Leu Lys Pro Phe Phe Val
1               5

<210> SEQ ID NO 100
<211> LENGTH: 10
<212> TYPE: PRT
<213> ORGANISM: Epstein-Barr virus

<400> SEQUENCE: 100

Phe Phe Gly Ala Glu Asp Asn Glu Val Phe
1               5                   10

<210> SEQ ID NO 101
<211> LENGTH: 10
<212> TYPE: PRT
<213> ORGANISM: Epstein-Barr virus

<400> SEQUENCE: 101

Phe Ile Glu Lys Gly Lys Phe Thr Trp Tyr
```

<210> SEQ ID NO 102
<211> LENGTH: 9
<212> TYPE: PRT
<213> ORGANISM: Epstein-Barr virus

<400> SEQUENCE: 102

Phe Ile Tyr Ala Gly Asp Pro Ser Ile
1               5

<210> SEQ ID NO 103
<211> LENGTH: 9
<212> TYPE: PRT
<213> ORGANISM: Epstein-Barr virus

<400> SEQUENCE: 103

Phe Leu Ser Gly Ser Pro Val Thr Ser
1               5

<210> SEQ ID NO 104
<211> LENGTH: 10
<212> TYPE: PRT
<213> ORGANISM: Epstein-Barr virus

<400> SEQUENCE: 104

Phe Met Arg Gly Val Trp Lys Tyr Glu Ile
1               5                   10

<210> SEQ ID NO 105
<211> LENGTH: 10
<212> TYPE: PRT
<213> ORGANISM: Epstein-Barr virus

<400> SEQUENCE: 105

Phe Thr Val Ala Phe Leu Phe Phe Gly Ala
1               5                   10

<210> SEQ ID NO 106
<211> LENGTH: 10
<212> TYPE: PRT
<213> ORGANISM: Epstein-Barr virus

<400> SEQUENCE: 106

Phe Thr Trp Tyr Ile Val Pro Ile Arg Leu
1               5                   10

<210> SEQ ID NO 107
<211> LENGTH: 10
<212> TYPE: PRT
<213> ORGANISM: Epstein-Barr virus

<400> SEQUENCE: 107

Phe Val Met His Ser Asp Gln Asp Ile Val
1               5                   10

<210> SEQ ID NO 108
<211> LENGTH: 9
<212> TYPE: PRT
<213> ORGANISM: Epstein-Barr virus

<400> SEQUENCE: 108

Gly Pro Leu Asn Val Lys Val Gly Met
1               5

<210> SEQ ID NO 109
<211> LENGTH: 10
<212> TYPE: PRT
<213> ORGANISM: Epstein-Barr virus

<400> SEQUENCE: 109

Gly Gln Ser Met Ala Gln Ala Phe Phe Ile
1               5                   10

<210> SEQ ID NO 110
<211> LENGTH: 10
<212> TYPE: PRT
<213> ORGANISM: Epstein-Barr virus

<400> SEQUENCE: 110

His Ser Asp Gln Asp Ile Val Leu Ser Val
1               5                   10

<210> SEQ ID NO 111
<211> LENGTH: 9
<212> TYPE: PRT
<213> ORGANISM: Epstein-Barr virus

<400> SEQUENCE: 111

His Ser Ser Asn Pro Val Phe Tyr Val
1               5

<210> SEQ ID NO 112
<211> LENGTH: 10
<212> TYPE: PRT
<213> ORGANISM: Epstein-Barr virus

<400> SEQUENCE: 112

His Ser Ser Asn Pro Val Phe Tyr Val Tyr
1               5                   10

<210> SEQ ID NO 113
<211> LENGTH: 10
<212> TYPE: PRT
<213> ORGANISM: Epstein-Barr virus

<400> SEQUENCE: 113

His Thr Phe Pro Gly Lys Val Cys Pro Val
1               5                   10

<210> SEQ ID NO 114
<211> LENGTH: 10
<212> TYPE: PRT
<213> ORGANISM: Epstein-Barr virus

<400> SEQUENCE: 114

Ile Ala Phe Arg Tyr Asn Pro Tyr Pro Lys
1               5                   10

<210> SEQ ID NO 115
<211> LENGTH: 10
<212> TYPE: PRT
<213> ORGANISM: Epstein-Barr virus

<400> SEQUENCE: 115

Ile Ile Pro Pro Asn Phe Ile Thr Glu Leu
1               5                   10

<210> SEQ ID NO 116

```
<211> LENGTH: 10
<212> TYPE: PRT
<213> ORGANISM: Epstein-Barr virus

<400> SEQUENCE: 116

Ile Leu Pro Gly Gln Ser Asp Ile Gln Leu
1               5                   10

<210> SEQ ID NO 117
<211> LENGTH: 9
<212> TYPE: PRT
<213> ORGANISM: Epstein-Barr virus

<400> SEQUENCE: 117

Ile Pro Pro Asn Phe Ile Thr Glu Leu
1               5

<210> SEQ ID NO 118
<211> LENGTH: 10
<212> TYPE: PRT
<213> ORGANISM: Epstein-Barr virus

<400> SEQUENCE: 118

Ile Thr Glu Leu Glu Tyr Asn Asn Thr Tyr
1               5                   10

<210> SEQ ID NO 119
<211> LENGTH: 10
<212> TYPE: PRT
<213> ORGANISM: Epstein-Barr virus

<400> SEQUENCE: 119

Ile Val Val Ser His Ser Ser Asn Pro Val
1               5                   10

<210> SEQ ID NO 120
<211> LENGTH: 9
<212> TYPE: PRT
<213> ORGANISM: Epstein-Barr virus

<400> SEQUENCE: 120

Lys Phe Thr Trp Tyr Ile Val Pro Ile
1               5

<210> SEQ ID NO 121
<211> LENGTH: 9
<212> TYPE: PRT
<213> ORGANISM: Epstein-Barr virus

<400> SEQUENCE: 121

Lys Leu Asn Thr Ser Glu Pro Gln Ile
1               5

<210> SEQ ID NO 122
<211> LENGTH: 9
<212> TYPE: PRT
<213> ORGANISM: Epstein-Barr virus

<400> SEQUENCE: 122

Lys Leu Pro Ser Phe Ser Phe Asn Thr
1               5

<210> SEQ ID NO 123
<211> LENGTH: 10
<212> TYPE: PRT
```

-continued

<213> ORGANISM: Epstein-Barr virus

<400> SEQUENCE: 123

Lys Leu Pro Ser Phe Ser Phe Asn Thr Thr
1               5                   10

<210> SEQ ID NO 124
<211> LENGTH: 9
<212> TYPE: PRT
<213> ORGANISM: Epstein-Barr virus

<400> SEQUENCE: 124

Lys Asn Pro Tyr Leu Tyr Leu Gln Ile
1               5

<210> SEQ ID NO 125
<211> LENGTH: 10
<212> TYPE: PRT
<213> ORGANISM: Epstein-Barr virus

<400> SEQUENCE: 125

Lys Pro Asp Thr Ser Phe Met Arg Gly Val
1               5                   10

<210> SEQ ID NO 126
<211> LENGTH: 10
<212> TYPE: PRT
<213> ORGANISM: Epstein-Barr virus

<400> SEQUENCE: 126

Lys Pro Gly Gln Thr Leu Lys Leu Thr Val
1               5                   10

<210> SEQ ID NO 127
<211> LENGTH: 9
<212> TYPE: PRT
<213> ORGANISM: Epstein-Barr virus

<400> SEQUENCE: 127

Lys Ser Tyr Ala Arg Ile His Thr Phe
1               5

<210> SEQ ID NO 128
<211> LENGTH: 10
<212> TYPE: PRT
<213> ORGANISM: Epstein-Barr virus

<400> SEQUENCE: 128

Lys Val Cys Pro Val Asn Ala Ile Arg Arg
1               5                   10

<210> SEQ ID NO 129
<211> LENGTH: 9
<212> TYPE: PRT
<213> ORGANISM: Epstein-Barr virus

<400> SEQUENCE: 129

Lys Tyr Glu Ile Phe Pro Ser Tyr Val
1               5

<210> SEQ ID NO 130
<211> LENGTH: 10
<212> TYPE: PRT
<213> ORGANISM: Epstein-Barr virus

```
<400> SEQUENCE: 130

Leu Ala Gln His Thr Pro Pro Phe Leu Lys
1               5                   10

<210> SEQ ID NO 131
<211> LENGTH: 10
<212> TYPE: PRT
<213> ORGANISM: Epstein-Barr virus

<400> SEQUENCE: 131

Leu Asp Asp Val Ile Ile Ala Phe Arg Tyr
1               5                   10

<210> SEQ ID NO 132
<211> LENGTH: 10
<212> TYPE: PRT
<213> ORGANISM: Epstein-Barr virus

<400> SEQUENCE: 132

Leu Phe Ile Glu Lys Gly Lys Phe Thr Trp
1               5                   10

<210> SEQ ID NO 133
<211> LENGTH: 9
<212> TYPE: PRT
<213> ORGANISM: Epstein-Barr virus

<400> SEQUENCE: 133

Leu Leu Ala Gln His Thr Pro Pro Phe
1               5

<210> SEQ ID NO 134
<211> LENGTH: 10
<212> TYPE: PRT
<213> ORGANISM: Epstein-Barr virus

<400> SEQUENCE: 134

Leu Leu Ala Gln His Thr Pro Pro Phe Leu
1               5                   10

<210> SEQ ID NO 135
<211> LENGTH: 9
<212> TYPE: PRT
<213> ORGANISM: Epstein-Barr virus

<400> SEQUENCE: 135

Leu Leu Asp Asp Val Ile Ile Ala Phe
1               5

<210> SEQ ID NO 136
<211> LENGTH: 9
<212> TYPE: PRT
<213> ORGANISM: Epstein-Barr virus

<400> SEQUENCE: 136

Leu Pro Gly Gln Ser Asp Ile Gln Leu
1               5

<210> SEQ ID NO 137
<211> LENGTH: 10
<212> TYPE: PRT
<213> ORGANISM: Epstein-Barr virus

<400> SEQUENCE: 137
```

Leu Pro Pro Cys Pro Ser Val Gly Gln Ile
1               5                   10

<210> SEQ ID NO 138
<211> LENGTH: 9
<212> TYPE: PRT
<213> ORGANISM: Epstein-Barr virus

<400> SEQUENCE: 138

Leu Pro Ser Phe Ser Phe Asn Thr Thr
1               5

<210> SEQ ID NO 139
<211> LENGTH: 10
<212> TYPE: PRT
<213> ORGANISM: Epstein-Barr virus

<400> SEQUENCE: 139

Leu Pro Ser Phe Ser Phe Asn Thr Thr Thr
1               5                   10

<210> SEQ ID NO 140
<211> LENGTH: 10
<212> TYPE: PRT
<213> ORGANISM: Epstein-Barr virus

<400> SEQUENCE: 140

Leu Gln Leu Asp Ala Gln Cys Gln Glu Leu
1               5                   10

<210> SEQ ID NO 141
<211> LENGTH: 9
<212> TYPE: PRT
<213> ORGANISM: Epstein-Barr virus

<400> SEQUENCE: 141

Leu Thr Leu Pro Gly Asn Ile Val Val
1               5

<210> SEQ ID NO 142
<211> LENGTH: 9
<212> TYPE: PRT
<213> ORGANISM: Epstein-Barr virus

<400> SEQUENCE: 142

Met Ala Gln Ala Phe Phe Ile Tyr Ala
1               5

<210> SEQ ID NO 143
<211> LENGTH: 9
<212> TYPE: PRT
<213> ORGANISM: Epstein-Barr virus

<400> SEQUENCE: 143

Asn Pro Tyr Leu Tyr Leu Gln Ile Leu
1               5

<210> SEQ ID NO 144
<211> LENGTH: 9
<212> TYPE: PRT
<213> ORGANISM: Epstein-Barr virus

<400> SEQUENCE: 144

Asn Ser Leu Arg Arg Leu Arg Pro Thr
1               5

<210> SEQ ID NO 145
<211> LENGTH: 9
<212> TYPE: PRT
<213> ORGANISM: Epstein-Barr virus

<400> SEQUENCE: 145

Asn Thr Thr Thr Tyr Gly Ser Arg Tyr
1               5

<210> SEQ ID NO 146
<211> LENGTH: 10
<212> TYPE: PRT
<213> ORGANISM: Epstein-Barr virus

<400> SEQUENCE: 146

Asn Thr Tyr Glu Ala Pro Leu Ser Ser Lys
1               5                   10

<210> SEQ ID NO 147
<211> LENGTH: 9
<212> TYPE: PRT
<213> ORGANISM: Epstein-Barr virus

<400> SEQUENCE: 147

Pro Phe Leu Lys Ser Tyr Ala Arg Ile
1               5

<210> SEQ ID NO 148
<211> LENGTH: 9
<212> TYPE: PRT
<213> ORGANISM: Epstein-Barr virus

<400> SEQUENCE: 148

Pro Ser Tyr Val Arg Val Thr Asn Lys
1               5

<210> SEQ ID NO 149
<211> LENGTH: 9
<212> TYPE: PRT
<213> ORGANISM: Epstein-Barr virus

<400> SEQUENCE: 149

Pro Tyr Pro Lys Ser His Trp Arg Trp
1               5

<210> SEQ ID NO 150
<211> LENGTH: 9
<212> TYPE: PRT
<213> ORGANISM: Epstein-Barr virus

<400> SEQUENCE: 150

Gln Ile Phe Leu Ser Gly Ser Pro Val
1               5

<210> SEQ ID NO 151
<211> LENGTH: 9
<212> TYPE: PRT
<213> ORGANISM: Epstein-Barr virus

<400> SEQUENCE: 151

Gln Leu Asp Ala Gln Cys Gln Glu Leu
1               5

```
<210> SEQ ID NO 152
<211> LENGTH: 9
<212> TYPE: PRT
<213> ORGANISM: Epstein-Barr virus

<400> SEQUENCE: 152

Gln Ser Met Ala Gln Ala Phe Phe Ile
1               5

<210> SEQ ID NO 153
<211> LENGTH: 10
<212> TYPE: PRT
<213> ORGANISM: Epstein-Barr virus

<400> SEQUENCE: 153

Gln Ser Met Ala Gln Ala Phe Phe Ile Tyr
1               5                   10

<210> SEQ ID NO 154
<211> LENGTH: 9
<212> TYPE: PRT
<213> ORGANISM: Epstein-Barr virus

<400> SEQUENCE: 154

Arg Leu Val Lys Asn Pro Tyr Leu Tyr
1               5

<210> SEQ ID NO 155
<211> LENGTH: 10
<212> TYPE: PRT
<213> ORGANISM: Epstein-Barr virus

<400> SEQUENCE: 155

Arg Leu Val Lys Asn Pro Tyr Leu Tyr Leu
1               5                   10

<210> SEQ ID NO 156
<211> LENGTH: 10
<212> TYPE: PRT
<213> ORGANISM: Epstein-Barr virus

<400> SEQUENCE: 156

Arg Pro Thr Glu Lys Pro Asp Thr Ser Phe
1               5                   10

<210> SEQ ID NO 157
<211> LENGTH: 9
<212> TYPE: PRT
<213> ORGANISM: Epstein-Barr virus

<400> SEQUENCE: 157

Arg Ser Leu Phe Ile Glu Lys Gly Lys
1               5

<210> SEQ ID NO 158
<211> LENGTH: 9
<212> TYPE: PRT
<213> ORGANISM: Epstein-Barr virus

<400> SEQUENCE: 158

Arg Ser Ser Phe Arg Asn Ser Leu Arg
1               5

<210> SEQ ID NO 159
<211> LENGTH: 10
```

<212> TYPE: PRT
<213> ORGANISM: Epstein-Barr virus

<400> SEQUENCE: 159

Arg Ser Ser Phe Arg Asn Ser Leu Arg Arg
1               5                   10

<210> SEQ ID NO 160
<211> LENGTH: 10
<212> TYPE: PRT
<213> ORGANISM: Epstein-Barr virus

<400> SEQUENCE: 160

Arg Val Ser Val Asp Thr Pro Asp Leu Lys
1               5                   10

<210> SEQ ID NO 161
<211> LENGTH: 9
<212> TYPE: PRT
<213> ORGANISM: Epstein-Barr virus

<400> SEQUENCE: 161

Arg Tyr Phe Gly Ser Pro Val Ile Ile
1               5

<210> SEQ ID NO 162
<211> LENGTH: 9
<212> TYPE: PRT
<213> ORGANISM: Epstein-Barr virus

<400> SEQUENCE: 162

Arg Tyr Phe Thr Val Ala Phe Leu Phe
1               5

<210> SEQ ID NO 163
<211> LENGTH: 10
<212> TYPE: PRT
<213> ORGANISM: Epstein-Barr virus

<400> SEQUENCE: 163

Arg Tyr Phe Thr Val Ala Phe Leu Phe Phe
1               5                   10

<210> SEQ ID NO 164
<211> LENGTH: 10
<212> TYPE: PRT
<213> ORGANISM: Epstein-Barr virus

<400> SEQUENCE: 164

Arg Tyr Ile Gln Arg Gln Gly Cys Ala Leu
1               5                   10

<210> SEQ ID NO 165
<211> LENGTH: 10
<212> TYPE: PRT
<213> ORGANISM: Epstein-Barr virus

<400> SEQUENCE: 165

Arg Tyr Asn Pro Tyr Pro Lys Ser His Trp
1               5                   10

<210> SEQ ID NO 166
<211> LENGTH: 9
<212> TYPE: PRT
<213> ORGANISM: Epstein-Barr virus

```
<400> SEQUENCE: 166

Ser Phe Lys Leu Pro Ser Phe Ser Phe
1               5

<210> SEQ ID NO 167
<211> LENGTH: 9
<212> TYPE: PRT
<213> ORGANISM: Epstein-Barr virus

<400> SEQUENCE: 167

Ser Phe Met Arg Gly Val Trp Lys Tyr
1               5

<210> SEQ ID NO 168
<211> LENGTH: 10
<212> TYPE: PRT
<213> ORGANISM: Epstein-Barr virus

<400> SEQUENCE: 168

Ser Leu Pro Thr Phe Glu Arg Ile Asn Lys
1               5                   10

<210> SEQ ID NO 169
<211> LENGTH: 10
<212> TYPE: PRT
<213> ORGANISM: Epstein-Barr virus

<400> SEQUENCE: 169

Ser Leu Arg Arg Leu Arg Pro Thr Glu Lys
1               5                   10

<210> SEQ ID NO 170
<211> LENGTH: 9
<212> TYPE: PRT
<213> ORGANISM: Epstein-Barr virus

<400> SEQUENCE: 170

Ser Met Ala Gln Ala Phe Phe Ile Tyr
1               5

<210> SEQ ID NO 171
<211> LENGTH: 10
<212> TYPE: PRT
<213> ORGANISM: Epstein-Barr virus

<400> SEQUENCE: 171

Ser Met Ala Gln Ala Phe Phe Ile Tyr Ala
1               5                   10

<210> SEQ ID NO 172
<211> LENGTH: 10
<212> TYPE: PRT
<213> ORGANISM: Epstein-Barr virus

<400> SEQUENCE: 172

Ser Pro Val Thr Ser Gln Asp Glu Cys Leu
1               5                   10

<210> SEQ ID NO 173
<211> LENGTH: 9
<212> TYPE: PRT
<213> ORGANISM: Epstein-Barr virus

<400> SEQUENCE: 173
```

```
Ser Gln Asp Glu Cys Leu Pro Tyr Leu
1               5
```

<210> SEQ ID NO 174
<211> LENGTH: 10
<212> TYPE: PRT
<213> ORGANISM: Epstein-Barr virus

<400> SEQUENCE: 174

```
Ser Gln Asp Glu Cys Leu Pro Tyr Leu Leu
1               5                   10
```

<210> SEQ ID NO 175
<211> LENGTH: 10
<212> TYPE: PRT
<213> ORGANISM: Epstein-Barr virus

<400> SEQUENCE: 175

```
Ser Arg Arg Ser Ser Phe Arg Asn Ser Leu
1               5                   10
```

<210> SEQ ID NO 176
<211> LENGTH: 9
<212> TYPE: PRT
<213> ORGANISM: Epstein-Barr virus

<400> SEQUENCE: 176

```
Ser Ser Phe Arg Asn Ser Leu Arg Arg
1               5
```

<210> SEQ ID NO 177
<211> LENGTH: 9
<212> TYPE: PRT
<213> ORGANISM: Epstein-Barr virus

<400> SEQUENCE: 177

```
Ser Ser Asn Pro Val Phe Tyr Val Tyr
1               5
```

<210> SEQ ID NO 178
<211> LENGTH: 9
<212> TYPE: PRT
<213> ORGANISM: Epstein-Barr virus

<400> SEQUENCE: 178

```
Ser Val Gly Gln Ile Leu Ser Phe Lys
1               5
```

<210> SEQ ID NO 179
<211> LENGTH: 9
<212> TYPE: PRT
<213> ORGANISM: Epstein-Barr virus

<400> SEQUENCE: 179

```
Thr Phe Glu Arg Ile Asn Lys Thr Phe
1               5
```

<210> SEQ ID NO 180
<211> LENGTH: 9
<212> TYPE: PRT
<213> ORGANISM: Epstein-Barr virus

<400> SEQUENCE: 180

```
Thr Ile Met Arg Arg Tyr Ile Gln Arg
```

```
1               5

<210> SEQ ID NO 181
<211> LENGTH: 9
<212> TYPE: PRT
<213> ORGANISM: Epstein-Barr virus

<400> SEQUENCE: 181

Thr Leu Leu Asp Asp Val Ile Ile Ala
1               5

<210> SEQ ID NO 182
<211> LENGTH: 10
<212> TYPE: PRT
<213> ORGANISM: Epstein-Barr virus

<400> SEQUENCE: 182

Thr Leu Leu Asp Asp Val Ile Ile Ala Phe
1               5                   10

<210> SEQ ID NO 183
<211> LENGTH: 10
<212> TYPE: PRT
<213> ORGANISM: Epstein-Barr virus

<400> SEQUENCE: 183

Thr Pro Asp Leu Lys Arg Glu Gly Pro Leu
1               5                   10

<210> SEQ ID NO 184
<211> LENGTH: 9
<212> TYPE: PRT
<213> ORGANISM: Epstein-Barr virus

<400> SEQUENCE: 184

Thr Ser Phe Met Arg Gly Val Trp Lys
1               5

<210> SEQ ID NO 185
<211> LENGTH: 10
<212> TYPE: PRT
<213> ORGANISM: Epstein-Barr virus

<400> SEQUENCE: 185

Thr Ser Phe Met Arg Gly Val Trp Lys Tyr
1               5                   10

<210> SEQ ID NO 186
<211> LENGTH: 9
<212> TYPE: PRT
<213> ORGANISM: Epstein-Barr virus

<400> SEQUENCE: 186

Thr Ser Gln Asp Glu Cys Leu Pro Tyr
1               5

<210> SEQ ID NO 187
<211> LENGTH: 10
<212> TYPE: PRT
<213> ORGANISM: Epstein-Barr virus

<400> SEQUENCE: 187

Thr Thr Tyr Gly Ser Arg Tyr Phe Thr Val
1               5                   10
```

```
<210> SEQ ID NO 188
<211> LENGTH: 9
<212> TYPE: PRT
<213> ORGANISM: Epstein-Barr virus

<400> SEQUENCE: 188

Thr Val Ala Phe Leu Phe Phe Gly Ala
1               5

<210> SEQ ID NO 189
<211> LENGTH: 10
<212> TYPE: PRT
<213> ORGANISM: Epstein-Barr virus

<400> SEQUENCE: 189

Thr Val Arg Asn Ile Ser Asn Asn Pro Ile
1               5                   10

<210> SEQ ID NO 190
<211> LENGTH: 9
<212> TYPE: PRT
<213> ORGANISM: Epstein-Barr virus

<400> SEQUENCE: 190

Thr Trp Tyr Ile Val Pro Ile Arg Leu
1               5

<210> SEQ ID NO 191
<211> LENGTH: 10
<212> TYPE: PRT
<213> ORGANISM: Epstein-Barr virus

<400> SEQUENCE: 191

Thr Tyr Glu Ala Pro Leu Ser Ser Lys Ile
1               5                   10

<210> SEQ ID NO 192
<211> LENGTH: 9
<212> TYPE: PRT
<213> ORGANISM: Epstein-Barr virus

<400> SEQUENCE: 192

Thr Tyr Gly Ser Arg Tyr Phe Thr Val
1               5

<210> SEQ ID NO 193
<211> LENGTH: 9
<212> TYPE: PRT
<213> ORGANISM: Epstein-Barr virus

<400> SEQUENCE: 193

Val Phe Leu Lys Pro Phe Phe Val Met
1               5

<210> SEQ ID NO 194
<211> LENGTH: 9
<212> TYPE: PRT
<213> ORGANISM: Epstein-Barr virus

<400> SEQUENCE: 194

Val Phe Tyr Val Tyr Pro Gln Glu Trp
1               5

<210> SEQ ID NO 195
```

```
<210> SEQ ID NO 195
<211> LENGTH: 10
<212> TYPE: PRT
<213> ORGANISM: Epstein-Barr virus

<400> SEQUENCE: 195

Val Phe Tyr Val Tyr Pro Gln Glu Trp Lys
1               5                   10

<210> SEQ ID NO 196
<211> LENGTH: 9
<212> TYPE: PRT
<213> ORGANISM: Epstein-Barr virus

<400> SEQUENCE: 196

Val Leu Asn Pro Arg Ser Leu Phe Ile
1               5

<210> SEQ ID NO 197
<211> LENGTH: 10
<212> TYPE: PRT
<213> ORGANISM: Epstein-Barr virus

<400> SEQUENCE: 197

Val Leu Ser Val Leu Asn Pro Arg Ser Leu
1               5                   10

<210> SEQ ID NO 198
<211> LENGTH: 9
<212> TYPE: PRT
<213> ORGANISM: Epstein-Barr virus

<400> SEQUENCE: 198

Val Met His Ser Asp Gln Asp Ile Val
1               5

<210> SEQ ID NO 199
<211> LENGTH: 10
<212> TYPE: PRT
<213> ORGANISM: Epstein-Barr virus

<400> SEQUENCE: 199

Val Met His Ser Asp Gln Asp Ile Val Leu
1               5                   10

<210> SEQ ID NO 200
<211> LENGTH: 10
<212> TYPE: PRT
<213> ORGANISM: Epstein-Barr virus

<400> SEQUENCE: 200

Val Ser His Ser Ser Asn Pro Val Phe Tyr
1               5                   10

<210> SEQ ID NO 201
<211> LENGTH: 10
<212> TYPE: PRT
<213> ORGANISM: Epstein-Barr virus

<400> SEQUENCE: 201

Val Thr Ser Gln Asp Glu Cys Leu Pro Tyr
1               5                   10

<210> SEQ ID NO 202
<211> LENGTH: 9
<212> TYPE: PRT
```

<213> ORGANISM: Epstein-Barr virus

<400> SEQUENCE: 202

Val Val Ser His Ser Ser Asn Pro Val
1               5

<210> SEQ ID NO 203
<211> LENGTH: 9
<212> TYPE: PRT
<213> ORGANISM: Epstein-Barr virus

<400> SEQUENCE: 203

Trp Tyr Ile Val Pro Ile Arg Leu Val
1               5

<210> SEQ ID NO 204
<211> LENGTH: 9
<212> TYPE: PRT
<213> ORGANISM: Epstein-Barr virus

<400> SEQUENCE: 204

Tyr Ala Arg Ile His Thr Phe Pro Gly
1               5

<210> SEQ ID NO 205
<211> LENGTH: 10
<212> TYPE: PRT
<213> ORGANISM: Epstein-Barr virus

<400> SEQUENCE: 205

Tyr Ala Arg Ile His Thr Phe Pro Gly Lys
1               5                   10

<210> SEQ ID NO 206
<211> LENGTH: 9
<212> TYPE: PRT
<213> ORGANISM: Epstein-Barr virus

<400> SEQUENCE: 206

Tyr Phe Thr Val Ala Phe Leu Phe Phe
1               5

<210> SEQ ID NO 207
<211> LENGTH: 9
<212> TYPE: PRT
<213> ORGANISM: Epstein-Barr virus

<400> SEQUENCE: 207

Tyr Ile Gln Arg Gln Gly Cys Ala Leu
1               5

<210> SEQ ID NO 208
<211> LENGTH: 9
<212> TYPE: PRT
<213> ORGANISM: Epstein-Barr virus

<400> SEQUENCE: 208

Tyr Ile Val Pro Ile Arg Leu Val Lys
1               5

<210> SEQ ID NO 209
<211> LENGTH: 10
<212> TYPE: PRT
<213> ORGANISM: Epstein-Barr virus

<400> SEQUENCE: 209

Tyr Leu Leu Ala Gln His Thr Pro Pro Phe
1               5                   10

<210> SEQ ID NO 210
<211> LENGTH: 9
<212> TYPE: PRT
<213> ORGANISM: Epstein-Barr virus

<400> SEQUENCE: 210

Tyr Leu Tyr Leu Gln Ile Leu Pro Gly
1               5

<210> SEQ ID NO 211
<211> LENGTH: 10
<212> TYPE: PRT
<213> ORGANISM: Epstein-Barr virus

<400> SEQUENCE: 211

Tyr Leu Tyr Leu Gln Ile Leu Pro Gly Gln
1               5                   10

<210> SEQ ID NO 212
<211> LENGTH: 9
<212> TYPE: PRT
<213> ORGANISM: Epstein-Barr virus

<400> SEQUENCE: 212

Tyr Pro Gly Gly Ala His Ala Ala Leu
1               5

<210> SEQ ID NO 213
<211> LENGTH: 10
<212> TYPE: PRT
<213> ORGANISM: Epstein-Barr virus

<400> SEQUENCE: 213

Tyr Pro Gly Gly Ala His Ala Ala Leu Ala
1               5                   10

<210> SEQ ID NO 214
<211> LENGTH: 10
<212> TYPE: PRT
<213> ORGANISM: Epstein-Barr virus

<400> SEQUENCE: 214

Tyr Val Arg Val Thr Asn Lys Gln Val Leu
1               5                   10

<210> SEQ ID NO 215
<211> LENGTH: 9
<212> TYPE: PRT
<213> ORGANISM: Epstein-Barr virus

<400> SEQUENCE: 215

Ala Gly Arg Tyr Arg Arg Ile Leu Leu
1               5

<210> SEQ ID NO 216
<211> LENGTH: 9
<212> TYPE: PRT
<213> ORGANISM: Epstein-Barr virus

<400> SEQUENCE: 216

```
Ala Ile Lys Cys Thr Cys Asn Ala Val
1               5

<210> SEQ ID NO 217
<211> LENGTH: 10
<212> TYPE: PRT
<213> ORGANISM: Epstein-Barr virus

<400> SEQUENCE: 217

Ala Leu Ala Ala His Thr Thr Arg Ser Leu
1               5                   10

<210> SEQ ID NO 218
<211> LENGTH: 9
<212> TYPE: PRT
<213> ORGANISM: Epstein-Barr virus

<400> SEQUENCE: 218

Ala Leu Ala Phe Asp Ile Glu Cys Leu
1               5

<210> SEQ ID NO 219
<211> LENGTH: 10
<212> TYPE: PRT
<213> ORGANISM: Epstein-Barr virus

<400> SEQUENCE: 219

Ala Leu Ala Pro Ser Pro Asp Ala Trp Ala
1               5                   10

<210> SEQ ID NO 220
<211> LENGTH: 9
<212> TYPE: PRT
<213> ORGANISM: Epstein-Barr virus

<400> SEQUENCE: 220

Ala Leu Lys Ala Ser Thr Phe Asp Arg
1               5

<210> SEQ ID NO 221
<211> LENGTH: 9
<212> TYPE: PRT
<213> ORGANISM: Epstein-Barr virus

<400> SEQUENCE: 221

Ala Leu Ser Pro Ala Asn Leu Gln Ala
1               5

<210> SEQ ID NO 222
<211> LENGTH: 10
<212> TYPE: PRT
<213> ORGANISM: Epstein-Barr virus

<400> SEQUENCE: 222

Ala Leu Ser Pro Ala Asn Leu Gln Ala Leu
1               5                   10

<210> SEQ ID NO 223
<211> LENGTH: 10
<212> TYPE: PRT
<213> ORGANISM: Epstein-Barr virus

<400> SEQUENCE: 223

Ala Leu Ser Val Leu Gln Asn Phe Thr Ala
1               5                   10
```

```
<210> SEQ ID NO 224
<211> LENGTH: 9
<212> TYPE: PRT
<213> ORGANISM: Epstein-Barr virus

<400> SEQUENCE: 224

Ala Pro Leu Asn Pro Glu Gly Gln Leu
1               5

<210> SEQ ID NO 225
<211> LENGTH: 9
<212> TYPE: PRT
<213> ORGANISM: Epstein-Barr virus

<400> SEQUENCE: 225

Ala Pro Gln Gly Leu Asp Val Glu Phe
1               5

<210> SEQ ID NO 226
<211> LENGTH: 10
<212> TYPE: PRT
<213> ORGANISM: Epstein-Barr virus

<400> SEQUENCE: 226

Ala Pro Ser Pro Asp Ala Trp Ala Pro Leu
1               5                   10

<210> SEQ ID NO 227
<211> LENGTH: 10
<212> TYPE: PRT
<213> ORGANISM: Epstein-Barr virus

<400> SEQUENCE: 227

Ala Ser Leu Leu Thr Ser Trp Leu Ala Lys
1               5                   10

<210> SEQ ID NO 228
<211> LENGTH: 9
<212> TYPE: PRT
<213> ORGANISM: Epstein-Barr virus

<400> SEQUENCE: 228

Ala Val Tyr Gly Phe Thr Gly Val Ala
1               5

<210> SEQ ID NO 229
<211> LENGTH: 9
<212> TYPE: PRT
<213> ORGANISM: Epstein-Barr virus

<400> SEQUENCE: 229

Ala Val Tyr Gln Lys Phe Val Glu Arg
1               5

<210> SEQ ID NO 230
<211> LENGTH: 10
<212> TYPE: PRT
<213> ORGANISM: Epstein-Barr virus

<400> SEQUENCE: 230

Ala Tyr Lys Ser Thr Gln Met Pro His Leu
1               5                   10
```

```
<210> SEQ ID NO 231
<211> LENGTH: 9
<212> TYPE: PRT
<213> ORGANISM: Epstein-Barr virus

<400> SEQUENCE: 231

Cys Leu Phe Asp Asn Asn Ser Gly Ala
1               5

<210> SEQ ID NO 232
<211> LENGTH: 10
<212> TYPE: PRT
<213> ORGANISM: Epstein-Barr virus

<400> SEQUENCE: 232

Cys Leu Phe Asp Asn Asn Ser Gly Ala Ala
1               5                   10

<210> SEQ ID NO 233
<211> LENGTH: 9
<212> TYPE: PRT
<213> ORGANISM: Epstein-Barr virus

<400> SEQUENCE: 233

Cys Leu Gly Glu Glu Gly Phe Pro Thr
1               5

<210> SEQ ID NO 234
<211> LENGTH: 10
<212> TYPE: PRT
<213> ORGANISM: Epstein-Barr virus

<400> SEQUENCE: 234

Cys Leu Gly Glu Glu Gly Phe Pro Thr Ala
1               5                   10

<210> SEQ ID NO 235
<211> LENGTH: 10
<212> TYPE: PRT
<213> ORGANISM: Epstein-Barr virus

<400> SEQUENCE: 235

Cys Leu Ser Ile Ala Glu Thr Val Thr Leu
1               5                   10

<210> SEQ ID NO 236
<211> LENGTH: 10
<212> TYPE: PRT
<213> ORGANISM: Epstein-Barr virus

<400> SEQUENCE: 236

Cys Val Asn Val Phe Gly Gln Gln Ala Tyr
1               5                   10

<210> SEQ ID NO 237
<211> LENGTH: 10
<212> TYPE: PRT
<213> ORGANISM: Epstein-Barr virus

<400> SEQUENCE: 237

Asp Ala Arg Val Lys Glu Ala Ala Ser Leu
1               5                   10

<210> SEQ ID NO 238
<211> LENGTH: 10
```

```
<212> TYPE: PRT
<213> ORGANISM: Epstein-Barr virus

<400> SEQUENCE: 238

Asp Leu Leu Asn His Phe Val Ile His Val
1               5                   10

<210> SEQ ID NO 239
<211> LENGTH: 9
<212> TYPE: PRT
<213> ORGANISM: Epstein-Barr virus

<400> SEQUENCE: 239

Asp Leu Arg Glu Gly Arg Val Pro Met
1               5

<210> SEQ ID NO 240
<211> LENGTH: 9
<212> TYPE: PRT
<213> ORGANISM: Epstein-Barr virus

<400> SEQUENCE: 240

Asp Met Leu Tyr Ala Phe Phe Gln Leu
1               5

<210> SEQ ID NO 241
<211> LENGTH: 10
<212> TYPE: PRT
<213> ORGANISM: Epstein-Barr virus

<400> SEQUENCE: 241

Asp Asn Asp Phe Val Thr Phe Gly Trp Tyr
1               5                   10

<210> SEQ ID NO 242
<211> LENGTH: 9
<212> TYPE: PRT
<213> ORGANISM: Epstein-Barr virus

<400> SEQUENCE: 242

Asp Arg Ala Arg His Ile Tyr Ser Ile
1               5

<210> SEQ ID NO 243
<211> LENGTH: 9
<212> TYPE: PRT
<213> ORGANISM: Epstein-Barr virus

<400> SEQUENCE: 243

Asp Val Arg Gly Pro Gln Pro Pro Leu
1               5

<210> SEQ ID NO 244
<211> LENGTH: 9
<212> TYPE: PRT
<213> ORGANISM: Epstein-Barr virus

<400> SEQUENCE: 244

Glu Ala Gly Arg Tyr Arg Arg Ile Leu
1               5

<210> SEQ ID NO 245
<211> LENGTH: 10
<212> TYPE: PRT
<213> ORGANISM: Epstein-Barr virus
```

```
<400> SEQUENCE: 245

Glu Leu Ser Arg Lys Leu Ser Ala Tyr Lys
1               5                   10

<210> SEQ ID NO 246
<211> LENGTH: 9
<212> TYPE: PRT
<213> ORGANISM: Epstein-Barr virus

<400> SEQUENCE: 246

Glu Met Ala Glu Asp Pro Ala Tyr Ala
1               5

<210> SEQ ID NO 247
<211> LENGTH: 10
<212> TYPE: PRT
<213> ORGANISM: Epstein-Barr virus

<400> SEQUENCE: 247

Glu Tyr Leu Arg Leu Ile Pro Lys Cys Phe
1               5                   10

<210> SEQ ID NO 248
<211> LENGTH: 9
<212> TYPE: PRT
<213> ORGANISM: Epstein-Barr virus

<400> SEQUENCE: 248

Phe Leu Ala Ser Leu Leu Thr Ser Trp
1               5

<210> SEQ ID NO 249
<211> LENGTH: 10
<212> TYPE: PRT
<213> ORGANISM: Epstein-Barr virus

<400> SEQUENCE: 249

Phe Leu Ala Ser Leu Leu Thr Ser Trp Leu
1               5                   10

<210> SEQ ID NO 250
<211> LENGTH: 10
<212> TYPE: PRT
<213> ORGANISM: Epstein-Barr virus

<400> SEQUENCE: 250

Phe Leu Arg Ala Asn Thr Lys Val Arg Ile
1               5                   10

<210> SEQ ID NO 251
<211> LENGTH: 9
<212> TYPE: PRT
<213> ORGANISM: Epstein-Barr virus

<400> SEQUENCE: 251

Phe Leu Arg Pro Asn Lys Gly Leu Leu
1               5

<210> SEQ ID NO 252
<211> LENGTH: 10
<212> TYPE: PRT
<213> ORGANISM: Epstein-Barr virus

<400> SEQUENCE: 252
```

Phe Leu Arg Pro Asn Lys Gly Leu Leu Lys
1               5                   10

<210> SEQ ID NO 253
<211> LENGTH: 10
<212> TYPE: PRT
<213> ORGANISM: Epstein-Barr virus

<400> SEQUENCE: 253

Phe Pro Thr Ala Thr Asn Glu Ala Asp Leu
1               5                   10

<210> SEQ ID NO 254
<211> LENGTH: 9
<212> TYPE: PRT
<213> ORGANISM: Epstein-Barr virus

<400> SEQUENCE: 254

Phe Gln Glu Ser Phe Thr Gln Gly Leu
1               5

<210> SEQ ID NO 255
<211> LENGTH: 9
<212> TYPE: PRT
<213> ORGANISM: Epstein-Barr virus

<400> SEQUENCE: 255

Phe Gln Leu Ile Arg Asp Leu Ser Val
1               5

<210> SEQ ID NO 256
<211> LENGTH: 9
<212> TYPE: PRT
<213> ORGANISM: Epstein-Barr virus

<400> SEQUENCE: 256

Phe Gln Thr Pro Gly Ala Ala Gly Val
1               5

<210> SEQ ID NO 257
<211> LENGTH: 10
<212> TYPE: PRT
<213> ORGANISM: Epstein-Barr virus

<400> SEQUENCE: 257

Phe Gln Thr Pro Gly Ala Ala Gly Val Val
1               5                   10

<210> SEQ ID NO 258
<211> LENGTH: 9
<212> TYPE: PRT
<213> ORGANISM: Epstein-Barr virus

<400> SEQUENCE: 258

Phe Ser Glu Ser Glu Thr Leu Arg Phe
1               5

<210> SEQ ID NO 259
<211> LENGTH: 10
<212> TYPE: PRT
<213> ORGANISM: Epstein-Barr virus

<400> SEQUENCE: 259

Phe Thr Gln Gly Leu Pro Val Gly Phe Leu

```
<210> SEQ ID NO 260
<211> LENGTH: 9
<212> TYPE: PRT
<213> ORGANISM: Epstein-Barr virus

<400> SEQUENCE: 260

Phe Val Ala Pro Ile Ser Leu Glu Ala
1               5

<210> SEQ ID NO 261
<211> LENGTH: 10
<212> TYPE: PRT
<213> ORGANISM: Epstein-Barr virus

<400> SEQUENCE: 261

Phe Val Glu Ala Leu Ser Pro Ala Asn Leu
1               5                   10

<210> SEQ ID NO 262
<211> LENGTH: 10
<212> TYPE: PRT
<213> ORGANISM: Epstein-Barr virus

<400> SEQUENCE: 262

Phe Val Ile His Val Glu Val Ala Glu Ile
1               5                   10

<210> SEQ ID NO 263
<211> LENGTH: 10
<212> TYPE: PRT
<213> ORGANISM: Epstein-Barr virus

<400> SEQUENCE: 263

Phe Val Lys Lys His Val His Glu Ser Phe
1               5                   10

<210> SEQ ID NO 264
<211> LENGTH: 9
<212> TYPE: PRT
<213> ORGANISM: Epstein-Barr virus

<400> SEQUENCE: 264

Phe Val Leu Asp Asn Asp Phe Val Thr
1               5

<210> SEQ ID NO 265
<211> LENGTH: 10
<212> TYPE: PRT
<213> ORGANISM: Epstein-Barr virus

<400> SEQUENCE: 265

Phe Val Leu Asp Asn Asp Phe Val Thr Phe
1               5                   10

<210> SEQ ID NO 266
<211> LENGTH: 9
<212> TYPE: PRT
<213> ORGANISM: Epstein-Barr virus

<400> SEQUENCE: 266

Phe Val Gln Thr Arg Cys Arg Arg Val
1               5
```

<210> SEQ ID NO 267
<211> LENGTH: 10
<212> TYPE: PRT
<213> ORGANISM: Epstein-Barr virus

<400> SEQUENCE: 267

Phe Val Gln Thr Arg Cys Arg Arg Val Leu
1               5                   10

<210> SEQ ID NO 268
<211> LENGTH: 9
<212> TYPE: PRT
<213> ORGANISM: Epstein-Barr virus

<400> SEQUENCE: 268

Phe Tyr Ala Ser Ala Pro Gln Gly Leu
1               5

<210> SEQ ID NO 269
<211> LENGTH: 9
<212> TYPE: PRT
<213> ORGANISM: Epstein-Barr virus

<400> SEQUENCE: 269

Gly Leu Asp Val Glu Phe Ala Val Leu
1               5

<210> SEQ ID NO 270
<211> LENGTH: 9
<212> TYPE: PRT
<213> ORGANISM: Epstein-Barr virus

<400> SEQUENCE: 270

Gly Leu Phe Pro Cys Leu Ser Ile Ala
1               5

<210> SEQ ID NO 271
<211> LENGTH: 9
<212> TYPE: PRT
<213> ORGANISM: Epstein-Barr virus

<400> SEQUENCE: 271

Gly Leu Phe Tyr Asn Pro Phe Leu Arg
1               5

<210> SEQ ID NO 272
<211> LENGTH: 9
<212> TYPE: PRT
<213> ORGANISM: Epstein-Barr virus

<400> SEQUENCE: 272

Gly Leu Ile Pro Ile Asp Met Tyr Ala
1               5

<210> SEQ ID NO 273
<211> LENGTH: 10
<212> TYPE: PRT
<213> ORGANISM: Epstein-Barr virus

<400> SEQUENCE: 273

Gly Leu Ile Pro Ile Asp Met Tyr Ala Val
1               5                   10

<210> SEQ ID NO 274

```
<211> LENGTH: 9
<212> TYPE: PRT
<213> ORGANISM: Epstein-Barr virus

<400> SEQUENCE: 274

Gly Leu Pro Val Gly Phe Leu Pro Val
1               5

<210> SEQ ID NO 275
<211> LENGTH: 10
<212> TYPE: PRT
<213> ORGANISM: Epstein-Barr virus

<400> SEQUENCE: 275

Gly Leu Pro Val Gly Phe Leu Pro Val Ile
1               5                   10

<210> SEQ ID NO 276
<211> LENGTH: 9
<212> TYPE: PRT
<213> ORGANISM: Epstein-Barr virus

<400> SEQUENCE: 276

Gly Met Tyr Cys Val Gln Asp Ser Ala
1               5

<210> SEQ ID NO 277
<211> LENGTH: 10
<212> TYPE: PRT
<213> ORGANISM: Epstein-Barr virus

<400> SEQUENCE: 277

Gly Met Tyr Cys Val Gln Asp Ser Ala Leu
1               5                   10

<210> SEQ ID NO 278
<211> LENGTH: 10
<212> TYPE: PRT
<213> ORGANISM: Epstein-Barr virus

<400> SEQUENCE: 278

Gly Pro Glu Gly Arg Arg Arg Leu Gly Met
1               5                   10

<210> SEQ ID NO 279
<211> LENGTH: 10
<212> TYPE: PRT
<213> ORGANISM: Epstein-Barr virus

<400> SEQUENCE: 279

Gly Gln Gln Ala Tyr Phe Tyr Ala Ser Ala
1               5                   10

<210> SEQ ID NO 280
<211> LENGTH: 10
<212> TYPE: PRT
<213> ORGANISM: Epstein-Barr virus

<400> SEQUENCE: 280

Gly Val Ala Asn Gly Leu Phe Pro Cys Leu
1               5                   10

<210> SEQ ID NO 281
<211> LENGTH: 9
<212> TYPE: PRT
```

<213> ORGANISM: Epstein-Barr virus

<400> SEQUENCE: 281

Gly Val Tyr His Phe Val Lys Lys His
1               5

<210> SEQ ID NO 282
<211> LENGTH: 9
<212> TYPE: PRT
<213> ORGANISM: Epstein-Barr virus

<400> SEQUENCE: 282

Gly Tyr Asn Val Ala Asn Phe Asp Trp
1               5

<210> SEQ ID NO 283
<211> LENGTH: 10
<212> TYPE: PRT
<213> ORGANISM: Epstein-Barr virus

<400> SEQUENCE: 283

His Ile Tyr Ser Ile Asn Pro Ala Ser Leu
1               5                   10

<210> SEQ ID NO 284
<211> LENGTH: 9
<212> TYPE: PRT
<213> ORGANISM: Epstein-Barr virus

<400> SEQUENCE: 284

His Leu Ala Val Tyr Gln Lys Phe Val
1               5

<210> SEQ ID NO 285
<211> LENGTH: 9
<212> TYPE: PRT
<213> ORGANISM: Epstein-Barr virus

<400> SEQUENCE: 285

His Pro Asn Ser Val Cys His Val Ala
1               5

<210> SEQ ID NO 286
<211> LENGTH: 10
<212> TYPE: PRT
<213> ORGANISM: Epstein-Barr virus

<400> SEQUENCE: 286

His Pro Asn Ser Val Cys His Val Ala Thr
1               5                   10

<210> SEQ ID NO 287
<211> LENGTH: 9
<212> TYPE: PRT
<213> ORGANISM: Epstein-Barr virus

<400> SEQUENCE: 287

His Val Ala Thr Trp Leu Gln Asp Lys
1               5

<210> SEQ ID NO 288
<211> LENGTH: 10
<212> TYPE: PRT
<213> ORGANISM: Epstein-Barr virus

```
<400> SEQUENCE: 288

His Val His Glu Ser Phe Leu Ala Ser Leu
1               5                   10

<210> SEQ ID NO 289
<211> LENGTH: 9
<212> TYPE: PRT
<213> ORGANISM: Epstein-Barr virus

<400> SEQUENCE: 289

His Val Tyr Asp Ile Leu Glu Thr Val
1               5

<210> SEQ ID NO 290
<211> LENGTH: 10
<212> TYPE: PRT
<213> ORGANISM: Epstein-Barr virus

<400> SEQUENCE: 290

His Val Tyr Asp Ile Leu Glu Thr Val Tyr
1               5                   10

<210> SEQ ID NO 291
<211> LENGTH: 9
<212> TYPE: PRT
<213> ORGANISM: Epstein-Barr virus

<400> SEQUENCE: 291

His Tyr Lys Glu Ile Pro Arg Leu Phe
1               5

<210> SEQ ID NO 292
<211> LENGTH: 10
<212> TYPE: PRT
<213> ORGANISM: Epstein-Barr virus

<400> SEQUENCE: 292

Ile Ala His Ile Pro Cys Arg Arg Val Leu
1               5                   10

<210> SEQ ID NO 293
<211> LENGTH: 9
<212> TYPE: PRT
<213> ORGANISM: Epstein-Barr virus

<400> SEQUENCE: 293

Ile Ile Gln Ala His Asn Leu Cys Tyr
1               5

<210> SEQ ID NO 294
<211> LENGTH: 9
<212> TYPE: PRT
<213> ORGANISM: Epstein-Barr virus

<400> SEQUENCE: 294

Ile Leu Asp Lys Gln Gln Leu Ala Ile
1               5

<210> SEQ ID NO 295
<211> LENGTH: 10
<212> TYPE: PRT
<213> ORGANISM: Epstein-Barr virus

<400> SEQUENCE: 295
```

```
Ile Leu Asp Lys Gln Gln Leu Ala Ile Lys
1               5                   10
```

<210> SEQ ID NO 296
<211> LENGTH: 9
<212> TYPE: PRT
<213> ORGANISM: Epstein-Barr virus

<400> SEQUENCE: 296

```
Ile Leu Asp Arg Ala Arg His Ile Tyr
1               5
```

<210> SEQ ID NO 297
<211> LENGTH: 10
<212> TYPE: PRT
<213> ORGANISM: Epstein-Barr virus

<400> SEQUENCE: 297

```
Ile Leu Glu Thr Val Tyr Thr His Glu Lys
1               5                   10
```

<210> SEQ ID NO 298
<211> LENGTH: 9
<212> TYPE: PRT
<213> ORGANISM: Epstein-Barr virus

<400> SEQUENCE: 298

```
Ile Leu Asn Gln Ala Tyr Thr Asp Leu
1               5
```

<210> SEQ ID NO 299
<211> LENGTH: 9
<212> TYPE: PRT
<213> ORGANISM: Epstein-Barr virus

<400> SEQUENCE: 299

```
Ile Leu Gln Ile Ser Cys Val Leu Trp
1               5
```

<210> SEQ ID NO 300
<211> LENGTH: 10
<212> TYPE: PRT
<213> ORGANISM: Epstein-Barr virus

<400> SEQUENCE: 300

```
Ile Pro Arg Leu Phe Ala Ala Gly Pro Glu
1               5                   10
```

<210> SEQ ID NO 301
<211> LENGTH: 10
<212> TYPE: PRT
<213> ORGANISM: Epstein-Barr virus

<400> SEQUENCE: 301

```
Ile Pro Arg Leu Gln His Arg Asp Ser Tyr
1               5                   10
```

<210> SEQ ID NO 302
<211> LENGTH: 9
<212> TYPE: PRT
<213> ORGANISM: Epstein-Barr virus

<400> SEQUENCE: 302

```
Ile Pro Ser Asp Lys Gln Gly Tyr Val
1               5
```

<210> SEQ ID NO 303
<211> LENGTH: 10
<212> TYPE: PRT
<213> ORGANISM: Epstein-Barr virus

<400> SEQUENCE: 303

Ile Pro Ser Asp Lys Gln Gly Tyr Val Val
1               5                   10

<210> SEQ ID NO 304
<211> LENGTH: 9
<212> TYPE: PRT
<213> ORGANISM: Epstein-Barr virus

<400> SEQUENCE: 304

Ile Gln Tyr Val Phe Val Glu Pro Lys
1               5

<210> SEQ ID NO 305
<211> LENGTH: 10
<212> TYPE: PRT
<213> ORGANISM: Epstein-Barr virus

<400> SEQUENCE: 305

Ile Thr Gly Leu Ile Pro Ile Asp Met Tyr
1               5                   10

<210> SEQ ID NO 306
<211> LENGTH: 9
<212> TYPE: PRT
<213> ORGANISM: Epstein-Barr virus

<400> SEQUENCE: 306

Ile Thr Lys Lys Arg Tyr Val Gly Val
1               5

<210> SEQ ID NO 307
<211> LENGTH: 10
<212> TYPE: PRT
<213> ORGANISM: Epstein-Barr virus

<400> SEQUENCE: 307

Ile Thr Lys Lys Arg Tyr Val Gly Val Leu
1               5                   10

<210> SEQ ID NO 308
<211> LENGTH: 9
<212> TYPE: PRT
<213> ORGANISM: Epstein-Barr virus

<400> SEQUENCE: 308

Ile Thr Leu Ser His Pro Asn Ser Val
1               5

<210> SEQ ID NO 309
<211> LENGTH: 10
<212> TYPE: PRT
<213> ORGANISM: Epstein-Barr virus

<400> SEQUENCE: 309

Ile Val Ile Lys Leu Leu Gly Arg Arg Lys
1               5                   10

```
<210> SEQ ID NO 310
<211> LENGTH: 9
<212> TYPE: PRT
<213> ORGANISM: Epstein-Barr virus

<400> SEQUENCE: 310

Ile Tyr Gly Asp Thr Asp Ser Leu Phe
1               5

<210> SEQ ID NO 311
<211> LENGTH: 10
<212> TYPE: PRT
<213> ORGANISM: Epstein-Barr virus

<400> SEQUENCE: 311

Ile Tyr Gly Asp Thr Asp Ser Leu Phe Ile
1               5                   10

<210> SEQ ID NO 312
<211> LENGTH: 9
<212> TYPE: PRT
<213> ORGANISM: Epstein-Barr virus

<400> SEQUENCE: 312

Ile Tyr Ser Ile Asn Pro Ala Ser Leu
1               5

<210> SEQ ID NO 313
<211> LENGTH: 9
<212> TYPE: PRT
<213> ORGANISM: Epstein-Barr virus

<400> SEQUENCE: 313

Lys Ala Ile Lys Lys Leu Leu Ala Ala
1               5

<210> SEQ ID NO 314
<211> LENGTH: 9
<212> TYPE: PRT
<213> ORGANISM: Epstein-Barr virus

<400> SEQUENCE: 314

Lys Glu Tyr Leu Arg Leu Ile Pro Lys
1               5

<210> SEQ ID NO 315
<211> LENGTH: 9
<212> TYPE: PRT
<213> ORGANISM: Epstein-Barr virus

<400> SEQUENCE: 315

Lys Gly Phe Leu Arg Ala Asn Thr Lys
1               5

<210> SEQ ID NO 316
<211> LENGTH: 9
<212> TYPE: PRT
<213> ORGANISM: Epstein-Barr virus

<400> SEQUENCE: 316

Lys Ile Ala His Ile Pro Cys Arg Arg
1               5

<210> SEQ ID NO 317
<211> LENGTH: 10
```

```
<212> TYPE: PRT
<213> ORGANISM: Epstein-Barr virus

<400> SEQUENCE: 317

Lys Ile Thr Leu Ser His Pro Asn Ser Val
1               5                   10

<210> SEQ ID NO 318
<211> LENGTH: 9
<212> TYPE: PRT
<213> ORGANISM: Epstein-Barr virus

<400> SEQUENCE: 318

Lys Leu Asp Thr Val Ala Arg His Leu
1               5

<210> SEQ ID NO 319
<211> LENGTH: 10
<212> TYPE: PRT
<213> ORGANISM: Epstein-Barr virus

<400> SEQUENCE: 319

Lys Leu Asp Thr Val Ala Arg His Leu Leu
1               5                   10

<210> SEQ ID NO 320
<211> LENGTH: 9
<212> TYPE: PRT
<213> ORGANISM: Epstein-Barr virus

<400> SEQUENCE: 320

Lys Leu Leu Gln Gly Ala Ala Asn Ile
1               5

<210> SEQ ID NO 321
<211> LENGTH: 10
<212> TYPE: PRT
<213> ORGANISM: Epstein-Barr virus

<400> SEQUENCE: 321

Lys Leu Leu Gln Gly Ala Ala Asn Ile Leu
1               5                   10

<210> SEQ ID NO 322
<211> LENGTH: 10
<212> TYPE: PRT
<213> ORGANISM: Epstein-Barr virus

<400> SEQUENCE: 322

Lys Leu Ser Ala Tyr Lys Ser Thr Gln Met
1               5                   10

<210> SEQ ID NO 323
<211> LENGTH: 9
<212> TYPE: PRT
<213> ORGANISM: Epstein-Barr virus

<400> SEQUENCE: 323

Lys Leu Ser Leu Ser Asp Tyr Lys Leu
1               5

<210> SEQ ID NO 324
<211> LENGTH: 9
<212> TYPE: PRT
<213> ORGANISM: Epstein-Barr virus
```

```
<400> SEQUENCE: 324

Lys Pro Asp Lys Glu Tyr Leu Arg Leu
1               5

<210> SEQ ID NO 325
<211> LENGTH: 10
<212> TYPE: PRT
<213> ORGANISM: Epstein-Barr virus

<400> SEQUENCE: 325

Lys Thr Ala Cys Lys Phe Val Gln Thr Arg
1               5                   10

<210> SEQ ID NO 326
<211> LENGTH: 10
<212> TYPE: PRT
<213> ORGANISM: Epstein-Barr virus

<400> SEQUENCE: 326

Lys Thr Glu Met Ala Glu Asp Pro Ala Tyr
1               5                   10

<210> SEQ ID NO 327
<211> LENGTH: 9
<212> TYPE: PRT
<213> ORGANISM: Epstein-Barr virus

<400> SEQUENCE: 327

Lys Thr Phe Ser Cys Leu Met Leu Ile
1               5

<210> SEQ ID NO 328
<211> LENGTH: 10
<212> TYPE: PRT
<213> ORGANISM: Epstein-Barr virus

<400> SEQUENCE: 328

Lys Thr Leu Met Lys Gly Val Glu Leu Val
1               5                   10

<210> SEQ ID NO 329
<211> LENGTH: 10
<212> TYPE: PRT
<213> ORGANISM: Epstein-Barr virus

<400> SEQUENCE: 329

Lys Val Arg Ile Thr Gly Leu Ile Pro Ile
1               5                   10

<210> SEQ ID NO 330
<211> LENGTH: 10
<212> TYPE: PRT
<213> ORGANISM: Epstein-Barr virus

<400> SEQUENCE: 330

Lys Val Thr Arg Arg Ser Ile Met Gly Tyr
1               5                   10

<210> SEQ ID NO 331
<211> LENGTH: 9
<212> TYPE: PRT
<213> ORGANISM: Epstein-Barr virus

<400> SEQUENCE: 331
```

Leu Ala Ala His Thr Thr Arg Ser Leu
1               5

<210> SEQ ID NO 332
<211> LENGTH: 10
<212> TYPE: PRT
<213> ORGANISM: Epstein-Barr virus

<400> SEQUENCE: 332

Leu Ala Lys Arg Lys Ala Ile Lys Lys Leu
1               5                   10

<210> SEQ ID NO 333
<211> LENGTH: 10
<212> TYPE: PRT
<213> ORGANISM: Epstein-Barr virus

<400> SEQUENCE: 333

Leu Asp Arg Ala Arg His Ile Tyr Ser Ile
1               5                   10

<210> SEQ ID NO 334
<211> LENGTH: 9
<212> TYPE: PRT
<213> ORGANISM: Epstein-Barr virus

<400> SEQUENCE: 334

Leu Ile Leu Gln Ile Ser Cys Val Leu
1               5

<210> SEQ ID NO 335
<211> LENGTH: 9
<212> TYPE: PRT
<213> ORGANISM: Epstein-Barr virus

<400> SEQUENCE: 335

Leu Ile Pro Ile Asp Met Tyr Ala Val
1               5

<210> SEQ ID NO 336
<211> LENGTH: 10
<212> TYPE: PRT
<213> ORGANISM: Epstein-Barr virus

<400> SEQUENCE: 336

Leu Ile Thr Lys Lys Arg Tyr Val Gly Val
1               5                   10

<210> SEQ ID NO 337
<211> LENGTH: 9
<212> TYPE: PRT
<213> ORGANISM: Epstein-Barr virus

<400> SEQUENCE: 337

Leu Leu Asn His Phe Val Ile His Val
1               5

<210> SEQ ID NO 338
<211> LENGTH: 9
<212> TYPE: PRT
<213> ORGANISM: Epstein-Barr virus

<400> SEQUENCE: 338

Leu Leu Gln Gly Ala Ala Asn Ile Leu

```
<210> SEQ ID NO 339
<211> LENGTH: 10
<212> TYPE: PRT
<213> ORGANISM: Epstein-Barr virus

<400> SEQUENCE: 339

Leu Leu Thr Ser Trp Leu Ala Lys Arg Lys
1               5                   10

<210> SEQ ID NO 340
<211> LENGTH: 10
<212> TYPE: PRT
<213> ORGANISM: Epstein-Barr virus

<400> SEQUENCE: 340

Leu Met Lys Gly Val Glu Leu Val Arg Lys
1               5                   10

<210> SEQ ID NO 341
<211> LENGTH: 10
<212> TYPE: PRT
<213> ORGANISM: Epstein-Barr virus

<400> SEQUENCE: 341

Leu Met Leu Ile Thr Lys Lys Arg Tyr Val
1               5                   10

<210> SEQ ID NO 342
<211> LENGTH: 9
<212> TYPE: PRT
<213> ORGANISM: Epstein-Barr virus

<400> SEQUENCE: 342

Leu Pro Val Gly Phe Leu Pro Val Ile
1               5

<210> SEQ ID NO 343
<211> LENGTH: 10
<212> TYPE: PRT
<213> ORGANISM: Epstein-Barr virus

<400> SEQUENCE: 343

Leu Gln Ile Ser Cys Val Leu Trp Ser Thr
1               5                   10

<210> SEQ ID NO 344
<211> LENGTH: 9
<212> TYPE: PRT
<213> ORGANISM: Epstein-Barr virus

<400> SEQUENCE: 344

Leu Ser Arg Lys Leu Ser Ala Tyr Lys
1               5

<210> SEQ ID NO 345
<211> LENGTH: 9
<212> TYPE: PRT
<213> ORGANISM: Epstein-Barr virus

<400> SEQUENCE: 345

Leu Thr Asp Gly Lys Thr Leu Met Lys
1               5
```

<210> SEQ ID NO 346
<211> LENGTH: 9
<212> TYPE: PRT
<213> ORGANISM: Epstein-Barr virus

<400> SEQUENCE: 346

Leu Thr Gly Gly Val Tyr His Phe Val
1               5

<210> SEQ ID NO 347
<211> LENGTH: 10
<212> TYPE: PRT
<213> ORGANISM: Epstein-Barr virus

<400> SEQUENCE: 347

Leu Thr Gly Gly Val Tyr His Phe Val Lys
1               5                   10

<210> SEQ ID NO 348
<211> LENGTH: 9
<212> TYPE: PRT
<213> ORGANISM: Epstein-Barr virus

<400> SEQUENCE: 348

Leu Thr Ser Trp Leu Ala Lys Arg Lys
1               5

<210> SEQ ID NO 349
<211> LENGTH: 10
<212> TYPE: PRT
<213> ORGANISM: Epstein-Barr virus

<400> SEQUENCE: 349

Leu Val Met Asp Leu Leu Asn His Phe Val
1               5                   10

<210> SEQ ID NO 350
<211> LENGTH: 9
<212> TYPE: PRT
<213> ORGANISM: Epstein-Barr virus

<400> SEQUENCE: 350

Leu Val Val Asp Phe Ala Ser Leu Tyr
1               5

<210> SEQ ID NO 351
<211> LENGTH: 9
<212> TYPE: PRT
<213> ORGANISM: Epstein-Barr virus

<400> SEQUENCE: 351

Met Leu Glu Arg Ala Lys Ala Phe Val
1               5

<210> SEQ ID NO 352
<211> LENGTH: 9
<212> TYPE: PRT
<213> ORGANISM: Epstein-Barr virus

<400> SEQUENCE: 352

Met Leu Ile Thr Lys Lys Arg Tyr Val
1               5

<210> SEQ ID NO 353

```
<211> LENGTH: 10
<212> TYPE: PRT
<213> ORGANISM: Epstein-Barr virus

<400> SEQUENCE: 353

Met Leu Ile Thr Lys Lys Arg Tyr Val Gly
1               5                   10

<210> SEQ ID NO 354
<211> LENGTH: 9
<212> TYPE: PRT
<213> ORGANISM: Epstein-Barr virus

<400> SEQUENCE: 354

Met Leu Tyr Ala Phe Phe Gln Leu Ile
1               5

<210> SEQ ID NO 355
<211> LENGTH: 10
<212> TYPE: PRT
<213> ORGANISM: Epstein-Barr virus

<400> SEQUENCE: 355

Met Leu Tyr Ala Phe Phe Gln Leu Ile Arg
1               5                   10

<210> SEQ ID NO 356
<211> LENGTH: 10
<212> TYPE: PRT
<213> ORGANISM: Epstein-Barr virus

<400> SEQUENCE: 356

Met Pro His Leu Ala Val Tyr Gln Lys Phe
1               5                   10

<210> SEQ ID NO 357
<211> LENGTH: 10
<212> TYPE: PRT
<213> ORGANISM: Epstein-Barr virus

<400> SEQUENCE: 357

Met Ser Gly Gly Leu Phe Tyr Asn Pro Phe
1               5                   10

<210> SEQ ID NO 358
<211> LENGTH: 9
<212> TYPE: PRT
<213> ORGANISM: Epstein-Barr virus

<400> SEQUENCE: 358

Met Tyr Ala Val Cys Arg Asp Lys Leu
1               5

<210> SEQ ID NO 359
<211> LENGTH: 9
<212> TYPE: PRT
<213> ORGANISM: Epstein-Barr virus

<400> SEQUENCE: 359

Asn Pro Glu Gly Gln Leu Arg Val Ile
1               5

<210> SEQ ID NO 360
<211> LENGTH: 10
<212> TYPE: PRT
```

<213> ORGANISM: Epstein-Barr virus

<400> SEQUENCE: 360

Asn Pro Phe Leu Arg Pro Asn Lys Gly Leu
1               5                   10

<210> SEQ ID NO 361
<211> LENGTH: 9
<212> TYPE: PRT
<213> ORGANISM: Epstein-Barr virus

<400> SEQUENCE: 361

Asn Thr Lys Val Arg Ile Thr Gly Leu
1               5

<210> SEQ ID NO 362
<211> LENGTH: 10
<212> TYPE: PRT
<213> ORGANISM: Epstein-Barr virus

<400> SEQUENCE: 362

Asn Thr Lys Val Arg Ile Thr Gly Leu Ile
1               5                   10

<210> SEQ ID NO 363
<211> LENGTH: 9
<212> TYPE: PRT
<213> ORGANISM: Epstein-Barr virus

<400> SEQUENCE: 363

Asn Val Ala Asn Phe Asp Trp Pro Tyr
1               5

<210> SEQ ID NO 364
<211> LENGTH: 10
<212> TYPE: PRT
<213> ORGANISM: Epstein-Barr virus

<400> SEQUENCE: 364

Asn Val Ala Asn Phe Asp Trp Pro Tyr Ile
1               5                   10

<210> SEQ ID NO 365
<211> LENGTH: 10
<212> TYPE: PRT
<213> ORGANISM: Epstein-Barr virus

<400> SEQUENCE: 365

Pro Leu Ser Gly Phe Tyr Asn Ser Pro Val
1               5                   10

<210> SEQ ID NO 366
<211> LENGTH: 9
<212> TYPE: PRT
<213> ORGANISM: Epstein-Barr virus

<400> SEQUENCE: 366

Gln Ile His Asp Arg Ile Gln Tyr Val
1               5

<210> SEQ ID NO 367
<211> LENGTH: 9
<212> TYPE: PRT
<213> ORGANISM: Epstein-Barr virus

```
<400> SEQUENCE: 367

Gln Ile Arg Val Phe Ser Cys Leu Leu
1               5

<210> SEQ ID NO 368
<211> LENGTH: 10
<212> TYPE: PRT
<213> ORGANISM: Epstein-Barr virus

<400> SEQUENCE: 368

Gln Leu Ile Arg Asp Leu Ser Val Glu Ile
1               5                   10

<210> SEQ ID NO 369
<211> LENGTH: 10
<212> TYPE: PRT
<213> ORGANISM: Epstein-Barr virus

<400> SEQUENCE: 369

Gln Met Pro His Leu Ala Val Tyr Gln Lys
1               5                   10

<210> SEQ ID NO 370
<211> LENGTH: 10
<212> TYPE: PRT
<213> ORGANISM: Epstein-Barr virus

<400> SEQUENCE: 370

Gln Gln Ile Arg Val Phe Ser Cys Leu Leu
1               5                   10

<210> SEQ ID NO 371
<211> LENGTH: 10
<212> TYPE: PRT
<213> ORGANISM: Epstein-Barr virus

<400> SEQUENCE: 371

Gln Thr Arg Cys Arg Arg Val Leu Asp Leu
1               5                   10

<210> SEQ ID NO 372
<211> LENGTH: 9
<212> TYPE: PRT
<213> ORGANISM: Epstein-Barr virus

<400> SEQUENCE: 372

Arg Ala Lys Ala Phe Val Glu Ala Leu
1               5

<210> SEQ ID NO 373
<211> LENGTH: 9
<212> TYPE: PRT
<213> ORGANISM: Epstein-Barr virus

<400> SEQUENCE: 373

Arg Ile Phe Glu Ala Asn Val Asp Ala
1               5

<210> SEQ ID NO 374
<211> LENGTH: 10
<212> TYPE: PRT
<213> ORGANISM: Epstein-Barr virus

<400> SEQUENCE: 374
```

-continued

Arg Ile Gln Tyr Val Phe Val Glu Pro Lys
1               5                   10

<210> SEQ ID NO 375
<211> LENGTH: 10
<212> TYPE: PRT
<213> ORGANISM: Epstein-Barr virus

<400> SEQUENCE: 375

Arg Leu Phe Ala Ala Gly Pro Glu Gly Arg
1               5                   10

<210> SEQ ID NO 376
<211> LENGTH: 9
<212> TYPE: PRT
<213> ORGANISM: Epstein-Barr virus

<400> SEQUENCE: 376

Arg Leu Ile Pro Lys Cys Phe Gln Thr
1               5

<210> SEQ ID NO 377
<211> LENGTH: 9
<212> TYPE: PRT
<213> ORGANISM: Epstein-Barr virus

<400> SEQUENCE: 377

Arg Leu Thr Gly Gly Val Tyr His Phe
1               5

<210> SEQ ID NO 378
<211> LENGTH: 10
<212> TYPE: PRT
<213> ORGANISM: Epstein-Barr virus

<400> SEQUENCE: 378

Arg Leu Thr Gly Gly Val Tyr His Phe Val
1               5                   10

<210> SEQ ID NO 379
<211> LENGTH: 9
<212> TYPE: PRT
<213> ORGANISM: Epstein-Barr virus

<400> SEQUENCE: 379

Arg Pro Gly Glu Asp Tyr Glu Ser Phe
1               5

<210> SEQ ID NO 380
<211> LENGTH: 9
<212> TYPE: PRT
<213> ORGANISM: Epstein-Barr virus

<400> SEQUENCE: 380

Arg Pro His Asp Ala Gly Lys Gly Phe
1               5

<210> SEQ ID NO 381
<211> LENGTH: 10
<212> TYPE: PRT
<213> ORGANISM: Epstein-Barr virus

<400> SEQUENCE: 381

Arg Pro His Asp Ala Gly Lys Gly Phe Leu
1               5                   10

```
<210> SEQ ID NO 382
<211> LENGTH: 10
<212> TYPE: PRT
<213> ORGANISM: Epstein-Barr virus

<400> SEQUENCE: 382

Arg Thr Met Leu Glu Arg Ala Lys Ala Phe
1               5                   10

<210> SEQ ID NO 383
<211> LENGTH: 10
<212> TYPE: PRT
<213> ORGANISM: Epstein-Barr virus

<400> SEQUENCE: 383

Arg Thr Pro Cys Arg Val Ser Val Glu Lys
1               5                   10

<210> SEQ ID NO 384
<211> LENGTH: 9
<212> TYPE: PRT
<213> ORGANISM: Epstein-Barr virus

<400> SEQUENCE: 384

Arg Val Phe Ser Cys Leu Leu Ala Ala
1               5

<210> SEQ ID NO 385
<211> LENGTH: 10
<212> TYPE: PRT
<213> ORGANISM: Epstein-Barr virus

<400> SEQUENCE: 385

Arg Val Phe Ser Cys Leu Leu Ala Ala Ala
1               5                   10

<210> SEQ ID NO 386
<211> LENGTH: 10
<212> TYPE: PRT
<213> ORGANISM: Epstein-Barr virus

<400> SEQUENCE: 386

Arg Val Ile Tyr Gly Asp Thr Asp Ser Leu
1               5                   10

<210> SEQ ID NO 387
<211> LENGTH: 9
<212> TYPE: PRT
<213> ORGANISM: Epstein-Barr virus

<400> SEQUENCE: 387

Arg Val Lys Glu Ala Ala Ser Leu Leu
1               5

<210> SEQ ID NO 388
<211> LENGTH: 10
<212> TYPE: PRT
<213> ORGANISM: Epstein-Barr virus

<400> SEQUENCE: 388

Arg Val Leu Asp Leu Val Leu Ala Asp Ala
1               5                   10
```

-continued

```
<210> SEQ ID NO 389
<211> LENGTH: 9
<212> TYPE: PRT
<213> ORGANISM: Epstein-Barr virus

<400> SEQUENCE: 389

Arg Tyr Arg Arg Ile Leu Leu Thr Leu
1               5

<210> SEQ ID NO 390
<211> LENGTH: 10
<212> TYPE: PRT
<213> ORGANISM: Epstein-Barr virus

<400> SEQUENCE: 390

Ser Phe Leu Ala Ser Leu Leu Thr Ser Trp
1               5                   10

<210> SEQ ID NO 391
<211> LENGTH: 10
<212> TYPE: PRT
<213> ORGANISM: Epstein-Barr virus

<400> SEQUENCE: 391

Ser Phe Thr Gln Gly Leu Pro Val Gly Phe
1               5                   10

<210> SEQ ID NO 392
<211> LENGTH: 9
<212> TYPE: PRT
<213> ORGANISM: Epstein-Barr virus

<400> SEQUENCE: 392

Ser Ile Met Gly Tyr Gly Asn His Ala
1               5

<210> SEQ ID NO 393
<211> LENGTH: 9
<212> TYPE: PRT
<213> ORGANISM: Epstein-Barr virus

<400> SEQUENCE: 393

Ser Ile Asn Pro Ala Ser Leu Gly Lys
1               5

<210> SEQ ID NO 394
<211> LENGTH: 9
<212> TYPE: PRT
<213> ORGANISM: Epstein-Barr virus

<400> SEQUENCE: 394

Ser Leu Phe Val Ala Pro Ile Ser Leu
1               5

<210> SEQ ID NO 395
<211> LENGTH: 9
<212> TYPE: PRT
<213> ORGANISM: Epstein-Barr virus

<400> SEQUENCE: 395

Ser Leu Leu Thr Ser Trp Leu Ala Lys
1               5

<210> SEQ ID NO 396
<211> LENGTH: 10
```

```
<212> TYPE: PRT
<213> ORGANISM: Epstein-Barr virus

<400> SEQUENCE: 396

Ser Leu Leu Thr Ser Trp Leu Ala Lys Arg
1               5                   10

<210> SEQ ID NO 397
<211> LENGTH: 10
<212> TYPE: PRT
<213> ORGANISM: Epstein-Barr virus

<400> SEQUENCE: 397

Ser Leu Ser Asp Tyr Lys Leu Asp Thr Val
1               5                   10

<210> SEQ ID NO 398
<211> LENGTH: 9
<212> TYPE: PRT
<213> ORGANISM: Epstein-Barr virus

<400> SEQUENCE: 398

Ser Leu Tyr Pro Ser Ile Ile Gln Ala
1               5

<210> SEQ ID NO 399
<211> LENGTH: 10
<212> TYPE: PRT
<213> ORGANISM: Epstein-Barr virus

<400> SEQUENCE: 399

Ser Leu Tyr Pro Ser Ile Ile Gln Ala His
1               5                   10

<210> SEQ ID NO 400
<211> LENGTH: 9
<212> TYPE: PRT
<213> ORGANISM: Epstein-Barr virus

<400> SEQUENCE: 400

Ser Pro Ala Asn Leu Gln Ala Leu Ala
1               5

<210> SEQ ID NO 401
<211> LENGTH: 10
<212> TYPE: PRT
<213> ORGANISM: Epstein-Barr virus

<400> SEQUENCE: 401

Ser Pro Leu Asp Phe His Val Tyr Asp Ile
1               5                   10

<210> SEQ ID NO 402
<211> LENGTH: 10
<212> TYPE: PRT
<213> ORGANISM: Epstein-Barr virus

<400> SEQUENCE: 402

Ser Thr Phe Asp Arg Arg Thr Pro Cys Arg
1               5                   10

<210> SEQ ID NO 403
<211> LENGTH: 9
<212> TYPE: PRT
<213> ORGANISM: Epstein-Barr virus
```

<400> SEQUENCE: 403

Ser Thr Gly Glu Glu Ala Gly Arg Tyr
1               5

<210> SEQ ID NO 404
<211> LENGTH: 10
<212> TYPE: PRT
<213> ORGANISM: Epstein-Barr virus

<400> SEQUENCE: 404

Ser Thr Gln Met Pro His Leu Ala Val Tyr
1               5                   10

<210> SEQ ID NO 405
<211> LENGTH: 9
<212> TYPE: PRT
<213> ORGANISM: Epstein-Barr virus

<400> SEQUENCE: 405

Ser Trp Leu Ala Lys Arg Lys Ala Ile
1               5

<210> SEQ ID NO 406
<211> LENGTH: 10
<212> TYPE: PRT
<213> ORGANISM: Epstein-Barr virus

<400> SEQUENCE: 406

Ser Trp Pro Ser Tyr Gln Ala Leu Ala Phe
1               5                   10

<210> SEQ ID NO 407
<211> LENGTH: 9
<212> TYPE: PRT
<213> ORGANISM: Epstein-Barr virus

<400> SEQUENCE: 407

Ser Tyr Gln Ala Leu Ala Phe Asp Ile
1               5

<210> SEQ ID NO 408
<211> LENGTH: 9
<212> TYPE: PRT
<213> ORGANISM: Epstein-Barr virus

<400> SEQUENCE: 408

Thr Lys Lys Arg Tyr Val Gly Val Leu
1               5

<210> SEQ ID NO 409
<211> LENGTH: 9
<212> TYPE: PRT
<213> ORGANISM: Epstein-Barr virus

<400> SEQUENCE: 409

Thr Leu Met Lys Gly Val Glu Leu Val
1               5

<210> SEQ ID NO 410
<211> LENGTH: 9
<212> TYPE: PRT
<213> ORGANISM: Epstein-Barr virus

<400> SEQUENCE: 410

```
Thr Met Leu Glu Arg Ala Lys Ala Phe
1               5

<210> SEQ ID NO 411
<211> LENGTH: 10
<212> TYPE: PRT
<213> ORGANISM: Epstein-Barr virus

<400> SEQUENCE: 411

Thr Met Leu Glu Arg Ala Lys Ala Phe Val
1               5                   10

<210> SEQ ID NO 412
<211> LENGTH: 10
<212> TYPE: PRT
<213> ORGANISM: Epstein-Barr virus

<400> SEQUENCE: 412

Thr Val Ala Arg His Leu Leu Gly Ala Lys
1               5                   10

<210> SEQ ID NO 413
<211> LENGTH: 9
<212> TYPE: PRT
<213> ORGANISM: Epstein-Barr virus

<400> SEQUENCE: 413

Val Ala Arg His Leu Leu Gly Ala Lys
1               5

<210> SEQ ID NO 414
<211> LENGTH: 10
<212> TYPE: PRT
<213> ORGANISM: Epstein-Barr virus

<400> SEQUENCE: 414

Val Ala Arg His Leu Leu Gly Ala Lys Lys
1               5                   10

<210> SEQ ID NO 415
<211> LENGTH: 9
<212> TYPE: PRT
<213> ORGANISM: Epstein-Barr virus

<400> SEQUENCE: 415

Val Ile Asp Ile Leu Asn Gln Ala Tyr
1               5

<210> SEQ ID NO 416
<211> LENGTH: 9
<212> TYPE: PRT
<213> ORGANISM: Epstein-Barr virus

<400> SEQUENCE: 416

Val Ile Lys Leu Leu Gly Arg Arg Lys
1               5

<210> SEQ ID NO 417
<211> LENGTH: 9
<212> TYPE: PRT
<213> ORGANISM: Epstein-Barr virus

<400> SEQUENCE: 417

Val Ile Gln Pro Leu Ser Gly Phe Tyr
```

```
<210> SEQ ID NO 418
<211> LENGTH: 9
<212> TYPE: PRT
<213> ORGANISM: Epstein-Barr virus

<400> SEQUENCE: 418

Val Ile Tyr Gly Asp Thr Asp Ser Leu
1               5

<210> SEQ ID NO 419
<211> LENGTH: 10
<212> TYPE: PRT
<213> ORGANISM: Epstein-Barr virus

<400> SEQUENCE: 419

Val Leu Ala Asp Ala Arg Val Lys Glu Ala
1               5                   10

<210> SEQ ID NO 420
<211> LENGTH: 10
<212> TYPE: PRT
<213> ORGANISM: Epstein-Barr virus

<400> SEQUENCE: 420

Val Leu Asp Asp Gly Gln Gln Ile Arg Val
1               5                   10

<210> SEQ ID NO 421
<211> LENGTH: 9
<212> TYPE: PRT
<213> ORGANISM: Epstein-Barr virus

<400> SEQUENCE: 421

Val Leu Asp Leu Val Leu Ala Asp Ala
1               5

<210> SEQ ID NO 422
<211> LENGTH: 10
<212> TYPE: PRT
<213> ORGANISM: Epstein-Barr virus

<400> SEQUENCE: 422

Val Leu Thr Asp Gly Lys Thr Leu Met Lys
1               5                   10

<210> SEQ ID NO 423
<211> LENGTH: 9
<212> TYPE: PRT
<213> ORGANISM: Epstein-Barr virus

<400> SEQUENCE: 423

Val Leu Val Val Asp Phe Ala Ser Leu
1               5

<210> SEQ ID NO 424
<211> LENGTH: 9
<212> TYPE: PRT
<213> ORGANISM: Epstein-Barr virus

<400> SEQUENCE: 424

Val Leu Trp Ser Thr Gly Glu Glu Ala
1               5
```

<210> SEQ ID NO 425
<211> LENGTH: 9
<212> TYPE: PRT
<213> ORGANISM: Epstein-Barr virus

<400> SEQUENCE: 425

Val Met Asp Leu Leu Asn His Phe Val
1               5

<210> SEQ ID NO 426
<211> LENGTH: 10
<212> TYPE: PRT
<213> ORGANISM: Epstein-Barr virus

<400> SEQUENCE: 426

Val Met Asp Leu Leu Asn His Phe Val Ile
1               5                   10

<210> SEQ ID NO 427
<211> LENGTH: 9
<212> TYPE: PRT
<213> ORGANISM: Epstein-Barr virus

<400> SEQUENCE: 427

Val Thr Phe Gly Trp Tyr Ser Cys Arg
1               5

<210> SEQ ID NO 428
<211> LENGTH: 10
<212> TYPE: PRT
<213> ORGANISM: Epstein-Barr virus

<400> SEQUENCE: 428

Val Thr Phe Gly Trp Tyr Ser Cys Arg Arg
1               5                   10

<210> SEQ ID NO 429
<211> LENGTH: 9
<212> TYPE: PRT
<213> ORGANISM: Epstein-Barr virus

<400> SEQUENCE: 429

Val Thr Arg Arg Ser Ile Met Gly Tyr
1               5

<210> SEQ ID NO 430
<211> LENGTH: 10
<212> TYPE: PRT
<213> ORGANISM: Epstein-Barr virus

<400> SEQUENCE: 430

Val Tyr Thr His Glu Lys Cys Ala Val Ile
1               5                   10

<210> SEQ ID NO 431
<211> LENGTH: 9
<212> TYPE: PRT
<213> ORGANISM: Epstein-Barr virus

<400> SEQUENCE: 431

Trp Leu Ala Lys Arg Lys Ala Ile Lys
1               5

<210> SEQ ID NO 432

```
<210> SEQ ID NO 432
<211> LENGTH: 10
<212> TYPE: PRT
<213> ORGANISM: Epstein-Barr virus

<400> SEQUENCE: 432

Trp Leu Ala Lys Arg Lys Ala Ile Lys Lys
1               5                   10

<210> SEQ ID NO 433
<211> LENGTH: 10
<212> TYPE: PRT
<213> ORGANISM: Epstein-Barr virus

<400> SEQUENCE: 433

Trp Leu Gln Asp Lys His Gly Cys Arg Ile
1               5                   10

<210> SEQ ID NO 434
<211> LENGTH: 9
<212> TYPE: PRT
<213> ORGANISM: Epstein-Barr virus

<400> SEQUENCE: 434

Trp Pro Ser Tyr Gln Ala Leu Ala Phe
1               5

<210> SEQ ID NO 435
<211> LENGTH: 10
<212> TYPE: PRT
<213> ORGANISM: Epstein-Barr virus

<400> SEQUENCE: 435

Trp Ser Thr Gly Glu Glu Ala Gly Arg Tyr
1               5                   10

<210> SEQ ID NO 436
<211> LENGTH: 9
<212> TYPE: PRT
<213> ORGANISM: Epstein-Barr virus

<400> SEQUENCE: 436

Tyr Ala Glu Arg His Gly Val Pro Val
1               5

<210> SEQ ID NO 437
<211> LENGTH: 10
<212> TYPE: PRT
<213> ORGANISM: Epstein-Barr virus

<400> SEQUENCE: 437

Tyr Ala Val Cys Arg Asp Lys Leu Ser Leu
1               5                   10

<210> SEQ ID NO 438
<211> LENGTH: 10
<212> TYPE: PRT
<213> ORGANISM: Epstein-Barr virus

<400> SEQUENCE: 438

Tyr Phe Tyr Ala Ser Ala Pro Gln Gly Leu
1               5                   10

<210> SEQ ID NO 439
<211> LENGTH: 9
<212> TYPE: PRT
```

<213> ORGANISM: Epstein-Barr virus

<400> SEQUENCE: 439

Tyr Ile Leu Asp Arg Ala Arg His Ile
1               5

<210> SEQ ID NO 440
<211> LENGTH: 9
<212> TYPE: PRT
<213> ORGANISM: Epstein-Barr virus

<400> SEQUENCE: 440

Tyr Leu Arg Leu Ile Pro Lys Cys Phe
1 5

<210> SEQ ID NO 441
<211> LENGTH: 10
<212> TYPE: PRT
<213> ORGANISM: Epstein-Barr virus

<400> SEQUENCE: 441

Tyr Pro Ser Ile Ile Gln Ala His Asn Leu
1 5 10

<210> SEQ ID NO 442
<211> LENGTH: 10
<212> TYPE: PRT
<213> ORGANISM: Epstein-Barr virus

<400> SEQUENCE: 442

Tyr Gln Gly Ala Thr Val Ile Gln Pro Leu
1 5 10

<210> SEQ ID NO 443
<211> LENGTH: 10
<212> TYPE: PRT
<213> ORGANISM: Epstein-Barr virus

<400> SEQUENCE: 443

Tyr Ser Ile Asn Pro Ala Ser Leu Gly Lys
1 5 10

<210> SEQ ID NO 444
<211> LENGTH: 9
<212> TYPE: PRT
<213> ORGANISM: Epstein-Barr virus

<400> SEQUENCE: 444

Tyr Thr Asp Leu Arg Glu Gly Arg Val
1 5

<210> SEQ ID NO 445
<211> LENGTH: 10
<212> TYPE: PRT
<213> ORGANISM: Epstein-Barr virus

<400> SEQUENCE: 445

Tyr Val Phe Val Glu Pro Lys Gly Gly Val
1 5 10

<210> SEQ ID NO 446
<211> LENGTH: 9
<212> TYPE: PRT
<213> ORGANISM: Epstein-Barr virus

```
<400> SEQUENCE: 446

Ala Tyr Ser Ala Arg Pro Pro Leu
1               5

<210> SEQ ID NO 447
<211> LENGTH: 10
<212> TYPE: PRT
<213> ORGANISM: Epstein-Barr virus

<400> SEQUENCE: 447

Cys Ala Tyr Ser Ala Arg Pro Pro Pro Leu
1               5                   10

<210> SEQ ID NO 448
<211> LENGTH: 10
<212> TYPE: PRT
<213> ORGANISM: Epstein-Barr virus

<400> SEQUENCE: 448

Gly Ala Arg Arg Arg Ala Arg Cys Pro Ala
1               5                   10

<210> SEQ ID NO 449
<211> LENGTH: 10
<212> TYPE: PRT
<213> ORGANISM: Epstein-Barr virus

<400> SEQUENCE: 449

Gly Pro Gly Arg Arg Ala Arg Ser Cys Leu
1               5                   10

<210> SEQ ID NO 450
<211> LENGTH: 10
<212> TYPE: PRT
<213> ORGANISM: Epstein-Barr virus

<400> SEQUENCE: 450

Met Ala Gly Ala Arg Arg Arg Ala Arg Cys
1               5                   10

<210> SEQ ID NO 451
<211> LENGTH: 10
<212> TYPE: PRT
<213> ORGANISM: Epstein-Barr virus

<400> SEQUENCE: 451

Arg Pro Gly Pro Gly Arg Arg Ala Arg Ser
1               5                   10

<210> SEQ ID NO 452
<211> LENGTH: 9
<212> TYPE: PRT
<213> ORGANISM: Epstein-Barr virus

<400> SEQUENCE: 452

Arg Pro Pro His Ser Arg Thr Arg Ala
1               5

<210> SEQ ID NO 453
<211> LENGTH: 10
<212> TYPE: PRT
<213> ORGANISM: Epstein-Barr virus

<400> SEQUENCE: 453
```

```
Arg Arg Arg Ala Arg Cys Pro Ala Ser Ala
1               5                   10

<210> SEQ ID NO 454
<211> LENGTH: 9
<212> TYPE: PRT
<213> ORGANISM: Epstein-Barr virus

<400> SEQUENCE: 454

Ser Gly Gln Pro Arg Trp Trp Pro Trp
1               5

<210> SEQ ID NO 455
<211> LENGTH: 9
<212> TYPE: PRT
<213> ORGANISM: Epstein-Barr virus

<400> SEQUENCE: 455

Ser Thr Arg Gly Arg Arg Ile Ser Ala
1               5

<210> SEQ ID NO 456
<211> LENGTH: 9
<212> TYPE: PRT
<213> ORGANISM: Epstein-Barr virus

<400> SEQUENCE: 456

Trp Pro Trp Gly Ser Pro Pro Pro Leu
1               5

<210> SEQ ID NO 457
<211> LENGTH: 10
<212> TYPE: PRT
<213> ORGANISM: Epstein-Barr virus

<400> SEQUENCE: 457

Trp Trp Pro Trp Gly Ser Pro Pro Pro Leu
1               5                   10

<210> SEQ ID NO 458
<211> LENGTH: 9
<212> TYPE: PRT
<213> ORGANISM: Epstein-Barr virus

<400> SEQUENCE: 458

Ala Met Phe Cys Ala Trp Lys Leu Tyr
1               5

<210> SEQ ID NO 459
<211> LENGTH: 10
<212> TYPE: PRT
<213> ORGANISM: Epstein-Barr virus

<400> SEQUENCE: 459

Ala Met Phe Cys Ala Trp Lys Leu Tyr Ser
1               5                   10

<210> SEQ ID NO 460
<211> LENGTH: 10
<212> TYPE: PRT
<213> ORGANISM: Epstein-Barr virus

<400> SEQUENCE: 460

Ala Val Lys Ala Ala Ala Gln Ser Ala Phe
1               5                   10
```

```
<210> SEQ ID NO 461
<211> LENGTH: 9
<212> TYPE: PRT
<213> ORGANISM: Epstein-Barr virus

<400> SEQUENCE: 461

Cys Ala Trp Lys Leu Tyr Ser Arg Lys
1               5

<210> SEQ ID NO 462
<211> LENGTH: 10
<212> TYPE: PRT
<213> ORGANISM: Epstein-Barr virus

<400> SEQUENCE: 462

Phe Ala Asp Ala Trp Arg Met Ala Arg Tyr
1               5                   10

<210> SEQ ID NO 463
<211> LENGTH: 9
<212> TYPE: PRT
<213> ORGANISM: Epstein-Barr virus

<400> SEQUENCE: 463

Lys Leu Tyr Ser Arg Lys Met Pro Ser
1               5

<210> SEQ ID NO 464
<211> LENGTH: 10
<212> TYPE: PRT
<213> ORGANISM: Epstein-Barr virus

<400> SEQUENCE: 464

Lys Leu Tyr Ser Arg Lys Met Pro Ser Arg
1               5                   10

<210> SEQ ID NO 465
<211> LENGTH: 10
<212> TYPE: PRT
<213> ORGANISM: Epstein-Barr virus

<400> SEQUENCE: 465

Lys Pro Pro Thr Val Leu Thr Arg Pro Ala
1               5                   10

<210> SEQ ID NO 466
<211> LENGTH: 10
<212> TYPE: PRT
<213> ORGANISM: Epstein-Barr virus

<400> SEQUENCE: 466

Lys Thr Leu Glu Ala Arg Cys Ser Ser Arg
1               5                   10

<210> SEQ ID NO 467
<211> LENGTH: 9
<212> TYPE: PRT
<213> ORGANISM: Epstein-Barr virus

<400> SEQUENCE: 467

Met Ala Arg Tyr Trp Gly Cys Ala Val
1               5
```

```
<210> SEQ ID NO 468
<211> LENGTH: 10
<212> TYPE: PRT
<213> ORGANISM: Epstein-Barr virus

<400> SEQUENCE: 468

Met Ala Arg Tyr Trp Gly Cys Ala Val Lys
1               5                   10

<210> SEQ ID NO 469
<211> LENGTH: 10
<212> TYPE: PRT
<213> ORGANISM: Epstein-Barr virus

<400> SEQUENCE: 469

Met Pro Ser Arg Ser Lys Thr Leu Glu Ala
1               5                   10

<210> SEQ ID NO 470
<211> LENGTH: 10
<212> TYPE: PRT
<213> ORGANISM: Epstein-Barr virus

<400> SEQUENCE: 470

Met Ser Met Pro Pro Lys Gly Phe Leu Lys
1               5                   10

<210> SEQ ID NO 471
<211> LENGTH: 10
<212> TYPE: PRT
<213> ORGANISM: Epstein-Barr virus

<400> SEQUENCE: 471

Pro Pro Thr Val Leu Thr Arg Pro Ala Met
1               5                   10

<210> SEQ ID NO 472
<211> LENGTH: 10
<212> TYPE: PRT
<213> ORGANISM: Epstein-Barr virus

<400> SEQUENCE: 472

Arg Gly Trp Arg Ala Arg Arg Leu Gly Lys
1               5                   10

<210> SEQ ID NO 473
<211> LENGTH: 10
<212> TYPE: PRT
<213> ORGANISM: Epstein-Barr virus

<400> SEQUENCE: 473

Arg Lys Met Pro Ser Arg Ser Lys Thr Leu
1               5                   10

<210> SEQ ID NO 474
<211> LENGTH: 9
<212> TYPE: PRT
<213> ORGANISM: Epstein-Barr virus

<400> SEQUENCE: 474

Arg Leu Gly Lys Glu Ser Trp Phe Ala
1               5

<210> SEQ ID NO 475
<211> LENGTH: 9
```

```
<212> TYPE: PRT
<213> ORGANISM: Epstein-Barr virus

<400> SEQUENCE: 475

Arg Leu Leu Asn Lys Pro Pro Thr Val
1               5

<210> SEQ ID NO 476
<211> LENGTH: 10
<212> TYPE: PRT
<213> ORGANISM: Epstein-Barr virus

<400> SEQUENCE: 476

Arg Leu Leu Asn Lys Pro Pro Thr Val Leu
1               5                   10

<210> SEQ ID NO 477
<211> LENGTH: 10
<212> TYPE: PRT
<213> ORGANISM: Epstein-Barr virus

<400> SEQUENCE: 477

Arg Met Ala Arg Tyr Trp Gly Cys Ala Val
1               5                   10

<210> SEQ ID NO 478
<211> LENGTH: 10
<212> TYPE: PRT
<213> ORGANISM: Epstein-Barr virus

<400> SEQUENCE: 478

Arg Pro Ala Met Phe Cys Ala Trp Lys Leu
1               5                   10

<210> SEQ ID NO 479
<211> LENGTH: 9
<212> TYPE: PRT
<213> ORGANISM: Epstein-Barr virus

<400> SEQUENCE: 479

Ser Met Pro Pro Lys Gly Phe Leu Lys
1               5

<210> SEQ ID NO 480
<211> LENGTH: 10
<212> TYPE: PRT
<213> ORGANISM: Epstein-Barr virus

<400> SEQUENCE: 480

Ser Met Pro Pro Lys Gly Phe Leu Lys Lys
1               5                   10

<210> SEQ ID NO 481
<211> LENGTH: 9
<212> TYPE: PRT
<213> ORGANISM: Epstein-Barr virus

<400> SEQUENCE: 481

Ser Pro Ala Cys Gln Thr Arg Asp Thr
1               5

<210> SEQ ID NO 482
<211> LENGTH: 9
<212> TYPE: PRT
<213> ORGANISM: Epstein-Barr virus
```

-continued

```
<400> SEQUENCE: 482

Ser Trp Phe Ala Asp Ala Trp Arg Met
1               5

<210> SEQ ID NO 483
<211> LENGTH: 10
<212> TYPE: PRT
<213> ORGANISM: Epstein-Barr virus

<400> SEQUENCE: 483

Val Leu Thr Arg Pro Ala Met Phe Cys Ala
1               5                   10

<210> SEQ ID NO 484
<211> LENGTH: 9
<212> TYPE: PRT
<213> ORGANISM: Epstein-Barr virus

<400> SEQUENCE: 484

Trp Arg Met Ala Arg Tyr Trp Gly Cys
1               5

<210> SEQ ID NO 485
<211> LENGTH: 10
<212> TYPE: PRT
<213> ORGANISM: Epstein-Barr virus

<400> SEQUENCE: 485

Trp Arg Met Ala Arg Tyr Trp Gly Cys Ala
1               5                   10

<210> SEQ ID NO 486
<211> LENGTH: 10
<212> TYPE: PRT
<213> ORGANISM: Epstein-Barr virus

<400> SEQUENCE: 486

Tyr Ser Arg Lys Met Pro Ser Arg Ser Lys
1               5                   10

<210> SEQ ID NO 487
<211> LENGTH: 9
<212> TYPE: PRT
<213> ORGANISM: Epstein-Barr virus

<400> SEQUENCE: 487

Ala Ala Arg Asp Arg Phe Pro Gly Leu
1               5

<210> SEQ ID NO 488
<211> LENGTH: 9
<212> TYPE: PRT
<213> ORGANISM: Epstein-Barr virus

<400> SEQUENCE: 488

Ala Ala Arg Gly Ser Thr Ser Ala Ala
1               5

<210> SEQ ID NO 489
<211> LENGTH: 10
<212> TYPE: PRT
<213> ORGANISM: Epstein-Barr virus

<400> SEQUENCE: 489
```

Ala Ala Arg Gly Ser Thr Ser Ala Ala Val
1               5                   10

<210> SEQ ID NO 490
<211> LENGTH: 10
<212> TYPE: PRT
<213> ORGANISM: Epstein-Barr virus

<400> SEQUENCE: 490

Ala Phe Leu Asp Lys Gly Thr Tyr Thr Leu
1               5                   10

<210> SEQ ID NO 491
<211> LENGTH: 10
<212> TYPE: PRT
<213> ORGANISM: Epstein-Barr virus

<400> SEQUENCE: 491

Ala Leu His Glu Gln Asn Gln Glu Gln Lys
1               5                   10

<210> SEQ ID NO 492
<211> LENGTH: 9
<212> TYPE: PRT
<213> ORGANISM: Epstein-Barr virus

<400> SEQUENCE: 492

Ala Pro Gly Lys Ser Leu Gly Thr Leu
1               5

<210> SEQ ID NO 493
<211> LENGTH: 9
<212> TYPE: PRT
<213> ORGANISM: Epstein-Barr virus

<400> SEQUENCE: 493

Ala Pro Pro Ala Ala Arg Gly Ser Thr
1               5

<210> SEQ ID NO 494
<211> LENGTH: 9
<212> TYPE: PRT
<213> ORGANISM: Epstein-Barr virus

<400> SEQUENCE: 494

Ala Gln Asn Ile Ala Gly Leu Arg Lys
1               5

<210> SEQ ID NO 495
<211> LENGTH: 9
<212> TYPE: PRT
<213> ORGANISM: Epstein-Barr virus

<400> SEQUENCE: 495

Ala Thr Leu Gln Thr Phe Ile Ser Leu
1               5

<210> SEQ ID NO 496
<211> LENGTH: 10
<212> TYPE: PRT
<213> ORGANISM: Epstein-Barr virus

<400> SEQUENCE: 496

Ala Thr Arg Gln Gln Thr Ser Phe Pro Phe

```
1               5                    10
```

<210> SEQ ID NO 497
<211> LENGTH: 9
<212> TYPE: PRT
<213> ORGANISM: Epstein-Barr virus

<400> SEQUENCE: 497

Ala Thr Val Gln Ile Gln Phe Ala Tyr
1               5

<210> SEQ ID NO 498
<211> LENGTH: 9
<212> TYPE: PRT
<213> ORGANISM: Epstein-Barr virus

<400> SEQUENCE: 498

Cys Leu Glu Gln Lys Arg Gln Asn Met
1               5

<210> SEQ ID NO 499
<211> LENGTH: 9
<212> TYPE: PRT
<213> ORGANISM: Epstein-Barr virus

<400> SEQUENCE: 499

Cys Leu Ile Thr Asp Met Met Ala Lys
1               5

<210> SEQ ID NO 500
<211> LENGTH: 9
<212> TYPE: PRT
<213> ORGANISM: Epstein-Barr virus

<400> SEQUENCE: 500

Cys Pro Leu Gln His Trp Gln Thr Phe
1               5

<210> SEQ ID NO 501
<211> LENGTH: 9
<212> TYPE: PRT
<213> ORGANISM: Epstein-Barr virus

<400> SEQUENCE: 501

Cys Gln Ala Thr Ser Gln Tyr Tyr Phe
1               5

<210> SEQ ID NO 502
<211> LENGTH: 9
<212> TYPE: PRT
<213> ORGANISM: Epstein-Barr virus

<400> SEQUENCE: 502

Cys Tyr Ser Arg Pro Leu Val Ser Phe
1               5

<210> SEQ ID NO 503
<211> LENGTH: 10
<212> TYPE: PRT
<213> ORGANISM: Epstein-Barr virus

<400> SEQUENCE: 503

Asp Met Met Ala Lys Ser Asn Ser Pro Phe
1               5                   10

<210> SEQ ID NO 504
<211> LENGTH: 10
<212> TYPE: PRT
<213> ORGANISM: Epstein-Barr virus

<400> SEQUENCE: 504

Asp Ser Phe His Val Arg Thr Asn Tyr Lys
1               5                   10

<210> SEQ ID NO 505
<211> LENGTH: 9
<212> TYPE: PRT
<213> ORGANISM: Epstein-Barr virus

<400> SEQUENCE: 505

Glu Leu Met Asp Ser Leu Gly Ser Val
1               5

<210> SEQ ID NO 506
<211> LENGTH: 10
<212> TYPE: PRT
<213> ORGANISM: Epstein-Barr virus

<400> SEQUENCE: 506

Glu Leu Tyr Asp Ala Pro Gly Trp Leu Ile
1               5                   10

<210> SEQ ID NO 507
<211> LENGTH: 9
<212> TYPE: PRT
<213> ORGANISM: Epstein-Barr virus

<400> SEQUENCE: 507

Glu Asn Arg Thr Ala Tyr Cys Pro Leu
1               5

<210> SEQ ID NO 508
<211> LENGTH: 9
<212> TYPE: PRT
<213> ORGANISM: Epstein-Barr virus

<400> SEQUENCE: 508

Glu Gln Lys Arg Gln Asn Met Val Leu
1               5

<210> SEQ ID NO 509
<211> LENGTH: 9
<212> TYPE: PRT
<213> ORGANISM: Epstein-Barr virus

<400> SEQUENCE: 509

Glu Thr Asp Gln Met Asp Thr Ile Tyr
1               5

<210> SEQ ID NO 510
<211> LENGTH: 9
<212> TYPE: PRT
<213> ORGANISM: Epstein-Barr virus

<400> SEQUENCE: 510

Glu Thr Met Cys Tyr Ser Arg Pro Leu
1               5

<210> SEQ ID NO 511

```
<211> LENGTH: 10
<212> TYPE: PRT
<213> ORGANISM: Epstein-Barr virus

<400> SEQUENCE: 511

Phe Phe Lys Asn Pro Phe Gly Gly Met Leu
1               5                   10

<210> SEQ ID NO 512
<211> LENGTH: 9
<212> TYPE: PRT
<213> ORGANISM: Epstein-Barr virus

<400> SEQUENCE: 512

Phe Ile Ser Leu Asn Thr Ser Leu Ile
1               5

<210> SEQ ID NO 513
<211> LENGTH: 9
<212> TYPE: PRT
<213> ORGANISM: Epstein-Barr virus

<400> SEQUENCE: 513

Phe Ile Thr Ser Gly Gly Leu Leu Leu
1               5

<210> SEQ ID NO 514
<211> LENGTH: 10
<212> TYPE: PRT
<213> ORGANISM: Epstein-Barr virus

<400> SEQUENCE: 514

Phe Ile Thr Ser Gly Gly Leu Leu Leu Ala
1               5                   10

<210> SEQ ID NO 515
<211> LENGTH: 9
<212> TYPE: PRT
<213> ORGANISM: Epstein-Barr virus

<400> SEQUENCE: 515

Phe Leu Asp Lys Gly Thr Tyr Thr Leu
1               5

<210> SEQ ID NO 516
<211> LENGTH: 10
<212> TYPE: PRT
<213> ORGANISM: Epstein-Barr virus

<400> SEQUENCE: 516

Phe Leu Asp Lys Gly Thr Tyr Thr Leu Ser
1               5                   10

<210> SEQ ID NO 517
<211> LENGTH: 9
<212> TYPE: PRT
<213> ORGANISM: Epstein-Barr virus

<400> SEQUENCE: 517

Phe Leu Thr Lys Lys Met Thr Glu Val
1               5

<210> SEQ ID NO 518
<211> LENGTH: 9
<212> TYPE: PRT
```

<213> ORGANISM: Epstein-Barr virus

<400> SEQUENCE: 518

Phe Pro Gly Leu Arg Arg Arg Arg Tyr
1               5

<210> SEQ ID NO 519
<211> LENGTH: 9
<212> TYPE: PRT
<213> ORGANISM: Epstein-Barr virus

<400> SEQUENCE: 519

Phe Gln Ala Gln Asn Ile Ala Gly Leu
1               5

<210> SEQ ID NO 520
<211> LENGTH: 9
<212> TYPE: PRT
<213> ORGANISM: Epstein-Barr virus

<400> SEQUENCE: 520

Phe Gln Ser Gly Asn Glu Ile His Val
1               5

<210> SEQ ID NO 521
<211> LENGTH: 10
<212> TYPE: PRT
<213> ORGANISM: Epstein-Barr virus

<400> SEQUENCE: 521

Phe Ser Phe Ile Asn Asp Thr Lys Thr Tyr
1               5                   10

<210> SEQ ID NO 522
<211> LENGTH: 9
<212> TYPE: PRT
<213> ORGANISM: Epstein-Barr virus

<400> SEQUENCE: 522

Phe Val Asp Gly Leu Gly Glu Leu Met
1               5

<210> SEQ ID NO 523
<211> LENGTH: 9
<212> TYPE: PRT
<213> ORGANISM: Epstein-Barr virus

<400> SEQUENCE: 523

Phe Val Thr Asn Thr Thr Val Gly Ile
1               5

<210> SEQ ID NO 524
<211> LENGTH: 10
<212> TYPE: PRT
<213> ORGANISM: Epstein-Barr virus

<400> SEQUENCE: 524

Phe Tyr Asp Gly Lys Asn Lys Glu Thr Phe
1               5                   10

<210> SEQ ID NO 525
<211> LENGTH: 10
<212> TYPE: PRT
<213> ORGANISM: Epstein-Barr virus

<400> SEQUENCE: 525

Gly Phe Ile Ser Phe Phe Lys Asn Pro Phe
1               5                   10

<210> SEQ ID NO 526
<211> LENGTH: 9
<212> TYPE: PRT
<213> ORGANISM: Epstein-Barr virus

<400> SEQUENCE: 526

Gly Ile Ala Thr Leu Gln Thr Phe Ile
1               5

<210> SEQ ID NO 527
<211> LENGTH: 10
<212> TYPE: PRT
<213> ORGANISM: Epstein-Barr virus

<400> SEQUENCE: 527

Gly Ile Phe Arg Glu Tyr Asn Phe Gln Ala
1               5                   10

<210> SEQ ID NO 528
<211> LENGTH: 9
<212> TYPE: PRT
<213> ORGANISM: Epstein-Barr virus

<400> SEQUENCE: 528

Gly Leu Phe Ser Ser Leu Val Ser Gly
1               5

<210> SEQ ID NO 529
<211> LENGTH: 10
<212> TYPE: PRT
<213> ORGANISM: Epstein-Barr virus

<400> SEQUENCE: 529

Gly Leu Phe Ser Ser Leu Val Ser Gly Phe
1               5                   10

<210> SEQ ID NO 530
<211> LENGTH: 9
<212> TYPE: PRT
<213> ORGANISM: Epstein-Barr virus

<400> SEQUENCE: 530

Gly Leu Gly Glu Leu Met Asp Ser Leu
1               5

<210> SEQ ID NO 531
<211> LENGTH: 9
<212> TYPE: PRT
<213> ORGANISM: Epstein-Barr virus

<400> SEQUENCE: 531

Gly Leu Leu Leu Ala Trp Leu Pro Leu
1               5

<210> SEQ ID NO 532
<211> LENGTH: 10
<212> TYPE: PRT
<213> ORGANISM: Epstein-Barr virus

<400> SEQUENCE: 532

```
Gly Leu Leu Leu Ala Trp Leu Pro Leu Thr
1               5                   10

<210> SEQ ID NO 533
<211> LENGTH: 10
<212> TYPE: PRT
<213> ORGANISM: Epstein-Barr virus

<400> SEQUENCE: 533

Gly Leu Leu Met Val Phe Lys Asp Asn Ile
1               5                   10

<210> SEQ ID NO 534
<211> LENGTH: 10
<212> TYPE: PRT
<213> ORGANISM: Epstein-Barr virus

<400> SEQUENCE: 534

Gly Leu Arg Lys Asp Leu Asp Asn Ala Val
1               5                   10

<210> SEQ ID NO 535
<211> LENGTH: 9
<212> TYPE: PRT
<213> ORGANISM: Epstein-Barr virus

<400> SEQUENCE: 535

Gly Met Leu Ile Leu Val Leu Val Ala
1               5

<210> SEQ ID NO 536
<211> LENGTH: 9
<212> TYPE: PRT
<213> ORGANISM: Epstein-Barr virus

<400> SEQUENCE: 536

Gly Pro Ser Val Ala Ser Arg Ala Leu
1               5

<210> SEQ ID NO 537
<211> LENGTH: 9
<212> TYPE: PRT
<213> ORGANISM: Epstein-Barr virus

<400> SEQUENCE: 537

Gly Gln Glu Ala Ile Thr Tyr Phe Ile
1               5

<210> SEQ ID NO 538
<211> LENGTH: 10
<212> TYPE: PRT
<213> ORGANISM: Epstein-Barr virus

<400> SEQUENCE: 538

Gly Thr Asp Asn Glu Ile Phe Leu Thr Lys
1               5                   10

<210> SEQ ID NO 539
<211> LENGTH: 9
<212> TYPE: PRT
<213> ORGANISM: Epstein-Barr virus

<400> SEQUENCE: 539

Gly Thr Leu Asn Asn Pro Ala Thr Val
1               5
```

-continued

<210> SEQ ID NO 540
<211> LENGTH: 9
<212> TYPE: PRT
<213> ORGANISM: Epstein-Barr virus

<400> SEQUENCE: 540

Gly Thr Tyr Thr Leu Ser Trp Lys Leu
1               5

<210> SEQ ID NO 541
<211> LENGTH: 9
<212> TYPE: PRT
<213> ORGANISM: Epstein-Barr virus

<400> SEQUENCE: 541

Gly Val Asn Ile Thr Val Asn Leu Lys
1               5

<210> SEQ ID NO 542
<211> LENGTH: 10
<212> TYPE: PRT
<213> ORGANISM: Epstein-Barr virus

<400> SEQUENCE: 542

His Thr Glu Gly Leu Leu Met Val Phe Lys
1               5                   10

<210> SEQ ID NO 543
<211> LENGTH: 10
<212> TYPE: PRT
<213> ORGANISM: Epstein-Barr virus

<400> SEQUENCE: 543

His Val Tyr Asn Asp Tyr His His Phe Lys
1               5                   10

<210> SEQ ID NO 544
<211> LENGTH: 9
<212> TYPE: PRT
<213> ORGANISM: Epstein-Barr virus

<400> SEQUENCE: 544

His Trp Gln Thr Phe Asp Ser Thr Ile
1               5

<210> SEQ ID NO 545
<211> LENGTH: 9
<212> TYPE: PRT
<213> ORGANISM: Epstein-Barr virus

<400> SEQUENCE: 545

Ile Leu Ile Tyr Asn Gly Trp Tyr Ala
1               5

<210> SEQ ID NO 546
<211> LENGTH: 9
<212> TYPE: PRT
<213> ORGANISM: Epstein-Barr virus

<400> SEQUENCE: 546

Ile Gln Phe Ala Tyr Asp Ser Leu Arg
1               5

```
<210> SEQ ID NO 547
<211> LENGTH: 10
<212> TYPE: PRT
<213> ORGANISM: Epstein-Barr virus

<400> SEQUENCE: 547

Ile Gln Phe Ala Tyr Asp Ser Leu Arg Arg
1               5                   10

<210> SEQ ID NO 548
<211> LENGTH: 10
<212> TYPE: PRT
<213> ORGANISM: Epstein-Barr virus

<400> SEQUENCE: 548

Ile Tyr Asn Gly Trp Tyr Ala Asp Ser Val
1               5                   10

<210> SEQ ID NO 549
<211> LENGTH: 10
<212> TYPE: PRT
<213> ORGANISM: Epstein-Barr virus

<400> SEQUENCE: 549

Ile Tyr Gln Cys Tyr Asn Ala Val Lys Met
1               5                   10

<210> SEQ ID NO 550
<211> LENGTH: 9
<212> TYPE: PRT
<213> ORGANISM: Epstein-Barr virus

<400> SEQUENCE: 550

Lys Gly Thr Tyr Thr Leu Ser Trp Lys
1               5

<210> SEQ ID NO 551
<211> LENGTH: 9
<212> TYPE: PRT
<213> ORGANISM: Epstein-Barr virus

<400> SEQUENCE: 551

Lys Ile Val Thr Asn Ile Leu Ile Tyr
1               5

<210> SEQ ID NO 552
<211> LENGTH: 9
<212> TYPE: PRT
<213> ORGANISM: Epstein-Barr virus

<400> SEQUENCE: 552

Lys Met Thr Glu Val Cys Gln Ala Thr
1               5

<210> SEQ ID NO 553
<211> LENGTH: 10
<212> TYPE: PRT
<213> ORGANISM: Epstein-Barr virus

<400> SEQUENCE: 553

Lys Met Thr Lys Asp Gly Leu Thr Arg Val
1               5                   10

<210> SEQ ID NO 554
<211> LENGTH: 10
```

<212> TYPE: PRT
<213> ORGANISM: Epstein-Barr virus

<400> SEQUENCE: 554

Lys Pro Thr Gly Gly Leu Ala Asn Gly Val
1               5                   10

<210> SEQ ID NO 555
<211> LENGTH: 10
<212> TYPE: PRT
<213> ORGANISM: Epstein-Barr virus

<400> SEQUENCE: 555

Lys Ser Asn Ser Pro Phe Asp Phe Phe Val
1               5                   10

<210> SEQ ID NO 556
<211> LENGTH: 10
<212> TYPE: PRT
<213> ORGANISM: Epstein-Barr virus

<400> SEQUENCE: 556

Lys Thr Met His Glu Lys Tyr Glu Ala Val
1               5                   10

<210> SEQ ID NO 557
<211> LENGTH: 10
<212> TYPE: PRT
<213> ORGANISM: Epstein-Barr virus

<400> SEQUENCE: 557

Leu Ala Arg Ala Trp Cys Leu Glu Gln Lys
1               5                   10

<210> SEQ ID NO 558
<211> LENGTH: 9
<212> TYPE: PRT
<213> ORGANISM: Epstein-Barr virus

<400> SEQUENCE: 558

Leu Phe Ser Ser Leu Val Ser Gly Phe
1               5

<210> SEQ ID NO 559
<211> LENGTH: 9
<212> TYPE: PRT
<213> ORGANISM: Epstein-Barr virus

<400> SEQUENCE: 559

Leu Ile Leu Val Leu Val Ala Gly Val
1               5

<210> SEQ ID NO 560
<211> LENGTH: 10
<212> TYPE: PRT
<213> ORGANISM: Epstein-Barr virus

<400> SEQUENCE: 560

Leu Ile Leu Val Leu Val Ala Gly Val Val
1               5                   10

<210> SEQ ID NO 561
<211> LENGTH: 9
<212> TYPE: PRT
<213> ORGANISM: Epstein-Barr virus

```
<400> SEQUENCE: 561

Leu Leu Ala Ala Leu Ala Cys Arg Leu
1               5

<210> SEQ ID NO 562
<211> LENGTH: 10
<212> TYPE: PRT
<213> ORGANISM: Epstein-Barr virus

<400> SEQUENCE: 562

Leu Leu Ala Trp Leu Pro Leu Thr Pro Arg
1               5                   10

<210> SEQ ID NO 563
<211> LENGTH: 9
<212> TYPE: PRT
<213> ORGANISM: Epstein-Barr virus

<400> SEQUENCE: 563

Leu Leu Leu Ala Trp Leu Pro Leu Thr
1               5

<210> SEQ ID NO 564
<211> LENGTH: 9
<212> TYPE: PRT
<213> ORGANISM: Epstein-Barr virus

<400> SEQUENCE: 564

Leu Leu Met Val Phe Lys Asp Asn Ile
1               5

<210> SEQ ID NO 565
<211> LENGTH: 10
<212> TYPE: PRT
<213> ORGANISM: Epstein-Barr virus

<400> SEQUENCE: 565

Leu Leu Met Val Phe Lys Asp Asn Ile Ile
1               5                   10

<210> SEQ ID NO 566
<211> LENGTH: 9
<212> TYPE: PRT
<213> ORGANISM: Epstein-Barr virus

<400> SEQUENCE: 566

Leu Pro Leu Thr Pro Arg Ser Leu Ala
1               5

<210> SEQ ID NO 567
<211> LENGTH: 10
<212> TYPE: PRT
<213> ORGANISM: Epstein-Barr virus

<400> SEQUENCE: 567

Leu Pro Leu Thr Pro Arg Ser Leu Ala Thr
1               5                   10

<210> SEQ ID NO 568
<211> LENGTH: 9
<212> TYPE: PRT
<213> ORGANISM: Epstein-Barr virus

<400> SEQUENCE: 568
```

Leu Arg Arg Gln Ile Asn Arg Met Leu
1               5

<210> SEQ ID NO 569
<211> LENGTH: 9
<212> TYPE: PRT
<213> ORGANISM: Epstein-Barr virus

<400> SEQUENCE: 569

Leu Thr Pro Arg Ser Leu Ala Thr Val
1               5

<210> SEQ ID NO 570
<211> LENGTH: 9
<212> TYPE: PRT
<213> ORGANISM: Epstein-Barr virus

<400> SEQUENCE: 570

Leu Val Ala Gly Val Val Ile Leu Val
1               5

<210> SEQ ID NO 571
<211> LENGTH: 10
<212> TYPE: PRT
<213> ORGANISM: Epstein-Barr virus

<400> SEQUENCE: 571

Leu Val Ser Gly Phe Ile Ser Phe Phe Lys
1               5                   10

<210> SEQ ID NO 572
<211> LENGTH: 9
<212> TYPE: PRT
<213> ORGANISM: Epstein-Barr virus

<400> SEQUENCE: 572

Leu Tyr Asp Ala Pro Gly Trp Leu Ile
1               5

<210> SEQ ID NO 573
<211> LENGTH: 10
<212> TYPE: PRT
<213> ORGANISM: Epstein-Barr virus

<400> SEQUENCE: 573

Leu Tyr Asp Ala Pro Gly Trp Leu Ile Trp
1               5                   10

<210> SEQ ID NO 574
<211> LENGTH: 10
<212> TYPE: PRT
<213> ORGANISM: Epstein-Barr virus

<400> SEQUENCE: 574

Met Cys Tyr Ser Arg Pro Leu Val Ser Phe
1               5                   10

<210> SEQ ID NO 575
<211> LENGTH: 10
<212> TYPE: PRT
<213> ORGANISM: Epstein-Barr virus

<400> SEQUENCE: 575

Met Leu Ile Leu Val Leu Val Ala Gly Val

```
1               5              10
```

<210> SEQ ID NO 576
<211> LENGTH: 9
<212> TYPE: PRT
<213> ORGANISM: Epstein-Barr virus

<400> SEQUENCE: 576

```
Met Leu Tyr Pro Gly Ile Asp Glu Leu
1               5
```

<210> SEQ ID NO 577
<211> LENGTH: 10
<212> TYPE: PRT
<213> ORGANISM: Epstein-Barr virus

<400> SEQUENCE: 577

```
Met Leu Tyr Pro Gly Ile Asp Glu Leu Ala
1               5                   10
```

<210> SEQ ID NO 578
<211> LENGTH: 9
<212> TYPE: PRT
<213> ORGANISM: Epstein-Barr virus

<400> SEQUENCE: 578

```
Met Met Ala Lys Ser Asn Ser Pro Phe
1               5
```

<210> SEQ ID NO 579
<211> LENGTH: 10
<212> TYPE: PRT
<213> ORGANISM: Epstein-Barr virus

<400> SEQUENCE: 579

```
Met Ser Gln Gln Pro Val Gln Met Leu Tyr
1               5                   10
```

<210> SEQ ID NO 580
<211> LENGTH: 9
<212> TYPE: PRT
<213> ORGANISM: Epstein-Barr virus

<400> SEQUENCE: 580

```
Met Thr Arg Arg Arg Val Leu Ser Val
1               5
```

<210> SEQ ID NO 581
<211> LENGTH: 10
<212> TYPE: PRT
<213> ORGANISM: Epstein-Barr virus

<400> SEQUENCE: 581

```
Met Thr Arg Arg Arg Val Leu Ser Val Val
1               5                   10
```

<210> SEQ ID NO 582
<211> LENGTH: 10
<212> TYPE: PRT
<213> ORGANISM: Epstein-Barr virus

<400> SEQUENCE: 582

```
Met Val Phe Lys Asp Asn Ile Ile Pro Tyr
1               5                   10
```

```
<210> SEQ ID NO 583
<211> LENGTH: 9
<212> TYPE: PRT
<213> ORGANISM: Epstein-Barr virus

<400> SEQUENCE: 583

Met Val Leu Arg Glu Leu Thr Lys Ile
1               5

<210> SEQ ID NO 584
<211> LENGTH: 10
<212> TYPE: PRT
<213> ORGANISM: Epstein-Barr virus

<400> SEQUENCE: 584

Asn Ile Asp Phe Ala Ser Leu Glu Leu Tyr
1               5                   10

<210> SEQ ID NO 585
<211> LENGTH: 9
<212> TYPE: PRT
<213> ORGANISM: Epstein-Barr virus

<400> SEQUENCE: 585

Asn Ile Ile Pro Tyr Ser Phe Lys Val
1               5

<210> SEQ ID NO 586
<211> LENGTH: 10
<212> TYPE: PRT
<213> ORGANISM: Epstein-Barr virus

<400> SEQUENCE: 586

Asn Ile Leu Ile Tyr Asn Gly Trp Tyr Ala
1               5                   10

<210> SEQ ID NO 587
<211> LENGTH: 9
<212> TYPE: PRT
<213> ORGANISM: Epstein-Barr virus

<400> SEQUENCE: 587

Asn Leu Thr Glu Leu Thr Thr Pro Thr
1               5

<210> SEQ ID NO 588
<211> LENGTH: 9
<212> TYPE: PRT
<213> ORGANISM: Epstein-Barr virus

<400> SEQUENCE: 588

Asn Met Val Leu Arg Glu Leu Thr Lys
1               5

<210> SEQ ID NO 589
<211> LENGTH: 9
<212> TYPE: PRT
<213> ORGANISM: Epstein-Barr virus

<400> SEQUENCE: 589

Asn Pro Ala Thr Val Gln Ile Gln Phe
1               5

<210> SEQ ID NO 590
```

<210> SEQ ID NO 590
<211> LENGTH: 9
<212> TYPE: PRT
<213> ORGANISM: Epstein-Barr virus

<400> SEQUENCE: 590

Asn Pro Phe Gly Gly Met Leu Ile Leu
1               5

<210> SEQ ID NO 591
<211> LENGTH: 9
<212> TYPE: PRT
<213> ORGANISM: Epstein-Barr virus

<400> SEQUENCE: 591

Asn Pro Gln Gly Glu Arg Arg Ala Phe
1               5

<210> SEQ ID NO 592
<211> LENGTH: 10
<212> TYPE: PRT
<213> ORGANISM: Epstein-Barr virus

<400> SEQUENCE: 592

Asn Pro Gln Gly Glu Arg Arg Ala Phe Leu
1               5                   10

<210> SEQ ID NO 593
<211> LENGTH: 9
<212> TYPE: PRT
<213> ORGANISM: Epstein-Barr virus

<400> SEQUENCE: 593

Asn Pro Thr Thr Val Met Ser Ser Ile
1               5

<210> SEQ ID NO 594
<211> LENGTH: 9
<212> TYPE: PRT
<213> ORGANISM: Epstein-Barr virus

<400> SEQUENCE: 594

Pro Pro Ala Ala Pro Gly Lys Ser Leu
1               5

<210> SEQ ID NO 595
<211> LENGTH: 10
<212> TYPE: PRT
<213> ORGANISM: Epstein-Barr virus

<400> SEQUENCE: 595

Pro Pro Ala Ala Arg Gly Ser Thr Ser Ala
1               5                   10

<210> SEQ ID NO 596
<211> LENGTH: 9
<212> TYPE: PRT
<213> ORGANISM: Epstein-Barr virus

<400> SEQUENCE: 596

Gln Met Asp Thr Ile Tyr Gln Cys Tyr
1               5

<210> SEQ ID NO 597
<211> LENGTH: 10
<212> TYPE: PRT

-continued

<213> ORGANISM: Epstein-Barr virus

<400> SEQUENCE: 597

Gln Met Leu Tyr Pro Gly Ile Asp Glu Leu
1               5                   10

<210> SEQ ID NO 598
<211> LENGTH: 9
<212> TYPE: PRT
<213> ORGANISM: Epstein-Barr virus

<400> SEQUENCE: 598

Gln Pro Ala Pro Pro Ala Thr Thr Val
1               5

<210> SEQ ID NO 599
<211> LENGTH: 9
<212> TYPE: PRT
<213> ORGANISM: Epstein-Barr virus

<400> SEQUENCE: 599

Gln Gln Thr Ser Phe Pro Phe Arg Val
1               5

<210> SEQ ID NO 600
<211> LENGTH: 9
<212> TYPE: PRT
<213> ORGANISM: Epstein-Barr virus

<400> SEQUENCE: 600

Gln Thr Val Glu Met Ser Pro Phe Tyr
1               5

<210> SEQ ID NO 601
<211> LENGTH: 9
<212> TYPE: PRT
<213> ORGANISM: Epstein-Barr virus

<400> SEQUENCE: 601

Gln Val Asn Lys Thr Met His Glu Lys
1               5

<210> SEQ ID NO 602
<211> LENGTH: 10
<212> TYPE: PRT
<213> ORGANISM: Epstein-Barr virus

<400> SEQUENCE: 602

Gln Tyr Tyr Phe Gln Ser Gly Asn Glu Ile
1               5                   10

<210> SEQ ID NO 603
<211> LENGTH: 9
<212> TYPE: PRT
<213> ORGANISM: Epstein-Barr virus

<400> SEQUENCE: 603

Arg Met Leu Gly Asp Leu Ala Arg Ala
1               5

<210> SEQ ID NO 604
<211> LENGTH: 10
<212> TYPE: PRT
<213> ORGANISM: Epstein-Barr virus -continued

```
<400> SEQUENCE: 604

Arg Met Leu Gly Asp Leu Ala Arg Ala Trp
1               5                   10

<210> SEQ ID NO 605
<211> LENGTH: 9
<212> TYPE: PRT
<213> ORGANISM: Epstein-Barr virus

<400> SEQUENCE: 605

Arg Pro Leu Val Ser Phe Ser Phe Ile
1               5

<210> SEQ ID NO 606
<211> LENGTH: 9
<212> TYPE: PRT
<213> ORGANISM: Epstein-Barr virus

<400> SEQUENCE: 606

Arg Gln Gln Thr Ser Phe Pro Phe Arg
1               5

<210> SEQ ID NO 607
<211> LENGTH: 10
<212> TYPE: PRT
<213> ORGANISM: Epstein-Barr virus

<400> SEQUENCE: 607

Arg Gln Gln Thr Ser Phe Pro Phe Arg Val
1               5                   10

<210> SEQ ID NO 608
<211> LENGTH: 9
<212> TYPE: PRT
<213> ORGANISM: Epstein-Barr virus

<400> SEQUENCE: 608

Arg Thr Ala Tyr Cys Pro Leu Gln His
1               5

<210> SEQ ID NO 609
<211> LENGTH: 9
<212> TYPE: PRT
<213> ORGANISM: Epstein-Barr virus

<400> SEQUENCE: 609

Arg Thr Asn Tyr Lys Ile Val Asp Tyr
1               5

<210> SEQ ID NO 610
<211> LENGTH: 10
<212> TYPE: PRT
<213> ORGANISM: Epstein-Barr virus

<400> SEQUENCE: 610

Arg Thr Arg Gln Met Ser Gln Gln Pro Val
1               5                   10

<210> SEQ ID NO 611
<211> LENGTH: 9
<212> TYPE: PRT
<213> ORGANISM: Epstein-Barr virus

<400> SEQUENCE: 611
```

```
Arg Thr Arg Thr Thr Val Asn Cys Leu
1               5

<210> SEQ ID NO 612
<211> LENGTH: 9
<212> TYPE: PRT
<213> ORGANISM: Epstein-Barr virus

<400> SEQUENCE: 612

Arg Val Leu Ser Val Val Val Leu Leu
1               5

<210> SEQ ID NO 613
<211> LENGTH: 10
<212> TYPE: PRT
<213> ORGANISM: Epstein-Barr virus

<400> SEQUENCE: 613

Arg Val Leu Ser Val Val Val Leu Leu Ala
1               5                   10

<210> SEQ ID NO 614
<211> LENGTH: 9
<212> TYPE: PRT
<213> ORGANISM: Epstein-Barr virus

<400> SEQUENCE: 614

Arg Tyr Ala Ser Gln Thr Glu Leu Tyr
1               5

<210> SEQ ID NO 615
<211> LENGTH: 9
<212> TYPE: PRT
<213> ORGANISM: Epstein-Barr virus

<400> SEQUENCE: 615

Arg Tyr Thr Lys Gly Gln Glu Ala Ile
1               5

<210> SEQ ID NO 616
<211> LENGTH: 9
<212> TYPE: PRT
<213> ORGANISM: Epstein-Barr virus

<400> SEQUENCE: 616

Ser Phe His Val Arg Thr Asn Tyr Lys
1               5

<210> SEQ ID NO 617
<211> LENGTH: 10
<212> TYPE: PRT
<213> ORGANISM: Epstein-Barr virus

<400> SEQUENCE: 617

Ser Phe His Val Arg Thr Asn Tyr Lys Ile
1               5                   10

<210> SEQ ID NO 618
<211> LENGTH: 10
<212> TYPE: PRT
<213> ORGANISM: Epstein-Barr virus

<400> SEQUENCE: 618

Ser Phe Lys Val Arg Ser Tyr Thr Lys Ile
1               5                   10
```

<210> SEQ ID NO 619
<211> LENGTH: 9
<212> TYPE: PRT
<213> ORGANISM: Epstein-Barr virus

<400> SEQUENCE: 619

Ser Phe Pro Phe Arg Val Cys Glu Leu
1               5

<210> SEQ ID NO 620
<211> LENGTH: 9
<212> TYPE: PRT
<213> ORGANISM: Epstein-Barr virus

<400> SEQUENCE: 620

Ser Ile Thr Asn Leu Val Ser Thr Val
1               5

<210> SEQ ID NO 621
<211> LENGTH: 9
<212> TYPE: PRT
<213> ORGANISM: Epstein-Barr virus

<400> SEQUENCE: 621

Ser Ile Tyr Gly Lys Ala Val Ala Ala
1               5

<210> SEQ ID NO 622
<211> LENGTH: 10
<212> TYPE: PRT
<213> ORGANISM: Epstein-Barr virus

<400> SEQUENCE: 622

Ser Ile Tyr Gly Lys Ala Val Ala Ala Lys
1               5                   10

<210> SEQ ID NO 623
<211> LENGTH: 9
<212> TYPE: PRT
<213> ORGANISM: Epstein-Barr virus

<400> SEQUENCE: 623

Ser Leu Gly Ser Val Gly Gln Ser Ile
1               5

<210> SEQ ID NO 624
<211> LENGTH: 9
<212> TYPE: PRT
<213> ORGANISM: Epstein-Barr virus

<400> SEQUENCE: 624

Ser Leu Ile Glu Asn Ile Asp Phe Ala
1               5

<210> SEQ ID NO 625
<211> LENGTH: 10
<212> TYPE: PRT
<213> ORGANISM: Epstein-Barr virus

<400> SEQUENCE: 625

Ser Leu Ile Glu Asn Ile Asp Phe Ala Ser
1               5                   10

```
<210> SEQ ID NO 626
<211> LENGTH: 10
<212> TYPE: PRT
<213> ORGANISM: Epstein-Barr virus

<400> SEQUENCE: 626

Ser Leu Asn Thr Ser Leu Ile Glu Asn Ile
1               5                   10

<210> SEQ ID NO 627
<211> LENGTH: 9
<212> TYPE: PRT
<213> ORGANISM: Epstein-Barr virus

<400> SEQUENCE: 627

Ser Leu Arg Arg Gln Ile Asn Arg Met
1               5

<210> SEQ ID NO 628
<211> LENGTH: 10
<212> TYPE: PRT
<213> ORGANISM: Epstein-Barr virus

<400> SEQUENCE: 628

Ser Leu Arg Arg Gln Ile Asn Arg Met Leu
1               5                   10

<210> SEQ ID NO 629
<211> LENGTH: 9
<212> TYPE: PRT
<213> ORGANISM: Epstein-Barr virus

<400> SEQUENCE: 629

Ser Leu Thr Arg Arg Thr Arg Gln Met
1               5

<210> SEQ ID NO 630
<211> LENGTH: 9
<212> TYPE: PRT
<213> ORGANISM: Epstein-Barr virus

<400> SEQUENCE: 630

Ser Leu Val Ser Gly Phe Ile Ser Phe
1               5

<210> SEQ ID NO 631
<211> LENGTH: 10
<212> TYPE: PRT
<213> ORGANISM: Epstein-Barr virus

<400> SEQUENCE: 631

Ser Leu Val Ser Gly Phe Ile Ser Phe Phe
1               5                   10

<210> SEQ ID NO 632
<211> LENGTH: 10
<212> TYPE: PRT
<213> ORGANISM: Epstein-Barr virus

<400> SEQUENCE: 632

Ser Met Arg Val Pro Gly Ser Glu Thr Met
1               5                   10

<210> SEQ ID NO 633
<211> LENGTH: 10
```

```
<212> TYPE: PRT
<213> ORGANISM: Epstein-Barr virus

<400> SEQUENCE: 633

Ser Pro Pro Ser Ser Pro Ser Pro Pro Ala
1               5                   10

<210> SEQ ID NO 634
<211> LENGTH: 9
<212> TYPE: PRT
<213> ORGANISM: Epstein-Barr virus

<400> SEQUENCE: 634

Ser Pro Ser Pro Pro Ala Pro Pro Ala
1               5

<210> SEQ ID NO 635
<211> LENGTH: 10
<212> TYPE: PRT
<213> ORGANISM: Epstein-Barr virus

<400> SEQUENCE: 635

Ser Pro Ser Pro Pro Ala Pro Pro Ala Ala
1               5                   10

<210> SEQ ID NO 636
<211> LENGTH: 9
<212> TYPE: PRT
<213> ORGANISM: Epstein-Barr virus

<400> SEQUENCE: 636

Ser Thr Ile Ala Thr Glu Thr Gly Lys
1               5

<210> SEQ ID NO 637
<211> LENGTH: 10
<212> TYPE: PRT
<213> ORGANISM: Epstein-Barr virus

<400> SEQUENCE: 637

Ser Thr Val Gly Gly Leu Phe Ser Ser Leu
1               5                   10

<210> SEQ ID NO 638
<211> LENGTH: 10
<212> TYPE: PRT
<213> ORGANISM: Epstein-Barr virus

<400> SEQUENCE: 638

Ser Val Gly Gln Ser Ile Thr Asn Leu Val
1               5                   10

<210> SEQ ID NO 639
<211> LENGTH: 9
<212> TYPE: PRT
<213> ORGANISM: Epstein-Barr virus

<400> SEQUENCE: 639

Ser Val Val Val Leu Leu Ala Ala Leu
1               5

<210> SEQ ID NO 640
<211> LENGTH: 9
<212> TYPE: PRT
<213> ORGANISM: Epstein-Barr virus
```

```
<400> SEQUENCE: 640

Ser Tyr Thr Lys Ile Val Thr Asn Ile
1               5

<210> SEQ ID NO 641
<211> LENGTH: 10
<212> TYPE: PRT
<213> ORGANISM: Epstein-Barr virus

<400> SEQUENCE: 641

Ser Tyr Thr Lys Ile Val Thr Asn Ile Leu
1               5                   10

<210> SEQ ID NO 642
<211> LENGTH: 9
<212> TYPE: PRT
<213> ORGANISM: Epstein-Barr virus

<400> SEQUENCE: 642

Thr Phe His Glu Arg Ala Asp Ser Phe
1               5

<210> SEQ ID NO 643
<211> LENGTH: 10
<212> TYPE: PRT
<213> ORGANISM: Epstein-Barr virus

<400> SEQUENCE: 643

Thr Phe Ile Ser Leu Asn Thr Ser Leu Ile
1               5                   10

<210> SEQ ID NO 644
<211> LENGTH: 9
<212> TYPE: PRT
<213> ORGANISM: Epstein-Barr virus

<400> SEQUENCE: 644

Thr Ile Tyr Gln Cys Tyr Asn Ala Val
1               5

<210> SEQ ID NO 645
<211> LENGTH: 10
<212> TYPE: PRT
<213> ORGANISM: Epstein-Barr virus

<400> SEQUENCE: 645

Thr Ile Tyr Gln Cys Tyr Asn Ala Val Lys
1               5                   10

<210> SEQ ID NO 646
<211> LENGTH: 9
<212> TYPE: PRT
<213> ORGANISM: Epstein-Barr virus

<400> SEQUENCE: 646

Thr Met Cys Tyr Ser Arg Pro Leu Val
1               5

<210> SEQ ID NO 647
<211> LENGTH: 9
<212> TYPE: PRT
<213> ORGANISM: Epstein-Barr virus

<400> SEQUENCE: 647
```

Thr Met His Glu Lys Tyr Glu Ala Val
1               5

<210> SEQ ID NO 648
<211> LENGTH: 10
<212> TYPE: PRT
<213> ORGANISM: Epstein-Barr virus

<400> SEQUENCE: 648

Thr Thr Val Met Ser Ser Ile Tyr Gly Lys
1               5                   10

<210> SEQ ID NO 649
<211> LENGTH: 10
<212> TYPE: PRT
<213> ORGANISM: Epstein-Barr virus

<400> SEQUENCE: 649

Thr Val Gly Gly Leu Phe Ser Ser Leu Val
1               5                   10

<210> SEQ ID NO 650
<211> LENGTH: 9
<212> TYPE: PRT
<213> ORGANISM: Epstein-Barr virus

<400> SEQUENCE: 650

Thr Val Met Ser Ser Ile Tyr Gly Lys
1               5

<210> SEQ ID NO 651
<211> LENGTH: 10
<212> TYPE: PRT
<213> ORGANISM: Epstein-Barr virus

<400> SEQUENCE: 651

Thr Tyr Phe Ile Thr Ser Gly Gly Leu Leu
1               5                   10

<210> SEQ ID NO 652
<211> LENGTH: 9
<212> TYPE: PRT
<213> ORGANISM: Epstein-Barr virus

<400> SEQUENCE: 652

Val Ile Leu Val Ile Ser Leu Thr Arg
1               5

<210> SEQ ID NO 653
<211> LENGTH: 10
<212> TYPE: PRT
<213> ORGANISM: Epstein-Barr virus

<400> SEQUENCE: 653

Val Ile Leu Val Ile Ser Leu Thr Arg Arg
1               5                   10

<210> SEQ ID NO 654
<211> LENGTH: 10
<212> TYPE: PRT
<213> ORGANISM: Epstein-Barr virus

<400> SEQUENCE: 654

Val Ile Ser Val Ser Gln Cys Val Pro Val

```
<210> SEQ ID NO 655
<211> LENGTH: 9
<212> TYPE: PRT
<213> ORGANISM: Epstein-Barr virus

<400> SEQUENCE: 655

Val Leu Leu Ala Ala Leu Ala Cys Arg
1               5

<210> SEQ ID NO 656
<211> LENGTH: 10
<212> TYPE: PRT
<213> ORGANISM: Epstein-Barr virus

<400> SEQUENCE: 656

Val Leu Leu Ala Ala Leu Ala Cys Arg Leu
1               5                   10

<210> SEQ ID NO 657
<211> LENGTH: 9
<212> TYPE: PRT
<213> ORGANISM: Epstein-Barr virus

<400> SEQUENCE: 657

Val Leu Arg Arg Arg Arg Arg Asp Ala
1               5

<210> SEQ ID NO 658
<211> LENGTH: 10
<212> TYPE: PRT
<213> ORGANISM: Epstein-Barr virus

<400> SEQUENCE: 658

Val Leu Arg Arg Arg Arg Arg Asp Ala Gly
1               5                   10

<210> SEQ ID NO 659
<211> LENGTH: 9
<212> TYPE: PRT
<213> ORGANISM: Epstein-Barr virus

<400> SEQUENCE: 659

Val Leu Ser Val Val Val Leu Leu Ala
1               5

<210> SEQ ID NO 660
<211> LENGTH: 10
<212> TYPE: PRT
<213> ORGANISM: Epstein-Barr virus

<400> SEQUENCE: 660

Val Leu Ser Val Val Val Leu Leu Ala Ala
1               5                   10

<210> SEQ ID NO 661
<211> LENGTH: 9
<212> TYPE: PRT
<213> ORGANISM: Epstein-Barr virus

<400> SEQUENCE: 661

Val Leu Val Ala Gly Val Val Ile Leu
1               5
```

<210> SEQ ID NO 662
<211> LENGTH: 10
<212> TYPE: PRT
<213> ORGANISM: Epstein-Barr virus

<400> SEQUENCE: 662

Val Leu Val Ala Gly Val Val Ile Leu Val
1               5                   10

<210> SEQ ID NO 663
<211> LENGTH: 9
<212> TYPE: PRT
<213> ORGANISM: Epstein-Barr virus

<400> SEQUENCE: 663

Val Met Ser Ser Ile Tyr Gly Lys Ala
1               5

<210> SEQ ID NO 664
<211> LENGTH: 10
<212> TYPE: PRT
<213> ORGANISM: Epstein-Barr virus

<400> SEQUENCE: 664

Val Met Ser Ser Ile Tyr Gly Lys Ala Val
1               5                   10

<210> SEQ ID NO 665
<211> LENGTH: 10
<212> TYPE: PRT
<213> ORGANISM: Epstein-Barr virus

<400> SEQUENCE: 665

Val Pro Pro Ala Ala Pro Gly Lys Ser Leu
1               5                   10

<210> SEQ ID NO 666
<211> LENGTH: 10
<212> TYPE: PRT
<213> ORGANISM: Epstein-Barr virus

<400> SEQUENCE: 666

Val Pro Val Asn Gln Ala Thr Val Thr Leu
1               5                   10

<210> SEQ ID NO 667
<211> LENGTH: 10
<212> TYPE: PRT
<213> ORGANISM: Epstein-Barr virus

<400> SEQUENCE: 667

Val Ser Phe Ser Phe Ile Asn Asp Thr Lys
1               5                   10

<210> SEQ ID NO 668
<211> LENGTH: 9
<212> TYPE: PRT
<213> ORGANISM: Epstein-Barr virus

<400> SEQUENCE: 668

Val Ser Gly Phe Ile Ser Phe Phe Lys
1               5

<210> SEQ ID NO 669

```
<211> LENGTH: 9
<212> TYPE: PRT
<213> ORGANISM: Epstein-Barr virus

<400> SEQUENCE: 669

Val Thr Asp Glu Gly Thr Ser Ser Phe
1               5

<210> SEQ ID NO 670
<211> LENGTH: 10
<212> TYPE: PRT
<213> ORGANISM: Epstein-Barr virus

<400> SEQUENCE: 670

Val Thr Asp Glu Gly Thr Ser Ser Phe Val
1               5                   10

<210> SEQ ID NO 671
<211> LENGTH: 10
<212> TYPE: PRT
<213> ORGANISM: Epstein-Barr virus

<400> SEQUENCE: 671

Val Tyr Val Asp Arg Asp Gly Val Asn Ile
1               5                   10

<210> SEQ ID NO 672
<211> LENGTH: 9
<212> TYPE: PRT
<213> ORGANISM: Epstein-Barr virus

<400> SEQUENCE: 672

Tyr Ala Asp Ser Val Thr Asn Arg His
1               5

<210> SEQ ID NO 673
<211> LENGTH: 10
<212> TYPE: PRT
<213> ORGANISM: Epstein-Barr virus

<400> SEQUENCE: 673

Tyr Cys Pro Leu Gln His Trp Gln Thr Phe
1               5                   10

<210> SEQ ID NO 674
<211> LENGTH: 10
<212> TYPE: PRT
<213> ORGANISM: Epstein-Barr virus

<400> SEQUENCE: 674

Tyr Phe Ile Thr Ser Gly Gly Leu Leu Leu
1               5                   10

<210> SEQ ID NO 675
<211> LENGTH: 10
<212> TYPE: PRT
<213> ORGANISM: Epstein-Barr virus

<400> SEQUENCE: 675

Tyr Ser Phe Lys Val Arg Ser Tyr Thr Lys
1               5                   10

<210> SEQ ID NO 676
<211> LENGTH: 10
<212> TYPE: PRT
```

```
<213> ORGANISM: Epstein-Barr virus

<400> SEQUENCE: 676

Tyr Ser Arg Pro Leu Val Ser Phe Ser Phe
1               5                   10

<210> SEQ ID NO 677
<211> LENGTH: 10
<212> TYPE: PRT
<213> ORGANISM: Epstein-Barr virus

<400> SEQUENCE: 677

Tyr Thr Lys Gly Gln Glu Ala Ile Thr Tyr
1               5                   10

<210> SEQ ID NO 678
<211> LENGTH: 9
<212> TYPE: PRT
<213> ORGANISM: Epstein-Barr virus

<400> SEQUENCE: 678

Tyr Tyr Phe Gln Ser Gly Asn Glu Ile
1               5

<210> SEQ ID NO 679
<211> LENGTH: 10
<212> TYPE: PRT
<213> ORGANISM: Epstein-Barr virus

<400> SEQUENCE: 679

Ala Ala Ala Tyr Ser Gln Val Tyr Ala Leu
1               5                   10

<210> SEQ ID NO 680
<211> LENGTH: 10
<212> TYPE: PRT
<213> ORGANISM: Epstein-Barr virus

<400> SEQUENCE: 680

Ala Ala Phe Glu Asn Ser Lys Tyr Ile Lys
1               5                   10

<210> SEQ ID NO 681
<211> LENGTH: 10
<212> TYPE: PRT
<213> ORGANISM: Epstein-Barr virus

<400> SEQUENCE: 681

Ala Ala Phe Thr Ala His Pro Gln Tyr Arg
1               5                   10

<210> SEQ ID NO 682
<211> LENGTH: 9
<212> TYPE: PRT
<213> ORGANISM: Epstein-Barr virus

<400> SEQUENCE: 682

Ala Ala Tyr Ser Gln Val Tyr Ala Leu
1               5

<210> SEQ ID NO 683
<211> LENGTH: 9
<212> TYPE: PRT
<213> ORGANISM: Epstein-Barr virus
```

```
<400> SEQUENCE: 683

Ala Gly Ala Arg Leu Thr His Leu Phe
1               5

<210> SEQ ID NO 684
<211> LENGTH: 9
<212> TYPE: PRT
<213> ORGANISM: Epstein-Barr virus

<400> SEQUENCE: 684

Ala Ile Leu Leu Pro Arg Leu Arg Arg
1               5

<210> SEQ ID NO 685
<211> LENGTH: 9
<212> TYPE: PRT
<213> ORGANISM: Epstein-Barr virus

<400> SEQUENCE: 685

Ala Ile Leu Gln Lys Arg Asn Glu Leu
1               5

<210> SEQ ID NO 686
<211> LENGTH: 9
<212> TYPE: PRT
<213> ORGANISM: Epstein-Barr virus

<400> SEQUENCE: 686

Ala Leu Ala Gly Ala Arg Leu Thr His
1               5

<210> SEQ ID NO 687
<211> LENGTH: 10
<212> TYPE: PRT
<213> ORGANISM: Epstein-Barr virus

<400> SEQUENCE: 687

Ala Leu Ala Gly Ala Arg Leu Thr His Leu
1               5                   10

<210> SEQ ID NO 688
<211> LENGTH: 9
<212> TYPE: PRT
<213> ORGANISM: Epstein-Barr virus

<400> SEQUENCE: 688

Ala Leu Ala Arg Cys Cys Asp Ala Ala
1               5

<210> SEQ ID NO 689
<211> LENGTH: 10
<212> TYPE: PRT
<213> ORGANISM: Epstein-Barr virus

<400> SEQUENCE: 689

Ala Leu Ala Val Glu Leu Ser Val Cys Ala
1               5                   10

<210> SEQ ID NO 690
<211> LENGTH: 10
<212> TYPE: PRT
<213> ORGANISM: Epstein-Barr virus

<400> SEQUENCE: 690
```

```
Ala Leu Asp Thr Tyr Asn Val Phe Ser Thr
1               5                   10

<210> SEQ ID NO 691
<211> LENGTH: 9
<212> TYPE: PRT
<213> ORGANISM: Epstein-Barr virus

<400> SEQUENCE: 691

Ala Leu Phe Ala Arg Glu Arg Arg Leu
1               5

<210> SEQ ID NO 692
<211> LENGTH: 9
<212> TYPE: PRT
<213> ORGANISM: Epstein-Barr virus

<400> SEQUENCE: 692

Ala Leu Lys Arg Lys Glu Gln Tyr Leu
1               5

<210> SEQ ID NO 693
<211> LENGTH: 9
<212> TYPE: PRT
<213> ORGANISM: Epstein-Barr virus

<400> SEQUENCE: 693

Ala Leu Leu Tyr Leu His Leu Gln Met
1               5

<210> SEQ ID NO 694
<211> LENGTH: 9
<212> TYPE: PRT
<213> ORGANISM: Epstein-Barr virus

<400> SEQUENCE: 694

Ala Leu Pro Pro Asp Gly Leu Tyr Leu
1               5

<210> SEQ ID NO 695
<211> LENGTH: 10
<212> TYPE: PRT
<213> ORGANISM: Epstein-Barr virus

<400> SEQUENCE: 695

Ala Leu Pro Pro Asp Gly Leu Tyr Leu Thr
1               5                   10

<210> SEQ ID NO 696
<211> LENGTH: 9
<212> TYPE: PRT
<213> ORGANISM: Epstein-Barr virus

<400> SEQUENCE: 696

Ala Leu Arg Glu Ala Val Leu Thr Val
1               5

<210> SEQ ID NO 697
<211> LENGTH: 9
<212> TYPE: PRT
<213> ORGANISM: Epstein-Barr virus

<400> SEQUENCE: 697

Ala Leu Ser Asp Ala Leu Lys Arg Lys
1               5
```

<210> SEQ ID NO 698
<211> LENGTH: 9
<212> TYPE: PRT
<213> ORGANISM: Epstein-Barr virus

<400> SEQUENCE: 698

Ala Leu Ser Leu Glu Leu Val His Leu
1               5

<210> SEQ ID NO 699
<211> LENGTH: 10
<212> TYPE: PRT
<213> ORGANISM: Epstein-Barr virus

<400> SEQUENCE: 699

Ala Leu Ser Leu Glu Leu Val His Leu Leu
1               5                   10

<210> SEQ ID NO 700
<211> LENGTH: 9
<212> TYPE: PRT
<213> ORGANISM: Epstein-Barr virus

<400> SEQUENCE: 700

Ala Leu Thr His Ser Leu Tyr Thr Phe
1               5

<210> SEQ ID NO 701
<211> LENGTH: 10
<212> TYPE: PRT
<213> ORGANISM: Epstein-Barr virus

<400> SEQUENCE: 701

Ala Leu Thr His Ser Leu Tyr Thr Phe Ile
1               5                   10

<210> SEQ ID NO 702
<211> LENGTH: 9
<212> TYPE: PRT
<213> ORGANISM: Epstein-Barr virus

<400> SEQUENCE: 702

Ala Pro Gly Ala Thr Glu Arg Leu Phe
1               5

<210> SEQ ID NO 703
<211> LENGTH: 9
<212> TYPE: PRT
<213> ORGANISM: Epstein-Barr virus

<400> SEQUENCE: 703

Ala Pro Gly Arg Lys Gly Thr Arg Val
1               5

<210> SEQ ID NO 704
<211> LENGTH: 10
<212> TYPE: PRT
<213> ORGANISM: Epstein-Barr virus

<400> SEQUENCE: 704

Ala Val Leu Thr Val Ser Leu Tyr Asn Lys
1               5                   10

```
<210> SEQ ID NO 705
<211> LENGTH: 9
<212> TYPE: PRT
<213> ORGANISM: Epstein-Barr virus

<400> SEQUENCE: 705

Ala Tyr Ser Gln Val Tyr Ala Leu Ala
1               5

<210> SEQ ID NO 706
<211> LENGTH: 10
<212> TYPE: PRT
<213> ORGANISM: Epstein-Barr virus

<400> SEQUENCE: 706

Ala Tyr Ser Gln Val Tyr Ala Leu Ala Val
1               5                   10

<210> SEQ ID NO 707
<211> LENGTH: 9
<212> TYPE: PRT
<213> ORGANISM: Epstein-Barr virus

<400> SEQUENCE: 707

Cys Ala Arg Leu Asp Pro Arg Ser Leu
1               5

<210> SEQ ID NO 708
<211> LENGTH: 9
<212> TYPE: PRT
<213> ORGANISM: Epstein-Barr virus

<400> SEQUENCE: 708

Cys Leu Ala Gln Gln Ser Glu Thr Leu
1               5

<210> SEQ ID NO 709
<211> LENGTH: 9
<212> TYPE: PRT
<213> ORGANISM: Epstein-Barr virus

<400> SEQUENCE: 709

Cys Leu Ile Asn Asp Ile Glu Ile Leu
1               5

<210> SEQ ID NO 710
<211> LENGTH: 10
<212> TYPE: PRT
<213> ORGANISM: Epstein-Barr virus

<400> SEQUENCE: 710

Cys Leu Ile Asn Asp Ile Glu Ile Leu Met
1               5                   10

<210> SEQ ID NO 711
<211> LENGTH: 9
<212> TYPE: PRT
<213> ORGANISM: Epstein-Barr virus

<400> SEQUENCE: 711

Asp Leu Leu Gly Arg Phe Arg Gly Val
1               5

<210> SEQ ID NO 712
<211> LENGTH: 10
```

```
<212> TYPE: PRT
<213> ORGANISM: Epstein-Barr virus

<400> SEQUENCE: 712

Asp Leu Tyr Ala Leu Leu Tyr Leu His Leu
1               5                   10

<210> SEQ ID NO 713
<211> LENGTH: 9
<212> TYPE: PRT
<213> ORGANISM: Epstein-Barr virus

<400> SEQUENCE: 713

Asp Pro Arg Leu Tyr Ile Thr Ser Val
1               5

<210> SEQ ID NO 714
<211> LENGTH: 10
<212> TYPE: PRT
<213> ORGANISM: Epstein-Barr virus

<400> SEQUENCE: 714

Asp Pro Arg Ser Leu Asp Val Ala Ala Val
1               5                   10

<210> SEQ ID NO 715
<211> LENGTH: 10
<212> TYPE: PRT
<213> ORGANISM: Epstein-Barr virus

<400> SEQUENCE: 715

Asp Ser Asp Arg Pro Leu Ile Leu Leu Tyr
1               5                   10

<210> SEQ ID NO 716
<211> LENGTH: 10
<212> TYPE: PRT
<213> ORGANISM: Epstein-Barr virus

<400> SEQUENCE: 716

Asp Trp Ile Glu Thr Ser Phe Asn Ser Phe
1               5                   10

<210> SEQ ID NO 717
<211> LENGTH: 10
<212> TYPE: PRT
<213> ORGANISM: Epstein-Barr virus

<400> SEQUENCE: 717

Glu Ile Leu Met Lys Arg Ile Asn Ser Val
1               5                   10

<210> SEQ ID NO 718
<211> LENGTH: 10
<212> TYPE: PRT
<213> ORGANISM: Epstein-Barr virus

<400> SEQUENCE: 718

Glu Leu Ala Arg Met Arg Asn His Phe Leu
1               5                   10

<210> SEQ ID NO 719
<211> LENGTH: 9
<212> TYPE: PRT
<213> ORGANISM: Epstein-Barr virus
```

```
<400> SEQUENCE: 719

Glu Leu Tyr Thr Arg Leu Asn Arg Ala
1               5

<210> SEQ ID NO 720
<211> LENGTH: 10
<212> TYPE: PRT
<213> ORGANISM: Epstein-Barr virus

<400> SEQUENCE: 720

Glu Leu Tyr Thr Arg Leu Asn Arg Ala Met
1               5                   10

<210> SEQ ID NO 721
<211> LENGTH: 10
<212> TYPE: PRT
<213> ORGANISM: Epstein-Barr virus

<400> SEQUENCE: 721

Glu Val Ala Glu Leu Ser Glu Leu Leu Tyr
1               5                   10

<210> SEQ ID NO 722
<211> LENGTH: 9
<212> TYPE: PRT
<213> ORGANISM: Epstein-Barr virus

<400> SEQUENCE: 722

Phe Ala Arg Glu Arg Arg Leu Ala Leu
1               5

<210> SEQ ID NO 723
<211> LENGTH: 10
<212> TYPE: PRT
<213> ORGANISM: Epstein-Barr virus

<400> SEQUENCE: 723

Phe Ala Arg Glu Arg Arg Leu Ala Leu Val
1               5                   10

<210> SEQ ID NO 724
<211> LENGTH: 9
<212> TYPE: PRT
<213> ORGANISM: Epstein-Barr virus

<400> SEQUENCE: 724

Phe Lys Asp Leu Tyr Ala Leu Leu Tyr
1               5

<210> SEQ ID NO 725
<211> LENGTH: 9
<212> TYPE: PRT
<213> ORGANISM: Epstein-Barr virus

<400> SEQUENCE: 725

Phe Leu Thr Ser Leu Ile Trp Pro Gly
1               5

<210> SEQ ID NO 726
<211> LENGTH: 10
<212> TYPE: PRT
<213> ORGANISM: Epstein-Barr virus

<400> SEQUENCE: 726
```

```
Phe Leu Thr Ser Leu Ile Trp Pro Gly Ile
1               5                   10

<210> SEQ ID NO 727
<211> LENGTH: 9
<212> TYPE: PRT
<213> ORGANISM: Epstein-Barr virus

<400> SEQUENCE: 727

Phe Leu Tyr Arg Arg Ala Phe Val Ser
1               5

<210> SEQ ID NO 728
<211> LENGTH: 10
<212> TYPE: PRT
<213> ORGANISM: Epstein-Barr virus

<400> SEQUENCE: 728

Phe Leu Tyr Arg Arg Ala Phe Val Ser Gly
1               5                   10

<210> SEQ ID NO 729
<211> LENGTH: 9
<212> TYPE: PRT
<213> ORGANISM: Epstein-Barr virus

<400> SEQUENCE: 729

Phe Pro Pro Pro Ser Asn Val Ala Leu
1               5

<210> SEQ ID NO 730
<211> LENGTH: 10
<212> TYPE: PRT
<213> ORGANISM: Epstein-Barr virus

<400> SEQUENCE: 730

Phe Tyr Cys Met Ser His Thr Met Gly Leu
1               5                   10

<210> SEQ ID NO 731
<211> LENGTH: 9
<212> TYPE: PRT
<213> ORGANISM: Epstein-Barr virus

<400> SEQUENCE: 731

Gly Gly His Ser Arg Leu Ser Ala Leu
1               5

<210> SEQ ID NO 732
<211> LENGTH: 9
<212> TYPE: PRT
<213> ORGANISM: Epstein-Barr virus

<400> SEQUENCE: 732

Gly Leu Ala Lys Leu Gln Ser Cys Leu
1               5

<210> SEQ ID NO 733
<211> LENGTH: 10
<212> TYPE: PRT
<213> ORGANISM: Epstein-Barr virus

<400> SEQUENCE: 733

Gly Leu Ala Lys Leu Gln Ser Cys Leu Ala
```

```
1               5                    10
```

<210> SEQ ID NO 734
<211> LENGTH: 10
<212> TYPE: PRT
<213> ORGANISM: Epstein-Barr virus

<400> SEQUENCE: 734

```
Gly Leu Phe Glu Asn Glu Val Arg Gln Ala
1               5                    10
```

<210> SEQ ID NO 735
<211> LENGTH: 9
<212> TYPE: PRT
<213> ORGANISM: Epstein-Barr virus

<400> SEQUENCE: 735

```
Gly Leu Phe Pro Pro Pro Ser Asn Val
1               5
```

<210> SEQ ID NO 736
<211> LENGTH: 10
<212> TYPE: PRT
<213> ORGANISM: Epstein-Barr virus

<400> SEQUENCE: 736

```
Gly Leu Phe Pro Pro Pro Ser Asn Val Ala
1               5                    10
```

<210> SEQ ID NO 737
<211> LENGTH: 10
<212> TYPE: PRT
<213> ORGANISM: Epstein-Barr virus

<400> SEQUENCE: 737

```
Gly Leu Leu Ala Ala Ala Tyr Ser Gln Val
1               5                    10
```

<210> SEQ ID NO 738
<211> LENGTH: 9
<212> TYPE: PRT
<213> ORGANISM: Epstein-Barr virus

<400> SEQUENCE: 738

```
Gly Leu Leu Ala Glu Leu Glu Ala Ile
1               5
```

<210> SEQ ID NO 739
<211> LENGTH: 10
<212> TYPE: PRT
<213> ORGANISM: Epstein-Barr virus

<400> SEQUENCE: 739

```
Gly Leu Leu Ala Glu Leu Glu Ala Ile Leu
1               5                    10
```

<210> SEQ ID NO 740
<211> LENGTH: 10
<212> TYPE: PRT
<213> ORGANISM: Epstein-Barr virus

<400> SEQUENCE: 740

```
Gly Pro Ser Gly Ala Leu Ser Asp Ala Leu
1               5                    10
```

```
<210> SEQ ID NO 741
<211> LENGTH: 10
<212> TYPE: PRT
<213> ORGANISM: Epstein-Barr virus

<400> SEQUENCE: 741

His Ala Leu Thr His Ser Leu Tyr Thr Phe
1               5                   10

<210> SEQ ID NO 742
<211> LENGTH: 9
<212> TYPE: PRT
<213> ORGANISM: Epstein-Barr virus

<400> SEQUENCE: 742

His Phe Leu Tyr Arg Arg Ala Phe Val
1               5

<210> SEQ ID NO 743
<211> LENGTH: 9
<212> TYPE: PRT
<213> ORGANISM: Epstein-Barr virus

<400> SEQUENCE: 743

His Leu Phe Asp Ala Val Ala Pro Gly
1               5

<210> SEQ ID NO 744
<211> LENGTH: 10
<212> TYPE: PRT
<213> ORGANISM: Epstein-Barr virus

<400> SEQUENCE: 744

His Leu Phe Asp Ala Val Ala Pro Gly Ala
1               5                   10

<210> SEQ ID NO 745
<211> LENGTH: 9
<212> TYPE: PRT
<213> ORGANISM: Epstein-Barr virus

<400> SEQUENCE: 745

His Leu His Ala Leu Thr His Ser Leu
1               5

<210> SEQ ID NO 746
<211> LENGTH: 10
<212> TYPE: PRT
<213> ORGANISM: Epstein-Barr virus

<400> SEQUENCE: 746

His Leu His Ala Leu Thr His Ser Leu Tyr
1               5                   10

<210> SEQ ID NO 747
<211> LENGTH: 9
<212> TYPE: PRT
<213> ORGANISM: Epstein-Barr virus

<400> SEQUENCE: 747

His Leu Leu Glu Ala Glu Glu Lys Ala
1               5

<210> SEQ ID NO 748
```

-continued

```
<211> LENGTH: 9
<212> TYPE: PRT
<213> ORGANISM: Epstein-Barr virus

<400> SEQUENCE: 748

His Leu Leu Glu Asn Ser Arg Glu Ala
1               5

<210> SEQ ID NO 749
<211> LENGTH: 9
<212> TYPE: PRT
<213> ORGANISM: Epstein-Barr virus

<400> SEQUENCE: 749

His Leu Gln Met Arg Asp Asp Ser Ala
1               5

<210> SEQ ID NO 750
<211> LENGTH: 9
<212> TYPE: PRT
<213> ORGANISM: Epstein-Barr virus

<400> SEQUENCE: 750

His Gln Lys Ala Phe Leu Thr Ser Leu
1               5

<210> SEQ ID NO 751
<211> LENGTH: 9
<212> TYPE: PRT
<213> ORGANISM: Epstein-Barr virus

<400> SEQUENCE: 751

His Val Ser Cys Asn His Leu Ala Val
1               5

<210> SEQ ID NO 752
<211> LENGTH: 10
<212> TYPE: PRT
<213> ORGANISM: Epstein-Barr virus

<400> SEQUENCE: 752

Ile Leu Cys Arg Ala Leu Arg Glu Ala Val
1               5                   10

<210> SEQ ID NO 753
<211> LENGTH: 10
<212> TYPE: PRT
<213> ORGANISM: Epstein-Barr virus

<400> SEQUENCE: 753

Ile Leu Leu Tyr Lys Gly Arg Gly Trp Val
1               5                   10

<210> SEQ ID NO 754
<211> LENGTH: 9
<212> TYPE: PRT
<213> ORGANISM: Epstein-Barr virus

<400> SEQUENCE: 754

Ile Leu Met Lys Arg Ile Asn Ser Val
1               5

<210> SEQ ID NO 755
<211> LENGTH: 10
<212> TYPE: PRT
```

-continued

<213> ORGANISM: Epstein-Barr virus

<400> SEQUENCE: 755

Ile Leu Met Lys Arg Ile Asn Ser Val Phe
1               5                   10

<210> SEQ ID NO 756
<211> LENGTH: 10
<212> TYPE: PRT
<213> ORGANISM: Epstein-Barr virus

<400> SEQUENCE: 756

Ile Trp Pro Gly Ile Glu Pro Ser Asp Trp
1               5                   10

<210> SEQ ID NO 757
<211> LENGTH: 9
<212> TYPE: PRT
<213> ORGANISM: Epstein-Barr virus

<400> SEQUENCE: 757

Lys Thr Trp Gly Arg Ser Leu Ile Leu
1               5

<210> SEQ ID NO 758
<211> LENGTH: 10
<212> TYPE: PRT
<213> ORGANISM: Epstein-Barr virus

<400> SEQUENCE: 758

Lys Thr Trp Gly Arg Ser Leu Ile Leu Arg
1               5                   10

<210> SEQ ID NO 759
<211> LENGTH: 9
<212> TYPE: PRT
<213> ORGANISM: Epstein-Barr virus

<400> SEQUENCE: 759

Lys Val Asp Val Ser Leu Cys Leu Ile
1               5

<210> SEQ ID NO 760
<211> LENGTH: 9
<212> TYPE: PRT
<213> ORGANISM: Epstein-Barr virus

<400> SEQUENCE: 760

Leu Ala Ala Ala Tyr Ser Gln Val Tyr
1               5

<210> SEQ ID NO 761
<211> LENGTH: 9
<212> TYPE: PRT
<213> ORGANISM: Epstein-Barr virus

<400> SEQUENCE: 761

Leu Ala Gly Ala Arg Leu Thr His Leu
1               5

<210> SEQ ID NO 762
<211> LENGTH: 9
<212> TYPE: PRT
<213> ORGANISM: Epstein-Barr virus

<400> SEQUENCE: 762

Leu Ala Arg Met Arg Asn His Phe Leu
1               5

<210> SEQ ID NO 763
<211> LENGTH: 10
<212> TYPE: PRT
<213> ORGANISM: Epstein-Barr virus

<400> SEQUENCE: 763

Leu Phe Ala Arg Glu Arg Arg Leu Ala Leu
1 5 10

<210> SEQ ID NO 764
<211> LENGTH: 10
<212> TYPE: PRT
<213> ORGANISM: Epstein-Barr virus

<400> SEQUENCE: 764

Leu Gly Arg Phe Arg Gly Val Ser Pro Ile
1 5 10

<210> SEQ ID NO 765
<211> LENGTH: 9
<212> TYPE: PRT
<213> ORGANISM: Epstein-Barr virus

<400> SEQUENCE: 765

Leu Ile Leu Arg Arg Ala Asp Ala Val
1 5

<210> SEQ ID NO 766
<211> LENGTH: 9
<212> TYPE: PRT
<213> ORGANISM: Epstein-Barr virus

<400> SEQUENCE: 766

Leu Ile Asn Asp Ile Glu Ile Leu Met
1 5

<210> SEQ ID NO 767
<211> LENGTH: 10
<212> TYPE: PRT
<213> ORGANISM: Epstein-Barr virus

<400> SEQUENCE: 767

Leu Ile Asn Asp Ile Glu Ile Leu Met Lys
1 5 10

<210> SEQ ID NO 768
<211> LENGTH: 9
<212> TYPE: PRT
<213> ORGANISM: Epstein-Barr virus

<400> SEQUENCE: 768

Leu Leu Ala Ala Ala Tyr Ser Gln Val
1 5

<210> SEQ ID NO 769
<211> LENGTH: 10
<212> TYPE: PRT
<213> ORGANISM: Epstein-Barr virus

<400> SEQUENCE: 769

```
Leu Leu Ala Ala Ala Tyr Ser Gln Val Tyr
1               5                   10

<210> SEQ ID NO 770
<211> LENGTH: 9
<212> TYPE: PRT
<213> ORGANISM: Epstein-Barr virus

<400> SEQUENCE: 770

Leu Leu Ala Glu Leu Glu Ala Ile Leu
1               5

<210> SEQ ID NO 771
<211> LENGTH: 10
<212> TYPE: PRT
<213> ORGANISM: Epstein-Barr virus

<400> SEQUENCE: 771

Leu Leu Ala Glu Leu Glu Ala Ile Leu Leu
1               5                   10

<210> SEQ ID NO 772
<211> LENGTH: 9
<212> TYPE: PRT
<213> ORGANISM: Epstein-Barr virus

<400> SEQUENCE: 772

Leu Leu Tyr Lys Gly Arg Gly Trp Val
1               5

<210> SEQ ID NO 773
<211> LENGTH: 10
<212> TYPE: PRT
<213> ORGANISM: Epstein-Barr virus

<400> SEQUENCE: 773

Leu Leu Tyr Lys Gly Arg Gly Trp Val Phe
1               5                   10

<210> SEQ ID NO 774
<211> LENGTH: 9
<212> TYPE: PRT
<213> ORGANISM: Epstein-Barr virus

<400> SEQUENCE: 774

Leu Leu Tyr Leu His Leu Gln Met Arg
1               5

<210> SEQ ID NO 775
<211> LENGTH: 9
<212> TYPE: PRT
<213> ORGANISM: Epstein-Barr virus

<400> SEQUENCE: 775

Leu Leu Tyr Trp Asn Ser Gly Gly His
1               5

<210> SEQ ID NO 776
<211> LENGTH: 10
<212> TYPE: PRT
<213> ORGANISM: Epstein-Barr virus

<400> SEQUENCE: 776

Leu Leu Tyr Trp Asn Ser Gly Gly His Ala
1               5                   10
```

```
<210> SEQ ID NO 777
<211> LENGTH: 9
<212> TYPE: PRT
<213> ORGANISM: Epstein-Barr virus

<400> SEQUENCE: 777

Leu Met Lys Arg Ile Asn Ser Val Phe
1               5

<210> SEQ ID NO 778
<211> LENGTH: 10
<212> TYPE: PRT
<213> ORGANISM: Epstein-Barr virus

<400> SEQUENCE: 778

Leu Met Lys Arg Ile Asn Ser Val Phe Tyr
1               5                   10

<210> SEQ ID NO 779
<211> LENGTH: 9
<212> TYPE: PRT
<213> ORGANISM: Epstein-Barr virus

<400> SEQUENCE: 779

Leu Pro Asn His Gly Asn Pro Ser Thr
1               5

<210> SEQ ID NO 780
<211> LENGTH: 10
<212> TYPE: PRT
<213> ORGANISM: Epstein-Barr virus

<400> SEQUENCE: 780

Leu Pro Asn His Gly Asn Pro Ser Thr Ala
1               5                   10

<210> SEQ ID NO 781
<211> LENGTH: 9
<212> TYPE: PRT
<213> ORGANISM: Epstein-Barr virus

<400> SEQUENCE: 781

Leu Ser Leu Glu Leu Val His Leu Leu
1               5

<210> SEQ ID NO 782
<211> LENGTH: 10
<212> TYPE: PRT
<213> ORGANISM: Epstein-Barr virus

<400> SEQUENCE: 782

Leu Val Arg Arg Ala Cys Glu Glu Ala Leu
1               5                   10

<210> SEQ ID NO 783
<211> LENGTH: 9
<212> TYPE: PRT
<213> ORGANISM: Epstein-Barr virus

<400> SEQUENCE: 783

Leu Tyr Ala Leu Leu Tyr Leu His Leu
1               5
```

-continued

```
<210> SEQ ID NO 784
<211> LENGTH: 9
<212> TYPE: PRT
<213> ORGANISM: Epstein-Barr virus

<400> SEQUENCE: 784

Leu Tyr Ile Thr Ser Val Pro Cys Trp
1               5

<210> SEQ ID NO 785
<211> LENGTH: 9
<212> TYPE: PRT
<213> ORGANISM: Epstein-Barr virus

<400> SEQUENCE: 785

Leu Tyr Lys Gly Arg Gly Trp Val Phe
1               5

<210> SEQ ID NO 786
<211> LENGTH: 10
<212> TYPE: PRT
<213> ORGANISM: Epstein-Barr virus

<400> SEQUENCE: 786

Leu Tyr Asn Lys Thr Trp Gly Arg Ser Leu
1               5                   10

<210> SEQ ID NO 787
<211> LENGTH: 9
<212> TYPE: PRT
<213> ORGANISM: Epstein-Barr virus

<400> SEQUENCE: 787

Leu Tyr Thr Phe Ile Thr Gly Pro Leu
1               5

<210> SEQ ID NO 788
<211> LENGTH: 10
<212> TYPE: PRT
<213> ORGANISM: Epstein-Barr virus

<400> SEQUENCE: 788

Leu Tyr Trp Asn Ser Gly Gly His Ala Ile
1               5                   10

<210> SEQ ID NO 789
<211> LENGTH: 9
<212> TYPE: PRT
<213> ORGANISM: Epstein-Barr virus

<400> SEQUENCE: 789

Met Ser Gly Leu Leu Ala Ala Ala Tyr
1               5

<210> SEQ ID NO 790
<211> LENGTH: 9
<212> TYPE: PRT
<213> ORGANISM: Epstein-Barr virus

<400> SEQUENCE: 790

Asn Ser Arg Glu Ala Ser Ala Ala Leu
1               5

<210> SEQ ID NO 791
<211> LENGTH: 10
```

```
<212> TYPE: PRT
<213> ORGANISM: Epstein-Barr virus

<400> SEQUENCE: 791

Asn Val Phe Ser Thr Val Pro Pro Glu Val
1               5                   10

<210> SEQ ID NO 792
<211> LENGTH: 9
<212> TYPE: PRT
<213> ORGANISM: Epstein-Barr virus

<400> SEQUENCE: 792

Pro Gln Tyr Arg Ala Ile Leu Gln Lys
1               5

<210> SEQ ID NO 793
<211> LENGTH: 9
<212> TYPE: PRT
<213> ORGANISM: Epstein-Barr virus

<400> SEQUENCE: 793

Gln Val Tyr Ala Leu Ala Val Glu Leu
1               5

<210> SEQ ID NO 794
<211> LENGTH: 10
<212> TYPE: PRT
<213> ORGANISM: Epstein-Barr virus

<400> SEQUENCE: 794

Arg Ala Ile Leu Gln Lys Arg Asn Glu Leu
1               5                   10

<210> SEQ ID NO 795
<211> LENGTH: 9
<212> TYPE: PRT
<213> ORGANISM: Epstein-Barr virus

<400> SEQUENCE: 795

Arg Leu Asp Pro Arg Ser Leu Asp Val
1               5

<210> SEQ ID NO 796
<211> LENGTH: 9
<212> TYPE: PRT
<213> ORGANISM: Epstein-Barr virus

<400> SEQUENCE: 796

Arg Leu Phe Cys Gly Gly Val Tyr Ser
1               5

<210> SEQ ID NO 797
<211> LENGTH: 10
<212> TYPE: PRT
<213> ORGANISM: Epstein-Barr virus

<400> SEQUENCE: 797

Arg Leu Phe Cys Gly Gly Val Tyr Ser Ser
1               5                   10

<210> SEQ ID NO 798
<211> LENGTH: 9
<212> TYPE: PRT
<213> ORGANISM: Epstein-Barr virus
```

<400> SEQUENCE: 798

Arg Leu Asn Arg Ala Met Gln Arg Leu
1               5

<210> SEQ ID NO 799
<211> LENGTH: 10
<212> TYPE: PRT
<213> ORGANISM: Epstein-Barr virus

<400> SEQUENCE: 799

Arg Leu Ser Ala Leu Phe Ala Arg Glu Arg
1               5                   10

<210> SEQ ID NO 800
<211> LENGTH: 9
<212> TYPE: PRT
<213> ORGANISM: Epstein-Barr virus

<400> SEQUENCE: 800

Arg Leu Thr His Leu Phe Asp Ala Val
1               5

<210> SEQ ID NO 801
<211> LENGTH: 9
<212> TYPE: PRT
<213> ORGANISM: Epstein-Barr virus

<400> SEQUENCE: 801

Arg Met Arg Asn His Phe Leu Tyr Arg
1               5

<210> SEQ ID NO 802
<211> LENGTH: 10
<212> TYPE: PRT
<213> ORGANISM: Epstein-Barr virus

<400> SEQUENCE: 802

Arg Met Arg Asn His Phe Leu Tyr Arg Arg
1               5                   10

<210> SEQ ID NO 803
<211> LENGTH: 9
<212> TYPE: PRT
<213> ORGANISM: Epstein-Barr virus

<400> SEQUENCE: 803

Arg Pro Ala Gly Ala Arg Glu Pro Gly
1               5

<210> SEQ ID NO 804
<211> LENGTH: 10
<212> TYPE: PRT
<213> ORGANISM: Epstein-Barr virus

<400> SEQUENCE: 804

Arg Pro Gly Gly Pro Glu Glu Gly Ala Val
1               5                   10

<210> SEQ ID NO 805
<211> LENGTH: 9
<212> TYPE: PRT
<213> ORGANISM: Epstein-Barr virus

<400> SEQUENCE: 805

Arg Gln Ala Gly Leu Gly His Leu Leu
1               5

<210> SEQ ID NO 806
<211> LENGTH: 10
<212> TYPE: PRT
<213> ORGANISM: Epstein-Barr virus

<400> SEQUENCE: 806

Arg Gln Val Ala Thr Glu Gly Leu Ala Lys
1               5                   10

<210> SEQ ID NO 807
<211> LENGTH: 9
<212> TYPE: PRT
<213> ORGANISM: Epstein-Barr virus

<400> SEQUENCE: 807

Arg Thr Pro Ser Val Ala Tyr Ser Val
1               5

<210> SEQ ID NO 808
<211> LENGTH: 10
<212> TYPE: PRT
<213> ORGANISM: Epstein-Barr virus

<400> SEQUENCE: 808

Ser Ala Ala Leu Leu Ala Pro Gly Arg Lys
1               5                   10

<210> SEQ ID NO 809
<211> LENGTH: 9
<212> TYPE: PRT
<213> ORGANISM: Epstein-Barr virus

<400> SEQUENCE: 809

Ser Leu Ala Ser Ser Gln Gln Ile Leu
1               5

<210> SEQ ID NO 810
<211> LENGTH: 10
<212> TYPE: PRT
<213> ORGANISM: Epstein-Barr virus

<400> SEQUENCE: 810

Ser Leu Cys Leu Ile Asn Asp Ile Glu Ile
1               5                   10

<210> SEQ ID NO 811
<211> LENGTH: 9
<212> TYPE: PRT
<213> ORGANISM: Epstein-Barr virus

<400> SEQUENCE: 811

Ser Leu Ile Leu Arg Arg Ala Asp Ala
1               5

<210> SEQ ID NO 812
<211> LENGTH: 10
<212> TYPE: PRT
<213> ORGANISM: Epstein-Barr virus

<400> SEQUENCE: 812

Ser Leu Ile Leu Arg Arg Ala Asp Ala Val

-continued

```
1               5               10

<210> SEQ ID NO 813
<211> LENGTH: 9
<212> TYPE: PRT
<213> ORGANISM: Epstein-Barr virus

<400> SEQUENCE: 813

Ser Leu Tyr Asn Lys Thr Trp Gly Arg
1               5

<210> SEQ ID NO 814
<211> LENGTH: 10
<212> TYPE: PRT
<213> ORGANISM: Epstein-Barr virus

<400> SEQUENCE: 814

Ser Leu Tyr Thr Phe Ile Thr Gly Pro Leu
1               5               10

<210> SEQ ID NO 815
<211> LENGTH: 10
<212> TYPE: PRT
<213> ORGANISM: Epstein-Barr virus

<400> SEQUENCE: 815

Ser Pro Glu Val Pro Arg Pro Ala Gly Ala
1               5               10

<210> SEQ ID NO 816
<211> LENGTH: 10
<212> TYPE: PRT
<213> ORGANISM: Epstein-Barr virus

<400> SEQUENCE: 816

Ser Pro Ile Pro Asp Pro Arg Leu Tyr Ile
1               5               10

<210> SEQ ID NO 817
<211> LENGTH: 10
<212> TYPE: PRT
<213> ORGANISM: Epstein-Barr virus

<400> SEQUENCE: 817

Ser Gln Val Tyr Ala Leu Ala Val Glu Leu
1               5               10

<210> SEQ ID NO 818
<211> LENGTH: 9
<212> TYPE: PRT
<213> ORGANISM: Epstein-Barr virus

<400> SEQUENCE: 818

Ser Val Ala Tyr Ser Val Glu Phe Tyr
1               5

<210> SEQ ID NO 819
<211> LENGTH: 9
<212> TYPE: PRT
<213> ORGANISM: Epstein-Barr virus

<400> SEQUENCE: 819

Ser Val Glu Phe Tyr Gly Gly His Lys
1               5
```

<210> SEQ ID NO 820
<211> LENGTH: 10
<212> TYPE: PRT
<213> ORGANISM: Epstein-Barr virus

<400> SEQUENCE: 820

Ser Val Phe Tyr Cys Met Ser His Thr Met
1               5                   10

<210> SEQ ID NO 821
<211> LENGTH: 10
<212> TYPE: PRT
<213> ORGANISM: Epstein-Barr virus

<400> SEQUENCE: 821

Thr Leu Ser Ser Glu His Leu His Ala Leu
1               5                   10

<210> SEQ ID NO 822
<211> LENGTH: 10
<212> TYPE: PRT
<213> ORGANISM: Epstein-Barr virus

<400> SEQUENCE: 822

Thr Leu Thr Glu Thr Leu Cys Leu Arg Val
1               5                   10

<210> SEQ ID NO 823
<211> LENGTH: 10
<212> TYPE: PRT
<213> ORGANISM: Epstein-Barr virus

<400> SEQUENCE: 823

Thr Pro Ser Val Ala Tyr Ser Val Glu Phe
1               5                   10

<210> SEQ ID NO 824
<211> LENGTH: 9
<212> TYPE: PRT
<213> ORGANISM: Epstein-Barr virus

<400> SEQUENCE: 824

Thr Ser Phe Asn Ser Phe Tyr Ser Val
1               5

<210> SEQ ID NO 825
<211> LENGTH: 9
<212> TYPE: PRT
<213> ORGANISM: Epstein-Barr virus

<400> SEQUENCE: 825

Thr Tyr Asp Ser Asp Arg Pro Leu Ile
1               5

<210> SEQ ID NO 826
<211> LENGTH: 9
<212> TYPE: PRT
<213> ORGANISM: Epstein-Barr virus

<400> SEQUENCE: 826

Val Ala Glu Leu Ser Glu Leu Leu Tyr
1               5

<210> SEQ ID NO 827

-continued

```
<211> LENGTH: 9
<212> TYPE: PRT
<213> ORGANISM: Epstein-Barr virus

<400> SEQUENCE: 827

Val Phe Lys Asp Leu Tyr Ala Leu Leu
1               5

<210> SEQ ID NO 828
<211> LENGTH: 9
<212> TYPE: PRT
<213> ORGANISM: Epstein-Barr virus

<400> SEQUENCE: 828

Val Phe Tyr Cys Met Ser His Thr Met
1               5

<210> SEQ ID NO 829
<211> LENGTH: 9
<212> TYPE: PRT
<213> ORGANISM: Epstein-Barr virus

<400> SEQUENCE: 829

Val Leu Thr Val Ser Leu Tyr Asn Lys
1               5

<210> SEQ ID NO 830
<211> LENGTH: 10
<212> TYPE: PRT
<213> ORGANISM: Epstein-Barr virus

<400> SEQUENCE: 830

Val Pro Cys Trp Arg Cys Val Gly Glu Leu
1               5                   10

<210> SEQ ID NO 831
<211> LENGTH: 9
<212> TYPE: PRT
<213> ORGANISM: Epstein-Barr virus

<400> SEQUENCE: 831

Val Pro Gly Pro Gly Arg Pro Glu Ala
1               5

<210> SEQ ID NO 832
<211> LENGTH: 9
<212> TYPE: PRT
<213> ORGANISM: Epstein-Barr virus

<400> SEQUENCE: 832

Val Pro Pro Leu Arg Thr Pro Ser Val
1               5

<210> SEQ ID NO 833
<211> LENGTH: 10
<212> TYPE: PRT
<213> ORGANISM: Epstein-Barr virus

<400> SEQUENCE: 833

Val Pro Pro Leu Arg Thr Pro Ser Val Ala
1               5                   10

<210> SEQ ID NO 834
<211> LENGTH: 9
<212> TYPE: PRT
```

<213> ORGANISM: Epstein-Barr virus

<400> SEQUENCE: 834

Val Pro Arg Pro Ala Gly Ala Arg Glu
1               5

<210> SEQ ID NO 835
<211> LENGTH: 10
<212> TYPE: PRT
<213> ORGANISM: Epstein-Barr virus

<400> SEQUENCE: 835

Val Pro Arg Pro Ala Gly Ala Arg Glu Pro
1               5                   10

<210> SEQ ID NO 836
<211> LENGTH: 10
<212> TYPE: PRT
<213> ORGANISM: Epstein-Barr virus

<400> SEQUENCE: 836

Val Val Tyr Trp Glu Leu Ala Arg Met Arg
1               5                   10

<210> SEQ ID NO 837
<211> LENGTH: 10
<212> TYPE: PRT
<213> ORGANISM: Epstein-Barr virus

<400> SEQUENCE: 837

Val Trp Gly Asp Val Val Tyr Trp Glu Leu
1               5                   10

<210> SEQ ID NO 838
<211> LENGTH: 10
<212> TYPE: PRT
<213> ORGANISM: Epstein-Barr virus

<400> SEQUENCE: 838

Val Tyr Ala Leu Ala Val Glu Leu Ser Val
1               5                   10

<210> SEQ ID NO 839
<211> LENGTH: 10
<212> TYPE: PRT
<213> ORGANISM: Epstein-Barr virus

<400> SEQUENCE: 839

Trp Ile Glu Thr Ser Phe Asn Ser Phe Tyr
1               5                   10

<210> SEQ ID NO 840
<211> LENGTH: 9
<212> TYPE: PRT
<213> ORGANISM: Epstein-Barr virus

<400> SEQUENCE: 840

Trp Val Phe Lys Asp Leu Tyr Ala Leu
1               5

<210> SEQ ID NO 841
<211> LENGTH: 10
<212> TYPE: PRT
<213> ORGANISM: Epstein-Barr virus

```
<400> SEQUENCE: 841

Trp Val Phe Lys Asp Leu Tyr Ala Leu Leu
1               5                   10

<210> SEQ ID NO 842
<211> LENGTH: 9
<212> TYPE: PRT
<213> ORGANISM: Epstein-Barr virus

<400> SEQUENCE: 842

Tyr Ala Leu Ala Val Glu Leu Ser Val
1               5

<210> SEQ ID NO 843
<211> LENGTH: 10
<212> TYPE: PRT
<213> ORGANISM: Epstein-Barr virus

<400> SEQUENCE: 843

Tyr Ala Leu Leu Tyr Leu His Leu Gln Met
1               5                   10

<210> SEQ ID NO 844
<211> LENGTH: 9
<212> TYPE: PRT
<213> ORGANISM: Epstein-Barr virus

<400> SEQUENCE: 844

Tyr Cys Met Ser His Thr Met Gly Leu
1               5

<210> SEQ ID NO 845
<211> LENGTH: 10
<212> TYPE: PRT
<213> ORGANISM: Epstein-Barr virus

<400> SEQUENCE: 845

Tyr Leu Arg Gln Val Ala Thr Glu Gly Leu
1               5                   10

<210> SEQ ID NO 846
<211> LENGTH: 10
<212> TYPE: PRT
<213> ORGANISM: Epstein-Barr virus

<400> SEQUENCE: 846

Tyr Leu Thr Tyr Asp Ser Asp Arg Pro Leu
1               5                   10

<210> SEQ ID NO 847
<211> LENGTH: 9
<212> TYPE: PRT
<213> ORGANISM: Epstein-Barr virus

<400> SEQUENCE: 847

Tyr Asn Lys Thr Trp Gly Arg Ser Leu
1               5

<210> SEQ ID NO 848
<211> LENGTH: 9
<212> TYPE: PRT
<213> ORGANISM: Epstein-Barr virus

<400> SEQUENCE: 848
```

```
Tyr Thr Phe Ile Thr Gly Pro Leu Ala
1               5

<210> SEQ ID NO 849
<211> LENGTH: 9
<212> TYPE: PRT
<213> ORGANISM: Epstein-Barr virus

<400> SEQUENCE: 849

Tyr Trp Asn Ser Gly Gly His Ala Ile
1               5

<210> SEQ ID NO 850
<211> LENGTH: 10
<212> TYPE: PRT
<213> ORGANISM: Epstein-Barr virus

<400> SEQUENCE: 850

Ala Ala Arg Pro Arg Leu Leu Leu Ser Leu
1               5                   10

<210> SEQ ID NO 851
<211> LENGTH: 9
<212> TYPE: PRT
<213> ORGANISM: Epstein-Barr virus

<400> SEQUENCE: 851

Ala Ala Arg Val Pro Ile Glu Glu Leu
1               5

<210> SEQ ID NO 852
<211> LENGTH: 9
<212> TYPE: PRT
<213> ORGANISM: Epstein-Barr virus

<400> SEQUENCE: 852

Ala Gly Met Ser Ala Thr Leu Pro Leu
1               5

<210> SEQ ID NO 853
<211> LENGTH: 10
<212> TYPE: PRT
<213> ORGANISM: Epstein-Barr virus

<400> SEQUENCE: 853

Ala Leu Leu Arg Gln Ala Gly Leu Gln Leu
1               5                   10

<210> SEQ ID NO 854
<211> LENGTH: 9
<212> TYPE: PRT
<213> ORGANISM: Epstein-Barr virus

<400> SEQUENCE: 854

Ala Leu Leu Trp Ala Ala Arg Pro Arg
1               5

<210> SEQ ID NO 855
<211> LENGTH: 10
<212> TYPE: PRT
<213> ORGANISM: Epstein-Barr virus

<400> SEQUENCE: 855

Ala Leu Leu Trp Ala Ala Arg Pro Arg Leu
1               5                   10
```

```
<210> SEQ ID NO 856
<211> LENGTH: 9
<212> TYPE: PRT
<213> ORGANISM: Epstein-Barr virus

<400> SEQUENCE: 856

Ala Leu Pro Gly Arg Leu Leu Leu Ala
1               5

<210> SEQ ID NO 857
<211> LENGTH: 9
<212> TYPE: PRT
<213> ORGANISM: Epstein-Barr virus

<400> SEQUENCE: 857

Ala Pro Ala Gly His Arg Gly Asp Val
1               5

<210> SEQ ID NO 858
<211> LENGTH: 10
<212> TYPE: PRT
<213> ORGANISM: Epstein-Barr virus

<400> SEQUENCE: 858

Ala Pro Ala Gly His Arg Gly Asp Val Glu
1               5                   10

<210> SEQ ID NO 859
<211> LENGTH: 9
<212> TYPE: PRT
<213> ORGANISM: Epstein-Barr virus

<400> SEQUENCE: 859

Ala Pro Gly Tyr Ala Val Glu Ala Val
1               5

<210> SEQ ID NO 860
<211> LENGTH: 10
<212> TYPE: PRT
<213> ORGANISM: Epstein-Barr virus

<400> SEQUENCE: 860

Ala Val Glu Ala Val Glu Gly Gly Leu Tyr
1               5                   10

<210> SEQ ID NO 861
<211> LENGTH: 9
<212> TYPE: PRT
<213> ORGANISM: Epstein-Barr virus

<400> SEQUENCE: 861

Ala Val Glu Gly Gly Leu Tyr Pro Val
1               5

<210> SEQ ID NO 862
<211> LENGTH: 10
<212> TYPE: PRT
<213> ORGANISM: Epstein-Barr virus

<400> SEQUENCE: 862

Ala Val Arg Leu Gln Arg Leu His Arg Val
1               5                   10
```

<210> SEQ ID NO 863
<211> LENGTH: 9
<212> TYPE: PRT
<213> ORGANISM: Epstein-Barr virus

<400> SEQUENCE: 863

Ala Val Arg Gln Arg Val Gln Val Leu
1               5

<210> SEQ ID NO 864
<211> LENGTH: 9
<212> TYPE: PRT
<213> ORGANISM: Epstein-Barr virus

<400> SEQUENCE: 864

Cys Pro Arg Gln Arg Leu Leu Ala Gly
1               5

<210> SEQ ID NO 865
<211> LENGTH: 10
<212> TYPE: PRT
<213> ORGANISM: Epstein-Barr virus

<400> SEQUENCE: 865

Cys Pro Ser Arg Pro Gly His Leu Arg Ala
1               5                   10

<210> SEQ ID NO 866
<211> LENGTH: 9
<212> TYPE: PRT
<213> ORGANISM: Epstein-Barr virus

<400> SEQUENCE: 866

Cys Thr Asp Ser Met Ala Ala Arg Val
1               5

<210> SEQ ID NO 867
<211> LENGTH: 9
<212> TYPE: PRT
<213> ORGANISM: Epstein-Barr virus

<400> SEQUENCE: 867

Glu Pro Arg Val Glu Leu Val Pro Leu
1               5

<210> SEQ ID NO 868
<211> LENGTH: 10
<212> TYPE: PRT
<213> ORGANISM: Epstein-Barr virus

<400> SEQUENCE: 868

Glu Pro Arg Val Glu Leu Val Pro Leu Leu
1               5                   10

<210> SEQ ID NO 869
<211> LENGTH: 9
<212> TYPE: PRT
<213> ORGANISM: Epstein-Barr virus

<400> SEQUENCE: 869

Phe Gln Ala Leu Gln Pro His Gly Val
1               5

<210> SEQ ID NO 870
<211> LENGTH: 10

<212> TYPE: PRT
<213> ORGANISM: Epstein-Barr virus

<400> SEQUENCE: 870

Gly Leu Ala Leu Leu Arg Gln Ala Gly Leu
1               5                   10

<210> SEQ ID NO 871
<211> LENGTH: 10
<212> TYPE: PRT
<213> ORGANISM: Epstein-Barr virus

<400> SEQUENCE: 871

Gly Leu Gly Lys Gln Val Cys Phe Asp Val
1               5                   10

<210> SEQ ID NO 872
<211> LENGTH: 9
<212> TYPE: PRT
<213> ORGANISM: Epstein-Barr virus

<400> SEQUENCE: 872

Gly Leu Gly Gln Gly Leu Ala Leu Leu
1               5

<210> SEQ ID NO 873
<211> LENGTH: 10
<212> TYPE: PRT
<213> ORGANISM: Epstein-Barr virus

<400> SEQUENCE: 873

Gly Met Ser Ala Thr Leu Pro Leu Pro Arg
1               5                   10

<210> SEQ ID NO 874
<211> LENGTH: 9
<212> TYPE: PRT
<213> ORGANISM: Epstein-Barr virus

<400> SEQUENCE: 874

Gly Pro Leu Cys Arg Gly Arg Val Ala
1               5

<210> SEQ ID NO 875
<211> LENGTH: 10
<212> TYPE: PRT
<213> ORGANISM: Epstein-Barr virus

<400> SEQUENCE: 875

Gly Pro Leu Cys Arg Gly Arg Val Ala Val
1               5                   10

<210> SEQ ID NO 876
<211> LENGTH: 10
<212> TYPE: PRT
<213> ORGANISM: Epstein-Barr virus

<400> SEQUENCE: 876

Gly Pro Pro His Gln Gly Gln Ala Thr Leu
1               5                   10

<210> SEQ ID NO 877
<211> LENGTH: 9
<212> TYPE: PRT
<213> ORGANISM: Epstein-Barr virus

<400> SEQUENCE: 877

Gly Pro Arg Asp Glu Gly Val Gln Ala
1               5

<210> SEQ ID NO 878
<211> LENGTH: 10
<212> TYPE: PRT
<213> ORGANISM: Epstein-Barr virus

<400> SEQUENCE: 878

Gly Pro Arg Asp Glu Gly Val Gln Ala Val
1               5                   10

<210> SEQ ID NO 879
<211> LENGTH: 9
<212> TYPE: PRT
<213> ORGANISM: Epstein-Barr virus

<400> SEQUENCE: 879

Gly Val Gln Arg Ser Gly Arg Pro Leu
1               5

<210> SEQ ID NO 880
<211> LENGTH: 10
<212> TYPE: PRT
<213> ORGANISM: Epstein-Barr virus

<400> SEQUENCE: 880

Gly Val Arg Arg Glu Gly Gly Gly Ala Val
1               5                   10

<210> SEQ ID NO 881
<211> LENGTH: 10
<212> TYPE: PRT
<213> ORGANISM: Epstein-Barr virus

<400> SEQUENCE: 881

His Ala Ile Lys His Ala Ile Asp Ser Leu
1               5                   10

<210> SEQ ID NO 882
<211> LENGTH: 9
<212> TYPE: PRT
<213> ORGANISM: Epstein-Barr virus

<400> SEQUENCE: 882

His Leu Ala Gln Val Leu Leu Leu Ala
1               5

<210> SEQ ID NO 883
<211> LENGTH: 10
<212> TYPE: PRT
<213> ORGANISM: Epstein-Barr virus

<400> SEQUENCE: 883

His Leu Ala Gln Val Leu Leu Leu Ala Leu
1               5                   10

<210> SEQ ID NO 884
<211> LENGTH: 9
<212> TYPE: PRT
<213> ORGANISM: Epstein-Barr virus

<400> SEQUENCE: 884

```
His Leu Arg Ala Leu Pro Gly Arg Leu
1               5
```

<210> SEQ ID NO 885
<211> LENGTH: 10
<212> TYPE: PRT
<213> ORGANISM: Epstein-Barr virus

<400> SEQUENCE: 885

```
His Leu Arg Ala Leu Pro Gly Arg Leu Leu
1               5                   10
```

<210> SEQ ID NO 886
<211> LENGTH: 10
<212> TYPE: PRT
<213> ORGANISM: Epstein-Barr virus

<400> SEQUENCE: 886

```
His Leu Arg Gly His Cys Arg Glu Asp Val
1               5                   10
```

<210> SEQ ID NO 887
<211> LENGTH: 9
<212> TYPE: PRT
<213> ORGANISM: Epstein-Barr virus

<400> SEQUENCE: 887

```
His Gln Leu Ala His Thr Ala Pro Ala
1               5
```

<210> SEQ ID NO 888
<211> LENGTH: 10
<212> TYPE: PRT
<213> ORGANISM: Epstein-Barr virus

<400> SEQUENCE: 888

```
Ile Leu Lys Gly Gly Thr Leu Ala Gly Ala
1               5                   10
```

<210> SEQ ID NO 889
<211> LENGTH: 10
<212> TYPE: PRT
<213> ORGANISM: Epstein-Barr virus

<400> SEQUENCE: 889

```
Lys Gln Val Cys Phe Asp Val Leu Gly Ile
1               5                   10
```

<210> SEQ ID NO 890
<211> LENGTH: 9
<212> TYPE: PRT
<213> ORGANISM: Epstein-Barr virus

<400> SEQUENCE: 890

```
Leu Ala Leu Leu Arg Gln Ala Gly Leu
1               5
```

<210> SEQ ID NO 891
<211> LENGTH: 9
<212> TYPE: PRT
<213> ORGANISM: Epstein-Barr virus

<400> SEQUENCE: 891

```
Leu Cys Arg Gly Arg Val Ala Val Val
```

```
<210> SEQ ID NO 892
<211> LENGTH: 9
<212> TYPE: PRT
<213> ORGANISM: Epstein-Barr virus

<400> SEQUENCE: 892

Leu Leu Ala Ser Ala Gln Pro Leu His
1               5

<210> SEQ ID NO 893
<211> LENGTH: 9
<212> TYPE: PRT
<213> ORGANISM: Epstein-Barr virus

<400> SEQUENCE: 893

Leu Leu Leu Ala Ser Ala Gln Pro Leu
1               5

<210> SEQ ID NO 894
<211> LENGTH: 10
<212> TYPE: PRT
<213> ORGANISM: Epstein-Barr virus

<400> SEQUENCE: 894

Leu Leu Gln Asp Gly Pro Val Leu Gly Val
1               5                   10

<210> SEQ ID NO 895
<211> LENGTH: 9
<212> TYPE: PRT
<213> ORGANISM: Epstein-Barr virus

<400> SEQUENCE: 895

Leu Leu Arg Gln Ala Gly Leu Gln Leu
1               5

<210> SEQ ID NO 896
<211> LENGTH: 10
<212> TYPE: PRT
<213> ORGANISM: Epstein-Barr virus

<400> SEQUENCE: 896

Leu Leu Val Arg Gln Arg Thr Cys Gly Val
1               5                   10

<210> SEQ ID NO 897
<211> LENGTH: 9
<212> TYPE: PRT
<213> ORGANISM: Epstein-Barr virus

<400> SEQUENCE: 897

Leu Leu Trp Ala Ala Arg Pro Arg Leu
1               5

<210> SEQ ID NO 898
<211> LENGTH: 10
<212> TYPE: PRT
<213> ORGANISM: Epstein-Barr virus

<400> SEQUENCE: 898

Leu Leu Trp Ala Ala Arg Pro Arg Leu Leu
1               5                   10
```

<210> SEQ ID NO 899
<211> LENGTH: 9
<212> TYPE: PRT
<213> ORGANISM: Epstein-Barr virus

<400> SEQUENCE: 899

Leu Pro Gly Lys Gln Gly Arg Glu Ala
1               5

<210> SEQ ID NO 900
<211> LENGTH: 10
<212> TYPE: PRT
<213> ORGANISM: Epstein-Barr virus

<400> SEQUENCE: 900

Leu Pro Gly Arg Leu Leu Leu Ala Ser Ala
1               5                   10

<210> SEQ ID NO 901
<211> LENGTH: 10
<212> TYPE: PRT
<213> ORGANISM: Epstein-Barr virus

<400> SEQUENCE: 901

Leu Pro Leu Pro Arg Cys Thr Asp Ser Met
1               5                   10

<210> SEQ ID NO 902
<211> LENGTH: 9
<212> TYPE: PRT
<213> ORGANISM: Epstein-Barr virus

<400> SEQUENCE: 902

Leu Pro Arg Cys Thr Asp Ser Met Ala
1               5

<210> SEQ ID NO 903
<211> LENGTH: 10
<212> TYPE: PRT
<213> ORGANISM: Epstein-Barr virus

<400> SEQUENCE: 903

Leu Pro Arg Cys Thr Asp Ser Met Ala Ala
1               5                   10

<210> SEQ ID NO 904
<211> LENGTH: 9
<212> TYPE: PRT
<213> ORGANISM: Epstein-Barr virus

<400> SEQUENCE: 904

Leu Gln Asp Gly Pro Val Leu Gly Val
1               5

<210> SEQ ID NO 905
<211> LENGTH: 9
<212> TYPE: PRT
<213> ORGANISM: Epstein-Barr virus

<400> SEQUENCE: 905

Leu Arg Ile His Arg His Arg Gln Val
1               5

<210> SEQ ID NO 906

```
<211> LENGTH: 10
<212> TYPE: PRT
<213> ORGANISM: Epstein-Barr virus

<400> SEQUENCE: 906

Leu Arg Ile His Arg His Arg Gln Val Val
1               5                   10

<210> SEQ ID NO 907
<211> LENGTH: 9
<212> TYPE: PRT
<213> ORGANISM: Epstein-Barr virus

<400> SEQUENCE: 907

Leu Val Arg Gln Arg Thr Cys Gly Val
1               5

<210> SEQ ID NO 908
<211> LENGTH: 10
<212> TYPE: PRT
<213> ORGANISM: Epstein-Barr virus

<400> SEQUENCE: 908

Leu Trp Ala Ala Arg Pro Arg Leu Leu Leu
1               5                   10

<210> SEQ ID NO 909
<211> LENGTH: 10
<212> TYPE: PRT
<213> ORGANISM: Epstein-Barr virus

<400> SEQUENCE: 909

Leu Tyr Pro Val Ala Arg Leu Asp Ala Trp
1               5                   10

<210> SEQ ID NO 910
<211> LENGTH: 9
<212> TYPE: PRT
<213> ORGANISM: Epstein-Barr virus

<400> SEQUENCE: 910

Met Ser Ala Thr Leu Pro Leu Pro Arg
1               5

<210> SEQ ID NO 911
<211> LENGTH: 9
<212> TYPE: PRT
<213> ORGANISM: Epstein-Barr virus

<400> SEQUENCE: 911

Pro Pro His Gln Gly Gln Ala Thr Leu
1               5

<210> SEQ ID NO 912
<211> LENGTH: 9
<212> TYPE: PRT
<213> ORGANISM: Epstein-Barr virus

<400> SEQUENCE: 912

Pro Pro Arg Ala Arg Asp Arg Ala Leu
1               5

<210> SEQ ID NO 913
<211> LENGTH: 10
<212> TYPE: PRT
```

<213> ORGANISM: Epstein-Barr virus

<400> SEQUENCE: 913

Pro Pro Arg Ala Arg Asp Arg Ala Leu Leu
1               5                   10

<210> SEQ ID NO 914
<211> LENGTH: 9
<212> TYPE: PRT
<213> ORGANISM: Epstein-Barr virus

<400> SEQUENCE: 914

Gln Pro Cys Pro Arg Gln Arg Leu Leu
1               5

<210> SEQ ID NO 915
<211> LENGTH: 9
<212> TYPE: PRT
<213> ORGANISM: Epstein-Barr virus

<400> SEQUENCE: 915

Gln Pro His Gly Val Arg His Ala Ile
1               5

<210> SEQ ID NO 916
<211> LENGTH: 10
<212> TYPE: PRT
<213> ORGANISM: Epstein-Barr virus

<400> SEQUENCE: 916

Gln Thr Leu Gly Gly His Leu Ala Gln Val
1               5                   10

<210> SEQ ID NO 917
<211> LENGTH: 10
<212> TYPE: PRT
<213> ORGANISM: Epstein-Barr virus

<400> SEQUENCE: 917

Gln Val Leu Arg Ala Gln Gly Leu Gly Lys
1               5                   10

<210> SEQ ID NO 918
<211> LENGTH: 10
<212> TYPE: PRT
<213> ORGANISM: Epstein-Barr virus

<400> SEQUENCE: 918

Arg Ala Leu Leu Trp Ala Ala Arg Pro Arg
1               5                   10

<210> SEQ ID NO 919
<211> LENGTH: 9
<212> TYPE: PRT
<213> ORGANISM: Epstein-Barr virus

<400> SEQUENCE: 919

Arg Ala Leu Pro Gly Arg Leu Leu Leu
1               5

<210> SEQ ID NO 920
<211> LENGTH: 10
<212> TYPE: PRT
<213> ORGANISM: Epstein-Barr virus -continued

<400> SEQUENCE: 920

Arg Ala Arg Asp Arg Ala Leu Leu Trp Ala
1               5                   10

<210> SEQ ID NO 921
<211> LENGTH: 9
<212> TYPE: PRT
<213> ORGANISM: Epstein-Barr virus

<400> SEQUENCE: 921

Arg Ile His Arg His Arg Gln Val Val
1               5

<210> SEQ ID NO 922
<211> LENGTH: 10
<212> TYPE: PRT
<213> ORGANISM: Epstein-Barr virus

<400> SEQUENCE: 922

Arg Leu Leu Leu Ala Ser Ala Gln Pro Leu
1               5                   10

<210> SEQ ID NO 923
<211> LENGTH: 9
<212> TYPE: PRT
<213> ORGANISM: Epstein-Barr virus

<400> SEQUENCE: 923

Arg Leu Leu Leu Ser Leu Gln Gln Val
1               5

<210> SEQ ID NO 924
<211> LENGTH: 10
<212> TYPE: PRT
<213> ORGANISM: Epstein-Barr virus

<400> SEQUENCE: 924

Arg Leu Arg Ile His Arg His Arg Gln Val
1               5                   10

<210> SEQ ID NO 925
<211> LENGTH: 10
<212> TYPE: PRT
<213> ORGANISM: Epstein-Barr virus

<400> SEQUENCE: 925

Arg Pro Gly His Leu Arg Ala Leu Pro Gly
1               5                   10

<210> SEQ ID NO 926
<211> LENGTH: 10
<212> TYPE: PRT
<213> ORGANISM: Epstein-Barr virus

<400> SEQUENCE: 926

Arg Pro Leu Cys Leu Arg Pro Pro Arg Ala
1               5                   10

<210> SEQ ID NO 927
<211> LENGTH: 9
<212> TYPE: PRT
<213> ORGANISM: Epstein-Barr virus

<400> SEQUENCE: 927

Arg Pro Pro Arg Ala Arg Asp Arg Ala
1               5

<210> SEQ ID NO 928
<211> LENGTH: 10
<212> TYPE: PRT
<213> ORGANISM: Epstein-Barr virus

<400> SEQUENCE: 928

Arg Pro Pro Arg Ala Arg Asp Arg Ala Leu
1               5                   10

<210> SEQ ID NO 929
<211> LENGTH: 10
<212> TYPE: PRT
<213> ORGANISM: Epstein-Barr virus

<400> SEQUENCE: 929

Arg Pro Arg Leu Leu Leu Ser Leu Gln Gln
1               5                   10

<210> SEQ ID NO 930
<211> LENGTH: 10
<212> TYPE: PRT
<213> ORGANISM: Epstein-Barr virus

<400> SEQUENCE: 930

Arg Val Gln Val Leu Arg Ala Gln Gly Leu
1               5                   10

<210> SEQ ID NO 931
<211> LENGTH: 9
<212> TYPE: PRT
<213> ORGANISM: Epstein-Barr virus

<400> SEQUENCE: 931

Arg Val Arg Glu Gly Ala Gly Arg Ala
1               5

<210> SEQ ID NO 932
<211> LENGTH: 10
<212> TYPE: PRT
<213> ORGANISM: Epstein-Barr virus

<400> SEQUENCE: 932

Arg Val Arg Glu Gly Ala Gly Arg Ala Gly
1               5                   10

<210> SEQ ID NO 933
<211> LENGTH: 10
<212> TYPE: PRT
<213> ORGANISM: Epstein-Barr virus

<400> SEQUENCE: 933

Arg Val Trp Asp Gly Thr Tyr Ala Pro Lys
1               5                   10

<210> SEQ ID NO 934
<211> LENGTH: 10
<212> TYPE: PRT
<213> ORGANISM: Epstein-Barr virus

<400> SEQUENCE: 934

Ser Leu Gln Gln Val Pro Glu Pro Ser Leu
1               5                   10

<210> SEQ ID NO 935
<211> LENGTH: 10
<212> TYPE: PRT
<213> ORGANISM: Epstein-Barr virus

<400> SEQUENCE: 935

Ser Gln Gly His Val Ala Gly Trp Gly Lys
1               5                   10

<210> SEQ ID NO 936
<211> LENGTH: 9
<212> TYPE: PRT
<213> ORGANISM: Epstein-Barr virus

<400> SEQUENCE: 936

Thr Leu Gly Gly His Leu Ala Gln Val
1               5

<210> SEQ ID NO 937
<211> LENGTH: 10
<212> TYPE: PRT
<213> ORGANISM: Epstein-Barr virus

<400> SEQUENCE: 937

Thr Leu Gly Gly His Leu Ala Gln Val Leu
1               5                   10

<210> SEQ ID NO 938
<211> LENGTH: 10
<212> TYPE: PRT
<213> ORGANISM: Epstein-Barr virus

<400> SEQUENCE: 938

Thr Tyr Ala Pro Lys Ala Ala Gln Gln Ile
1               5                   10

<210> SEQ ID NO 939
<211> LENGTH: 9
<212> TYPE: PRT
<213> ORGANISM: Epstein-Barr virus

<400> SEQUENCE: 939

Val Leu Leu Leu Ala Leu Glu Arg Val
1               5

<210> SEQ ID NO 940
<211> LENGTH: 9
<212> TYPE: PRT
<213> ORGANISM: Epstein-Barr virus

<400> SEQUENCE: 940

Val Leu Arg Ala Gln Gly Leu Gly Lys
1               5

<210> SEQ ID NO 941
<211> LENGTH: 9
<212> TYPE: PRT
<213> ORGANISM: Epstein-Barr virus

<400> SEQUENCE: 941

Val Pro Ile Glu Glu Leu Arg Glu Phe
1               5

```
<210> SEQ ID NO 942
<211> LENGTH: 9
<212> TYPE: PRT
<213> ORGANISM: Epstein-Barr virus

<400> SEQUENCE: 942

Val Pro Leu Leu Gln Asp Gly Pro Val
1               5

<210> SEQ ID NO 943
<211> LENGTH: 10
<212> TYPE: PRT
<213> ORGANISM: Epstein-Barr virus

<400> SEQUENCE: 943

Val Pro Leu Leu Gln Asp Gly Pro Val Leu
1               5                   10

<210> SEQ ID NO 944
<211> LENGTH: 10
<212> TYPE: PRT
<213> ORGANISM: Epstein-Barr virus

<400> SEQUENCE: 944

Val Val Ala His Ala Gly Gln Leu Pro Val
1               5                   10

<210> SEQ ID NO 945
<211> LENGTH: 9
<212> TYPE: PRT
<213> ORGANISM: Epstein-Barr virus

<400> SEQUENCE: 945

Trp Ala Ala Arg Pro Arg Leu Leu Leu
1               5

<210> SEQ ID NO 946
<211> LENGTH: 10
<212> TYPE: PRT
<213> ORGANISM: Epstein-Barr virus

<400> SEQUENCE: 946

Trp Pro Tyr Gln Gly Ser Gln Glu Arg Leu
1               5                   10

<210> SEQ ID NO 947
<211> LENGTH: 9
<212> TYPE: PRT
<213> ORGANISM: Epstein-Barr virus

<400> SEQUENCE: 947

Tyr Pro Val Ala Arg Leu Asp Ala Trp
1               5
```